US009758827B2

(12) United States Patent
Keller et al.

(10) Patent No.: US 9,758,827 B2
(45) Date of Patent: Sep. 12, 2017

(54) MIRNA FINGERPRINT IN THE DIAGNOSIS OF LUNG CANCER

(75) Inventors: Andreas Keller, Puettlingen (DE); Eckart Meese, Huetschenhausen (DE); Anne Borries, Heidelberg (DE); Markus Beier, Weinheim (DE)

(73) Assignee: Comprehensive Biomarker Center GmbH, Heidelberg (DE)

(*) Notice: Subject to any disclaimer, the term of this patent is extended or adjusted under 35 U.S.C. 154(b) by 0 days.

(21) Appl. No.: 13/376,281

(22) PCT Filed: Jun. 7, 2010

(86) PCT No.: PCT/EP2010/057942

§ 371 (c)(1),
(2), (4) Date: Jan. 19, 2012

(87) PCT Pub. No.: WO2010/139810

PCT Pub. Date: Dec. 9, 2010

(65) Prior Publication Data

US 2012/0108462 A1 May 3, 2012

Related U.S. Application Data

(60) Provisional application No. 61/184,452, filed on Jun. 5, 2009, provisional application No. 61/213,971, filed on Aug. 3, 2009, provisional application No. 61/287,521, filed on Dec. 17, 2009.

(30) Foreign Application Priority Data

Dec. 17, 2009 (EP) .................................... 09015668

(51) Int. Cl.

| | |
|---|---|
| ***C12Q 1/68*** | (2006.01) |
| ***G06F 19/24*** | (2011.01) |
| ***G06F 19/20*** | (2011.01) |

(52) U.S. Cl.

CPC ......... *C12Q 1/6883* (2013.01); *C12Q 1/6809* (2013.01); *C12Q 1/6886* (2013.01); *G06F 19/20* (2013.01); *G06F 19/24* (2013.01); *C12Q 2600/106* (2013.01); *C12Q 2600/112* (2013.01); *C12Q 2600/158* (2013.01); *C12Q 2600/178* (2013.01)

(58) Field of Classification Search

CPC ................ C12Q 1/6886; C12Q 1/6809; C12Q 2600/178; C12Q 2600/158; C12Q 2525/207; C12Q 2600/112; C12Q 2600/118

See application file for complete search history.

(56) References Cited

U.S. PATENT DOCUMENTS

2002/0172968 A1 11/2002 Liu et al.
2006/0019258 A1* 1/2006 Yeakley ........................... 435/6
2007/0050146 A1* 3/2007 Bentwich et al. .............. 702/19
2010/0184034 A1* 7/2010 Bankaitis-Davis .. C12Q 1/6886 435/6.12
2011/0251098 A1* 10/2011 Showe ............... G01N 33/5091 506/9

FOREIGN PATENT DOCUMENTS

| | | | |
|---|---|---|---|
| EP | 2 327 800 | A1 | 6/2011 |
| WO | 2008/104984 | A2 | 9/2008 |
| WO | 2008/117278 | A2 | 10/2008 |
| WO | 2009/025790 | A1 | 2/2009 |
| WO | 2009/033185 | A1 | 3/2009 |
| WO | 2009/036332 | A1 | 3/2009 |
| WO | 2009/055979 | A1 | 5/2009 |
| WO | 2009/057113 | A2 | 5/2009 |
| WO | 2009/070653 | A1 | 6/2009 |
| WO | 2009/099905 | A2 | 8/2009 |
| WO | 2009/108866 | A2 | 9/2009 |
| WO | 2009/147525 | A1 | 12/2009 |

OTHER PUBLICATIONS

Volinia et al. A microRNA expression signature of human solid tumors defines cancer target genes. Proceedings of the National Academy of Sciences, USA, vol. 103, No. 7, pp. 2257-2261, Feb. 2006, including Supporting Information printed as pp. 1/17-17/17.*
Kruhøffer et al. Isolation of microarray-grade total RNA, MicroRNA, and DNA from a signle PAXgene Blood RNA tube. Journal of Molecular Diagnostics, vol. 9, No. 4, pp. 452-458, Sep. 2007.*
Young et al. Wheater's Functional Histology: A Text and Colour Atlas, 5th edition, Churchill Livingstone, Elsevier, 2006, page on "Blood cell types," printed as p. 1/1.*
Debey-Pascher et al. "Chapter 22: Blood-based miRNA preparation for noninvasive marker development." in Next-Generation MicroRNA Expression Profiling Technology: Methods and Protocols, vol. 822, Jian-Bing Fan (ed.), pp. 307-338, 2012.*
PAXgene® Blood RNA Kit Handbook, Version 2, Mar. 2009, printed as pp. 1-56.*
PAXgene® Blood RNA Kit Handbook, Jun. 2005, printed as pp. 1-36.*
McShane et al. REporting recommendations for tumor MARKer prognostic studies (REMARK). British Journal of Cancer, vol. 93, pp. 387-391, 2005.*
Schneider, BJ. Non-small cell lung cancer staging: proposed revisions to the TNM system. Cancer Imaging, vol. 8, pp. 181-185, 2008.*
Guo et al. Confirmation of gene expression-based prediction of survival in non-small cell lung cancer. Clinical Cancer Research, vol. 14, No. 24, pp. 8213-8220, Dec. 15, 2008.*
Krell et al. microRNAs in the cancer clinic. Frontiers in Bioscience (Elite Edition), vol. 5, pp. 204-213, Jan. 2013.*
Quantilect™ SYBR® Green PCR Handbook: for quantitative, real-time PCR and two-step RT-PCR, www.qiagen.com, pp. 1-40, Aug. 2003.*
Moss et al. SCG3 transcript in peripheral blood is a prognostic biomarker for REST-deficient small cell lung cancer. Clinical Cancer Research, vol. 15, No. 1, pp. 274-283, Jan. 1, 2009.*
Chen et al. Characterization of microRNAs in serum: a novel class of biomarkers for diagnosis of cancer and other diseases. Cell Research, vol. 18, pp. 997-1006, Sep. 2, 2008, including Supplementary Tables 1-5.*

(Continued)

*Primary Examiner* — Jennifer Dunston

(74) *Attorney, Agent, or Firm* — Kilpatrick Townsend & Stockton LLP

(57) ABSTRACT

The present invention provides novel methods for diagnosing diseases based on the determination of specific miRNAs that have altered expression levels in disease states compared to healthy controls.

9 Claims, 104 Drawing Sheets

(56) References Cited

OTHER PUBLICATIONS

Figure 1:
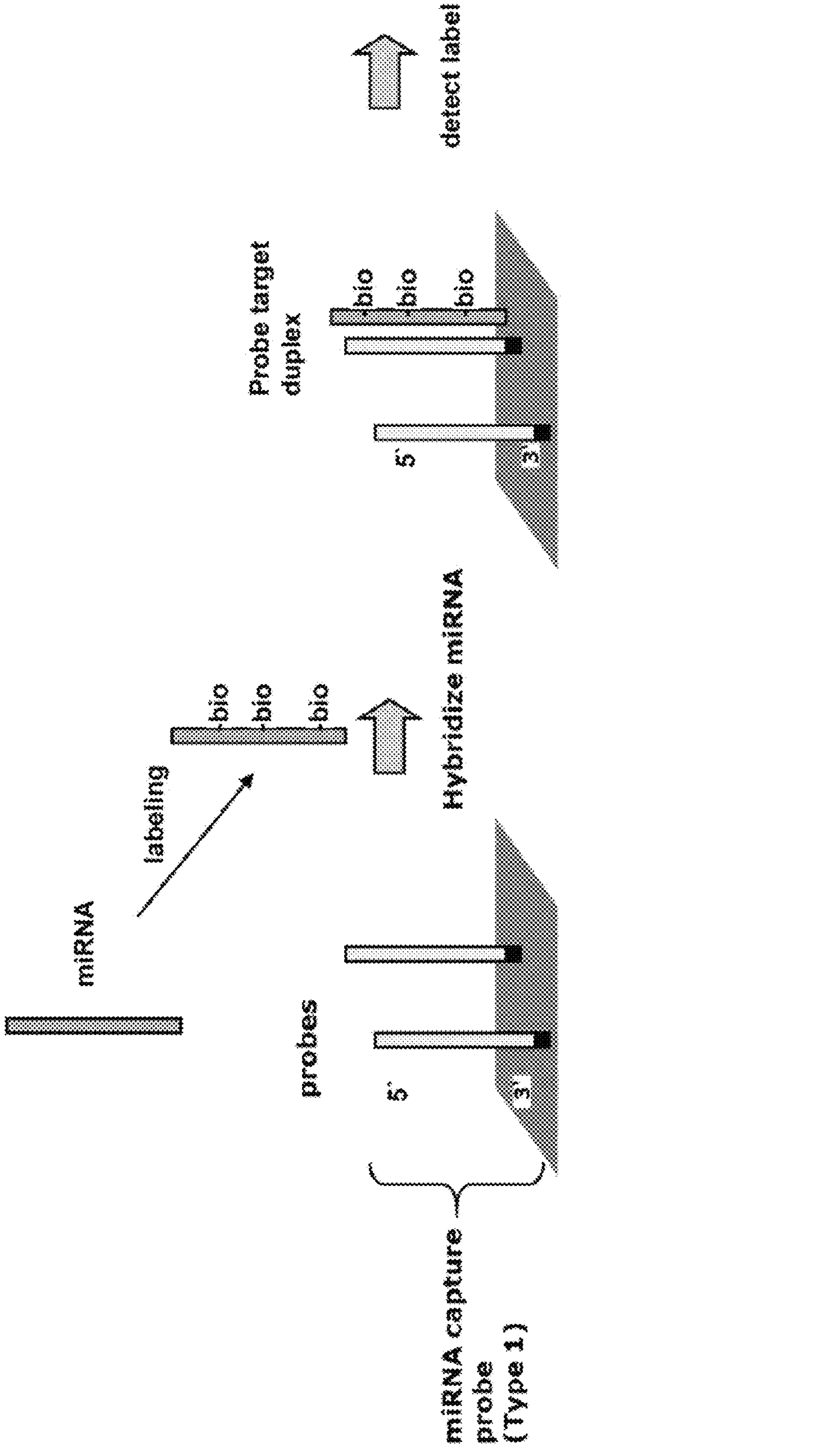

Shaffer, Jonathan, Martin Schlumpberger, and Eric Lader. "miRNA profiling from blood—challenges and recommendations." Qiagen Scientific article. pp. 1-10, 2012.*

Rabinowits Guilherme et al: "Exosomal microRNA: a diagnostic marker for lung cancer." Clinical Lung Cancer Jan. 2009 LNKD—PUBMED:19289371, vol. 10, No. 1, Jan. 2009 (Jan. 2009), pp. 42-46, XP002595815 ISSN: 1525-7304 the whole document.

Chen X et al: "Characterization of microRNAs in serum: a novel class of biomarkers for diagnosis of cancer and other diseases" Cell Research—Xibao Yanjiu, Nature Publishing Group, GB, CN LNKD D01:10.1038/CR.2008.282, vol. 18, No. 10, Oct. 1, 2008 (Oct. 1, 2008), pp. 997-1006, XP002552942 ISSN: 1001-0602 [retrieved on Sep. 2, 2008] cited in the application the whole document.

Keller Andreas et al: "miRNAs in lung cancer—Studying complex fingerprints in patient's blood cells by microarray experiments" BMC Cancer, Biomed Central, London, GB LNKD—D01:10.1186/1471-2407-9-353, vol. 9, No. 1, Oct. 6, 2009 (Oct. 6, 2009), p. 353, XP021062692 ISSN: 1471-2407 the whole document.

Keller Andreas et al: "Multiple Sclerosis: MicroRNA Expression Profiles Accurately Differentiate Patients with Relapsing-Remitting Disease from Healthy Controls" PLOS One, vol. 4, No. 10, Oct. 2009 (Oct. 2009), XP002596072 ISSN: 1932-6203 the whole document.

Lu Ming et al: "An Analysis of Human MicroRNA and Disease Associations" PLOS One, vol. 3, No. 10, Oct. 2008 (Oct. 2008), XP002596074 ISSN: 1932-6203 the whole documents.

Otaegui David et al: "Differential Micro RNA Expression in PBMC from Multiple Sclerosis Patients" PLOS One, vol. 4, No. 7, Jul. 2009 (Jul. 2009), XP002596073 ISSN: 1932-6203 table 2.

Leidinger Petra et al: "High-throughput miRNA profiling of human melanoma blood samples." BMC Cancer 2010 LNKD—PUBMED:20529253, vol. 10, Jun. 7, 2010 (Jun. 7, 2010), p. 262, XP002597623 ISSN: 1471-2407 the whole document.

Mitchell Patrick S et al: "Circulating microRNAs as stable blood-based markers for cancer detection" Jul. 29, 2008 (Jul. 29, 2008), Proceedings of the National Academy of Sciences of the United States (PNAS), National Academy of Science, US LNKD D01:10.1073/PNAS.0804549105, pp. 10513-10518 , XP002518102 ISSN: 0027-8424 [retrieved on Jul. 28, 2008] the whole document.

Molnar et al: "Changes in miRNA expression in solid tumors: An miRNA profiling in melanomas" Seminars in Cancer Biology, Saunders Scientific Publications, Philadelphia, PA, US LNKD DOI:10.1016/J. Semcancer.2008.01.001, vol. 18, No. 2, Jan. 15, 2008 (Jan. 15, 2008), pp. 111-122, XP022517940 ISSN: 1044-579X the whole document.

Office Action dated Nov. 6, 2014 in U.S. Appl. No. 13/376,225, 28 pages.

* cited by examiner

<u>Example :</u> human mature miRNA let-7a
ID : hsa-let-7a
Accession-Nr.: MIMAT0000062
Sequence: 5'-UGAGGUAGUAGGUUGUAUAGUU-3' miRNA capture probes :

- Type 1 (miRNA Hybridization Assay)

surface-3'-ACTCCATCATCCAACATATCAA-5'
  surface-5'-AACTATACAACCTACTACCTCA-3'

- Type 2 (miRNA Tandem Hybridization Assay)

surface-3'-ACTCCATCATCCAACATATCAA-SP-ACTCCATCATCCAACATATCAA-5'
  surface-5'-AACTATACAACCTACTACCTCA-SP-AACTATACAACCTACTACCTCA-3'

- Type 3 (miRNA RAKE-Assay)

surface-5'-AACTATACAACCTACTACCTCA-EL-3'

- Type 4 (miRNA MPEA-Assay)

surface-3'-EL-ACTCCATCATCCAACATATCAA-5'

Figure 5

Type 2 (miRNA Tandem Hybridization Assay)

surface-3'-ACTCCATCATCCAACATATCAA-SP-ACTCCATCATCCAACATATCAA-5'
surface-5'-AACTATACAACCTACTACCTCA-SP-AACTATACAACCTACTACCTCA-3'

With SP :

• nucleotide sequence with n = 0 –12 nucleotides chosen on the basis of showing low complementarity to potential target sequences, therefore resulting in no to low degree of crosshybridisation to target mixture preferentially : n = 0, no spacer between the 2 miRNA probe sequence stretches

Figure 6

Type 3 (miRNA RAKE-Assay)

surface-5'-AACTATACAACCTACTACCTCA-EL-3'

Type 4 (miRNA MPEA-Assay)

surface-3'-EL-ACTCCATCATCCAACATATCAA-5'

With EL :

• nucleotide sequence with n = 0 – 30 nucleotides chosen on the basis of showing low complementarity to potential target sequences, therefore resulting in no to low degree of crosshybridisation to target mixture preferentially : homomeric sequence stretch, $-N_n-$ with n = 1-30, N = A or C, or T, or G especially preferentially homomeric sequence stretch, $-N_n-$ with n = 1-12, N = A or C, or T, or G

Figure 7

| SEQ ID NO | No. | microRNA | Sequence | Median Cancer | Median Normal | Fold Quotient | Mutual Information |
|---|---|---|---|---|---|---|---|
| SEQ ID NO: 21 | 1 | hsa-miR-361-5p | uuaucagaaucuccaggguac | 606.46 | 53.00 | 11.44 | 0.45 |
| SEQ ID NO: 118 | 2 | hsa-miR-23b | aucacauugccagggauuacc | 3976.97 | 2099.43 | 1.89 | 0.42 |
| SEQ ID NO: 1 | 3 | hsa-miR-126 | ucguaccgugaguaauaaugcg | 606.46 | 3428.42 | 0.18 | 0.42 |
| SEQ ID NO: 838 | 4 | hsa-miR-527 | cugcaaagggaagcccuuuc | 74.78 | 68.44 | 1.09 | 0.42 |
| SEQ ID NO: 28 | 5 | hsa-miR-29a | uagcaccaucugaaaucgguua | 447.00 | 108.56 | 4.12 | 0.36 |
| SEQ ID NO: 3 | 6 | hsa-let-7i | ugagguaguaguuugugcuguu | 4106.11 | 6349.31 | 0.65 | 0.34 |
| SEQ ID NO: 8 | 7 | hsa-miR-19a | ugugcaaaucuaugcaaaacuga | 420.06 | 1.00 | 420.06 | 0.34 |
| SEQ ID NO: 146 | 8 | hsa-miR-28-5p | aaggagcucacagucuauugag | 454.22 | 108.56 | 4.18 | 0.33 |
| SEQ ID NO: 594 | 9 | hsa-miR-185* | aggggcuggcuuuccucugguc | 55.56 | 47.06 | 1.18 | 0.31 |
| SEQ ID NO: 147 | 10 | hsa-miR-23a | aucacauugccagggauuucc | 3428.42 | 1797.04 | 1.91 | 0.30 |
| SEQ ID NO: 529 | 11 | hsa-miR-1914* | ggaggggucccgcacugggagg | 249.39 | 153.00 | 1.63 | 0.30 |
| SEQ ID NO: 409 | 12 | hsa-miR-29c | uagcaccauuugaaaucgguua | 340.89 | 36.11 | 9.44 | 0.29 |
| SEQ ID NO: 36 | 13 | hsa-miR-505* | gggagccaggaaguauugaugu | 280.11 | 90.78 | 3.09 | 0.29 |
| SEQ ID NO: 4 | 14 | hsa-let-7d | agagguaguagguugcauaguu | 6795.89 | 13307.74 | 0.51 | 0.29 |
| SEQ ID NO: 139 | 15 | hsa-miR-378 | acuggacuuggagucagaagg | 284.22 | 21.56 | 13.19 | 0.29 |
| SEQ ID NO: 156 | 16 | hsa-miR-29b | uagcaccauuugaaaucaguguu | 337.83 | 82.06 | 4.12 | 0.29 |
| SEQ ID NO: 25 | 17 | hsa-miR-604 | aggcugcggaauucaggac | 245.00 | 90.78 | 2.70 | 0.29 |
| SEQ ID NO: 5 | 18 | hsa-miR-22 | aagcugccaguugaagaacugu | 7978.50 | 3868.50 | 2.06 | 0.28 |
| SEQ ID NO: 53 | 19 | hsa-let-7b | ugagguaguagguugugugguu | 6349.31 | 9746.17 | 0.65 | 0.28 |
| SEQ ID NO: 663 | 20 | hsa-miR-299-3p | uaugugggaugguaaaccgcuu | 58.78 | 55.22 | 1.06 | 0.28 |
| SEQ ID NO: 26 | 21 | hsa-miR-423-3p | agcucggucugaggccccucagu | 1797.04 | 463.22 | 3.88 | 0.27 |
| SEQ ID NO: 23 | 22 | hsa-miR-18a* | acugcccuaagugcuccuucugg | 1040.44 | 119.89 | 8.68 | 0.27 |
| SEQ ID NO: 687 | 23 | hsa-miR-1909 | cgcaggggccgggugcucaccg | 154.22 | 132.56 | 1.16 | 0.26 |
| SEQ ID NO: 15 | 24 | hsa-let-7c | ugagguaguagguuguaugguu | 5660.31 | 8969.72 | 0.63 | 0.26 |
| SEQ ID NO: 6 | 25 | hsa-miR-15a | uagcagcacauaaugguuugug | 3428.42 | 5944.79 | 0.58 | 0.25 |
| SEQ ID NO: 37 | 26 | hsa-miR-425 | aaugacacgaucacucccguuga | 11838.82 | 7392.17 | 1.60 | 0.25 |
| SEQ ID NO: 27 | 27 | hsa-miR-93* | acugcugagcuagcacuucccg | 480.44 | 30.44 | 15.78 | 0.25 |
| SEQ ID NO: 157 | 28 | hsa-miR-665 | accaggaggcugaggccccu | 212.00 | 191.33 | 1.11 | 0.25 |
| SEQ ID NO: 50 | 29 | hsa-miR-30e | uguaaacauccuugacuggaag | 369.89 | 129.44 | 2.86 | 0.25 |

Figure 10A

| | | | | | | | |
|---|---|---|---|---|---|---|---|
| SEQ ID NO: 38 | 30 | hsa-miR-339-3p | ugagcgccucgacgacagagccg | 209.67 | 109.67 | 1.91 | 0.25 |
| SEQ ID NO: 761 | 31 | hsa-miR-1307 | acucggcguggcgucggucgug | 82.06 | 70.67 | 1.16 | 0.25 |
| SEQ ID NO: 579 | 32 | hsa-miR-625* | gacuauagaacuuucccccuca | 52.00 | 21.89 | 2.38 | 0.23 |
| SEQ ID NO: 677 | 33 | hsa-miR-193a-5p | ugggucuuugcgggcgagauga | 46.89 | 30.44 | 1.54 | 0.23 |
| SEQ ID NO: 622 | 34 | hsa-miR-130b | cagugcaaugaugaaagggcau | 388.00 | 185.22 | 2.09 | 0.23 |
| SEQ ID NO: 734 | 35 | hsa-miR-17* | acugcagugaaggcacuuguag | 194.00 | 90.78 | 2.14 | 0.23 |
| SEQ ID NO: 9 | 36 | hsa-miR-574-5p | ugagugugugugugugagugugu | 108.56 | 30.22 | 3.59 | 0.22 |
| SEQ ID NO: 10 | 37 | hsa-miR-324-3p | acugccccaggugcugcugg | 1221.94 | 700.50 | 1.74 | 0.22 |
| SEQ ID NO: 358 | 38 | hsa-miR-24 | uggcucaguucagcaggaacag | 511.89 | 331.06 | 1.55 | 0.21 |
| SEQ ID NO: 688 | 39 | hsa-miR-629 | uggguuuacguugggagaacu | 106.11 | 63.11 | 1.68 | 0.21 |
| SEQ ID NO: 605 | 40 | hsa-miR-1323 | ucaaaacugaggggcauuuucu | 68.22 | 44.00 | 1.55 | 0.21 |
| SEQ ID NO: 18 | 41 | hsa-let-7g | ugagguaguaguuuguacaguu | 3428.42 | 6795.89 | 0.50 | 0.21 |
| SEQ ID NO: 77 | 42 | hsa-miR-1246 | aauggauuuuuggagcagg | 4915.83 | 3572.67 | 1.38 | 0.21 |
| SEQ ID NO: 131 | 43 | hsa-miR-215 | augaccuaugaauugacagac | 1085.22 | 463.22 | 2.34 | 0.21 |
| SEQ ID NO: 196 | 44 | hsa-miR-151-3p | cuagacugaagcuccuugagg | 344.56 | 90.78 | 3.80 | 0.21 |
| SEQ ID NO: 731 | 45 | hsa-miR-1471 | gcccgcguguggagccaggugu | 37.89 | 33.78 | 1.12 | 0.21 |
| SEQ ID NO: 109 | 46 | hsa-miR-652 | aauggcgccacuaggguugug | 1388.26 | 961.58 | 1.44 | 0.21 |
| SEQ ID NO: 41 | 47 | hsa-miR-15b* | cgaaucauuauuugcugcucua | 46.89 | 1.00 | 46.89 | 0.21 |
| SEQ ID NO: 30 | 48 | hsa-miR-210 | cugugcgugugacagcggcuga | 412.67 | 58.89 | 7.01 | 0.21 |
| SEQ ID NO: 20 | 49 | hsa-miR-339-5p | ucccuguccuccaggagcucacg | 312.11 | 12.44 | 25.08 | 0.21 |
| SEQ ID NO: 11 | 50 | hsa-miR-20b | caaagugcucauagugcagguag | 1118.35 | 2947.83 | 0.38 | 0.20 |
| SEQ ID NO: 716 | 51 | hsa-miR-654-5p | uggugggccgcagaacaugugc | 124.11 | 98.56 | 1.26 | 0.20 |
| SEQ ID NO: 719 | 52 | hsa-miR-328 | cuggcccucucugcccuuccgu | 72.22 | 68.44 | 1.06 | 0.19 |
| SEQ ID NO: 454 | 53 | hsa-miR-659 | cuugguucagggagggucccca | 150.56 | 133.11 | 1.13 | 0.19 |
| SEQ ID NO: 45 | 54 | hsa-miR-20a | uaaagugcuuauagugcagguag | 2319.90 | 4202.14 | 0.55 | 0.19 |
| SEQ ID NO: 16 | 55 | hsa-let-7f | ugagguaguagauuguauaguu | 5382.15 | 9746.17 | 0.55 | 0.19 |
| SEQ ID NO: 24 | 56 | hsa-miR-26b | uucaaguaauucaggauaggu | 1085.22 | 2058.85 | 0.53 | 0.18 |
| SEQ ID NO: 568 | 57 | hsa-miR-296 | agcagaagcagggagguucuccca | 71.56 | 53.33 | 1.34 | 0.18 |
| SEQ ID NO: 787 | 58 | hsa-miR-557 | guuugcacggguggggccuugucu | 114.67 | 132.00 | 0.87 | 0.18 |
| SEQ ID NO: 19 | 59 | hsa-miR-140-3p | uaccacaggguagaaccacgg | 9312.50 | 4621.29 | 2.02 | 0.18 |
| SEQ ID NO: 849 | 60 | hsa-miR-664* | acuggcuagggaaaaugauuggau | 61.56 | 39.44 | 1.56 | 0.18 |

Figure 10A (cont'd)

| | | | | | | | |
|---|---|---|---|---|---|---|---|
| SEQ ID NO: 7 | 61 | hsa-miR-98 | ugagguaguaaguuguauuguu | 322.44 | 1440.75 | 0.22 | 0.18 |
| SEQ ID NO: 701 | 62 | hsa-miR-1303 | uuuagagacggggucuugcucu | 41.89 | 31.33 | 1.34 | 0.18 |
| SEQ ID NO: 698 | 63 | hsa-miR-744 | ugcggggcuagggcuaacagca | 364.22 | 388.00 | 0.94 | 0.18 |
| SEQ ID NO: 134 | 64 | hsa-miR-378* | cuccugacuccagguccugugu | 111.78 | 28.00 | 3.99 | 0.18 |
| SEQ ID NO: 88 | 65 | hsa-miR-1207-3p | ucagcuggcccucauuuc | 1.00 | 18.11 | 0.06 | 0.18 |
| SEQ ID NO: 33 | 66 | hsa-miR-126* | cauuauuacuuuugguacgcg | 1.00 | 33.78 | 0.03 | 0.18 |
| SEQ ID NO: 70 | 67 | hsa-miR-1288 | uggacugcccugaucuggaga | 1.00 | 1.00 | 1.00 | 0.18 |
| SEQ ID NO: 47 | 68 | hsa-miR-145* | ggauuccuggaaauacuguucu | 1.00 | 1.00 | 1.00 | 0.18 |
| SEQ ID NO: 158 | 69 | hsa-miR-18a | uaaggugcaucuagugcagauag | 143.78 | 58.89 | 2.44 | 0.18 |
| SEQ ID NO: 78 | 70 | hsa-miR-338-5p | aacaauauccuggugcugagug | 1.00 | 1.00 | 1.00 | 0.18 |
| SEQ ID NO: 46 | 71 | hsa-miR-374a | uuauaauacaaccugauaagug | 225.11 | 692.94 | 0.32 | 0.18 |
| SEQ ID NO: 197 | 72 | hsa-miR-454 | uagugcaauauugcuuauagggu | 90.44 | 26.56 | 3.41 | 0.18 |
| SEQ ID NO: 71 | 73 | hsa-miR-503 | uagcagcgggaacaguucugcag | 68.67 | 73.33 | 0.94 | 0.18 |
| SEQ ID NO: 72 | 74 | hsa-miR-563 | agguugacauacguuuccc | 1.00 | 1.00 | 1.00 | 0.18 |
| SEQ ID NO: 2 | 75 | hsa-miR-423-5p | ugaggggcagagagcgagacuuu | 6795.89 | 3976.97 | 1.71 | 0.17 |
| SEQ ID NO: 89 | 76 | hsa-miR-16 | uagcagcacguaaauauuggcg | 20349.58 | 24783.94 | 0.82 | 0.17 |
| SEQ ID NO: 846 | 77 | hsa-miR-637 | acugggggcuuucgggcucugcgu | 90.11 | 70.89 | 1.27 | 0.17 |
| SEQ ID NO: 12 | 78 | hsa-miR-25 | cauugcacuugucucggucuga | 12517.64 | 7639.53 | 1.64 | 0.17 |
| SEQ ID NO: 342 | 79 | hsa-miR-1182 | gagggucuugggagggaugugac | 708.06 | 674.69 | 1.05 | 0.17 |
| SEQ ID NO: 159 | 80 | hsa-miR-1224-5p | gugaggacucgggaggugg | 586.78 | 388.00 | 1.51 | 0.17 |
| SEQ ID NO: 636 | 81 | hsa-miR-144* | ggauaucaucauauacuguaag | 340.89 | 450.61 | 0.76 | 0.17 |
| SEQ ID NO: 60 | 82 | hsa-miR-361-3p | ucccccaggugugauucugauuu | 367.06 | 256.44 | 1.43 | 0.16 |
| SEQ ID NO: 69 | 83 | hsa-miR-151-5p | ucgaggagcucacagucuagu | 1732.86 | 1024.56 | 1.69 | 0.16 |
| SEQ ID NO: 14 | 84 | hsa-let-7e | ugagguaggagguuguauaguu | 1297.51 | 2947.83 | 0.44 | 0.15 |
| SEQ ID NO: 17 | 85 | hsa-let-7a | ugagguaguagguuguauaguu | 6795.89 | 12517.64 | 0.54 | 0.15 |
| SEQ ID NO: 237 | 86 | hsa-miR-194 | uguaacagcaacuccaugugga | 1853.10 | 1440.75 | 1.29 | 0.15 |
| SEQ ID NO: 376 | 87 | hsa-miR-921 | cuagugagggacagaaccaggauuc | 260.22 | 207.33 | 1.26 | 0.15 |
| SEQ ID NO: 238 | 88 | hsa-miR-15b | uagcagcacaucaugguuuaca | 20349.58 | 23734.72 | 0.86 | 0.15 |
| SEQ ID NO: 756 | 89 | hsa-miR-187* | ggcuacaacacaggacccgggc | 88.56 | 68.44 | 1.29 | 0.14 |
| SEQ ID NO: 51 | 90 | hsa-miR-223 | ugucaguuugucaaauacccca | 3080.08 | 5660.31 | 0.54 | 0.14 |
| SEQ ID NO: 493 | 91 | hsa-miR-1255a | aggaugagcaaagaaaguagauu | 46.44 | 28.44 | 1.63 | 0.14 |

Figure 10A (cont'd)

| | | | | | | | |
|---|---|---|---|---|---|---|---|
| SEQ ID NO: 110 | 92 | hsa-miR-1256 | aggcauugacuucucacuagcu | 1.00 | 1.00 | 1.00 | 0.14 |
| SEQ ID NO: 22 | 93 | hsa-miR-1283 | ucuacaaaggaaagcgcuuucu | 2.33 | 22.22 | 0.11 | 0.14 |
| SEQ ID NO: 93 | 94 | hsa-miR-136 | acuccauuuguuuugaugaugga | 1.00 | 1.56 | 0.64 | 0.14 |
| SEQ ID NO: 140 | 95 | hsa-miR-143* | ggugcagugcugcaucucuggu | 1.00 | 1.00 | 1.00 | 0.14 |
| SEQ ID NO: 98 | 96 | hsa-miR-186* | gcccaaaggugaauuuuuuggg | 1.00 | 1.00 | 1.00 | 0.14 |
| SEQ ID NO: 34 | 97 | hsa-miR-188-3p | cucccacaugcaggguuugca | 1.00 | 4.44 | 0.23 | 0.14 |
| SEQ ID NO: 61 | 98 | hsa-miR-19a* | aguuuugcauaguugcacuaca | 1.00 | 1.00 | 1.00 | 0.14 |
| SEQ ID NO: 185 | 99 | hsa-miR-208b | auaagacgaacaaaagguuugu | 6.78 | 1.00 | 6.78 | 0.14 |
| SEQ ID NO: 337 | 100 | hsa-miR-27b* | agagcuuagcugauuggugaac | 8.44 | 4.22 | 2.00 | 0.14 |
| SEQ ID NO: 79 | 101 | hsa-miR-297 | auguaugugugcaugugcaug | 1.00 | 12.11 | 0.08 | 0.14 |
| SEQ ID NO: 48 | 102 | hsa-miR-302b | uaagugcuuccauguuuuaguag | 1.00 | 1.00 | 1.00 | 0.14 |
| SEQ ID NO: 485 | 103 | hsa-miR-30e* | cuuucagucggauguuuacagc | 20.56 | 8.33 | 2.47 | 0.14 |
| SEQ ID NO: 239 | 104 | hsa-miR-342-5p | aggggugcuaucugugauuga | 82.44 | 73.33 | 1.12 | 0.14 |
| SEQ ID NO: 62 | 105 | hsa-miR-433 | aucaugaugggcuccucggugu | 1.00 | 1.00 | 1.00 | 0.14 |
| SEQ ID NO: 32 | 106 | hsa-miR-453 | agguuguccgugguggaguucgca | 6.78 | 57.00 | 0.12 | 0.14 |
| SEQ ID NO: 343 | 107 | hsa-miR-532-3p | ccucccacacccaaggcuugca | 88.11 | 114.67 | 0.77 | 0.14 |
| SEQ ID NO: 54 | 108 | hsa-miR-542-3p | ugugacagauugauaacugaaa | 1.00 | 18.72 | 0.05 | 0.14 |
| SEQ ID NO: 94 | 109 | hsa-miR-548d-3p | caaaaaccacaguuucuuuugc | 1.00 | 1.00 | 1.00 | 0.14 |
| SEQ ID NO: 148 | 110 | hsa-miR-645 | ucuaggcugguacugcuga | 1.00 | 1.00 | 1.00 | 0.14 |
| SEQ ID NO: 149 | 111 | hsa-miR-647 | guggcugcacucacuuccuuc | 1.00 | 1.00 | 1.00 | 0.14 |
| SEQ ID NO: 73 | 112 | hsa-miR-663b | gguggcccggccgugccugagg | 5.56 | 4.44 | 1.25 | 0.14 |
| SEQ ID NO: 443 | 113 | hsa-miR-30a | uguaaacauccucgacuggaag | 1175.03 | 1056.33 | 1.11 | 0.14 |
| SEQ ID NO: 552 | 114 | hsa-miR-365 | uaaugccccuaaaaauccuuau | 24.00 | 42.78 | 0.56 | 0.14 |
| SEQ ID NO: 678 | 115 | hsa-miR-671-3p | uccgguucucagggcuccacc | 21.11 | 13.72 | 1.54 | 0.13 |
| SEQ ID NO: 74 | 116 | hsa-let-7d* | cuauacgaccugcugccuuucu | 39.44 | 6.00 | 6.57 | 0.13 |
| SEQ ID NO: 29 | 117 | hsa-miR-1248 | accuucuuguauaagcacugugcuaaa | 154.22 | 31.33 | 4.92 | 0.13 |
| SEQ ID NO: 410 | 118 | hsa-miR-1268 | cgggcgugguggugggg | 901.96 | 1056.33 | 0.85 | 0.13 |
| SEQ ID NO: 99 | 119 | hsa-miR-145 | guccaguuuucccaggaaucccu | 571.78 | 101.11 | 5.66 | 0.13 |
| SEQ ID NO: 271 | 120 | hsa-miR-198 | gguccagaggggagauagguuc | 428.39 | 382.00 | 1.12 | 0.13 |
| SEQ ID NO: 75 | 121 | hsa-miR-199a-5p | cccaguguucagacuaccuguuc | 145.33 | 36.11 | 4.02 | 0.13 |
| SEQ ID NO: 795 | 122 | hsa-miR-323-5p | agguggguccgugggcgcguucgc | 58.33 | 67.44 | 0.86 | 0.13 |

Figure 10A (cont'd)

| | | | | | | | |
|---|---|---|---|---|---|---|---|
| SEQ ID NO: 31 | 123 | hsa-miR-19b | ugugcaaauccaugcaaaacuga | 3428.42 | 1853.10 | 1.85 | 0.13 |
| SEQ ID NO: 49 | 124 | hsa-miR-106a | aaaagugcuuacagugcagguag | 4462.58 | 6349.31 | 0.70 | 0.13 |
| SEQ ID NO: 619 | 125 | hsa-miR-885-3p | aggcagcgggguguaguggaua | 463.22 | 1040.44 | 0.45 | 0.12 |
| SEQ ID NO: 13 | 126 | hsa-miR-195 | uagcagcacagaaauauuggc | 2575.72 | 4462.58 | 0.58 | 0.12 |
| SEQ ID NO: 198 | 127 | hsa-miR-101 | uacaguacugugauaacugaa | 94.56 | 138.61 | 0.68 | 0.12 |
| SEQ ID NO: 834 | 128 | hsa-miR-130a | cagugcaauguuaaaagggcau | 746.29 | 874.97 | 0.85 | 0.12 |
| SEQ ID NO: 67 | 129 | hsa-miR-192 | cugaccuaugaauugacagcc | 3080.08 | 1675.67 | 1.84 | 0.12 |
| SEQ ID NO: 865 | 130 | hsa-miR-638 | agggaucgcgggcggguggcggccu | 4915.83 | 5944.79 | 0.83 | 0.12 |
| SEQ ID NO: 840 | 131 | hsa-miR-1238 | cuuccucgucugucugcccc | 52.00 | 58.89 | 0.88 | 0.11 |
| SEQ ID NO: 753 | 132 | hsa-miR-106b | uaaagugcugacagugcagau | 3080.08 | 2319.90 | 1.33 | 0.11 |
| SEQ ID NO: 90 | 133 | hsa-miR-1 | uggaauguaaagaaguauguau | 1.00 | 1.00 | 1.00 | 0.11 |
| SEQ ID NO: 160 | 134 | hsa-miR-10a* | caaauucguaucuaggggaaua | 1.00 | 4.44 | 0.23 | 0.11 |
| SEQ ID NO: 63 | 135 | hsa-miR-1200 | cuccugagccauucugagccuc | 1.00 | 5.11 | 0.20 | 0.11 |
| SEQ ID NO: 105 | 136 | hsa-miR-1204 | ucguggccuggucuccauuau | 1.00 | 4.44 | 0.23 | 0.11 |
| SEQ ID NO: 377 | 137 | hsa-miR-1206 | uguucauguagauguuuaagc | 1.00 | 10.44 | 0.10 | 0.11 |
| SEQ ID NO: 466 | 138 | hsa-miR-124 | uaaggcacgcggugaaugcc | 20.56 | 11.33 | 1.81 | 0.11 |
| SEQ ID NO: 68 | 139 | hsa-miR-1245 | aagugaucuaaaggccuacau | 1.00 | 1.00 | 1.00 | 0.11 |
| SEQ ID NO: 378 | 140 | hsa-miR-1259 | auauaugaugacuuagcuuuu | 112.44 | 106.11 | 1.06 | 0.11 |
| SEQ ID NO: 240 | 141 | hsa-miR-125b-2* | ucacaagucaggcucuugggac | 1.00 | 3.67 | 0.27 | 0.11 |
| SEQ ID NO: 80 | 142 | hsa-miR-1261 | auggauaaggcuuuggcuu | 1.00 | 10.44 | 0.10 | 0.11 |
| SEQ ID NO: 141 | 143 | hsa-miR-1266 | ccucagggcuguagaacagggcu | 17.11 | 29.94 | 0.57 | 0.11 |
| SEQ ID NO: 221 | 144 | hsa-miR-1278 | uaguacugugcauaucaucuau | 1.00 | 1.00 | 1.00 | 0.11 |
| SEQ ID NO: 241 | 145 | hsa-miR-1297 | uucaaguaauucaggug | 1.00 | 1.00 | 1.00 | 0.11 |
| SEQ ID NO: 119 | 146 | hsa-miR-1302 | uugggacauacuuaugcuaaa | 1.00 | 1.00 | 1.00 | 0.11 |
| SEQ ID NO: 318 | 147 | hsa-miR-1304 | uuugaggcuacagugagaugug | 20.56 | 28.00 | 0.73 | 0.11 |
| SEQ ID NO: 222 | 148 | hsa-miR-135b | uauggcuuuucauuccuauguga | 1.00 | 1.00 | 1.00 | 0.11 |
| SEQ ID NO: 161 | 149 | hsa-miR-181a* | accaucgaccguugauuguacc | 1.00 | 1.00 | 1.00 | 0.11 |
| SEQ ID NO: 685 | 150 | hsa-miR-181c | aacauucaaccugucggugagu | 130.44 | 21.78 | 5.99 | 0.11 |
| SEQ ID NO: 199 | 151 | hsa-miR-19b-1* | aguuuugcagguuugcauccagc | 1.00 | 1.00 | 1.00 | 0.11 |
| SEQ ID NO: 489 | 152 | hsa-miR-205 | uccuucauuccaccggagucug | 1.00 | 1.00 | 1.00 | 0.11 |
| SEQ ID NO: 111 | 153 | hsa-miR-20b* | acuguaguaugggcacuuccag | 1.00 | 4.44 | 0.23 | 0.11 |

Figure 10A (cont'd)

| | | | | | | | |
|---|---|---|---|---|---|---|---|
| SEQ ID NO: 162 | 154 | hsa-miR-218-2* | caugguucugucaagcaccgcg | 1.00 | 1.00 | 1.00 | 0.11 |
| SEQ ID NO: 319 | 155 | hsa-miR-220b | ccaccaccgugucugacacuu | 2.67 | 1.00 | 2.67 | 0.11 |
| SEQ ID NO: 135 | 156 | hsa-miR-221* | accuggcauacaauguagauuu | 1.00 | 1.00 | 1.00 | 0.11 |
| SEQ ID NO: 211 | 157 | hsa-miR-23b* | uggguuccuggcaugcugauuu | 1.00 | 1.00 | 1.00 | 0.11 |
| SEQ ID NO: 192 | 158 | hsa-miR-24-2* | ugccuacugagcugaaacacag | 1.00 | 1.00 | 1.00 | 0.11 |
| SEQ ID NO: 289 | 159 | hsa-miR-28-3p | cacuagauugugagcuccugga | 29.11 | 21.11 | 1.38 | 0.11 |
| SEQ ID NO: 150 | 160 | hsa-miR-302b* | acuuuaacauggaagugcuuuc | 1.00 | 1.00 | 1.00 | 0.11 |
| SEQ ID NO: 86 | 161 | hsa-miR-335* | uuuuucauuauugcuccugacc | 1.00 | 1.56 | 0.64 | 0.11 |
| SEQ ID NO: 136 | 162 | hsa-miR-34b | caaucacuaacuccacugccau | 2.67 | 19.78 | 0.13 | 0.11 |
| SEQ ID NO: 163 | 163 | hsa-miR-371-3p | aagugccgccaucuuuugagugu | 1.00 | 1.00 | 1.00 | 0.11 |
| SEQ ID NO: 616 | 164 | hsa-miR-374b | auauaauacaaccugcuaagug | 126.44 | 21.56 | 5.87 | 0.11 |
| SEQ ID NO: 164 | 165 | hsa-miR-377 | aucacacaaaggcaacuuuugu | 1.00 | 1.00 | 1.00 | 0.11 |
| SEQ ID NO: 117 | 166 | hsa-miR-411 | uaguagaccguauagcguacg | 1.00 | 1.00 | 1.00 | 0.11 |
| SEQ ID NO: 112 | 167 | hsa-miR-424* | caaaacgugaggcgcugcuau | 34.00 | 46.11 | 0.74 | 0.11 |
| SEQ ID NO: 530 | 168 | hsa-miR-425* | aucgggaaugucguguccgccc | 98.00 | 33.78 | 2.90 | 0.11 |
| SEQ ID NO: 120 | 169 | hsa-miR-449a | uggcaguguauuguuagcuggu | 1.00 | 1.00 | 1.00 | 0.11 |
| SEQ ID NO: 56 | 170 | hsa-miR-451 | aaaccguuaccauuacugaguu | 1118.35 | 4106.11 | 0.27 | 0.11 |
| SEQ ID NO: 200 | 171 | hsa-miR-509-5p | uacugcagacaguggcaauca | 1.00 | 1.00 | 1.00 | 0.11 |
| SEQ ID NO: 55 | 172 | hsa-miR-516b* | ugcuuccuuucagagggu | 9.56 | 31.33 | 0.30 | 0.11 |
| SEQ ID NO: 113 | 173 | hsa-miR-517a | aucgugcaucccuuuagagugu | 1.00 | 1.00 | 1.00 | 0.11 |
| SEQ ID NO: 64 | 174 | hsa-miR-522 | aaaaugguucccuuuagagugu | 1.00 | 8.33 | 0.12 | 0.11 |
| SEQ ID NO: 379 | 175 | hsa-miR-525-5p | cuccagagggaugcacuuucu | 1.89 | 4.22 | 0.45 | 0.11 |
| SEQ ID NO: 763 | 176 | hsa-miR-532-5p | caugccuugaguguaggaccgu | 121.44 | 92.56 | 1.31 | 0.11 |
| SEQ ID NO: 121 | 177 | hsa-miR-548f | aaaaacuguaauuacuuuu | 1.00 | 1.00 | 1.00 | 0.11 |
| SEQ ID NO: 96 | 178 | hsa-miR-548h | aaaaguaaucgcgguuuuuguc | 1.00 | 1.00 | 1.00 | 0.11 |
| SEQ ID NO: 187 | 179 | hsa-miR-551b | gcgacccauacuugguuucag | 1.00 | 1.00 | 1.00 | 0.11 |
| SEQ ID NO: 142 | 180 | hsa-miR-554 | gcuaguccugacucagccagu | 1.00 | 1.00 | 1.00 | 0.11 |
| SEQ ID NO: 122 | 181 | hsa-miR-597 | ugugucacucgaugaccacugu | 1.00 | 1.00 | 1.00 | 0.11 |
| SEQ ID NO: 116 | 182 | hsa-miR-599 | guugugucaguuuaucaaac | 1.00 | 1.00 | 1.00 | 0.11 |
| SEQ ID NO: 59 | 183 | hsa-miR-602 | gacacgggcgacagcugcggccc | 20.56 | 44.00 | 0.47 | 0.11 |
| SEQ ID NO: 123 | 184 | hsa-miR-603 | cacacacugcaauuacuuuugc | 1.00 | 1.56 | 0.64 | 0.11 |

Figure 10A (cont'd)

| | | | | | | | |
|---|---|---|---|---|---|---|---|
| SEQ ID NO: 151 | 185 | hsa-miR-607 | guucaaauccagaucuauaac | 1.00 | 1.00 | 1.00 | 0.11 |
| SEQ ID NO: 107 | 186 | hsa-miR-619 | gaccuggacauguuugugcccagu | 1.00 | 1.00 | 1.00 | 0.11 |
| SEQ ID NO: 143 | 187 | hsa-miR-631 | agaccuggcccagaccucagc | 2.67 | 13.72 | 0.19 | 0.11 |
| SEQ ID NO: 234 | 188 | hsa-miR-874 | cugcccuggcccgagggaccga | 34.00 | 35.83 | 0.95 | 0.11 |
| SEQ ID NO: 320 | 189 | hsa-miR-891a | ugcaacgaaccugagccacuga | 6.78 | 6.56 | 1.03 | 0.11 |
| SEQ ID NO: 81 | 190 | hsa-miR-922 | gcagcagagaauaggacuacguc | 1.00 | 18.72 | 0.05 | 0.11 |
| SEQ ID NO: 242 | 191 | hsa-miR-933 | ugugcgcagggagaccucuccc | 18.11 | 28.44 | 0.64 | 0.11 |
| SEQ ID NO: 553 | 192 | hsa-miR-99b | cacccguagaaccgaccuugcg | 73.33 | 33.56 | 2.19 | 0.11 |
| SEQ ID NO: 106 | 193 | hsa-miR-106b* | ccgcacuguggguacuugcugc | 901.96 | 137.56 | 6.56 | 0.11 |
| SEQ ID NO: 42 | 194 | hsa-miR-29c* | ugaccgauuucuccugguguuc | 61.11 | 1.00 | 61.11 | 0.11 |
| SEQ ID NO: 243 | 195 | hsa-miR-493* | uuguacaugguaggcuuucauu | 1.56 | 3.11 | 0.50 | 0.11 |
| SEQ ID NO: 725 | 196 | hsa-miR-886-5p | cgggucggaguuagcucaagcgg | 126.44 | 87.67 | 1.44 | 0.11 |
| SEQ ID NO: 808 | 197 | hsa-miR-197 | uucaccaccuucuccacccagc | 143.78 | 111.78 | 1.29 | 0.10 |
| SEQ ID NO: 639 | 198 | hsa-miR-183 | uauggcacugguagaauucacu | 90.11 | 26.56 | 3.39 | 0.10 |
| SEQ ID NO: 526 | 199 | hsa-miR-500 | uaauccuugcuaccugggugaga | 136.17 | 58.78 | 2.32 | 0.10 |
| SEQ ID NO: 359 | 200 | hsa-miR-484 | ucaggcucaguccccucccgau | 3778.89 | 2575.72 | 1.47 | 0.10 |
| SEQ ID NO: 82 | 201 | hsa-miR-185 | uggagagaaaggcaguuccuga | 15421.86 | 13307.74 | 1.16 | 0.10 |
| SEQ ID NO: 39 | 202 | hsa-miR-668 | ugucacucggcucggcccacuac | 276.44 | 92.56 | 2.99 | 0.10 |
| SEQ ID NO: 471 | 203 | hsa-miR-936 | acaguagagggaggaaucgcag | 683.82 | 660.47 | 1.04 | 0.10 |
| SEQ ID NO: 97 | 204 | hsa-miR-331-3p | gccccugggccuauccuagaa | 723.61 | 403.89 | 1.79 | 0.10 |
| SEQ ID NO: 83 | 205 | hsa-miR-611 | gcgaggaccccucggggucugac | 30.44 | 18.11 | 1.68 | 0.10 |
| SEQ ID NO: 723 | 206 | hsa-miR-1469 | cucggcgcggggcgcgggcucc | 961.58 | 1297.51 | 0.74 | 0.10 |
| SEQ ID NO: 780 | 207 | hsa-miR-564 | aggcacggugucagcaggc | 56.78 | 47.06 | 1.21 | 0.09 |
| SEQ ID NO: 560 | 208 | hsa-miR-103 | agcagcauuguacagggcuauga | 3868.50 | 5362.15 | 0.72 | 0.09 |
| SEQ ID NO: 696 | 209 | hsa-miR-1273 | gggcgacaaagcaagacucuuucuu | 26.44 | 31.33 | 0.84 | 0.09 |
| SEQ ID NO: 344 | 210 | hsa-miR-181b | aacauucauugcugucgguggguu | 61.11 | 27.78 | 2.20 | 0.09 |
| SEQ ID NO: 130 | 211 | hsa-miR-658 | ggcggagggaaguagguccguuggu | 2425.74 | 1118.35 | 2.17 | 0.09 |
| SEQ ID NO: 598 | 212 | hsa-miR-125a-3p | acaggugagguucuugggagcc | 58.33 | 39.22 | 1.49 | 0.08 |
| SEQ ID NO: 165 | 213 | hsa-miR-140-5p | cagugguuuuacccuaugguag | 1.00 | 1.00 | 1.00 | 0.08 |
| SEQ ID NO: 166 | 214 | hsa-miR-301a | cagugcaauaguauugucaaagc | 16.78 | 21.56 | 0.78 | 0.08 |
| SEQ ID NO: 321 | 215 | hsa-miR-1253 | agagaagaagaucagccugca | 1.00 | 1.00 | 1.00 | 0.08 |

Figure 10A (cont'd)

| | | | | | | | |
|---|---|---|---|---|---|---|---|
| SEQ ID NO: 713 | 216 | hsa-miR-663 | aggcggggcgccgcgggaccgc | 715.83 | 1175.03 | 0.61 | 0.08 |
| SEQ ID NO: 223 | 217 | hsa-let-7c* | uagaguuacacccugggaguua | 1.00 | 1.00 | 1.00 | 0.08 |
| SEQ ID NO: 102 | 218 | hsa-let-7f-1* | cuauacaaucuauugccuuccc | 1.00 | 1.00 | 1.00 | 0.08 |
| SEQ ID NO: 290 | 219 | hsa-let-7f-2* | cuauacagucuacugucuuucc | 1.00 | 1.00 | 1.00 | 0.08 |
| SEQ ID NO: 360 | 220 | hsa-miR-103-as | ucauagcccuguacaaugcugcu | 1.00 | 1.00 | 1.00 | 0.08 |
| SEQ ID NO: 244 | 221 | hsa-miR-105 | ucaaaugcucagacuccuguggu | 1.00 | 1.00 | 1.00 | 0.08 |
| SEQ ID NO: 689 | 222 | hsa-miR-10a | uacccuguagauccgaauuugug | 34.22 | 30.44 | 1.12 | 0.08 |
| SEQ ID NO: 284 | 223 | hsa-miR-1185 | agaggauacccuuuguauguu | 1.00 | 1.00 | 1.00 | 0.08 |
| SEQ ID NO: 527 | 224 | hsa-miR-1201 | agccugauuaaacacaugcucuga | 37.89 | 18.11 | 2.09 | 0.08 |
| SEQ ID NO: 322 | 225 | hsa-miR-1205 | ucugcaggguuugcuuugag | 1.00 | 1.00 | 1.00 | 0.08 |
| SEQ ID NO: 411 | 226 | hsa-miR-122 | uggagugugacaaugguguuug | 17.11 | 21.11 | 0.81 | 0.08 |
| SEQ ID NO: 124 | 227 | hsa-miR-1247 | acccgucccguucguccccgga | 9.56 | 16.33 | 0.59 | 0.08 |
| SEQ ID NO: 455 | 228 | hsa-miR-1251 | acucuagcugccaaaggcgcu | 1.00 | 1.00 | 1.00 | 0.08 |
| SEQ ID NO: 212 | 229 | hsa-miR-1262 | augggugaauuuguagaaggau | 1.00 | 11.33 | 0.09 | 0.08 |
| SEQ ID NO: 629 | 230 | hsa-miR-1270 | cuggagauauggaagagcugugu | 31.56 | 30.44 | 1.04 | 0.08 |
| SEQ ID NO: 84 | 231 | hsa-miR-1272 | gaugaugauggcagcaaauucugaaa | 1.00 | 1.00 | 1.00 | 0.08 |
| SEQ ID NO: 167 | 232 | hsa-miR-1277 | uacguagauauauauguauuuu | 1.00 | 1.00 | 1.00 | 0.08 |
| SEQ ID NO: 114 | 233 | hsa-miR-1284 | ucuauacagacccuggcuuuuc | 1.00 | 11.56 | 0.09 | 0.08 |
| SEQ ID NO: 152 | 234 | hsa-miR-1289 | uggaguccaggaaucugcauuuu | 1.00 | 4.44 | 0.23 | 0.08 |
| SEQ ID NO: 168 | 235 | hsa-miR-130a* | uucacauugugcuacugucugc | 1.00 | 1.00 | 1.00 | 0.08 |
| SEQ ID NO: 291 | 236 | hsa-miR-1322 | gaugaugcugcugaugcug | 1.56 | 6.56 | 0.24 | 0.08 |
| SEQ ID NO: 153 | 237 | hsa-miR-1324 | ccagacagaauucuaugcacuuuc | 1.00 | 1.00 | 1.00 | 0.08 |
| SEQ ID NO: 613 | 238 | hsa-miR-133a | uuugguccccuucaaccagcug | 34.22 | 21.11 | 1.62 | 0.08 |
| SEQ ID NO: 610 | 239 | hsa-miR-135b* | auguagggcuaaaagccauggg | 34.22 | 12.11 | 2.83 | 0.08 |
| SEQ ID NO: 323 | 240 | hsa-miR-137 | uuauugcuuaagaauacgcguag | 1.00 | 1.00 | 1.00 | 0.08 |
| SEQ ID NO: 245 | 241 | hsa-miR-141 | uaacacugucugguaaagaugg | 1.00 | 1.00 | 1.00 | 0.08 |
| SEQ ID NO: 550 | 242 | hsa-miR-142-5p | cauaaaguagaaagcacuacu | 29.11 | 10.44 | 2.79 | 0.08 |
| SEQ ID NO: 201 | 243 | hsa-miR-144 | uacaguauagaugauguacu | 40.67 | 82.06 | 0.50 | 0.08 |
| SEQ ID NO: 224 | 244 | hsa-miR-1468 | cuccguuugccuguuucgcug | 1.00 | 4.22 | 0.24 | 0.08 |
| SEQ ID NO: 355 | 245 | hsa-miR-146a* | ccucugaaauucaguucuucag | 1.00 | 1.00 | 1.00 | 0.08 |
| SEQ ID NO: 188 | 246 | hsa-miR-146b-3p | ugcccuguggacucaguucugg | 1.00 | 1.00 | 1.00 | 0.08 |

Figure 10A (cont'd)

| | | | | | | | |
|---|---|---|---|---|---|---|---|
| SEQ ID NO: 486 | 247 | hsa-miR-147 | guguguggaaaugcuucugc | 4.00 | 1.00 | 4.00 | 0.08 |
| SEQ ID NO: 132 | 248 | hsa-miR-147b | gugugcggaaaugcuucugcua | 1.00 | 1.00 | 1.00 | 0.08 |
| SEQ ID NO: 542 | 249 | hsa-miR-149 | ucuggcucccgugucuucacuccc | 9.56 | 11.33 | 0.84 | 0.08 |
| SEQ ID NO: 213 | 250 | hsa-miR-153 | uugcauagucacaaaagugauc | 1.00 | 1.00 | 1.00 | 0.08 |
| SEQ ID NO: 125 | 251 | hsa-miR-1539 | uccugcgcgucccagaugccc | 5.22 | 21.11 | 0.25 | 0.08 |
| SEQ ID NO: 324 | 252 | hsa-miR-154* | aaucauacacgguugaccuauu | 1.00 | 1.00 | 1.00 | 0.08 |
| SEQ ID NO: 186 | 253 | hsa-miR-16-1* | ccaguauuaacugugcugcuga | 1.00 | 1.56 | 0.64 | 0.08 |
| SEQ ID NO: 246 | 254 | hsa-miR-181c* | aaccaucgaccguugaguggac | 1.00 | 1.00 | 1.00 | 0.08 |
| SEQ ID NO: 292 | 255 | hsa-miR-1827 | ugaggcaguagauugaau | 9.56 | 4.44 | 2.15 | 0.08 |
| SEQ ID NO: 399 | 256 | hsa-miR-18b | uaaggugcaucuagugcaguuag | 137.22 | 234.33 | 0.59 | 0.08 |
| SEQ ID NO: 126 | 257 | hsa-miR-1911 | ugaguaccgccaugucuguuggg | 1.00 | 1.56 | 0.64 | 0.08 |
| SEQ ID NO: 235 | 258 | hsa-miR-1911* | caccaggcauuguggucucc | 1.00 | 1.00 | 1.00 | 0.08 |
| SEQ ID NO: 169 | 259 | hsa-miR-1912 | uacccagagcaugcagugugaa | 1.00 | 1.56 | 0.64 | 0.08 |
| SEQ ID NO: 293 | 260 | hsa-miR-192* | cugccaauuccauaggucacag | 1.00 | 1.00 | 1.00 | 0.08 |
| SEQ ID NO: 247 | 261 | hsa-miR-193a-3p | aacuggccuacaaagucccagu | 20.83 | 21.11 | 0.99 | 0.08 |
| SEQ ID NO: 170 | 262 | hsa-miR-193b | aacuggcccucaaagucccgcu | 1.00 | 1.56 | 0.64 | 0.08 |
| SEQ ID NO: 115 | 263 | hsa-miR-199b-3p | acaguagucugcacauugguua | 1.00 | 11.56 | 0.09 | 0.08 |
| SEQ ID NO: 380 | 264 | hsa-miR-200a* | caucuuaccggacagugcugga | 1.00 | 1.00 | 1.00 | 0.08 |
| SEQ ID NO: 351 | 265 | hsa-miR-200b | uaauacugccugguaaugauga | 1.00 | 1.00 | 1.00 | 0.08 |
| SEQ ID NO: 468 | 266 | hsa-miR-200c | uaauacugccggguaaugaugga | 7.44 | 10.44 | 0.71 | 0.08 |
| SEQ ID NO: 602 | 267 | hsa-miR-212 | uaacagucuccagucacggcc | 7.44 | 4.44 | 1.68 | 0.08 |
| SEQ ID NO: 171 | 268 | hsa-miR-214* | ugccugucuacacuugcugugc | 1.00 | 1.00 | 1.00 | 0.08 |
| SEQ ID NO: 172 | 269 | hsa-miR-216b | aaaucucugcaggcaaauguga | 1.00 | 1.00 | 1.00 | 0.08 |
| SEQ ID NO: 285 | 270 | hsa-miR-29b-2* | cugguuucacauggugcuuag | 34.44 | 47.22 | 0.73 | 0.08 |
| SEQ ID NO: 248 | 271 | hsa-miR-302c | uaagugcuuccauguuucagugg | 1.00 | 1.00 | 1.00 | 0.08 |
| SEQ ID NO: 294 | 272 | hsa-miR-302e | uaagugcuuccaugcuu | 1.00 | 1.00 | 1.00 | 0.08 |
| SEQ ID NO: 173 | 273 | hsa-miR-302f | uaauugcuuccauguuu | 1.00 | 1.00 | 1.00 | 0.08 |
| SEQ ID NO: 273 | 274 | hsa-miR-30d* | cuuucagucagauguuugcugc | 1.00 | 1.00 | 1.00 | 0.08 |
| SEQ ID NO: 127 | 275 | hsa-miR-325 | ccuaguaggguguccaguaagugu | 1.00 | 14.89 | 0.07 | 0.08 |
| SEQ ID NO: 108 | 276 | hsa-miR-34a* | caaucagcaaguauacugcccu | 1.00 | 1.00 | 1.00 | 0.08 |
| SEQ ID NO: 44 | 277 | hsa-miR-34c-3p | aaucacuaaccacacggccagg | 4.00 | 28.44 | 0.14 | 0.08 |

Figure 10A (cont'd)

| | | | | | | | |
|---|---|---|---|---|---|---|---|
| SEQ ID NO: 366 | 278 | hsa-miR-369-5p | agaucgaccguguuauauucgc | 1.00 | 1.00 | 1.00 | 0.08 |
| SEQ ID NO: 375 | 279 | hsa-miR-374a* | cuuaucagauuguauuguaauu | 1.00 | 1.00 | 1.00 | 0.08 |
| SEQ ID NO: 225 | 280 | hsa-miR-374b* | cuuagcagguuguauuaucauu | 1.00 | 1.00 | 1.00 | 0.08 |
| SEQ ID NO: 494 | 281 | hsa-miR-380* | ugguugaccauagaacaugcgc | 1.00 | 1.00 | 1.00 | 0.08 |
| SEQ ID NO: 282 | 282 | hsa-miR-384 | auuccuagaaauuguucaua | 1.00 | 1.00 | 1.00 | 0.08 |
| SEQ ID NO: 128 | 283 | hsa-miR-409-5p | agguuacccgagcaacuuugcau | 1.00 | 1.00 | 1.00 | 0.08 |
| SEQ ID NO: 295 | 284 | hsa-miR-411* | uauguaacacgguccacuaacc | 1.00 | 1.56 | 0.64 | 0.08 |
| SEQ ID NO: 296 | 285 | hsa-miR-424 | cagcagcaauucauguuuugaa | 53.00 | 40.78 | 1.30 | 0.08 |
| SEQ ID NO: 190 | 286 | hsa-miR-449b | aggcaguguauuguuagcuggc | 1.00 | 1.00 | 1.00 | 0.08 |
| SEQ ID NO: 274 | 287 | hsa-miR-452* | cucaucugcaaagaaguaagug | 1.00 | 1.00 | 1.00 | 0.08 |
| SEQ ID NO: 249 | 288 | hsa-miR-485-5p | agaggcuggccgugaugaauuc | 39.67 | 50.89 | 0.78 | 0.08 |
| SEQ ID NO: 487 | 289 | hsa-miR-487b | aaucguacagggucauccacuu | 20.56 | 12.11 | 1.70 | 0.08 |
| SEQ ID NO: 250 | 290 | hsa-miR-499-3p | aacaucacagcaagucugugcu | 1.00 | 1.00 | 1.00 | 0.08 |
| SEQ ID NO: 202 | 291 | hsa-miR-508-5p | uacuccagagggcgucacucaug | 22.67 | 31.33 | 0.72 | 0.08 |
| SEQ ID NO: 154 | 292 | hsa-miR-513a-3p | uaaauuucaccuuucugagaagg | 1.00 | 1.00 | 1.00 | 0.08 |
| SEQ ID NO: 226 | 293 | hsa-miR-514 | auugacacuucugugaguaga | 1.00 | 1.00 | 1.00 | 0.08 |
| SEQ ID NO: 193 | 294 | hsa-miR-518f | gaaagcgcuucucuuuagagg | 1.00 | 1.00 | 1.00 | 0.08 |
| SEQ ID NO: 57 | 295 | hsa-miR-519c-3p | aaagugcaucuuuuuagaggau | 1.00 | 12.00 | 0.08 | 0.08 |
| SEQ ID NO: 189 | 296 | hsa-miR-520b | aaagugcuuccuuuuagaggg | 1.00 | 1.00 | 1.00 | 0.08 |
| SEQ ID NO: 214 | 297 | hsa-miR-520e | aaagugcuuccuuuuugaggg | 1.00 | 1.00 | 1.00 | 0.08 |
| SEQ ID NO: 191 | 298 | hsa-miR-520g | acaaagugcuucccuuuagagugu | 1.00 | 1.00 | 1.00 | 0.08 |
| SEQ ID NO: 345 | 299 | hsa-miR-521 | aacgcacuucccuuuagagugu | 1.00 | 4.44 | 0.23 | 0.08 |
| SEQ ID NO: 174 | 300 | hsa-miR-522* | cucuagagggaagcgcuuucug | 4.00 | 12.11 | 0.33 | 0.08 |
| SEQ ID NO: 335 | 301 | hsa-miR-523 | gaacgcgcuucccuauagagggu | 1.00 | 1.00 | 1.00 | 0.08 |
| SEQ ID NO: 251 | 302 | hsa-miR-545 | ucagcaaacauuuauugugugc | 1.00 | 1.00 | 1.00 | 0.08 |
| SEQ ID NO: 275 | 303 | hsa-miR-548b-3p | caagaaccucaguugcuuuugu | 1.00 | 1.00 | 1.00 | 0.08 |
| SEQ ID NO: 252 | 304 | hsa-miR-548b-5p | aaaaguaauugugguuuuggcc | 1.00 | 1.00 | 1.00 | 0.08 |
| SEQ ID NO: 175 | 305 | hsa-miR-548j | aaaaguaauugcggucuuuggu | 1.00 | 1.00 | 1.00 | 0.08 |
| SEQ ID NO: 253 | 306 | hsa-miR-549 | ugacaacuauggaugagcucu | 1.00 | 1.00 | 1.00 | 0.08 |
| SEQ ID NO: 387 | 307 | hsa-miR-551a | gcgacccacucuugguuucca | 1.00 | 1.00 | 1.00 | 0.08 |
| SEQ ID NO: 325 | 308 | hsa-miR-555 | aggguaagcugaaccucugau | 1.00 | 1.00 | 1.00 | 0.08 |

Figure 10A (cont'd)

| | | | | | | | |
|---|---|---|---|---|---|---|---|
| SEQ ID NO: 314 | 309 | hsa-miR-558 | ugagcugcuguaccaaaau | 1.00 | 1.00 | 1.00 | 0.08 |
| SEQ ID NO: 95 | 310 | hsa-miR-561 | caaaguuuaagauccuugaagu | 1.00 | 1.00 | 1.00 | 0.08 |
| SEQ ID NO: 176 | 311 | hsa-miR-568 | auguauaaauguauacacac | 1.00 | 1.00 | 1.00 | 0.08 |
| SEQ ID NO: 203 | 312 | hsa-miR-569 | aguuaaugaauccuggaaagu | 1.00 | 1.00 | 1.00 | 0.08 |
| SEQ ID NO: 469 | 313 | hsa-miR-572 | guccgcucggcgguggccca | 6.78 | 4.44 | 1.53 | 0.08 |
| SEQ ID NO: 254 | 314 | hsa-miR-576-5p | auucuaauuucuccacgucuuu | 1.00 | 4.22 | 0.24 | 0.08 |
| SEQ ID NO: 255 | 315 | hsa-miR-577 | uagauaaaauauugguaccug | 1.00 | 1.00 | 1.00 | 0.08 |
| SEQ ID NO: 578 | 316 | hsa-miR-581 | ucuuguguucucuagaucagu | 1.00 | 1.00 | 1.00 | 0.08 |
| SEQ ID NO: 297 | 317 | hsa-miR-582-3p | uaacugguugaacaacugaacc | 4.00 | 4.22 | 0.95 | 0.08 |
| SEQ ID NO: 256 | 318 | hsa-miR-583 | caaagaggaaggucccauuac | 49.56 | 55.22 | 0.90 | 0.08 |
| SEQ ID NO: 609 | 319 | hsa-miR-584 | uuaugguuugccugggacugag | 119.89 | 114.67 | 1.05 | 0.08 |
| SEQ ID NO: 257 | 320 | hsa-miR-587 | uuuccauaggugaugagucac | 1.00 | 1.56 | 0.64 | 0.08 |
| SEQ ID NO: 227 | 321 | hsa-miR-590-3p | uaauuuuauguauaagcuagu | 1.00 | 1.00 | 1.00 | 0.08 |
| SEQ ID NO: 137 | 322 | hsa-miR-593* | aggcaccagccaggcauugcucagc | 1.00 | 12.11 | 0.08 | 0.08 |
| SEQ ID NO: 228 | 323 | hsa-miR-606 | aaacuacugaaaaucaaagau | 1.00 | 1.00 | 1.00 | 0.08 |
| SEQ ID NO: 144 | 324 | hsa-miR-609 | aggguguuucucucaucucu | 1.00 | 1.00 | 1.00 | 0.08 |
| SEQ ID NO: 341 | 325 | hsa-miR-618 | aaacucuacuuguccuucugagu | 1.00 | 1.00 | 1.00 | 0.08 |
| SEQ ID NO: 258 | 326 | hsa-miR-624 | cacaagguauugguauuaccu | 1.00 | 1.00 | 1.00 | 0.08 |
| SEQ ID NO: 298 | 327 | hsa-miR-629* | guucucccaacguaagcccagc | 31.56 | 33.56 | 0.94 | 0.08 |
| SEQ ID NO: 204 | 328 | hsa-miR-636 | ugugcuugcucgucccgcccgca | 46.89 | 49.22 | 0.95 | 0.08 |
| SEQ ID NO: 739 | 329 | hsa-miR-641 | aaagacauaggauagagucaccuc | 34.00 | 21.56 | 1.58 | 0.08 |
| SEQ ID NO: 283 | 330 | hsa-miR-644 | aguguggcuuucuuagagc | 1.00 | 1.00 | 1.00 | 0.08 |
| SEQ ID NO: 259 | 331 | hsa-miR-646 | aagcagcugccucugaggc | 1.00 | 1.00 | 1.00 | 0.08 |
| SEQ ID NO: 177 | 332 | hsa-miR-648 | aagugugcagggcacuggu | 1.00 | 1.00 | 1.00 | 0.08 |
| SEQ ID NO: 194 | 333 | hsa-miR-649 | aaaccuguguuguucaagaguc | 1.00 | 1.00 | 1.00 | 0.08 |
| SEQ ID NO: 367 | 334 | hsa-miR-653 | guguugaaacaaucucuacug | 1.00 | 1.00 | 1.00 | 0.08 |
| SEQ ID NO: 260 | 335 | hsa-miR-655 | auaauacaugguuaaccucuuu | 1.00 | 1.00 | 1.00 | 0.08 |
| SEQ ID NO: 178 | 336 | hsa-miR-662 | ucccacguuguggcccagcag | 1.00 | 3.11 | 0.32 | 0.08 |
| SEQ ID NO: 456 | 337 | hsa-miR-664 | uauucauuuauccccagccuaca | 8.44 | 11.33 | 0.75 | 0.08 |
| SEQ ID NO: 412 | 338 | hsa-miR-7-2* | caacaaaucccagucuaccuaa | 13.00 | 12.11 | 1.07 | 0.08 |
| SEQ ID NO: 569 | 339 | hsa-miR-758 | uuugugaccugguccacuaacc | 9.11 | 14.89 | 0.61 | 0.08 |

Figure 10A (cont'd)

| | | | | | | | |
|---|---|---|---|---|---|---|---|
| SEQ ID NO: 368 | 340 | hsa-miR-767-3p | ucugcucauaccccaugguuucu | 16.78 | 18.72 | 0.90 | 0.08 |
| SEQ ID NO: 280 | 341 | hsa-miR-876-5p | uauaccucaguuuuaucaggug | 1.00 | 1.00 | 1.00 | 0.08 |
| SEQ ID NO: 261 | 342 | hsa-miR-885-5p | uccauuacacuacccugccucu | 5.56 | 28.00 | 0.20 | 0.08 |
| SEQ ID NO: 326 | 343 | hsa-miR-887 | gugaacgggcgccaucccgagg | 22.67 | 31.33 | 0.72 | 0.08 |
| SEQ ID NO: 205 | 344 | hsa-miR-937 | auccgcgcucugacucucugcc | 4.00 | 10.44 | 0.38 | 0.08 |
| SEQ ID NO: 327 | 345 | hsa-miR-363 | aauugcacgguauccaucugua | 2790.67 | 3303.71 | 0.84 | 0.08 |
| SEQ ID NO: 145 | 346 | hsa-miR-30c | uguaaacauccuacacucucagc | 8969.72 | 4779.31 | 1.88 | 0.08 |
| SEQ ID NO: 547 | 347 | hsa-miR-148a | ucagugcacuacagaacuuugu | 382.00 | 901.96 | 0.42 | 0.08 |
| SEQ ID NO: 101 | 348 | hsa-miR-30b | uguaaacauccuacacucagcu | 5530.88 | 3303.71 | 1.67 | 0.08 |
| SEQ ID NO: 473 | 349 | hsa-miR-21 | uagcuuaucagacugauguuga | 708.06 | 857.30 | 0.83 | 0.08 |
| SEQ ID NO: 671 | 350 | hsa-miR-1908 | cggcggggacggcgauugguc | 5944.79 | 6597.61 | 0.90 | 0.08 |
| SEQ ID NO: 512 | 351 | hsa-miR-1207-5p | uggcagggaggcugggaggggg | 5382.15 | 4318.58 | 1.25 | 0.08 |
| SEQ ID NO: 236 | 352 | hsa-miR-1292 | ugggaacggguuccggcagacgcug | 252.11 | 158.89 | 1.59 | 0.08 |
| SEQ ID NO: 179 | 353 | hsa-miR-222 | agcuacaucuggcuacugggu | 320.78 | 1.00 | 320.78 | 0.08 |
| SEQ ID NO: 786 | 354 | hsa-miR-518a-5p | cugcaaagggaagcccuuuc | 55.33 | 34.00 | 1.63 | 0.07 |
| SEQ ID NO: 315 | 355 | hsa-miR-26a | uucaaguaauccaggauaggcu | 8969.72 | 11137.35 | 0.81 | 0.07 |
| SEQ ID NO: 864 | 356 | hsa-miR-335 | ucaagagcaauaacgaaaaaugu | 115.33 | 67.44 | 1.71 | 0.07 |
| SEQ ID NO: 778 | 357 | hsa-miR-1301 | uugcagcugccugggagugacuuc | 22.67 | 18.11 | 1.25 | 0.07 |
| SEQ ID NO: 91 | 358 | hsa-miR-1291 | uggcccugacugaagaccagcagu | 30.44 | 1.00 | 30.44 | 0.07 |
| SEQ ID NO: 58 | 359 | hsa-miR-1244 | aaguaguugguuuguaugagaugguu | 25.56 | 1.00 | 25.56 | 0.07 |
| SEQ ID NO: 565 | 360 | hsa-miR-1913 | ucugcccccuccgcugcugcca | 34.22 | 51.56 | 0.66 | 0.06 |
| SEQ ID NO: 40 | 361 | hsa-miR-363* | cggguggaucacgaugcaauuu | 2425.74 | 723.61 | 3.35 | 0.06 |
| SEQ ID NO: 155 | 362 | hsa-miR-939 | uggggagcugaggcucuggggggug | 203.17 | 58.78 | 3.46 | 0.06 |
| SEQ ID NO: 100 | 363 | hsa-miR-17 | caaagugcuuacagugcagguag | 3976.97 | 5242.15 | 0.76 | 0.06 |
| SEQ ID NO: 381 | 364 | hsa-miR-1293 | uggguggucuggagauuugugc | 50.56 | 21.11 | 2.39 | 0.06 |
| SEQ ID NO: 823 | 365 | hsa-miR-92b* | agggacgggacgcggugcagug | 1344.42 | 2425.74 | 0.55 | 0.06 |
| SEQ ID NO: 52 | 366 | hsa-miR-1269 | cuggacugagccgugcuacugg | 4.00 | 34.44 | 0.12 | 0.06 |
| SEQ ID NO: 611 | 367 | hsa-miR-1295 | uuaggccgcagaucuggguga | 8.44 | 11.33 | 0.75 | 0.06 |
| SEQ ID NO: 648 | 368 | hsa-miR-155 | uuaaugcuaaucgugauaggggu | 128.44 | 14.89 | 8.63 | 0.06 |
| SEQ ID NO: 299 | 369 | hsa-miR-491-3p | cuuaugcaagauucccuucuac | 1.00 | 1.00 | 1.00 | 0.06 |
| SEQ ID NO: 300 | 370 | hsa-miR-519b-3p | aaagugcauccuuuuagagguu | 1.00 | 1.00 | 1.00 | 0.06 |

Figure 10A (cont'd)

| | | | | | | | |
|---|---|---|---|---|---|---|---|
| SEQ ID NO: 65 | 371 | hsa-miR-520f | aagugcuuccuuuuagaggguu | 1.00 | 4.22 | 0.24 | 0.06 |
| SEQ ID NO: 35 | 372 | hsa-miR-624* | uaguaccaguaccuuguguuca | 1.00 | 27.78 | 0.04 | 0.06 |
| SEQ ID NO: 215 | 373 | hsa-miR-632 | gugucugcuuccugugga | 2.67 | 4.44 | 0.60 | 0.06 |
| SEQ ID NO: 262 | 374 | hsa-miR-194* | ccaguggggcugcuguuaucug | 6.78 | 5.11 | 1.33 | 0.06 |
| SEQ ID NO: 637 | 375 | hsa-miR-23a* | gggguuccuggggaugggauuu | 74.00 | 122.44 | 0.60 | 0.06 |
| SEQ ID NO: 138 | 376 | hsa-miR-552 | aacaggugacugguuagacaa | 4.00 | 22.22 | 0.18 | 0.06 |
| SEQ ID NO: 577 | 377 | hsa-miR-576-3p | aagauguggaaaaauuggaauc | 1.00 | 11.33 | 0.09 | 0.06 |
| SEQ ID NO: 133 | 378 | hsa-miR-30d | uguaaacauccccgacuggaag | 6349.31 | 4318.58 | 1.47 | 0.06 |
| SEQ ID NO: 538 | 379 | hsa-miR-494 | ugaaacauacacgggaaaccuc | 20349.58 | 20349.58 | 1.00 | 0.06 |
| SEQ ID NO: 788 | 380 | hsa-miR-1228* | gugggcgggggcaggugugug | 5944.79 | 5802.55 | 1.02 | 0.05 |
| SEQ ID NO: 129 | 381 | hsa-miR-182 | uuuggcaaugguagaacucacacu | 7639.53 | 5073.69 | 1.51 | 0.05 |
| SEQ ID NO: 216 | 382 | hsa-miR-106a* | cugcaauguaagcacuucuuac | 1.00 | 4.44 | 0.23 | 0.05 |
| SEQ ID NO: 301 | 383 | hsa-miR-1197 | uaggacacauggucuacuucu | 1.00 | 1.56 | 0.64 | 0.05 |
| SEQ ID NO: 356 | 384 | hsa-miR-122* | aacgccauuaucacacuaaaua | 1.00 | 1.00 | 1.00 | 0.05 |
| SEQ ID NO: 444 | 385 | hsa-miR-1224-3p | ccccaccuccucucuccucag | 25.56 | 67.44 | 0.38 | 0.05 |
| SEQ ID NO: 510 | 386 | hsa-miR-124* | cguguucacagcggaccuugau | 2.67 | 1.00 | 2.67 | 0.05 |
| SEQ ID NO: 511 | 387 | hsa-miR-1254 | agccuggaagcuggagccugcagu | 245.00 | 723.61 | 0.34 | 0.05 |
| SEQ ID NO: 806 | 388 | hsa-miR-125a-5p | ucccugagacccuuuaaccuguga | 82.89 | 21.56 | 3.85 | 0.05 |
| SEQ ID NO: 316 | 389 | hsa-miR-1263 | augguacccuggcauacugagu | 1.00 | 1.00 | 1.00 | 0.05 |
| SEQ ID NO: 302 | 390 | hsa-miR-127-5p | cugaagcucagagggcucugau | 5.56 | 21.56 | 0.26 | 0.05 |
| SEQ ID NO: 630 | 391 | hsa-miR-1271 | cuuggcaccuagcaagcacuca | 15.78 | 1.56 | 10.14 | 0.05 |
| SEQ ID NO: 770 | 392 | hsa-miR-1285 | ucugggcaacaaagugagaccu | 300.67 | 53.00 | 5.67 | 0.05 |
| SEQ ID NO: 303 | 393 | hsa-miR-1286 | ugcaggaccaagaugagcccu | 12.44 | 12.00 | 1.04 | 0.05 |
| SEQ ID NO: 180 | 394 | hsa-miR-1287 | ugcuggaucagugguucgaguc | 1.00 | 12.44 | 0.08 | 0.05 |
| SEQ ID NO: 548 | 395 | hsa-miR-1294 | ugugagguuggcauuguugucu | 29.11 | 18.72 | 1.55 | 0.05 |
| SEQ ID NO: 304 | 396 | hsa-miR-132* | accguggcuuucgauuguuacu | 1.00 | 1.00 | 1.00 | 0.05 |
| SEQ ID NO: 92 | 397 | hsa-miR-138-2* | gcuauuucacgacaccaggguu | 1.00 | 4.44 | 0.23 | 0.05 |
| SEQ ID NO: 328 | 398 | hsa-miR-1537 | aaaaccgucuaguuacaguugu | 1.00 | 1.00 | 1.00 | 0.05 |
| SEQ ID NO: 413 | 399 | hsa-miR-15a* | caggccauauugugcugccuca | 1.00 | 1.00 | 1.00 | 0.05 |
| SEQ ID NO: 589 | 400 | hsa-miR-16-2* | ccaauauuacugugcugcuuua | 40.56 | 30.22 | 1.34 | 0.05 |
| SEQ ID NO: 414 | 401 | hsa-miR-181d | aacauucauuguugucggugggu | 2.67 | 2.67 | 1.00 | 0.05 |

Figure 10A (cont'd)

| | | | | | | | |
|---|---|---|---|---|---|---|---|
| SEQ ID NO: 474 | 402 | hsa-miR-182* | ugguucuagacuugccaacua | 1.00 | 1.00 | 1.00 | 0.05 |
| SEQ ID NO: 388 | 403 | hsa-miR-196b | uagguaguuuccuguuguuggg | 1.00 | 21.56 | 0.05 | 0.05 |
| SEQ ID NO: 438 | 404 | hsa-miR-202* | uuccuaugcauauacuucuuug | 1.00 | 1.00 | 1.00 | 0.05 |
| SEQ ID NO: 430 | 405 | hsa-miR-21* | caacaccagucgaugggcugu | 1.00 | 1.00 | 1.00 | 0.05 |
| SEQ ID NO: 329 | 406 | hsa-miR-219-1-3p | agaguugagucuggacgucccg | 1.00 | 1.00 | 1.00 | 0.05 |
| SEQ ID NO: 415 | 407 | hsa-miR-219-5p | ugauuguccaaacgcaauucu | 1.00 | 1.00 | 1.00 | 0.05 |
| SEQ ID NO: 330 | 408 | hsa-miR-220a | ccacaccguaucugacacuuu | 1.00 | 1.00 | 1.00 | 0.05 |
| SEQ ID NO: 331 | 409 | hsa-miR-222* | cucaguagccaguguagauccu | 1.00 | 1.00 | 1.00 | 0.05 |
| SEQ ID NO: 263 | 410 | hsa-miR-299-5p | ugguuuaccgucccacauacau | 1.00 | 1.00 | 1.00 | 0.05 |
| SEQ ID NO: 543 | 411 | hsa-miR-300 | uauacaagggcagacucucucu | 1.00 | 1.00 | 1.00 | 0.05 |
| SEQ ID NO: 590 | 412 | hsa-miR-301b | cagugcaaugauauugucaaagc | 1.00 | 1.00 | 1.00 | 0.05 |
| SEQ ID NO: 336 | 413 | hsa-miR-302a* | acuuaaacguggauguacuugcu | 1.00 | 1.00 | 1.00 | 0.05 |
| SEQ ID NO: 416 | 414 | hsa-miR-302d | uaagugcuuccauguuugagugu | 1.00 | 1.00 | 1.00 | 0.05 |
| SEQ ID NO: 217 | 415 | hsa-miR-31* | ugcuaugccaacauauugccau | 1.00 | 1.00 | 1.00 | 0.05 |
| SEQ ID NO: 195 | 416 | hsa-miR-32 | uauugcacauuacuaaguugca | 1.00 | 3.67 | 0.27 | 0.05 |
| SEQ ID NO: 389 | 417 | hsa-miR-32* | caauuuagugugugugauauuu | 1.00 | 1.00 | 1.00 | 0.05 |
| SEQ ID NO: 332 | 418 | hsa-miR-323-3p | cacauuacacggucgaccucu | 1.00 | 1.00 | 1.00 | 0.05 |
| SEQ ID NO: 852 | 419 | hsa-miR-324-5p | cgcauccccuagggcauuggugu | 232.67 | 56.22 | 4.14 | 0.05 |
| SEQ ID NO: 641 | 420 | hsa-miR-330-3p | gcaaagcacacggccugcagaga | 15.33 | 11.11 | 1.38 | 0.05 |
| SEQ ID NO: 264 | 421 | hsa-miR-337-3p | cuccuauaugaugccuuucuuc | 1.00 | 4.44 | 0.23 | 0.05 |
| SEQ ID NO: 390 | 422 | hsa-miR-33a | gugcauuguaguugcauugca | 1.00 | 1.00 | 1.00 | 0.05 |
| SEQ ID NO: 305 | 423 | hsa-miR-33b | gugcauugcuguugcauugc | 1.00 | 1.56 | 0.64 | 0.05 |
| SEQ ID NO: 218 | 424 | hsa-miR-33b* | cagugccucggcagugcagccc | 1.00 | 1.00 | 1.00 | 0.05 |
| SEQ ID NO: 206 | 425 | hsa-miR-346 | ugucugcccgcaugccugccucu | 1.00 | 1.00 | 1.00 | 0.05 |
| SEQ ID NO: 417 | 426 | hsa-miR-34a | uggcagugucuuagcugguugu | 1.00 | 1.00 | 1.00 | 0.05 |
| SEQ ID NO: 475 | 427 | hsa-miR-34c-5p | aggcaguguaguuagcugauugc | 1.00 | 1.00 | 1.00 | 0.05 |
| SEQ ID NO: 465 | 428 | hsa-miR-367 | aauugcacuuuagcaaugguga | 1.00 | 1.00 | 1.00 | 0.05 |
| SEQ ID NO: 229 | 429 | hsa-miR-369-3p | aauaauacaugguugaucuuu | 1.00 | 1.00 | 1.00 | 0.05 |
| SEQ ID NO: 382 | 430 | hsa-miR-372 | aaagugcugcgacauuugagcgu | 1.00 | 1.00 | 1.00 | 0.05 |
| SEQ ID NO: 509 | 431 | hsa-miR-376a | aucauagaggaaaauccacgu | 1.00 | 3.11 | 0.32 | 0.05 |
| SEQ ID NO: 340 | 432 | hsa-miR-376a* | guagauucuccuucuaugagua | 1.00 | 1.00 | 1.00 | 0.05 |

Figure 10A (cont'd)

| | | | | | | | |
|---|---|---|---|---|---|---|---|
| SEQ ID NO: 333 | 433 | hsa-miR-376b | aucauagaggaaaauccauguu | 1.00 | 6.56 | 0.15 | 0.05 |
| SEQ ID NO: 361 | 434 | hsa-miR-380 | uauguaauaugguccacaucuu | 1.00 | 1.00 | 1.00 | 0.05 |
| SEQ ID NO: 418 | 435 | hsa-miR-410 | aauauaacacagauggccugu | 1.00 | 1.00 | 1.00 | 0.05 |
| SEQ ID NO: 826 | 436 | hsa-miR-422a | acuggacuuagggucagaaggc | 166.44 | 1.00 | 166.44 | 0.05 |
| SEQ ID NO: 476 | 437 | hsa-miR-429 | uaauacugucugguaaaaccgu | 1.00 | 1.00 | 1.00 | 0.05 |
| SEQ ID NO: 281 | 438 | hsa-miR-431* | caggucgucuugcagggcuucu | 1.00 | 1.00 | 1.00 | 0.05 |
| SEQ ID NO: 400 | 439 | hsa-miR-432* | cuggauggcuccuccaugucu | 1.00 | 1.00 | 1.00 | 0.05 |
| SEQ ID NO: 357 | 440 | hsa-miR-450b-3p | uugggaucauuuugcauccaua | 1.00 | 1.00 | 1.00 | 0.05 |
| SEQ ID NO: 352 | 441 | hsa-miR-455-5p | uaugugccuuuggacuacaucg | 1.00 | 1.00 | 1.00 | 0.05 |
| SEQ ID NO: 230 | 442 | hsa-miR-488 | uugaaaggcuauuucuugguc | 1.00 | 1.00 | 1.00 | 0.05 |
| SEQ ID NO: 457 | 443 | hsa-miR-488* | cccagauaauggcacucucaa | 1.00 | 1.00 | 1.00 | 0.05 |
| SEQ ID NO: 286 | 444 | hsa-miR-489 | gugacaucacauauacggcagc | 1.00 | 1.00 | 1.00 | 0.05 |
| SEQ ID NO: 334 | 445 | hsa-miR-490-5p | ccauggaucuccaggugggu | 1.00 | 4.22 | 0.24 | 0.05 |
| SEQ ID NO: 690 | 446 | hsa-miR-491-5p | aguggggaacccuuccaugagg | 101.11 | 96.94 | 1.04 | 0.05 |
| SEQ ID NO: 691 | 447 | hsa-miR-492 | aggaccugcgggacaagauucuu | 88.56 | 87.67 | 1.01 | 0.05 |
| SEQ ID NO: 265 | 448 | hsa-miR-493 | ugaaggucuacugugugccagg | 1.00 | 1.00 | 1.00 | 0.05 |
| SEQ ID NO: 87 | 449 | hsa-miR-497 | cagcagcacacugugguuugu | 15.78 | 39.44 | 0.40 | 0.05 |
| SEQ ID NO: 266 | 450 | hsa-miR-497* | caaaccacacugugguguuaga | 1.00 | 1.00 | 1.00 | 0.05 |
| SEQ ID NO: 207 | 451 | hsa-miR-506 | uaaggcacccuucugaguaga | 1.00 | 1.00 | 1.00 | 0.05 |
| SEQ ID NO: 401 | 452 | hsa-miR-509-3p | ugauugguacgucugugggguag | 1.89 | 1.56 | 1.21 | 0.05 |
| SEQ ID NO: 442 | 453 | hsa-miR-511 | gugucuuuugcucugcaguca | 1.00 | 1.00 | 1.00 | 0.05 |
| SEQ ID NO: 531 | 454 | hsa-miR-515-3p | gagugccuucuuuuggagcguu | 1.00 | 1.00 | 1.00 | 0.05 |
| SEQ ID NO: 369 | 455 | hsa-miR-516a-3p | ugcuuccuuucagagggu | 1.00 | 1.00 | 1.00 | 0.05 |
| SEQ ID NO: 782 | 456 | hsa-miR-518b | caaagcgcuccccuuuagaggu | 20.56 | 4.44 | 4.63 | 0.05 |
| SEQ ID NO: 267 | 457 | hsa-miR-519a | aaagugcauccuuuuagagugu | 1.00 | 1.00 | 1.00 | 0.05 |
| SEQ ID NO: 595 | 458 | hsa-miR-519d | caaagugccucccuuuagagug | 1.00 | 1.00 | 1.00 | 0.05 |
| SEQ ID NO: 516 | 459 | hsa-miR-520a-3p | aaagugcuucccuuuggacugu | 1.00 | 1.00 | 1.00 | 0.05 |
| SEQ ID NO: 370 | 460 | hsa-miR-520c-3p | aaagugcuuccuuuuagagggu | 1.00 | 1.00 | 1.00 | 0.05 |
| SEQ ID NO: 445 | 461 | hsa-miR-525-3p | gaaggcgcuucccuuuagagcg | 1.00 | 1.00 | 1.00 | 0.05 |
| SEQ ID NO: 346 | 462 | hsa-miR-545* | ucaguaaauguuuauuagauga | 1.00 | 1.00 | 1.00 | 0.05 |
| SEQ ID NO: 383 | 463 | hsa-miR-548a-5p | aaaaguaauugcgaguuuuacc | 1.00 | 1.00 | 1.00 | 0.05 |

Figure 10A (cont'd)

| | | | | | | | |
|---|---|---|---|---|---|---|---|
| SEQ ID NO: 391 | 464 | hsa-miR-548d-5p | aaaaguaauuguggguuuugcc | 1.00 | 1.00 | 1.00 | 0.05 |
| SEQ ID NO: 458 | 465 | hsa-miR-548g | aaaacuguaauuacuuuuguac | 1.00 | 1.00 | 1.00 | 0.05 |
| SEQ ID NO: 384 | 466 | hsa-miR-548k | aaaaguacuugcggauuuugcu | 1.00 | 1.00 | 1.00 | 0.05 |
| SEQ ID NO: 472 | 467 | hsa-miR-548n | caaaaguaauuguggauuuugu | 1.00 | 1.00 | 1.00 | 0.05 |
| SEQ ID NO: 699 | 468 | hsa-miR-550 | agugccugagggaguaagagccc | 136.17 | 90.78 | 1.50 | 0.05 |
| SEQ ID NO: 306 | 469 | hsa-miR-553 | aaaacggugagauuuuguuuu | 1.00 | 1.00 | 1.00 | 0.05 |
| SEQ ID NO: 365 | 470 | hsa-miR-556-5p | gaugagcucauuguaauaugag | 1.00 | 1.00 | 1.00 | 0.05 |
| SEQ ID NO: 287 | 471 | hsa-miR-566 | gggcgccugugaucccaac | 1.00 | 1.00 | 1.00 | 0.05 |
| SEQ ID NO: 507 | 472 | hsa-miR-567 | aguauguucuuccaggacagaac | 1.00 | 1.00 | 1.00 | 0.05 |
| SEQ ID NO: 449 | 473 | hsa-miR-570 | cgaaaacagcaauuaccuuugc | 1.00 | 1.00 | 1.00 | 0.05 |
| SEQ ID NO: 632 | 474 | hsa-miR-574-3p | cacgcucaugcacacacccaca | 48.00 | 58.78 | 0.82 | 0.05 |
| SEQ ID NO: 517 | 475 | hsa-miR-585 | ugggcguaucuguaugcua | 1.00 | 1.00 | 1.00 | 0.05 |
| SEQ ID NO: 453 | 476 | hsa-miR-590-5p | gagcuuauucauaaaagugcag | 1.00 | 1.00 | 1.00 | 0.05 |
| SEQ ID NO: 338 | 477 | hsa-miR-591 | agaccauggguucucauugu | 1.00 | 1.00 | 1.00 | 0.05 |
| SEQ ID NO: 596 | 478 | hsa-miR-605 | uaaaucccaugguggccuucuccu | 6.78 | 3.67 | 1.85 | 0.05 |
| SEQ ID NO: 557 | 479 | hsa-miR-612 | gcugggcagggcuucugagcuccuu | 24.56 | 33.44 | 0.73 | 0.05 |
| SEQ ID NO: 448 | 480 | hsa-miR-615-3p | uccgagccugggucucccucuu | 1.00 | 1.00 | 1.00 | 0.05 |
| SEQ ID NO: 392 | 481 | hsa-miR-616 | agucauuggaggguuugagcag | 27.00 | 30.44 | 0.89 | 0.05 |
| SEQ ID NO: 405 | 482 | hsa-miR-617 | agacuucccauuugaagguggc | 2.67 | 4.44 | 0.60 | 0.05 |
| SEQ ID NO: 307 | 483 | hsa-miR-620 | auggagauagauauagaaau | 1.00 | 1.56 | 0.64 | 0.05 |
| SEQ ID NO: 607 | 484 | hsa-miR-628-3p | ucuaguaagaguggcagucga | 49.56 | 34.44 | 1.44 | 0.05 |
| SEQ ID NO: 477 | 485 | hsa-miR-628-5p | augcugacauauuuacuagagg | 1.00 | 1.00 | 1.00 | 0.05 |
| SEQ ID NO: 350 | 486 | hsa-miR-635 | acuugggcacugaaacaaugucc | 1.00 | 1.00 | 1.00 | 0.05 |
| SEQ ID NO: 431 | 487 | hsa-miR-657 | ggcagguucucacccucucuagg | 1.00 | 1.00 | 1.00 | 0.05 |
| SEQ ID NO: 824 | 488 | hsa-miR-660 | uacccauugcauaucggaguug | 130.44 | 57.00 | 2.29 | 0.05 |
| SEQ ID NO: 518 | 489 | hsa-miR-675b | cuguaugcccucaccgcuca | 4.00 | 4.44 | 0.90 | 0.05 |
| SEQ ID NO: 308 | 490 | hsa-miR-708 | aaggagcuuacaaucuagcuggg | 1.00 | 1.00 | 1.00 | 0.05 |
| SEQ ID NO: 371 | 491 | hsa-miR-708* | caacuagacugugagcuucuag | 1.00 | 1.00 | 1.00 | 0.05 |
| SEQ ID NO: 599 | 492 | hsa-miR-744* | cuguugccacuaaccucaaccu | 15.33 | 11.33 | 1.35 | 0.05 |
| SEQ ID NO: 459 | 493 | hsa-miR-802 | caguaacaaagauucauccuugu | 1.00 | 1.00 | 1.00 | 0.05 |
| SEQ ID NO: 353 | 494 | hsa-miR-876-3p | uggugguuuacaaaguaauuca | 1.00 | 1.00 | 1.00 | 0.05 |

Figure 10A (cont'd)

| | | | | | | | |
|---|---|---|---|---|---|---|---|
| SEQ ID NO: 393 | 495 | hsa-miR-876-5p | uggauuucuuugugaaucacca | 1.00 | 1.00 | 1.00 | 0.05 |
| SEQ ID NO: 339 | 496 | hsa-miR-888 | uacucaaaaagcugucaguca | 1.00 | 1.00 | 1.00 | 0.05 |
| SEQ ID NO: 181 | 497 | hsa-miR-891b | ugcaacuuaccugagucauuga | 1.00 | 1.00 | 1.00 | 0.05 |
| SEQ ID NO: 309 | 498 | hsa-miR-892b | cacuggcuccuuucuggguaga | 1.00 | 1.00 | 1.00 | 0.05 |
| SEQ ID NO: 406 | 499 | hsa-miR-9 | ucuuugguuaucuagcuguauga | 1.00 | 1.00 | 1.00 | 0.05 |
| SEQ ID NO: 347 | 500 | hsa-miR-9* | auaaagcuagauaaccgaaagu | 1.00 | 1.00 | 1.00 | 0.05 |
| SEQ ID NO: 372 | 501 | hsa-miR-924 | agagucuugugaugucuugc | 1.00 | 1.00 | 1.00 | 0.05 |
| SEQ ID NO: 272 | 502 | hsa-miR-934 | ugucuacuacuggagacacugg | 1.00 | 1.00 | 1.00 | 0.05 |
| SEQ ID NO: 519 | 503 | hsa-miR-943 | cugacuguugccguccuccag | 1.00 | 1.00 | 1.00 | 0.05 |
| SEQ ID NO: 398 | 504 | hsa-miR-96* | aaucaugugcagugccaauaug | 1.00 | 1.00 | 1.00 | 0.05 |
| SEQ ID NO: 268 | 505 | hsa-miR-99a* | caagcucgcuucuaugggucug | 1.00 | 1.00 | 1.00 | 0.05 |
| SEQ ID NO: 220 | 506 | hsa-miR-99b* | caagcucgugucuguggguccg | 1.00 | 1.00 | 1.00 | 0.05 |
| SEQ ID NO: 450 | 507 | hsa-miR-320a | aaaagcuggguugagagggcga | 10047.96 | 8310.31 | 1.21 | 0.05 |
| SEQ ID NO: 231 | 508 | hsa-miR-128 | ucacagugaaccggucucuuu | 773.97 | 21.56 | 35.91 | 0.05 |
| SEQ ID NO: 269 | 509 | hsa-miR-1280 | ucccaccgcugccaccc | 237.33 | 158.89 | 1.49 | 0.05 |
| SEQ ID NO: 478 | 510 | hsa-miR-29a* | acugauuucuuuugguguucag | 2.22 | 1.00 | 2.22 | 0.05 |
| SEQ ID NO: 419 | 511 | hsa-miR-33a* | caauguuuccacagugcaucac | 1.00 | 1.00 | 1.00 | 0.05 |
| SEQ ID NO: 232 | 512 | hsa-miR-362-5p | aauccuuggaaccuaggugugagu | 260.22 | 14.89 | 17.48 | 0.05 |
| SEQ ID NO: 479 | 513 | hsa-miR-370 | gccugcugggguggaaccuggu | 194.00 | 156.56 | 1.24 | 0.05 |
| SEQ ID NO: 420 | 514 | hsa-miR-502-3p | aaugcaccugggcaaggauuca | 364.22 | 14.89 | 24.46 | 0.05 |
| SEQ ID NO: 43 | 515 | hsa-miR-550* | ugucuuacucccucaggcacau | 331.06 | 5.11 | 64.77 | 0.05 |
| SEQ ID NO: 276 | 516 | hsa-miR-586 | uaugcauuguauuuuuaggucc | 1.00 | 1.00 | 1.00 | 0.05 |
| SEQ ID NO: 432 | 517 | hsa-miR-651 | uuuaggauaagcuugacuuuug | 1.00 | 1.00 | 1.00 | 0.05 |
| SEQ ID NO: 433 | 518 | hsa-miR-765 | uggaggagaaggaaggugaug | 1065.22 | 1101.78 | 0.98 | 0.05 |
| SEQ ID NO: 505 | 519 | hsa-miR-942 | ucuucucuguuuuggccaugug | 52.00 | 18.11 | 2.87 | 0.05 |
| SEQ ID NO: 668 | 520 | hsa-miR-125b-1* | acggguuaggcucuugggagcu | 49.56 | 56.22 | 0.88 | 0.05 |
| SEQ ID NO: 544 | 521 | hsa-miR-1826 | auugaucaucgacacuucgaacgcaau | 35853.42 | 35853.42 | 1.00 | 0.05 |
| SEQ ID NO: 182 | 522 | hsa-miR-342-3p | ucucacacagaaaucgcacccgu | 3428.42 | 2319.90 | 1.48 | 0.05 |
| SEQ ID NO: 711 | 523 | hsa-miR-513c | uucucaaggaggugucguuuau | 68.67 | 45.11 | 1.52 | 0.04 |
| SEQ ID NO: 495 | 524 | hsa-miR-1275 | gugggggagaggcuguc | 1146.69 | 901.96 | 1.27 | 0.04 |
| SEQ ID NO: 460 | 525 | hsa-miR-542-5p | ucggggaucaucaugucacgaga | 6.78 | 1.00 | 6.78 | 0.04 |

Figure 10A (cont'd)

| | | | | | | | |
|---|---|---|---|---|---|---|---|
| SEQ ID NO: 692 | 526 | hsa-miR-516a-5p | uucucgaggaaagaagcacuuuc | 39.67 | 58.78 | 0.67 | 0.04 |
| SEQ ID NO: 843 | 527 | hsa-miR-524-5p | cuacaaagggaagcacuuucuc | 31.11 | 29.44 | 1.06 | 0.04 |
| SEQ ID NO: 627 | 528 | hsa-miR-923 | gucagcggaggaaaagaaacu | 24783.94 | 20349.58 | 1.22 | 0.04 |
| SEQ ID NO: 277 | 529 | hsa-miR-92b | uauugcacucgucccggccucc | 4260.36 | 5530.88 | 0.77 | 0.04 |
| SEQ ID NO: 85 | 530 | hsa-miR-1299 | uucuggaauucugugugaggga | 1.00 | 29.94 | 0.03 | 0.04 |
| SEQ ID NO: 720 | 531 | hsa-miR-146b-5p | ugagaacugaauuccauaggcu | 92.56 | 67.44 | 1.37 | 0.04 |
| SEQ ID NO: 437 | 532 | hsa-miR-302a | uaagugcuuccauguuuugguga | 1.00 | 1.00 | 1.00 | 0.04 |
| SEQ ID NO: 208 | 533 | hsa-miR-379* | uauguaacaugguccacuaacu | 1.00 | 1.56 | 0.64 | 0.04 |
| SEQ ID NO: 394 | 534 | hsa-miR-508-3p | ugauuguagccuuuuggaguaga | 1.00 | 1.00 | 1.00 | 0.04 |
| SEQ ID NO: 183 | 535 | hsa-miR-512-3p | aagugcugucauagcugagguc | 1.00 | 1.00 | 1.00 | 0.04 |
| SEQ ID NO: 278 | 536 | hsa-miR-517b | ucgugcaucccuuuagaguguu | 1.00 | 1.00 | 1.00 | 0.04 |
| SEQ ID NO: 310 | 537 | hsa-miR-520h | acaaagugcuucccuuuagagu | 1.00 | 1.00 | 1.00 | 0.04 |
| SEQ ID NO: 279 | 538 | hsa-miR-548a-3p | caaaacuggcaauuacuuuugc | 1.00 | 1.00 | 1.00 | 0.04 |
| SEQ ID NO: 210 | 539 | hsa-miR-579 | uucauuugguauaaaccgcgauu | 1.00 | 1.00 | 1.00 | 0.04 |
| SEQ ID NO: 839 | 540 | hsa-miR-877* | uccucuucucccuccucccag | 20.83 | 21.11 | 0.99 | 0.04 |
| SEQ ID NO: 488 | 541 | hsa-miR-888* | gacugacaccucuuugggugaa | 1.00 | 6.56 | 0.15 | 0.04 |
| SEQ ID NO: 103 | 542 | hsa-miR-1305 | uuuucaacucuaaugggagaga | 1.00 | 3.67 | 0.27 | 0.04 |
| SEQ ID NO: 354 | 543 | hsa-miR-373* | acucaaaaugggggcgcuuucc | 79.67 | 116.33 | 0.68 | 0.04 |
| SEQ ID NO: 421 | 544 | hsa-miR-379 | ugguagacuauggaacguagg | 25.56 | 39.22 | 0.65 | 0.04 |
| SEQ ID NO: 836 | 545 | hsa-miR-432 | ucuuggaguaggucauuggugg | 41.89 | 39.22 | 1.07 | 0.04 |
| SEQ ID NO: 693 | 546 | hsa-miR-510 | uacucaggagaguggcaaucac | 26.78 | 8.33 | 3.21 | 0.04 |
| SEQ ID NO: 625 | 547 | hsa-miR-518e* | cucuagagggaagcgcuuucug | 2.22 | 2.67 | 0.83 | 0.04 |
| SEQ ID NO: 66 | 548 | hsa-miR-519c-5p | cucuagagggaagcgcuuucug | 1.56 | 13.72 | 0.11 | 0.04 |
| SEQ ID NO: 373 | 549 | hsa-miR-520d-5p | cuacaaagggaagcccuuuc | 37.67 | 44.89 | 0.84 | 0.04 |
| SEQ ID NO: 631 | 550 | hsa-miR-610 | ugagcuaaaugugugcuggga | 24.00 | 36.11 | 0.66 | 0.04 |
| SEQ ID NO: 348 | 551 | hsa-miR-920 | ggggagcuguggaagcagua | 50.56 | 80.11 | 0.63 | 0.04 |
| SEQ ID NO: 789 | 552 | hsa-miR-22* | aguucuucaguggcaagcuuua | 69.67 | 36.11 | 1.93 | 0.03 |
| SEQ ID NO: 861 | 553 | hsa-miR-92a | uauugcacuugucccggccugu | 22685.50 | 18004.17 | 1.26 | 0.03 |
| SEQ ID NO: 649 | 554 | hsa-miR-1202 | gugccagcugcaguggggag | 71.56 | 86.67 | 0.83 | 0.03 |
| SEQ ID NO: 362 | 555 | hsa-miR-513a-5p | uucacagggaggugucau | 450.61 | 348.22 | 1.29 | 0.03 |
| SEQ ID NO: 681 | 556 | hsa-miR-1308 | gcaugggugguucagugg | 15421.86 | 9312.50 | 1.66 | 0.03 |

Figure 10A (cont'd)

| | | | | | | | |
|---|---|---|---|---|---|---|---|
| SEQ ID NO: 402 | 557 | hsa-miR-1183 | cacuguaggugauggugagagugggca | 120.44 | 82.89 | 1.45 | 0.03 |
| SEQ ID NO: 446 | 558 | hsa-miR-1225-5p | guggguacggcccaguggggggg | 142.83 | 194.00 | 0.74 | 0.03 |
| SEQ ID NO: 385 | 559 | hsa-miR-1300 | uugagaaggaggcugcug | 327.33 | 192.67 | 1.70 | 0.03 |
| SEQ ID NO: 816 | 560 | hsa-miR-139-3p | ggagacgcggcccuguuggagu | 43.11 | 33.78 | 1.28 | 0.03 |
| SEQ ID NO: 697 | 561 | hsa-miR-25* | aggcggagacuugggcaauug | 111.78 | 68.44 | 1.63 | 0.03 |
| SEQ ID NO: 395 | 562 | hsa-miR-26a-2* | ccuauucuugauuacuuguuuc | 1.00 | 1.00 | 1.00 | 0.03 |
| SEQ ID NO: 496 | 563 | hsa-miR-330-5p | ucucugggccugugucuuaggc | 1.00 | 1.00 | 1.00 | 0.03 |
| SEQ ID NO: 724 | 564 | hsa-miR-338-3p | uccagcaucagugauuuuguug | 13.72 | 1.00 | 13.72 | 0.03 |
| SEQ ID NO: 422 | 565 | hsa-miR-498 | uuucaagccagggggcguuuuuc | 101.11 | 58.78 | 1.72 | 0.03 |
| SEQ ID NO: 311 | 566 | hsa-miR-500* | augcaccugggcaaggauucug | 254.28 | 8.33 | 30.51 | 0.03 |
| SEQ ID NO: 423 | 567 | hsa-miR-518d-5p | cucuagagggaagcacuuucug | 36.78 | 19.78 | 1.86 | 0.03 |
| SEQ ID NO: 600 | 568 | hsa-miR-520c-5p | cucuagagggaagcacuuucug | 31.56 | 30.44 | 1.04 | 0.03 |
| SEQ ID NO: 434 | 569 | hsa-miR-548m | caaagguauuugugguuuuug | 1.00 | 1.00 | 1.00 | 0.03 |
| SEQ ID NO: 312 | 570 | hsa-miR-551b* | gaaaucaagcgugggugagacc | 97.33 | 87.67 | 1.11 | 0.03 |
| SEQ ID NO: 233 | 571 | hsa-miR-671-5p | aggaagcccuggaggggcuggag | 272.00 | 168.11 | 1.62 | 0.03 |
| SEQ ID NO: 76 | 572 | hsa-miR-720 | ucucgcuggggccucca | 189.89 | 61.56 | 3.08 | 0.03 |
| SEQ ID NO: 737 | 573 | hsa-miR-766 | acuccagccccacagccucagc | 106.11 | 70.89 | 1.50 | 0.03 |
| SEQ ID NO: 597 | 574 | hsa-miR-877 | guagaggagauggcgcaggg | 364.22 | 450.61 | 0.81 | 0.03 |
| SEQ ID NO: 480 | 575 | hsa-let-7a* | cuauacaaucuacugucuuuc | 4.78 | 4.22 | 1.13 | 0.03 |
| SEQ ID NO: 655 | 576 | hsa-let-7e* | cuauacggccuccuagcuuucc | 1.00 | 1.00 | 1.00 | 0.03 |
| SEQ ID NO: 620 | 577 | hsa-let-7i* | cugcgcaagcuacugccuugcu | 5.22 | 1.00 | 5.22 | 0.03 |
| SEQ ID NO: 585 | 578 | hsa-miR-100* | caagcuuguaucuauagguaug | 1.00 | 1.00 | 1.00 | 0.03 |
| SEQ ID NO: 481 | 579 | hsa-miR-101* | caguuaucacagugcugaugcu | 1.00 | 1.00 | 1.00 | 0.03 |
| SEQ ID NO: 497 | 580 | hsa-miR-1243 | aacuggaucaauuauaggagug | 1.00 | 1.00 | 1.00 | 0.03 |
| SEQ ID NO: 545 | 581 | hsa-miR-127-3p | ucggauccgucugagcuuggcu | 1.00 | 1.00 | 1.00 | 0.03 |
| SEQ ID NO: 583 | 582 | hsa-miR-133b | uuugguccccuucaaccagcua | 24.00 | 19.78 | 1.21 | 0.03 |
| SEQ ID NO: 683 | 583 | hsa-miR-135a | uauggcuuuuuauuccuauguga | 1.00 | 1.00 | 1.00 | 0.03 |
| SEQ ID NO: 498 | 584 | hsa-miR-136* | caucaucgucucaaaugagucu | 1.00 | 1.00 | 1.00 | 0.03 |
| SEQ ID NO: 499 | 585 | hsa-miR-141* | caucuuccaguacaguguugga | 1.00 | 1.00 | 1.00 | 0.03 |
| SEQ ID NO: 558 | 586 | hsa-miR-183* | gugaauuaccgaagggccauaa | 82.06 | 72.22 | 1.14 | 0.03 |
| SEQ ID NO: 461 | 587 | hsa-miR-190 | ugauauguuugauauauuaggu | 1.00 | 1.00 | 1.00 | 0.03 |

Figure 10A (cont'd)

| | | | | | | | |
|---|---|---|---|---|---|---|---|
| SEQ ID NO: 555 | 588 | hsa-miR-200a | uaacacugucugguaacgaugu | 1.00 | 1.00 | 1.00 | 0.03 |
| SEQ ID NO: 554 | 589 | hsa-miR-200b* | caucuuacugggcagcauugga | 7.44 | 4.22 | 1.76 | 0.03 |
| SEQ ID NO: 682 | 590 | hsa-miR-208a | auaagacgagcaaaaagcuugu | 19.89 | 14.89 | 1.34 | 0.03 |
| SEQ ID NO: 528 | 591 | hsa-miR-20a* | acugcauuaugagcacuuaaag | 1.00 | 1.00 | 1.00 | 0.03 |
| SEQ ID NO: 483 | 592 | hsa-miR-217 | uacugcaucaggaacugauugga | 1.00 | 1.00 | 1.00 | 0.03 |
| SEQ ID NO: 462 | 593 | hsa-miR-218-1* | augguuccgucaagcaccaugg | 1.00 | 1.00 | 1.00 | 0.03 |
| SEQ ID NO: 506 | 594 | hsa-miR-26a-1* | ccuauucuugguuacuugcacg | 1.00 | 1.00 | 1.00 | 0.03 |
| SEQ ID NO: 522 | 595 | hsa-miR-27a* | agggcuuagcugcuugugagca | 1.00 | 1.00 | 1.00 | 0.03 |
| SEQ ID NO: 617 | 596 | hsa-miR-329 | aacacaccugguuaaccucuuu | 1.00 | 1.56 | 0.64 | 0.03 |
| SEQ ID NO: 684 | 597 | hsa-miR-331-5p | cuagguaugguucccagggaucc | 22.22 | 21.11 | 1.05 | 0.03 |
| SEQ ID NO: 582 | 598 | hsa-miR-337-5p | gaacggcuucauacaggaguu | 2.67 | 8.33 | 0.32 | 0.03 |
| SEQ ID NO: 463 | 599 | hsa-miR-367* | acuguugcuaauaugcaacucu | 1.00 | 1.00 | 1.00 | 0.03 |
| SEQ ID NO: 566 | 600 | hsa-miR-373 | gaagugcuucgauuuuggggugu | 1.00 | 1.56 | 0.64 | 0.03 |
| SEQ ID NO: 532 | 601 | hsa-miR-377* | agagguugcccuuggugaauuc | 1.00 | 1.00 | 1.00 | 0.03 |
| SEQ ID NO: 664 | 602 | hsa-miR-381 | uauacaagggcaagcucucugu | 7.44 | 1.00 | 7.44 | 0.03 |
| SEQ ID NO: 570 | 603 | hsa-miR-412 | acuucaccugguccacuagccgu | 4.00 | 1.56 | 2.57 | 0.03 |
| SEQ ID NO: 539 | 604 | hsa-miR-448 | uugcauauguaggaugucccau | 1.00 | 1.00 | 1.00 | 0.03 |
| SEQ ID NO: 464 | 605 | hsa-miR-450a | uuuugcgauguguuccuaauau | 1.00 | 1.00 | 1.00 | 0.03 |
| SEQ ID NO: 660 | 606 | hsa-miR-452 | aacuguuugcagaggaaacuga | 2.67 | 1.00 | 2.67 | 0.03 |
| SEQ ID NO: 614 | 607 | hsa-miR-485-3p | gucauacacggcucuccucucu | 1.00 | 1.56 | 0.64 | 0.03 |
| SEQ ID NO: 541 | 608 | hsa-miR-487a | aaucauacagggacauccaguu | 1.56 | 1.56 | 1.00 | 0.03 |
| SEQ ID NO: 533 | 609 | hsa-miR-504 | agacccuggucugcacucuauc | 1.00 | 1.00 | 1.00 | 0.03 |
| SEQ ID NO: 374 | 610 | hsa-miR-512-5p | cacucagccuugagggcacuuuc | 1.00 | 4.22 | 0.24 | 0.03 |
| SEQ ID NO: 500 | 611 | hsa-miR-517c | aucgugcauccuuuuagagugu | 1.00 | 1.00 | 1.00 | 0.03 |
| SEQ ID NO: 571 | 612 | hsa-miR-518c | caaagcgcuucucuuuagagugu | 1.00 | 1.00 | 1.00 | 0.03 |
| SEQ ID NO: 556 | 613 | hsa-miR-518e | aaagcgcuucccuucagagug | 1.00 | 1.00 | 1.00 | 0.03 |
| SEQ ID NO: 515 | 614 | hsa-miR-539 | ggagaaauuauccuugguguguu | 1.00 | 1.00 | 1.00 | 0.03 |
| SEQ ID NO: 534 | 615 | hsa-miR-548c-3p | caaaaaucucaauuacuuuugc | 1.00 | 1.00 | 1.00 | 0.03 |
| SEQ ID NO: 561 | 616 | hsa-miR-548o | ccaaaacugcaguuacuuuugc | 1.00 | 1.00 | 1.00 | 0.03 |
| SEQ ID NO: 424 | 617 | hsa-miR-556-3p | auauuaccauuagcucaucuuu | 1.00 | 1.00 | 1.00 | 0.03 |
| SEQ ID NO: 482 | 618 | hsa-miR-559 | uaaaguaaauaugcaccaaaa | 1.00 | 1.00 | 1.00 | 0.03 |

Figure 10A (cont'd)

| | | | | | | | |
|---|---|---|---|---|---|---|---|
| SEQ ID NO: 520 | 619 | hsa-miR-573 | cugaagugauguguaacugaucag | 1.00 | 1.00 | 1.00 | 0.03 |
| SEQ ID NO: 513 | 620 | hsa-miR-580 | uugagaaugaugaaucauuagg | 1.00 | 1.00 | 1.00 | 0.03 |
| SEQ ID NO: 452 | 621 | hsa-miR-582-5p | uuacaguuguucaaccaguuacu | 1.00 | 3.11 | 0.32 | 0.03 |
| SEQ ID NO: 572 | 622 | hsa-miR-589* | ucagaacaaaugccgguucccaga | 22.67 | 20.56 | 1.10 | 0.03 |
| SEQ ID NO: 523 | 623 | hsa-miR-613 | aggaauguuccuucuuugcc | 1.00 | 1.00 | 1.00 | 0.03 |
| SEQ ID NO: 501 | 624 | hsa-miR-621 | ggcuagcaacagcgcuuaccu | 1.00 | 1.00 | 1.00 | 0.03 |
| SEQ ID NO: 403 | 625 | hsa-miR-626 | agcugucugaaaaugucuu | 1.00 | 1.00 | 1.00 | 0.03 |
| SEQ ID NO: 540 | 626 | hsa-miR-633 | cuaauaguaucuaccacaauaaa | 1.00 | 1.00 | 1.00 | 0.03 |
| SEQ ID NO: 702 | 627 | hsa-miR-650 | aggaggcagcgcucucaggac | 14.89 | 12.44 | 1.20 | 0.03 |
| SEQ ID NO: 832 | 628 | hsa-miR-661 | ugccugggucucuggccugcgcgu | 4.00 | 1.00 | 4.00 | 0.03 |
| SEQ ID NO: 467 | 629 | hsa-miR-767-5p | ugcaccaugguugucugagcaug | 1.00 | 1.00 | 1.00 | 0.03 |
| SEQ ID NO: 451 | 630 | hsa-miR-770-5p | uccaguaccacgugucagggcca | 9.11 | 11.33 | 0.80 | 0.03 |
| SEQ ID NO: 621 | 631 | hsa-miR-935 | ccaguuaccgcuuccgcuaccgc | 1.00 | 1.00 | 1.00 | 0.03 |
| SEQ ID NO: 783 | 632 | hsa-miR-941 | cacccggcugugugcacaugugc | 39.67 | 4.22 | 9.39 | 0.03 |
| SEQ ID NO: 576 | 633 | hsa-miR-944 | aaauuauuguacaucggaugag | 1.00 | 1.00 | 1.00 | 0.03 |
| SEQ ID NO: 396 | 634 | hsa-miR-187 | ucgugucuuguguugcagccgg | 1.00 | 4.44 | 0.23 | 0.03 |
| SEQ ID NO: 767 | 635 | hsa-miR-191* | gcugcgcuuggauuucgucccc | 53.00 | 47.06 | 1.13 | 0.03 |
| SEQ ID NO: 714 | 636 | hsa-miR-320c | aaaagcugggouugagagggu | 5382.15 | 6141.96 | 0.88 | 0.02 |
| SEQ ID NO: 703 | 637 | hsa-miR-1227 | cgugccacccuuuuccccag | 32.00 | 29.94 | 1.07 | 0.02 |
| SEQ ID NO: 559 | 638 | hsa-miR-148b | ucagugcaucacagaacuuugu | 364.22 | 1.00 | 364.22 | 0.02 |
| SEQ ID NO: 313 | 639 | hsa-miR-186 | caaagaauucuccuuuugggcu | 39.67 | 18.72 | 2.12 | 0.02 |
| SEQ ID NO: 591 | 640 | hsa-miR-190b | ugauauguuugauauuggguu | 1.00 | 1.00 | 1.00 | 0.02 |
| SEQ ID NO: 665 | 641 | hsa-miR-340 | uuauaaagcaaugagacugauu | 79.67 | 21.56 | 3.70 | 0.02 |
| SEQ ID NO: 618 | 642 | hsa-miR-483-5p | aagacgggaggaaagaagggag | 4541.94 | 3572.67 | 1.27 | 0.02 |
| SEQ ID NO: 425 | 643 | hsa-miR-502-5p | auccuugcuaucugggugcua | 6.78 | 1.00 | 6.78 | 0.02 |
| SEQ ID NO: 586 | 644 | hsa-miR-589 | ugagaaccacgucugcucugag | 6.78 | 1.00 | 6.78 | 0.02 |
| SEQ ID NO: 715 | 645 | hsa-miR-320b | aaaagcuggguugagagggcaa | 6349.31 | 6349.31 | 1.00 | 0.02 |
| SEQ ID NO: 288 | 646 | hsa-miR-1538 | cggcccgggcugcugcuguuccu | 48.00 | 18.72 | 2.56 | 0.02 |
| SEQ ID NO: 546 | 647 | hsa-miR-486-5p | uccuguacugagcugccccgag | 42197.28 | 42197.28 | 1.00 | 0.02 |
| SEQ ID NO: 791 | 648 | hsa-miR-149* | agggagggacgggggcugugc | 18004.17 | 13307.74 | 1.35 | 0.02 |
| SEQ ID NO: 514 | 649 | hsa-let-7b* | cuauacaaccuacugccuuccc | 22.22 | 13.72 | 1.62 | 0.02 |

Figure 10A (cont'd)

| | | | | | | | |
|---|---|---|---|---|---|---|---|
| SEQ ID NO: 819 | 650 | hsa-miR-1180 | uuuccggcucgcgugggugugu | 61.11 | 21.11 | 2.89 | 0.02 |
| SEQ ID NO: 562 | 651 | hsa-miR-1203 | cccggagccaggaugcagcuc | 43.11 | 28.00 | 1.54 | 0.02 |
| SEQ ID NO: 490 | 652 | hsa-miR-1257 | agugaaugaugggguucugacc | 2.67 | 1.56 | 1.71 | 0.02 |
| SEQ ID NO: 844 | 653 | hsa-miR-1258 | aguuaggauuaggucguggaa | 15.78 | 12.44 | 1.27 | 0.02 |
| SEQ ID NO: 386 | 654 | hsa-miR-1264 | caagucuuauuugagcaccuguu | 1.00 | 1.00 | 1.00 | 0.02 |
| SEQ ID NO: 850 | 655 | hsa-miR-1470 | gcccuccgcccgugcaccccg | 20.56 | 12.11 | 1.70 | 0.02 |
| SEQ ID NO: 657 | 656 | hsa-miR-18b* | ugcccuaaaugccccuucuggc | 24.56 | 18.11 | 1.36 | 0.02 |
| SEQ ID NO: 502 | 657 | hsa-miR-1915* | accuugccuugcugcccgggcc | 1.00 | 11.33 | 0.09 | 0.02 |
| SEQ ID NO: 680 | 658 | hsa-miR-19b-2* | aguuuugcagguuugcauuuca | 1.00 | 1.00 | 1.00 | 0.02 |
| SEQ ID NO: 797 | 659 | hsa-miR-203 | gugaaauguuuaggaccacuag | 1.00 | 1.00 | 1.00 | 0.02 |
| SEQ ID NO: 439 | 660 | hsa-miR-206 | uggaauguaaggaagugugugg | 15.78 | 28.44 | 0.55 | 0.02 |
| SEQ ID NO: 317 | 661 | hsa-miR-211 | uucccuuugucauccuucgccu | 1.00 | 3.67 | 0.27 | 0.02 |
| SEQ ID NO: 435 | 662 | hsa-miR-219-2-3p | agaauuguggcuggacaucugu | 4.00 | 1.00 | 4.00 | 0.02 |
| SEQ ID NO: 524 | 663 | hsa-miR-220c | acacagggcuguugugaagacu | 1.00 | 3.11 | 0.32 | 0.02 |
| SEQ ID NO: 447 | 664 | hsa-miR-223* | cguguauuugacaagcugaguu | 1.00 | 4.44 | 0.23 | 0.02 |
| SEQ ID NO: 588 | 665 | hsa-miR-224 | caagucacuagugguuccguu | 1.00 | 1.00 | 1.00 | 0.02 |
| SEQ ID NO: 809 | 666 | hsa-miR-27b | uucacaguggcuaaguucugc | 73.33 | 33.78 | 2.17 | 0.02 |
| SEQ ID NO: 492 | 667 | hsa-miR-296-5p | agggcccccccucaauccugu | 48.00 | 58.89 | 0.82 | 0.02 |
| SEQ ID NO: 792 | 668 | hsa-miR-30c-1* | cugggagaggguuguuuacucc | 101.11 | 101.11 | 1.00 | 0.02 |
| SEQ ID NO: 426 | 669 | hsa-miR-31 | aggcaagaugcuggcauagcu | 8.44 | 3.67 | 2.30 | 0.02 |
| SEQ ID NO: 647 | 670 | hsa-miR-382 | gaaguuguucgugguggauucg | 9.56 | 1.56 | 6.14 | 0.02 |
| SEQ ID NO: 648 | 671 | hsa-miR-454* | acccuaucaauauugucucugc | 27.00 | 21.11 | 1.28 | 0.02 |
| SEQ ID NO: 675 | 672 | hsa-miR-486-3p | cggggcagcucaguacaggau | 37.89 | 18.72 | 2.02 | 0.02 |
| SEQ ID NO: 363 | 673 | hsa-miR-509-3-5p | uacugcagacguggcaaucaug | 1.00 | 1.00 | 1.00 | 0.02 |
| SEQ ID NO: 771 | 674 | hsa-miR-518f* | cucuagagggaagcacuuucuc | 25.17 | 58.89 | 0.43 | 0.02 |
| SEQ ID NO: 484 | 675 | hsa-miR-519b-5p | cucuagagggaagcgcuuucug | 1.56 | 4.44 | 0.35 | 0.02 |
| SEQ ID NO: 407 | 676 | hsa-miR-519e | aagugccuccuuuuagaguguu | 1.00 | 1.00 | 1.00 | 0.02 |
| SEQ ID NO: 440 | 677 | hsa-miR-520d-3p | aaagugcuucucuuugguggguu | 1.00 | 1.00 | 1.00 | 0.02 |
| SEQ ID NO: 270 | 678 | hsa-miR-523* | cucuagagggaagcgcuuucug | 6.78 | 18.72 | 0.36 | 0.02 |
| SEQ ID NO: 525 | 679 | hsa-miR-524-3p | gaaggcgcuucccuuuggagu | 1.00 | 1.00 | 1.00 | 0.02 |
| SEQ ID NO: 503 | 680 | hsa-miR-541 | uggugggcacagaaucuggacu | 16.78 | 28.44 | 0.59 | 0.02 |

Figure 10A (cont'd)

| | | | | | | | |
|---|---|---|---|---|---|---|---|
| SEQ ID NO: 504 | 681 | hsa-miR-543 | aaacauucgcggugcacuucuu | 1.00 | 1.00 | 1.00 | 0.02 |
| SEQ ID NO: 712 | 682 | hsa-miR-548c-5p | aaaaguaauugcgguuuuugcc | 1.00 | 1.00 | 1.00 | 0.02 |
| SEQ ID NO: 606 | 683 | hsa-miR-548e | aaaaacugagacuacuuuugca | 1.00 | 1.00 | 1.00 | 0.02 |
| SEQ ID NO: 441 | 684 | hsa-miR-548i | aaaaguaauugcggauuuugcc | 1.00 | 1.00 | 1.00 | 0.02 |
| SEQ ID NO: 549 | 685 | hsa-miR-548l | aaaaguauuugcggguuuuguc | 1.00 | 1.00 | 1.00 | 0.02 |
| SEQ ID NO: 593 | 686 | hsa-miR-548p | uagcaaaaacugcaguuacuuu | 1.00 | 1.00 | 1.00 | 0.02 |
| SEQ ID NO: 349 | 687 | hsa-miR-571 | ugaguuggccaucugagugag | 1.00 | 1.00 | 1.00 | 0.02 |
| SEQ ID NO: 676 | 688 | hsa-miR-596 | aagccugcccggcuccucggg | 1.00 | 3.11 | 0.32 | 0.02 |
| SEQ ID NO: 774 | 689 | hsa-miR-598 | uacgucaucguugucaucguca | 12.22 | 1.00 | 12.22 | 0.02 |
| SEQ ID NO: 738 | 690 | hsa-miR-600 | acuuacagacaagagccuugcuc | 1.00 | 1.00 | 1.00 | 0.02 |
| SEQ ID NO: 184 | 691 | hsa-miR-623 | aucccuugcaggggcuguugggu | 1.00 | 1.00 | 1.00 | 0.02 |
| SEQ ID NO: 658 | 692 | hsa-miR-630 | aguauucuguaccagggaaggu | 4.00 | 6.56 | 0.61 | 0.02 |
| SEQ ID NO: 758 | 693 | hsa-miR-642 | gucccucuccaaaugugucuug | 1.00 | 1.00 | 1.00 | 0.02 |
| SEQ ID NO: 573 | 694 | hsa-miR-643 | acuuguaugcuagcucagguag | 1.00 | 1.00 | 1.00 | 0.02 |
| SEQ ID NO: 219 | 695 | hsa-miR-654-3p | uaugucugcugaccaucaccuu | 1.00 | 1.00 | 1.00 | 0.02 |
| SEQ ID NO: 364 | 696 | hsa-miR-873 | gcaggaacuugugagucuccu | 1.00 | 5.11 | 0.20 | 0.02 |
| SEQ ID NO: 700 | 697 | hsa-miR-890 | uacuuggaaaggcaucaguug | 20.56 | 11.56 | 1.78 | 0.02 |
| SEQ ID NO: 863 | 698 | hsa-miR-150 | ucucccaacccuuguaccagug | 600.34 | 839.63 | 0.72 | 0.02 |
| SEQ ID NO: 757 | 699 | hsa-miR-125b | ucccugagacccuaacuuguga | 65.56 | 38.33 | 1.71 | 0.01 |
| SEQ ID NO: 628 | 700 | hsa-miR-196a* | cggcaacaagaaacugccugag | 15.33 | 18.72 | 0.82 | 0.01 |
| SEQ ID NO: 397 | 701 | hsa-miR-199a-3p | acaguagucugcacauugguua | 1.00 | 19.78 | 0.05 | 0.01 |
| SEQ ID NO: 730 | 702 | hsa-miR-421 | aucaacagacauuaauugggcgc | 217.67 | 1.00 | 217.67 | 0.01 |
| SEQ ID NO: 643 | 703 | hsa-miR-483-3p | ucacuccucuccucccgucuu | 13.00 | 30.44 | 0.43 | 0.01 |
| SEQ ID NO: 779 | 704 | hsa-miR-515-5p | uucuccaaaagaaagcacuuucug | 1.00 | 1.00 | 1.00 | 0.01 |
| SEQ ID NO: 615 | 705 | hsa-miR-541* | aaaggauucugcugucggucccacu | 1.00 | 1.00 | 1.00 | 0.01 |
| SEQ ID NO: 535 | 706 | hsa-miR-1276 | uaaagagcccuguggagaca | 24.56 | 30.44 | 0.81 | 0.01 |
| SEQ ID NO: 749 | 707 | hsa-miR-191 | caacggaaucccaaaagcagcug | 31577.57 | 27467.24 | 1.15 | 0.01 |
| SEQ ID NO: 798 | 708 | hsa-miR-302c* | uuuaacauggggguaccugcug | 66.67 | 18.72 | 3.67 | 0.01 |
| SEQ ID NO: 745 | 709 | hsa-miR-30b* | cugggagguggauguuuacuuc | 88.56 | 98.56 | 0.90 | 0.01 |
| SEQ ID NO: 768 | 710 | hsa-miR-221 | agcuacauugucugcuggguuuc | 382.00 | 539.56 | 0.71 | 0.01 |
| SEQ ID NO: 694 | 711 | hsa-miR-1915 | ccccagggcgacgcggcggg | 2223.89 | 3080.08 | 0.72 | 0.01 |

Figure 10A (cont'd)

| | | | | | | | |
|---|---|---|---|---|---|---|---|
| SEQ ID NO: 818 | 712 | hsa-miR-1228 | ucacaccugccucgcccccc | 39.67 | 140.78 | 0.28 | 0.01 |
| SEQ ID NO: 656 | 713 | hsa-miR-1237 | uccuucugcuccgucccccag | 37.89 | 30.44 | 1.24 | 0.01 |
| SEQ ID NO: 104 | 714 | hsa-miR-129-5p | cuuuuugcggucugggcuugc | 33.78 | 14.89 | 2.27 | 0.01 |
| SEQ ID NO: 732 | 715 | hsa-miR-150* | cugguacaggccugggggacag | 101.11 | 101.78 | 0.99 | 0.01 |
| SEQ ID NO: 722 | 716 | hsa-miR-1909* | ugagugccggugccugcccug | 20.56 | 16.33 | 1.26 | 0.01 |
| SEQ ID NO: 728 | 717 | hsa-miR-1910 | ccaguccugugccugccgccu | 7.44 | 11.56 | 0.64 | 0.01 |
| SEQ ID NO: 650 | 718 | hsa-miR-202 | agagguauagggcaugggaa | 111.78 | 61.11 | 1.83 | 0.01 |
| SEQ ID NO: 587 | 719 | hsa-miR-218 | uugugcuugaucuaaccaugu | 1.00 | 1.00 | 1.00 | 0.01 |
| SEQ ID NO: 759 | 720 | hsa-miR-30a* | cuuucagucggauguuugcagc | 1.00 | 1.00 | 1.00 | 0.01 |
| SEQ ID NO: 717 | 721 | hsa-miR-326 | ccucugggcccuuccuccag | 20.56 | 19.78 | 1.04 | 0.01 |
| SEQ ID NO: 567 | 722 | hsa-miR-371-5p | acucaaacugugggggcacu | 98.00 | 93.22 | 1.05 | 0.01 |
| SEQ ID NO: 603 | 723 | hsa-miR-505 | cgucaacacuugcugguuuccu | 53.00 | 11.33 | 4.68 | 0.01 |
| SEQ ID NO: 820 | 724 | hsa-miR-575 | gagccaguuggacaggagc | 58.78 | 70.67 | 0.83 | 0.01 |
| SEQ ID NO: 491 | 725 | hsa-miR-7 | uggaagacuagugauuuuguugu | 256.44 | 1.00 | 256.44 | 0.01 |
| SEQ ID NO: 828 | 726 | hsa-miR-938 | ugcccuuaaaggugaacccagu | 2.22 | 1.00 | 2.22 | 0.01 |
| SEQ ID NO: 740 | 727 | hsa-miR-340* | uccgucucaguuacuuuauagc | 4.00 | 1.00 | 4.00 | 0.01 |
| SEQ ID NO: 427 | 728 | hsa-miR-100 | aacccguagauccgaacuugug | 212.00 | 98.56 | 2.15 | 0.01 |
| SEQ ID NO: 733 | 729 | hsa-miR-1229 | cucucaccacugcccucccacag | 27.89 | 33.78 | 0.83 | 0.01 |
| SEQ ID NO: 772 | 730 | hsa-miR-1233 | ugagcccuguccucccgcag | 8.44 | 12.44 | 0.68 | 0.01 |
| SEQ ID NO: 810 | 731 | hsa-miR-1236 | ccucuuccccuugucucuccag | 39.67 | 44.00 | 0.90 | 0.01 |
| SEQ ID NO: 623 | 732 | hsa-miR-1274a | gucccuguucaggcgcca | 93.89 | 12.00 | 7.82 | 0.01 |
| SEQ ID NO: 633 | 733 | hsa-miR-1282 | ucguuugccuuuuucugcuu | 29.44 | 1.56 | 18.93 | 0.01 |
| SEQ ID NO: 754 | 734 | hsa-miR-129-3p | aagcccuuaccccaaaaagcau | 4.00 | 28.33 | 0.14 | 0.01 |
| SEQ ID NO: 853 | 735 | hsa-miR-129* | aagcccuuaccccaaaaaguau | 8.44 | 1.00 | 8.44 | 0.01 |
| SEQ ID NO: 766 | 736 | hsa-miR-1296 | uuagggcccuggcuccaucucc | 14.56 | 4.22 | 3.45 | 0.01 |
| SEQ ID NO: 781 | 737 | hsa-miR-634 | aaccagcaccccaacuuuggac | 36.78 | 49.22 | 0.75 | 0.01 |
| SEQ ID NO: 762 | 738 | hsa-miR-769-3p | cugggaucuccggggucuugguu | 25.56 | 15.56 | 1.64 | 0.01 |
| SEQ ID NO: 735 | 739 | hsa-miR-320d | aaaagcugggguugagagga | 4318.58 | 4390.58 | 0.98 | 0.01 |
| SEQ ID NO: 521 | 740 | hsa-miR-93 | caaagugcuguucgugcagguag | 4779.31 | 5660.31 | 0.84 | 0.01 |
| SEQ ID NO: 642 | 741 | hsa-let-7g* | cuguacaggccacugccuugc | 1.00 | 1.00 | 1.00 | 0.01 |
| SEQ ID NO: 672 | 742 | hsa-miR-1267 | ccuguugaaguguaaucccca | 9.56 | 1.56 | 6.14 | 0.01 |

Figure 10A (cont'd)

| | | | | | | | |
|---|---|---|---|---|---|---|---|
| SEQ ID NO: 817 | 743 | hsa-miR-130b* | acucuuucccuguugcacuac | 2.67 | 1.00 | 2.67 | 0.01 |
| SEQ ID NO: 666 | 744 | hsa-miR-132 | uaacagucuacagccauggucg | 24.56 | 4.22 | 5.82 | 0.01 |
| SEQ ID NO: 747 | 745 | hsa-miR-138-1* | gcuacuucacaacaccagggcc | 19.89 | 4.22 | 4.71 | 0.01 |
| SEQ ID NO: 667 | 746 | hsa-miR-142-3p | uguaguguuuccuacuuuaugga | 1.00 | 1.00 | 1.00 | 0.01 |
| SEQ ID NO: 785 | 747 | hsa-miR-195* | ccaauauuggcugugcugcucc | 1.00 | 1.00 | 1.00 | 0.01 |
| SEQ ID NO: 436 | 748 | hsa-miR-501-3p | aaugcacccgggcaaggauucu | 286.11 | 21.56 | 13.27 | 0.01 |
| SEQ ID NO: 563 | 749 | hsa-miR-135a* | uauagggauuggagccguggcg | 644.90 | 480.44 | 1.34 | 0.01 |
| SEQ ID NO: 536 | 750 | hsa-miR-138 | agcugguguugugaaucaggccg | 8.44 | 1.00 | 8.44 | 0.01 |
| SEQ ID NO: 644 | 751 | hsa-miR-214 | acagcaggcacagacaggcagu | 29.11 | 3.11 | 9.36 | 0.01 |
| SEQ ID NO: 428 | 752 | hsa-miR-296-3p | gaggguuggguggaggcucucc | 606.46 | 408.44 | 1.48 | 0.01 |
| SEQ ID NO: 829 | 753 | hsa-miR-608 | agggguggguguugggacagcuccgu | 106.89 | 96.94 | 1.10 | 0.01 |
| SEQ ID NO: 634 | 754 | hsa-miR-10b* | acagauucgauucuaggggaau | 1.00 | 1.00 | 1.00 | 0.01 |
| SEQ ID NO: 209 | 755 | hsa-miR-1184 | ccugcagcgacuugauggcuucc | 1.00 | 1.00 | 1.00 | 0.01 |
| SEQ ID NO: 796 | 756 | hsa-miR-1231 | gugucugggcggacagcugc | 43.11 | 30.44 | 1.42 | 0.01 |
| SEQ ID NO: 581 | 757 | hsa-miR-1281 | ucgccuccucccucucc | 8.44 | 35.83 | 0.24 | 0.01 |
| SEQ ID NO: 773 | 758 | hsa-miR-1290 | uggauuuuuggaucaggga | 39.67 | 28.33 | 1.40 | 0.01 |
| SEQ ID NO: 710 | 759 | hsa-miR-1321 | cagggaggugaaugugau | 74.22 | 58.78 | 1.26 | 0.01 |
| SEQ ID NO: 821 | 760 | hsa-miR-134 | ugugacugguugaccagagggg | 55.67 | 34.00 | 1.64 | 0.01 |
| SEQ ID NO: 601 | 761 | hsa-miR-148a* | aaaguucugagacacuccgacu | 1.00 | 1.00 | 1.00 | 0.01 |
| SEQ ID NO: 807 | 762 | hsa-miR-152 | ucagugcaugacagaacuugg | 16.78 | 12.11 | 1.39 | 0.01 |
| SEQ ID NO: 718 | 763 | hsa-miR-1825 | uccagugcccuccucucc | 21.11 | 30.44 | 0.69 | 0.01 |
| SEQ ID NO: 608 | 764 | hsa-miR-1914 | cccugugcccggcccacuucug | 6.78 | 14.89 | 0.46 | 0.01 |
| SEQ ID NO: 408 | 765 | hsa-miR-204 | uucccuuugucauccuaugccu | 1.00 | 1.00 | 1.00 | 0.01 |
| SEQ ID NO: 661 | 766 | hsa-miR-26b* | ccuguucuccauuacuuggcuc | 1.00 | 4.22 | 0.24 | 0.01 |
| SEQ ID NO: 669 | 767 | hsa-miR-30c-2* | cugggagaaggcuguuuacucu | 68.67 | 56.78 | 1.21 | 0.01 |
| SEQ ID NO: 645 | 768 | hsa-miR-34b* | uaggcagugucauuagcugauug | 1.00 | 1.00 | 1.00 | 0.01 |
| SEQ ID NO: 592 | 769 | hsa-miR-375 | uuuguucguucggcucgcguga | 1.00 | 1.00 | 1.00 | 0.01 |
| SEQ ID NO: 564 | 770 | hsa-miR-383 | agaucagaaggugauuguggcu | 15.33 | 18.67 | 0.82 | 0.01 |
| SEQ ID NO: 837 | 771 | hsa-miR-409-3p | gaauguugcucggugaaccccu | 97.33 | 68.44 | 1.42 | 0.01 |
| SEQ ID NO: 835 | 772 | hsa-miR-450b-5p | uuuugcaauauguuccugaaua | 1.00 | 1.00 | 1.00 | 0.01 |
| SEQ ID NO: 707 | 773 | hsa-miR-455-3p | gcaguccaugggcauauacac | 1.00 | 1.00 | 1.00 | 0.01 |

Figure 10A (cont'd)

| | | | | | | | |
|---|---|---|---|---|---|---|---|
| SEQ ID NO: 640 | 774 | hsa-miR-490-3p | caaccuggaggacuccaugcug | 1.00 | 1.00 | 1.00 | 0.01 |
| SEQ ID NO: 811 | 775 | hsa-miR-495 | aaacaaacauggugcacuucuu | 2.67 | 3.67 | 0.73 | 0.01 |
| SEQ ID NO: 748 | 776 | hsa-miR-501-5p | aauccuuugucccugggugaga | 4.78 | 3.11 | 1.54 | 0.01 |
| SEQ ID NO: 662 | 777 | hsa-miR-516b | aucuggagguaagaagcacuuu | 52.00 | 56.22 | 0.92 | 0.01 |
| SEQ ID NO: 742 | 778 | hsa-miR-520a-5p | cuccagagggaaguacuuucu | 15.33 | 18.72 | 0.82 | 0.01 |
| SEQ ID NO: 652 | 779 | hsa-miR-593 | ugucucugcuggggguuucu | 30.44 | 46.44 | 0.66 | 0.01 |
| SEQ ID NO: 854 | 780 | hsa-miR-625 | agggggaaaguucuauagucc | 182.44 | 109.67 | 1.66 | 0.01 |
| SEQ ID NO: 814 | 781 | hsa-miR-675 | uggugcggagagggcccacagug | 185.22 | 172.44 | 1.07 | 0.01 |
| SEQ ID NO: 653 | 782 | hsa-miR-760 | cggcucugggucugugggga | 34.89 | 53.33 | 0.65 | 0.01 |
| SEQ ID NO: 775 | 783 | hsa-miR-769-5p | ugagaccucuggguucugagcu | 15.33 | 3.67 | 4.18 | 0.01 |
| SEQ ID NO: 822 | 784 | hsa-miR-875-3p | ccuggaaacacugagguugug | 6.78 | 1.00 | 6.78 | 0.01 |
| SEQ ID NO: 769 | 785 | hsa-miR-92a-1* | agguugggaucgguugcaaugcu | 20.56 | 21.56 | 0.95 | 0.01 |
| SEQ ID NO: 750 | 786 | hsa-miR-107 | agcagcauuguacagggcuauca | 4106.11 | 4916.83 | 0.84 | 0.00 |
| SEQ ID NO: 624 | 787 | hsa-miR-1226 | ucaccagcccuguguucccuag | 1.00 | 4.44 | 0.23 | 0.00 |
| SEQ ID NO: 580 | 788 | hsa-miR-1260 | aucccaccucugccacca | 84.17 | 51.33 | 1.64 | 0.00 |
| SEQ ID NO: 815 | 789 | hsa-miR-1274b | ucccuguucgggcgcca | 176.56 | 63.61 | 2.78 | 0.00 |
| SEQ ID NO: 760 | 790 | hsa-miR-139-5p | ucuacagugcacgugucuccag | 1.56 | 4.22 | 0.37 | 0.00 |
| SEQ ID NO: 793 | 791 | hsa-miR-200c* | cgucuuacccagcaguguuugg | 1.00 | 1.00 | 1.00 | 0.00 |
| SEQ ID NO: 646 | 792 | hsa-miR-302d* | acuuuaacauggaggcacuugc | 1.00 | 11.33 | 0.09 | 0.00 |
| SEQ ID NO: 537 | 793 | hsa-miR-431 | ugucuugcaggccgucaugca | 1.00 | 3.67 | 0.27 | 0.00 |
| SEQ ID NO: 638 | 794 | hsa-miR-499-5p | uuaagacuugcagugauguuu | 1.00 | 1.00 | 1.00 | 0.00 |
| SEQ ID NO: 802 | 795 | hsa-miR-526b* | gaaagugcuuccuuuuagaggc | 1.00 | 1.00 | 1.00 | 0.00 |
| SEQ ID NO: 776 | 796 | hsa-miR-614 | gaacgccuguucuugccaggugg | 9.11 | 4.22 | 2.16 | 0.00 |
| SEQ ID NO: 551 | 797 | hsa-miR-889 | uuaauaucggacaaccauugu | 1.00 | 1.00 | 1.00 | 0.00 |
| SEQ ID NO: 709 | 798 | hsa-miR-96 | uuuggcacuagcacauuuuugcu | 106.89 | 36.11 | 2.96 | 0.00 |
| SEQ ID NO: 842 | 799 | hsa-miR-193b* | cggggguuuugagggcgagauga | 81.11 | 108.56 | 0.75 | 0.00 |
| SEQ ID NO: 695 | 800 | hsa-miR-518c* | ucucuggagggaagcacuuucug | 109.67 | 63.61 | 1.72 | 0.00 |
| SEQ ID NO: 855 | 801 | hsa-miR-519a* | cucuagagggaagcgcuuucug | 1.00 | 4.44 | 0.23 | 0.00 |
| SEQ ID NO: 470 | 802 | hsa-miR-526a | cucuagagggaagcacuuucug | 27.00 | 56.22 | 0.48 | 0.00 |
| SEQ ID NO: 704 | 803 | hsa-miR-595 | gaagugugccguggugugucu | 12.00 | 11.33 | 1.06 | 0.00 |
| SEQ ID NO: 799 | 804 | hsa-miR-99a | aacccguagauccgaucuugug | 92.56 | 22.22 | 4.17 | 0.00 |

Figure 10A (cont'd)

| | | | | | | | |
|---|---|---|---|---|---|---|---|
| SEQ ID NO: 584 | 805 | hsa-miR-92a-2* | ggguggggauuuguugcauuac | 148.44 | 67.44 | 2.20 | 0.00 |
| SEQ ID NO: 804 | 806 | hsa-miR-181a | aacauucaacgcugucggugagu | 586.78 | 133.11 | 4.41 | 0.00 |
| SEQ ID NO: 800 | 807 | hsa-miR-146a | ugagaacugaauuccauggguu | 136.17 | 129.44 | 1.05 | 0.00 |
| SEQ ID NO: 851 | 808 | hsa-miR-105* | acggauguuugagcaugugcua | 2.67 | 1.00 | 2.67 | 0.00 |
| SEQ ID NO: 830 | 809 | hsa-miR-1279 | ucauauugcuucuuucu | 1.00 | 1.00 | 1.00 | 0.00 |
| SEQ ID NO: 845 | 810 | hsa-miR-154 | uagguuauccguguugccuucg | 1.00 | 1.00 | 1.00 | 0.00 |
| SEQ ID NO: 784 | 811 | hsa-miR-376c | aacauagaggaaauuccacgu | 1.00 | 1.00 | 1.00 | 0.00 |
| SEQ ID NO: 404 | 812 | hsa-miR-513b | uucacaaggaggugucauuuau | 91.17 | 72.22 | 1.26 | 0.00 |
| SEQ ID NO: 574 | 813 | hsa-miR-592 | uugugucaauaugcgaugaugu | 1.00 | 1.00 | 1.00 | 0.00 |
| SEQ ID NO: 705 | 814 | hsa-miR-1255b | cggaugagcaaagaaagugguu | 87.67 | 76.56 | 1.15 | 0.00 |
| SEQ ID NO: 825 | 815 | hsa-miR-526b | cucuugagggaagcacuuucugu | 67.78 | 33.78 | 2.01 | 0.00 |
| SEQ ID NO: 847 | 816 | hsa-miR-588 | uuggccacaauggguuagaac | 1.56 | 1.56 | 1.00 | 0.00 |
| SEQ ID NO: 743 | 817 | hsa-miR-1179 | aagcauucuuucauugguugg | 1.00 | 1.00 | 1.00 | 0.00 |
| SEQ ID NO: 833 | 818 | hsa-miR-1208 | ucacuguucagacaggcgga | 27.00 | 18.72 | 1.44 | 0.00 |
| SEQ ID NO: 626 | 819 | hsa-miR-1225-3p | ugagccccugugccgcccccag | 39.67 | 42.78 | 0.93 | 0.00 |
| SEQ ID NO: 729 | 820 | hsa-miR-1226* | gugagggcaugcaggccuggaugggg | 99.11 | 96.94 | 1.02 | 0.00 |
| SEQ ID NO: 790 | 821 | hsa-miR-1234 | ucggccugaccacccaccccac | 53.67 | 82.06 | 0.65 | 0.00 |
| SEQ ID NO: 831 | 822 | hsa-miR-1249 | acgcccuucccccccuucuuca | 24.56 | 30.22 | 0.81 | 0.00 |
| SEQ ID NO: 812 | 823 | hsa-miR-143 | ugagaugaagcacuguagcuc | 20.56 | 12.00 | 1.71 | 0.00 |
| SEQ ID NO: 856 | 824 | hsa-miR-181a-2* | accacugaccguugacuguacc | 115.33 | 67.44 | 1.71 | 0.00 |
| SEQ ID NO: 508 | 825 | hsa-miR-184 | uggacggagaacugauaagggu | 94.56 | 56.78 | 1.67 | 0.00 |
| SEQ ID NO: 765 | 826 | hsa-miR-196a | uagguaguuucauguuguuggg | 4.00 | 1.00 | 4.00 | 0.00 |
| SEQ ID NO: 857 | 827 | hsa-miR-199b-5p | cccaguguuuagacuaucuguuc | 4.00 | 1.00 | 4.00 | 0.00 |
| SEQ ID NO: 635 | 828 | hsa-miR-216a | uaaucucagcuggcaacuguga | 1.00 | 1.00 | 1.00 | 0.00 |
| SEQ ID NO: 858 | 829 | hsa-miR-27a | uucacaguggcuaaguuccgc | 150.56 | 55.22 | 2.73 | 0.00 |
| SEQ ID NO: 708 | 830 | hsa-miR-345 | gcugacuccuaguccagggcuc | 168.11 | 34.44 | 4.88 | 0.00 |
| SEQ ID NO: 813 | 831 | hsa-miR-362-3p | aacacaccuauucaaggauuca | 16.44 | 14.89 | 1.10 | 0.00 |
| SEQ ID NO: 673 | 832 | hsa-miR-507 | uuuugcaccuuuuggagugaa | 1.00 | 1.00 | 1.00 | 0.00 |
| SEQ ID NO: 841 | 833 | hsa-miR-517* | ccucuagauggaagcacugucu | 16.78 | 12.11 | 1.39 | 0.00 |
| SEQ ID NO: 859 | 834 | hsa-miR-518a-3p | gaaagcgcuucccuuugcugga | 1.00 | 1.00 | 1.00 | 0.00 |
| SEQ ID NO: 777 | 835 | hsa-miR-578 | cuucuugugcucuaggauugu | 1.00 | 1.00 | 1.00 | 0.00 |

Figure 10A (cont'd)

| | | | | | | | |
|---|---|---|---|---|---|---|---|
| SEQ ID NO: 726 | 836 | hsa-miR-601 | uggucuaggauuguuggaggag | 20.56 | 21.89 | 0.94 | 0.00 |
| SEQ ID NO: 429 | 837 | hsa-miR-615-5p | ggggguccccggugcucggauc | 34.00 | 12.11 | 2.81 | 0.00 |
| SEQ ID NO: 805 | 838 | hsa-miR-622 | acagucugcugagguuggagc | 6.78 | 3.11 | 2.18 | 0.00 |
| SEQ ID NO: 751 | 839 | hsa-miR-639 | aucgcugcgguugcgagcgcugu | 1.00 | 1.00 | 1.00 | 0.00 |
| SEQ ID NO: 721 | 840 | hsa-miR-886-3p | cgcgggugcuuacugacccuu | 12.33 | 1.00 | 12.33 | 0.00 |
| SEQ ID NO: 654 | 841 | hsa-miR-940 | aaggcagggcccccgcuccc | 112.44 | 67.44 | 1.67 | 0.00 |
| SEQ ID NO: 736 | 842 | hsa-miR-10b | uacccuguagaaccgaauuugug | 22.22 | 8.33 | 2.67 | 0.00 |
| SEQ ID NO: 744 | 843 | hsa-miR-1178 | uugcucacuguucuucccuag | 1.00 | 1.00 | 1.00 | 0.00 |
| SEQ ID NO: 794 | 844 | hsa-miR-1181 | ccgucgccgccacccgagccg | 21.11 | 28.00 | 0.75 | 0.00 |
| SEQ ID NO: 706 | 845 | hsa-miR-1252 | agaaggaaauugaauucauuua | 1.00 | 1.00 | 1.00 | 0.00 |
| SEQ ID NO: 727 | 846 | hsa-miR-1298 | uucauucggcuguccagaugua | 1.00 | 1.00 | 1.00 | 0.00 |
| SEQ ID NO: 803 | 847 | hsa-miR-148b* | aaguucuguuauacacucaggc | 1.00 | 1.00 | 1.00 | 0.00 |
| SEQ ID NO: 746 | 848 | hsa-miR-155* | cuccuacauauuagcauuaaca | 1.00 | 1.00 | 1.00 | 0.00 |
| SEQ ID NO: 679 | 849 | hsa-miR-24-1* | ugccuacugagcugauaucagu | 1.00 | 1.00 | 1.00 | 0.00 |
| SEQ ID NO: 862 | 850 | hsa-miR-29b-1* | gcugguuucauauggugguuuaga | 1.00 | 1.00 | 1.00 | 0.00 |
| SEQ ID NO: 604 | 851 | hsa-miR-496 | ugaguauuacauggccaaucuc | 15.33 | 4.44 | 3.45 | 0.00 |
| SEQ ID NO: 752 | 852 | hsa-miR-518d-3p | caaagcgcuucccuuuggagc | 1.00 | 1.00 | 1.00 | 0.00 |
| SEQ ID NO: 651 | 853 | hsa-miR-544 | auucugcauuuuuagcaaguuc | 1.00 | 1.00 | 1.00 | 0.00 |
| SEQ ID NO: 741 | 854 | hsa-miR-616* | acucaaaacccuucagugacuu | 1.00 | 1.56 | 0.64 | 0.00 |
| SEQ ID NO: 686 | 855 | hsa-miR-640 | augauccaggaaccugccucu | 4.00 | 4.44 | 0.90 | 0.00 |
| SEQ ID NO: 801 | 856 | hsa-miR-656 | aauauuauacagucaaccucu | 1.00 | 1.00 | 1.00 | 0.00 |
| SEQ ID NO: 764 | 857 | hsa-miR-7-1* | caacaaaucacagucugccaua | 15.78 | 28.33 | 0.56 | 0.00 |
| SEQ ID NO: 575 | 858 | hsa-miR-892a | cacuguguccuuucugcguag | 7.89 | 14.89 | 0.53 | 0.00 |
| SEQ ID NO: 612 | 859 | hsa-miR-95 | uucaacggguauuuauugagca | 1.00 | 1.00 | 1.00 | 0.00 |
| SEQ ID NO: 827 | 860 | hsa-miR-1250 | acggugcuggauguggccuuu | 37.67 | 40.78 | 0.92 | 0.00 |
| SEQ ID NO: 860 | 861 | hsa-miR-1265 | caggauguggucaaguguuguu | 6.78 | 1.56 | 4.36 | 0.00 |
| SEQ ID NO: 755 | 862 | hsa-miR-1306 | acguuggcucuggguggug | 6.78 | 4.22 | 1.61 | 0.00 |
| SEQ ID NO: 674 | 863 | hsa-miR-188-5p | caucccuugcaugguggaggg | 21.44 | 22.22 | 0.97 | 0.00 |
| SEQ ID NO: 659 | 864 | hsa-miR-519e* | uucuccaaaagggagcacuuuc | 17.11 | 19.78 | 0.87 | 0.00 |
| SEQ ID NO: 670 | 865 | hsa-miR-627 | gugagucucuaagaaaagagga | 1.00 | 1.00 | 1.00 | 0.00 |

Figure 10A (cont'd)

| SEQ ID NO | No. | microRNA | Sequence | Median Cancer | Median Normal | Fold Quotient | t-test significance |
|---|---|---|---|---|---|---|---|
| SEQ ID NO: 1 | 1 | hsa-miR-126 | ucguaccgugaguaauaaugcg | 606 | 3428 | 0.18 | 3.43E-05 |
| SEQ ID NO: 2 | 2 | hsa-miR-423-5p | ugaggggcagagagcgagacuuu | 6796 | 3977 | 1.71 | 9.78E-04 |
| SEQ ID NO: 3 | 3 | hsa-let-7i | ugagguaguaguuugugcuguu | 4106 | 6349 | 0.65 | 2.72E-03 |
| SEQ ID NO: 4 | 4 | hsa-let-7d | agagguaguagguugcauaguu | 6796 | 13308 | 0.51 | 2.72E-03 |
| SEQ ID NO: 5 | 5 | hsa-miR-22 | aagcugccaguugaagaacugu | 7979 | 3869 | 2.06 | 8.78E-03 |
| SEQ ID NO: 6 | 6 | hsa-miR-15a | uagcagcacauaaugguuugug | 3428 | 5945 | 0.58 | 8.78E-03 |
| SEQ ID NO: 7 | 7 | hsa-miR-98 | ugagguaguaaguuguauuguu | 322 | 1441 | 0.22 | 8.78E-03 |
| SEQ ID NO: 8 | 8 | hsa-miR-19a | ugugcaaaucuaugcaaaacuga | 420 | 1 | 420.06 | 1.52E-02 |
| SEQ ID NO: 9 | 9 | hsa-miR-574-5p | ugagugugugugugugagugugu | 109 | 30 | 3.59 | 1.52E-02 |
| SEQ ID NO: 10 | 10 | hsa-miR-324-3p | acugccccaggugcugcugg | 1222 | 701 | 1.74 | 1.52E-02 |
| SEQ ID NO: 11 | 11 | hsa-miR-20b | caaagugcucauagugcagguag | 1118 | 2948 | 0.38 | 1.52E-02 |
| SEQ ID NO: 12 | 12 | hsa-miR-25 | cauugcacuugucucggucuga | 12518 | 7640 | 1.64 | 1.83E-02 |
| SEQ ID NO: 13 | 13 | hsa-miR-195 | uagcagcacagaaauauuggc | 2576 | 4463 | 0.58 | 1.83E-02 |
| SEQ ID NO: 14 | 14 | hsa-let-7e | ugagguaggagguuguauaguu | 1298 | 2948 | 0.44 | 1.97E-02 |
| SEQ ID NO: 15 | 15 | hsa-let-7c | ugagguaguagguuguaugguu | 5660 | 8970 | 0.63 | 1.99E-02 |
| SEQ ID NO: 16 | 16 | hsa-let-7f | ugagguaguagauuguauaguu | 5382 | 9746 | 0.55 | 2.00E-02 |
| SEQ ID NO: 17 | 17 | hsa-let-7a | ugagguaguagguuguauaguu | 6796 | 12518 | 0.54 | 2.30E-02 |
| SEQ ID NO: 18 | 18 | hsa-let-7g | ugagguaguaguuuguacaguu | 3428 | 6796 | 0.50 | 2.36E-02 |
| SEQ ID NO: 19 | 19 | hsa-miR-140-3p | uaccacaggguagaaccacgg | 9313 | 4621 | 2.02 | 2.46E-02 |
| SEQ ID NO: 20 | 20 | hsa-miR-339-5p | ucccuguccuccaggagcucacg | 312 | 12 | 25.08 | 2.56E-02 |
| SEQ ID NO: 21 | 21 | hsa-miR-361-5p | uuaucagaaucuccagggguac | 606 | 53 | 11.44 | 3.08E-02 |
| SEQ ID NO: 22 | 22 | hsa-miR-1283 | ucuacaaaggaaagcgcuuucu | 2 | 22 | 0.11 | 3.71E-02 |
| SEQ ID NO: 23 | 23 | hsa-miR-18a* | acugcccuaagugcuccuucugg | 1040 | 120 | 8.68 | 4.39E-02 |
| SEQ ID NO: 24 | 24 | hsa-miR-26b | uucaaguaauucaggauaggu | 1065 | 2059 | 0.53 | 4.41E-02 |
| SEQ ID NO: 25 | 25 | hsa-miR-604 | aggcugcggaauucaggac | 245 | 91 | 2.70 | 4.80E-02 |
| SEQ ID NO: 26 | 26 | hsa-miR-423-3p | agcucggucugaggccccucagu | 1797 | 463 | 3.88 | 4.95E-02 |
| SEQ ID NO: 27 | 27 | hsa-miR-93* | acugcugagcuagcacuucccg | 480 | 30 | 15.78 | 4.95E-02 |
| SEQ ID NO: 28 | 28 | hsa-miR-29a | uagcaccaucugaaaucgguua | 447 | 109 | 4.12 | 6.80E-02 |
| SEQ ID NO: 29 | 29 | hsa-miR-1248 | accuucuuguauaagcacugugcuaaa | 154 | 31 | 4.92 | 7.60E-02 |

Figure 10B

| | | | | | | | |
|---|---|---|---|---|---|---|---|
| SEQ ID NO: 30 | 30 | hsa-miR-210 | cugugcgugugacagcggcuga | 413 | 59 | 7.01 | 7.61E-02 |
| SEQ ID NO: 31 | 31 | hsa-miR-19b | ugugcaaauccaugcaaaacuga | 3428 | 1853 | 1.85 | 7.61E-02 |
| SEQ ID NO: 32 | 32 | hsa-miR-453 | agguuguccguggugaguucgca | 7 | 57 | 0.12 | 9.14E-02 |
| SEQ ID NO: 33 | 33 | hsa-miR-126* | cauuauuacuuuugguacgcg | 1 | 34 | 0.03 | 9.30E-02 |
| SEQ ID NO: 34 | 34 | hsa-miR-188-3p | cucccacaugcaggguuugca | 1 | 4 | 0.23 | 9.30E-02 |
| SEQ ID NO: 35 | 35 | hsa-miR-624* | uaguaccaguaccuuguguuca | 1 | 28 | 0.04 | 9.30E-02 |
| SEQ ID NO: 36 | 36 | hsa-miR-505* | gggagccaggaaguauugaugu | 280 | 91 | 3.09 | 9.85E-02 |
| SEQ ID NO: 37 | 37 | hsa-miR-425 | aaugacacgaucacucccguuga | 11839 | 7392 | 1.60 | 9.85E-02 |
| SEQ ID NO: 38 | 38 | hsa-miR-339-3p | ugagcgccucgacgacagagccg | 210 | 110 | 1.91 | 9.85E-02 |
| SEQ ID NO: 39 | 39 | hsa-miR-668 | ugucacucggcucggcccacuac | 276 | 93 | 2.99 | 9.85E-02 |
| SEQ ID NO: 40 | 40 | hsa-miR-363* | cggguggaucacgaugcaauuu | 2426 | 724 | 3.35 | 9.85E-02 |
| SEQ ID NO: 41 | 41 | hsa-miR-15b* | cgaaucauuauuugcugcucua | 47 | 1 | 46.89 | 1.01E-01 |
| SEQ ID NO: 42 | 42 | hsa-miR-29c* | ugaccgauuucuccugguguuc | 61 | 1 | 61.11 | 1.05E-01 |
| SEQ ID NO: 43 | 43 | hsa-miR-550* | ugucuuacucccucaggcacau | 331 | 5 | 64.77 | 1.11E-01 |
| SEQ ID NO: 44 | 44 | hsa-miR-34c-3p | aaucacuaaccacacggccagg | 4 | 28 | 0.14 | 1.33E-01 |
| SEQ ID NO: 45 | 45 | hsa-miR-20a | uaaagugcuuauagugcagguag | 2320 | 4202 | 0.55 | 1.33E-01 |
| SEQ ID NO: 46 | 46 | hsa-miR-374a | uuauaauacaaccugauaagug | 225 | 693 | 0.32 | 1.36E-01 |
| SEQ ID NO: 47 | 47 | hsa-miR-145* | ggauuccuggaaauacuguucu | 1 | 1 | 1.00 | 1.38E-01 |
| SEQ ID NO: 48 | 48 | hsa-miR-302b | uaagugcuuccauguuuuaguag | 1 | 1 | 1.00 | 1.42E-01 |
| SEQ ID NO: 49 | 49 | hsa-miR-106a | aaaagugcuuacagugcagguag | 4463 | 6349 | 0.70 | 1.53E-01 |
| SEQ ID NO: 50 | 50 | hsa-miR-30e | uguaaacauccuugacuggaag | 370 | 129 | 2.86 | 1.65E-01 |
| SEQ ID NO: 51 | 51 | hsa-miR-223 | ugucaguuugucaaauacccca | 3080 | 5660 | 0.54 | 1.70E-01 |
| SEQ ID NO: 52 | 52 | hsa-miR-1269 | cuggacugagccgugcuacugg | 4 | 34 | 0.12 | 1.70E-01 |
| SEQ ID NO: 53 | 53 | hsa-let-7b | ugagguaguagguugugugguu | 6349 | 9746 | 0.65 | 1.71E-01 |
| SEQ ID NO: 54 | 54 | hsa-miR-542-3p | ugugacagauugauaacugaaa | 1 | 19 | 0.05 | 1.71E-01 |
| SEQ ID NO: 55 | 55 | hsa-miR-516b* | ugcuucccuuucagagggu | 10 | 31 | 0.30 | 1.71E-01 |
| SEQ ID NO: 56 | 56 | hsa-miR-451 | aaaccguuaccauuacugaguu | 1118 | 4106 | 0.27 | 1.72E-01 |
| SEQ ID NO: 57 | 57 | hsa-miR-519c-3p | aaagugcaucuuuuuagaggau | 1 | 12 | 0.08 | 1.72E-01 |
| SEQ ID NO: 58 | 58 | hsa-miR-1244 | aaguaguugguuuguaugagaugguu | 26 | 1 | 25.56 | 1.72E-01 |
| SEQ ID NO: 59 | 59 | hsa-miR-602 | gacacgggcgacagcugcggccc | 21 | 44 | 0.47 | 1.89E-01 |
| SEQ ID NO: 60 | 60 | hsa-miR-361-3p | ucccccaggugugauucugauuu | 367 | 256 | 1.43 | 1.90E-01 |

Figure 10B (cont'd)

| | | | | | | | |
|---|---|---|---|---|---|---|---|
| SEQ ID NO: 61 | 61 | hsa-miR-19a* | aguuuugcauaguugcacuaca | 1 | 1 | 1.00 | 1.91E-01 |
| SEQ ID NO: 62 | 62 | hsa-miR-433 | aucaugaugggcuccucggugu | 1 | 1 | 1.00 | 1.91E-01 |
| SEQ ID NO: 63 | 63 | hsa-miR-1200 | cuccugagccauucugagccuc | 1 | 5 | 0.20 | 2.02E-01 |
| SEQ ID NO: 64 | 64 | hsa-miR-522 | aaaaugguucccuuuagagugu | 1 | 8 | 0.12 | 2.02E-01 |
| SEQ ID NO: 65 | 65 | hsa-miR-520f | aagugcuuccuuuuagaggguu | 1 | 4 | 0.24 | 2.02E-01 |
| SEQ ID NO: 66 | 66 | hsa-miR-519c-5p | cucuagagggaagcgcuuucug | 2 | 14 | 0.11 | 2.02E-01 |
| SEQ ID NO: 67 | 67 | hsa-miR-192 | cugaccuaugaauugacagcc | 3080 | 1676 | 1.84 | 2.07E-01 |
| SEQ ID NO: 68 | 68 | hsa-miR-1245 | aagugaucuaaaggccuacau | 1 | 1 | 1.00 | 2.07E-01 |
| SEQ ID NO: 69 | 69 | hsa-miR-151-5p | ucgaggagcucacagucuagu | 1733 | 1025 | 1.69 | 2.10E-01 |
| SEQ ID NO: 70 | 70 | hsa-miR-1288 | uggacugcccugaucuggaga | 1 | 1 | 1.00 | 2.12E-01 |
| SEQ ID NO: 71 | 71 | hsa-miR-503 | uagcagcgggaacaguucugcag | 69 | 73 | 0.94 | 2.12E-01 |
| SEQ ID NO: 72 | 72 | hsa-miR-563 | agguugacauacguuuccc | 1 | 1 | 1.00 | 2.12E-01 |
| SEQ ID NO: 73 | 73 | hsa-miR-663b | gguggcccggccgugccugagg | 6 | 4 | 1.25 | 2.12E-01 |
| SEQ ID NO: 74 | 74 | hsa-let-7d* | cuauacgaccugcugccuuucu | 39 | 6 | 6.57 | 2.12E-01 |
| SEQ ID NO: 75 | 75 | hsa-miR-199a-5p | cccaguguucagacuaccuguuc | 145 | 36 | 4.02 | 2.12E-01 |
| SEQ ID NO: 76 | 76 | hsa-miR-720 | ucucgcuggggccucca | 190 | 62 | 3.08 | 2.12E-01 |
| SEQ ID NO: 77 | 77 | hsa-miR-1246 | aauggauuuuuggagcagg | 4916 | 3573 | 1.38 | 2.14E-01 |
| SEQ ID NO: 78 | 78 | hsa-miR-338-5p | aacaauauccuggugcugagug | 1 | 1 | 1.00 | 2.14E-01 |
| SEQ ID NO: 79 | 79 | hsa-miR-297 | auguaugugugcaugugcaug | 1 | 12 | 0.08 | 2.14E-01 |
| SEQ ID NO: 80 | 80 | hsa-miR-1261 | auggauaaggcuuuggcuu | 1 | 10 | 0.10 | 2.14E-01 |
| SEQ ID NO: 81 | 81 | hsa-miR-922 | gcagcagagaauaggacuacguc | 1 | 19 | 0.05 | 2.14E-01 |
| SEQ ID NO: 82 | 82 | hsa-miR-185 | uggagagaaaggcaguuccuga | 15422 | 13308 | 1.16 | 2.14E-01 |
| SEQ ID NO: 83 | 83 | hsa-miR-611 | gcgaggaccccucggggucugac | 30 | 18 | 1.68 | 2.14E-01 |
| SEQ ID NO: 84 | 84 | hsa-miR-1272 | gaugaugauggcagcaaauucugaaa | 1 | 1 | 1.00 | 2.14E-01 |
| SEQ ID NO: 85 | 85 | hsa-miR-1299 | uucuggaauucugugugaggga | 1 | 30 | 0.03 | 2.14E-01 |
| SEQ ID NO: 86 | 86 | hsa-miR-335* | uuuuucauuauugcuccugacc | 1 | 2 | 0.64 | 2.15E-01 |
| SEQ ID NO: 87 | 87 | hsa-miR-497 | cagcagcacacugugguuugu | 16 | 39 | 0.40 | 2.15E-01 |
| SEQ ID NO: 88 | 88 | hsa-miR-1207-3p | ucagcuggcccucauuuc | 1 | 18 | 0.06 | 2.23E-01 |
| SEQ ID NO: 89 | 89 | hsa-miR-16 | uagcagcacguaaauauuggcg | 20350 | 24784 | 0.82 | 2.23E-01 |
| SEQ ID NO: 90 | 90 | hsa-miR-1 | uggaauguaaagaaguauguau | 1 | 1 | 1.00 | 2.23E-01 |
| SEQ ID NO: 91 | 91 | hsa-miR-1291 | uggcccugacugaagaccagcagu | 30 | 1 | 30.44 | 2.23E-01 |

Figure 10B (cont'd)

| | | | | | | | |
|---|---|---|---|---|---|---|---|
| SEQ ID NO: 92 | 92 | hsa-miR-138-2* | gcuauuucacgacaccaggguu | 1 | 4 | 0.23 | 2.23E-01 |
| SEQ ID NO: 93 | 93 | hsa-miR-136 | acuccauuuguuuugaugaugga | 1 | 2 | 0.64 | 2.23E-01 |
| SEQ ID NO: 94 | 94 | hsa-miR-548d-3p | caaaaaccacaguuucuuuugc | 1 | 1 | 1.00 | 2.23E-01 |
| SEQ ID NO: 95 | 95 | hsa-miR-561 | caaaguuuaagauccuugaagu | 1 | 1 | 1.00 | 2.23E-01 |
| SEQ ID NO: 96 | 96 | hsa-miR-548h | aaaaguaaucgcgguuuuuguc | 1 | 1 | 1.00 | 2.23E-01 |
| SEQ ID NO: 97 | 97 | hsa-miR-331-3p | gccccugggccuauccuagaa | 724 | 404 | 1.79 | 2.23E-01 |
| SEQ ID NO: 98 | 98 | hsa-miR-186* | gcccaaaggugaauuuuuuggg | 1 | 1 | 1.00 | 2.30E-01 |
| SEQ ID NO: 99 | 99 | hsa-miR-145 | guccaguuuucccaggaaucccu | 572 | 101 | 5.66 | 2.30E-01 |
| SEQ ID NO: 100 | 100 | hsa-miR-17 | caaagugcuuacagugcagguag | 3977 | 5242 | 0.76 | 2.30E-01 |
| SEQ ID NO: 101 | 101 | hsa-miR-30b | uguaaacauccuacacucagcu | 5531 | 3304 | 1.67 | 2.39E-01 |
| SEQ ID NO: 102 | 102 | hsa-let-7f-1* | cuauacaaucuauugccuuccc | 1 | 1 | 1.00 | 2.50E-01 |
| SEQ ID NO: 103 | 103 | hsa-miR-1305 | uuuucaacucuaaugggagaga | 1 | 4 | 0.27 | 2.56E-01 |
| SEQ ID NO: 104 | 104 | hsa-miR-129-5p | cuuuuugcggucugggcuugc | 34 | 15 | 2.27 | 2.64E-01 |
| SEQ ID NO: 105 | 105 | hsa-miR-1204 | ucguggccuggucuccauuau | 1 | 4 | 0.23 | 2.66E-01 |
| SEQ ID NO: 106 | 106 | hsa-miR-106b* | ccgcacugugggguacuugcugc | 902 | 138 | 6.56 | 2.66E-01 |
| SEQ ID NO: 107 | 107 | hsa-miR-619 | gaccuggacauguuugugcccagu | 1 | 1 | 1.00 | 2.74E-01 |
| SEQ ID NO: 108 | 108 | hsa-miR-34a* | caaucagcaaguauacugcccu | 1 | 1 | 1.00 | 2.74E-01 |
| SEQ ID NO: 109 | 109 | hsa-miR-652 | aauggcgccacuaggguugug | 1388 | 962 | 1.44 | 2.78E-01 |
| SEQ ID NO: 110 | 110 | hsa-miR-1256 | aggcauugacuucucacuagcu | 1 | 1 | 1.00 | 2.78E-01 |
| SEQ ID NO: 111 | 111 | hsa-miR-20b* | acuguaguaugggcacuuccag | 1 | 4 | 0.23 | 2.78E-01 |
| SEQ ID NO: 112 | 112 | hsa-miR-424* | caaaacgugaggcgcugcuau | 34 | 46 | 0.74 | 2.78E-01 |
| SEQ ID NO: 113 | 113 | hsa-miR-517a | aucgugcaucccuuuagagugu | 1 | 1 | 1.00 | 2.78E-01 |
| SEQ ID NO: 114 | 114 | hsa-miR-1284 | ucuauacagacccuggcuuuuc | 1 | 12 | 0.09 | 2.78E-01 |
| SEQ ID NO: 115 | 115 | hsa-miR-199b-3p | acaguagucugcacauugguua | 1 | 12 | 0.09 | 2.78E-01 |
| SEQ ID NO: 116 | 116 | hsa-miR-599 | guugugucaguuuaucaaac | 1 | 1 | 1.00 | 2.85E-01 |
| SEQ ID NO: 117 | 117 | hsa-miR-411 | uaguagaccguauagcguacg | 1 | 1 | 1.00 | 2.89E-01 |
| SEQ ID NO: 118 | 118 | hsa-miR-23b | aucacauugccagggauuacc | 3977 | 2099 | 1.89 | 2.91E-01 |
| SEQ ID NO: 119 | 119 | hsa-miR-1302 | uugggacauacuuaugcuaaa | 1 | 1 | 1.00 | 2.91E-01 |
| SEQ ID NO: 120 | 120 | hsa-miR-449a | uggcaguguauuguuagcuggu | 1 | 1 | 1.00 | 2.91E-01 |
| SEQ ID NO: 121 | 121 | hsa-miR-548l | aaaaacuguaauuacuuuu | 1 | 1 | 1.00 | 2.91E-01 |
| SEQ ID NO: 122 | 122 | hsa-miR-597 | ugugucacucgaugaccacugu | 1 | 1 | 1.00 | 2.91E-01 |

Figure 10B (cont'd)

| | | | | | | | |
|---|---|---|---|---|---|---|---|
| SEQ ID NO: 123 | 123 | hsa-miR-603 | cacacacugcaauuacuuuugc | 1 | 2 | 0.64 | 2.91E-01 |
| SEQ ID NO: 124 | 124 | hsa-miR-1247 | acccgucccguucguccccgga | 10 | 16 | 0.59 | 2.91E-01 |
| SEQ ID NO: 125 | 125 | hsa-miR-1539 | uccugcgcgucccagaugccc | 5 | 21 | 0.25 | 2.91E-01 |
| SEQ ID NO: 126 | 126 | hsa-miR-1911 | ugaguaccgccaugucuguuggg | 1 | 2 | 0.64 | 2.91E-01 |
| SEQ ID NO: 127 | 127 | hsa-miR-325 | ccuaguagguguccaguaagugu | 1 | 15 | 0.07 | 2.91E-01 |
| SEQ ID NO: 128 | 128 | hsa-miR-409-5p | agguuacccgagcaacuuugcau | 1 | 1 | 1.00 | 2.91E-01 |
| SEQ ID NO: 129 | 129 | hsa-miR-182 | uuuggcaaugguagaacucacacu | 7640 | 5074 | 1.51 | 2.91E-01 |
| SEQ ID NO: 130 | 130 | hsa-miR-658 | ggcggagggaaguagguccguuggu | 2426 | 1118 | 2.17 | 2.93E-01 |
| SEQ ID NO: 131 | 131 | hsa-miR-215 | augaccuaugaauugacagac | 1085 | 463 | 2.34 | 2.98E-01 |
| SEQ ID NO: 132 | 132 | hsa-miR-147b | gugugcggaaaugcuucugcua | 1 | 1 | 1.00 | 2.98E-01 |
| SEQ ID NO: 133 | 133 | hsa-miR-30d | uguaaacauccccgacuggaag | 6349 | 4319 | 1.47 | 2.98E-01 |
| SEQ ID NO: 134 | 134 | hsa-miR-378* | cuccugacuccagguccugugu | 112 | 28 | 3.99 | 2.98E-01 |
| SEQ ID NO: 135 | 135 | hsa-miR-221* | accuggcauacaauguagauuu | 1 | 1 | 1.00 | 2.98E-01 |
| SEQ ID NO: 136 | 136 | hsa-miR-34b | caaucacuaacuccacugccau | 3 | 20 | 0.13 | 2.98E-01 |
| SEQ ID NO: 137 | 137 | hsa-miR-593* | aggcaccagccaggcauugcucagc | 1 | 12 | 0.08 | 2.98E-01 |
| SEQ ID NO: 138 | 138 | hsa-miR-552 | aacaggugacugguuagacaa | 4 | 22 | 0.18 | 2.98E-01 |
| SEQ ID NO: 139 | 139 | hsa-miR-378 | acuggacuuggagucagaagg | 284 | 22 | 13.19 | 2.99E-01 |
| SEQ ID NO: 140 | 140 | hsa-miR-143* | ggugcagugcugcaucucuggu | 1 | 1 | 1.00 | 2.99E-01 |
| SEQ ID NO: 141 | 141 | hsa-miR-1266 | ccucagggcuguagaacagggcu | 17 | 30 | 0.57 | 2.99E-01 |
| SEQ ID NO: 142 | 142 | hsa-miR-554 | gcuaguccugacucagccagu | 1 | 1 | 1.00 | 2.99E-01 |
| SEQ ID NO: 143 | 143 | hsa-miR-631 | agaccuggcccagaccucagc | 3 | 14 | 0.19 | 2.99E-01 |
| SEQ ID NO: 144 | 144 | hsa-miR-609 | aggguguuucucucaucucu | 1 | 1 | 1.00 | 2.99E-01 |
| SEQ ID NO: 145 | 145 | hsa-miR-30c | uguaaacauccuacacucucagc | 8970 | 4779 | 1.88 | 2.99E-01 |
| SEQ ID NO: 146 | 146 | hsa-miR-28-5p | aaggagcucacagucuauugag | 454 | 109 | 4.18 | 3.02E-01 |
| SEQ ID NO: 147 | 147 | hsa-miR-23a | aucacauugccagggauuucc | 3428 | 1797 | 1.91 | 3.02E-01 |
| SEQ ID NO: 148 | 148 | hsa-miR-645 | ucuaggcugguacugcuga | 1 | 1 | 1.00 | 3.02E-01 |
| SEQ ID NO: 149 | 149 | hsa-miR-647 | guggcugcacucacuuccuuc | 1 | 1 | 1.00 | 3.02E-01 |
| SEQ ID NO: 150 | 150 | hsa-miR-302b* | acuuuaacauggaagugcuuuc | 1 | 1 | 1.00 | 3.02E-01 |
| SEQ ID NO: 151 | 151 | hsa-miR-607 | guucaaauccagaucuauaac | 1 | 1 | 1.00 | 3.02E-01 |
| SEQ ID NO: 152 | 152 | hsa-miR-1289 | uggaguccaggaaucugcauuuu | 1 | 4 | 0.23 | 3.02E-01 |
| SEQ ID NO: 153 | 153 | hsa-miR-1324 | ccagacagaauucuaugcacuuuc | 1 | 1 | 1.00 | 3.02E-01 |

Figure 10B (cont'd)

| | | | | | | | |
|---|---|---|---|---|---|---|---|
| SEQ ID NO: 154 | 154 | hsa-miR-513a-3p | uaaauuucaccuuucugagaagg | 1 | 1 | 1.00 | 3.02E-01 |
| SEQ ID NO: 155 | 155 | hsa-miR-939 | uggggagcugaggcucugggggug | 203 | 59 | 3.46 | 3.02E-01 |
| SEQ ID NO: 156 | 156 | hsa-miR-29b | uagcaccauuugaaaucaguguu | 338 | 82 | 4.12 | 3.03E-01 |
| SEQ ID NO: 157 | 157 | hsa-miR-665 | accaggaggcugaggccccu | 212 | 191 | 1.11 | 3.03E-01 |
| SEQ ID NO: 158 | 158 | hsa-miR-18a | uaaggugcaucuagugcagauag | 144 | 59 | 2.44 | 3.03E-01 |
| SEQ ID NO: 159 | 159 | hsa-miR-1224-5p | gugaggacucgggaggugg | 587 | 388 | 1.51 | 3.03E-01 |
| SEQ ID NO: 160 | 160 | hsa-miR-10a* | caaauucguaucuaggggaaua | 1 | 4 | 0.23 | 3.03E-01 |
| SEQ ID NO: 161 | 161 | hsa-miR-181a* | accaucgaccguugauuguacc | 1 | 1 | 1.00 | 3.03E-01 |
| SEQ ID NO: 162 | 162 | hsa-miR-218-2* | caugguucugucaagcaccgcg | 1 | 1 | 1.00 | 3.03E-01 |
| SEQ ID NO: 163 | 163 | hsa-miR-371-3p | aagugccgccaucuuuugagugu | 1 | 1 | 1.00 | 3.03E-01 |
| SEQ ID NO: 164 | 164 | hsa-miR-377 | aucacacaaaggcaacuuuugu | 1 | 1 | 1.00 | 3.03E-01 |
| SEQ ID NO: 165 | 165 | hsa-miR-140-5p | cagugguuuuacccuaugguag | 1 | 1 | 1.00 | 3.03E-01 |
| SEQ ID NO: 166 | 166 | hsa-miR-301a | cagugcaauaguauugucaaagc | 17 | 22 | 0.78 | 3.03E-01 |
| SEQ ID NO: 167 | 167 | hsa-miR-1277 | uacguagauauauauguauuuu | 1 | 1 | 1.00 | 3.03E-01 |
| SEQ ID NO: 168 | 168 | hsa-miR-130a* | uucacauugugcuacugucugc | 1 | 1 | 1.00 | 3.03E-01 |
| SEQ ID NO: 169 | 169 | hsa-miR-1912 | uacccagagcaugcagugugaa | 1 | 2 | 0.64 | 3.03E-01 |
| SEQ ID NO: 170 | 170 | hsa-miR-193b | aacuggcccucaaagucccgcu | 1 | 2 | 0.64 | 3.03E-01 |
| SEQ ID NO: 171 | 171 | hsa-miR-214* | ugccugucuacacuugcugugc | 1 | 1 | 1.00 | 3.03E-01 |
| SEQ ID NO: 172 | 172 | hsa-miR-216b | aaaucucugcaggcaaauguga | 1 | 1 | 1.00 | 3.03E-01 |
| SEQ ID NO: 173 | 173 | hsa-miR-302f | uaauugcuuccauguuu | 1 | 1 | 1.00 | 3.03E-01 |
| SEQ ID NO: 174 | 174 | hsa-miR-522* | cucuagagggaagcgcuuucug | 4 | 12 | 0.33 | 3.03E-01 |
| SEQ ID NO: 175 | 175 | hsa-miR-548j | aaaaguaauugcggucuuuggu | 1 | 1 | 1.00 | 3.03E-01 |
| SEQ ID NO: 176 | 176 | hsa-miR-568 | auguauaaauguauacacac | 1 | 1 | 1.00 | 3.03E-01 |
| SEQ ID NO: 177 | 177 | hsa-miR-648 | aagugugcagggcacuggu | 1 | 1 | 1.00 | 3.03E-01 |
| SEQ ID NO: 178 | 178 | hsa-miR-662 | ucccacguuguggcccagcag | 1 | 3 | 0.32 | 3.03E-01 |
| SEQ ID NO: 179 | 179 | hsa-miR-222 | agcuacaucuggcuacugggu | 321 | 1 | 320.78 | 3.03E-01 |
| SEQ ID NO: 180 | 180 | hsa-miR-1287 | ugcuggaucagugguucgaguc | 1 | 12 | 0.08 | 3.03E-01 |
| SEQ ID NO: 181 | 181 | hsa-miR-891b | ugcaacuuaccugagucauuga | 1 | 1 | 1.00 | 3.03E-01 |
| SEQ ID NO: 182 | 182 | hsa-miR-342-3p | ucucacacagaaaucgcacccgu | 3428 | 2320 | 1.48 | 3.03E-01 |
| SEQ ID NO: 183 | 183 | hsa-miR-512-3p | aagugcugucauagcugagguc | 1 | 1 | 1.00 | 3.03E-01 |
| SEQ ID NO: 184 | 184 | hsa-miR-623 | aucccuugcaggggcuguugggu | 1 | 1 | 1.00 | 3.03E-01 |

Figure 10B (cont'd)

| | | | | | | | |
|---|---|---|---|---|---|---|---|
| SEQ ID NO: 185 | 185 | hsa-miR-208b | auaagacgaacaaaagguuugu | 7 | 1 | 6.78 | 3.03E-01 |
| SEQ ID NO: 186 | 186 | hsa-miR-16-1* | ccaguauuaacugugcugcuga | 1 | 2 | 0.64 | 3.06E-01 |
| SEQ ID NO: 187 | 187 | hsa-miR-551b | gcgacccauacuugguuucag | 1 | 1 | 1.00 | 3.08E-01 |
| SEQ ID NO: 188 | 188 | hsa-miR-146b-3p | ugcccuguggacucaguucugg | 1 | 1 | 1.00 | 3.08E-01 |
| SEQ ID NO: 189 | 189 | hsa-miR-520b | aaagugcuuccuuuuagaggg | 1 | 1 | 1.00 | 3.09E-01 |
| SEQ ID NO: 190 | 190 | hsa-miR-449b | aggcaguguauuguuagcuggc | 1 | 1 | 1.00 | 3.11E-01 |
| SEQ ID NO: 191 | 191 | hsa-miR-520g | acaaagugcuucccuuuagagugu | 1 | 1 | 1.00 | 3.12E-01 |
| SEQ ID NO: 192 | 192 | hsa-miR-24-2* | ugccuacugagcugaaacacag | 1 | 1 | 1.00 | 3.14E-01 |
| SEQ ID NO: 193 | 193 | hsa-miR-518f | gaaagcgcuucucuuuagagg | 1 | 1 | 1.00 | 3.16E-01 |
| SEQ ID NO: 194 | 194 | hsa-miR-649 | aaaccuguguuguucaagaguc | 1 | 1 | 1.00 | 3.18E-01 |
| SEQ ID NO: 195 | 195 | hsa-miR-32 | uauugcacauuacuaaguugca | 1 | 4 | 0.27 | 3.18E-01 |
| SEQ ID NO: 196 | 196 | hsa-miR-151-3p | cuagacugaagcuccuugagg | 345 | 91 | 3.80 | 3.19E-01 |
| SEQ ID NO: 197 | 197 | hsa-miR-454 | uagugcaauauugcuuauagggu | 90 | 27 | 3.41 | 3.19E-01 |
| SEQ ID NO: 198 | 198 | hsa-miR-101 | uacaguacugugauaacugaa | 95 | 139 | 0.68 | 3.19E-01 |
| SEQ ID NO: 199 | 199 | hsa-miR-19b-1* | aguuuugcagguuugcauccagc | 1 | 1 | 1.00 | 3.19E-01 |
| SEQ ID NO: 200 | 200 | hsa-miR-509-5p | uacugcagacaguggcaauca | 1 | 1 | 1.00 | 3.19E-01 |
| SEQ ID NO: 201 | 201 | hsa-miR-144 | uacaguauagaugauguacu | 41 | 82 | 0.50 | 3.19E-01 |
| SEQ ID NO: 202 | 202 | hsa-miR-508-5p | uacuccagagggcgucacucaug | 23 | 31 | 0.72 | 3.19E-01 |
| SEQ ID NO: 203 | 203 | hsa-miR-569 | aguuaaugaauccuggaaagu | 1 | 1 | 1.00 | 3.19E-01 |
| SEQ ID NO: 204 | 204 | hsa-miR-636 | ugugcuugcucgucccgcccgca | 47 | 49 | 0.95 | 3.19E-01 |
| SEQ ID NO: 205 | 205 | hsa-miR-937 | auccgcgcucugacucucugcc | 4 | 10 | 0.38 | 3.19E-01 |
| SEQ ID NO: 206 | 206 | hsa-miR-346 | ugucugcccgcaugccugccucu | 1 | 1 | 1.00 | 3.19E-01 |
| SEQ ID NO: 207 | 207 | hsa-miR-506 | uaaggcacccuucugaguaga | 1 | 1 | 1.00 | 3.19E-01 |
| SEQ ID NO: 208 | 208 | hsa-miR-379* | uauguaacaugguccacuaacu | 1 | 2 | 0.64 | 3.19E-01 |
| SEQ ID NO: 209 | 209 | hsa-miR-1184 | ccugcagcgacuugauggcuucc | 1 | 1 | 1.00 | 3.19E-01 |
| SEQ ID NO: 210 | 210 | hsa-miR-579 | uucauuugguauaaaccgcgauu | 1 | 1 | 1.00 | 3.19E-01 |
| SEQ ID NO: 211 | 211 | hsa-miR-23b* | uggguuccuggcaugcugauuu | 1 | 1 | 1.00 | 3.21E-01 |
| SEQ ID NO: 212 | 212 | hsa-miR-1262 | augggugaauuuguagaaggau | 1 | 11 | 0.09 | 3.21E-01 |
| SEQ ID NO: 213 | 213 | hsa-miR-153 | uugcauagucacaaaagugauc | 1 | 1 | 1.00 | 3.21E-01 |
| SEQ ID NO: 214 | 214 | hsa-miR-520e | aaagugcuuccuuuuugaggg | 1 | 1 | 1.00 | 3.21E-01 |
| SEQ ID NO: 215 | 215 | hsa-miR-632 | gugucugcuuccugugga | 3 | 4 | 0.60 | 3.21E-01 |

Figure 10B (cont'd)

| | | | | | | | |
|---|---|---|---|---|---|---|---|
| SEQ ID NO: 216 | 216 | hsa-miR-106a* | cugcaauguaagcacuucuuac | 1 | 4 | 0.23 | 3.21E-01 |
| SEQ ID NO: 217 | 217 | hsa-miR-31* | ugcuaugccaacauauugccau | 1 | 1 | 1.00 | 3.21E-01 |
| SEQ ID NO: 218 | 218 | hsa-miR-33b* | cagugccucggcagugcagccc | 1 | 1 | 1.00 | 3.21E-01 |
| SEQ ID NO: 219 | 219 | hsa-miR-654-3p | uaugucugcugaccaucaccuu | 1 | 1 | 1.00 | 3.21E-01 |
| SEQ ID NO: 220 | 220 | hsa-miR-99b* | caagcucgugucuguggguccg | 1 | 1 | 1.00 | 3.23E-01 |
| SEQ ID NO: 221 | 221 | hsa-miR-1278 | uaguacugugcauaucaucuau | 1 | 1 | 1.00 | 3.24E-01 |
| SEQ ID NO: 222 | 222 | hsa-miR-135b | uauggcuuuucauuccuaugugaa | 1 | 1 | 1.00 | 3.24E-01 |
| SEQ ID NO: 223 | 223 | hsa-let-7c* | uagaguuacacccugggaguua | 1 | 1 | 1.00 | 3.24E-01 |
| SEQ ID NO: 224 | 224 | hsa-miR-1468 | cuccguuugccuguuucgcug | 1 | 4 | 0.24 | 3.24E-01 |
| SEQ ID NO: 225 | 225 | hsa-miR-374b* | cuuagcagguuguauuaucauu | 1 | 1 | 1.00 | 3.24E-01 |
| SEQ ID NO: 226 | 226 | hsa-miR-514 | auugacacuucugugaguaga | 1 | 1 | 1.00 | 3.24E-01 |
| SEQ ID NO: 227 | 227 | hsa-miR-590-3p | uaauuuuauguauaagcuagu | 1 | 1 | 1.00 | 3.24E-01 |
| SEQ ID NO: 228 | 228 | hsa-miR-606 | aaacuacugaaaaucaaagau | 1 | 1 | 1.00 | 3.24E-01 |
| SEQ ID NO: 229 | 229 | hsa-miR-369-3p | aauaauacaugguugaucuuu | 1 | 1 | 1.00 | 3.24E-01 |
| SEQ ID NO: 230 | 230 | hsa-miR-488 | uugaaaggcuauuucuugguc | 1 | 1 | 1.00 | 3.24E-01 |
| SEQ ID NO: 231 | 231 | hsa-miR-128 | ucacagugaaccggucucuuu | 774 | 22 | 35.91 | 3.24E-01 |
| SEQ ID NO: 232 | 232 | hsa-miR-362-5p | aauccuuggaaccuaggugugagu | 260 | 15 | 17.48 | 3.24E-01 |
| SEQ ID NO: 233 | 233 | hsa-miR-671-5p | aggaagcccuggaggggcuggag | 272 | 168 | 1.62 | 3.24E-01 |
| SEQ ID NO: 234 | 234 | hsa-miR-874 | cugcccuggcccgagggaccga | 34 | 36 | 0.95 | 3.27E-01 |
| SEQ ID NO: 235 | 235 | hsa-miR-1911* | caccaggcauugugguucucc | 1 | 1 | 1.00 | 3.27E-01 |
| SEQ ID NO: 236 | 236 | hsa-miR-1292 | ugggaacggguuccggcagacgcug | 252 | 159 | 1.59 | 3.28E-01 |
| SEQ ID NO: 237 | 237 | hsa-miR-194 | uguaacagcaacuccaugugga | 1853 | 1441 | 1.29 | 3.29E-01 |
| SEQ ID NO: 238 | 238 | hsa-miR-15b | uagcagcacaucaugguuuaca | 20350 | 23735 | 0.86 | 3.29E-01 |
| SEQ ID NO: 239 | 239 | hsa-miR-342-5p | aggggugcuaucugugauuga | 82 | 73 | 1.12 | 3.29E-01 |
| SEQ ID NO: 240 | 240 | hsa-miR-125b-2* | ucacaagucaggcucuugggac | 1 | 4 | 0.27 | 3.29E-01 |
| SEQ ID NO: 241 | 241 | hsa-miR-1297 | uucaaguaauucaggug | 1 | 1 | 1.00 | 3.29E-01 |
| SEQ ID NO: 242 | 242 | hsa-miR-933 | ugugcgcagggagaccucuccc | 18 | 28 | 0.64 | 3.29E-01 |
| SEQ ID NO: 243 | 243 | hsa-miR-493* | uuguacaugguaggcuuucauu | 2 | 3 | 0.50 | 3.29E-01 |
| SEQ ID NO: 244 | 244 | hsa-miR-105 | ucaaaugcucagacuccugugggu | 1 | 1 | 1.00 | 3.29E-01 |
| SEQ ID NO: 245 | 245 | hsa-miR-141 | uaacacugucugguaaagaugg | 1 | 1 | 1.00 | 3.29E-01 |
| SEQ ID NO: 246 | 246 | hsa-miR-181c* | aaccaucgaccguugaguggac | 1 | 1 | 1.00 | 3.29E-01 |

Figure 10B (cont'd)

| | | | | | | | |
|---|---|---|---|---|---|---|---|
| SEQ ID NO: 247 | 247 | hsa-miR-193a-3p | aacuggccuacaaagucccagu | 21 | 21 | 0.99 | 3.29E-01 |
| SEQ ID NO: 248 | 248 | hsa-miR-302c | uaagugcuuccauguuucagugg | 1 | 1 | 1.00 | 3.29E-01 |
| SEQ ID NO: 249 | 249 | hsa-miR-485-5p | agaggcuggccgugaugaauuc | 40 | 51 | 0.78 | 3.29E-01 |
| SEQ ID NO: 250 | 250 | hsa-miR-499-3p | aacaucacagcaagucugugcu | 1 | 1 | 1.00 | 3.29E-01 |
| SEQ ID NO: 251 | 251 | hsa-miR-545 | ucagcaaacauuuauugugugc | 1 | 1 | 1.00 | 3.29E-01 |
| SEQ ID NO: 252 | 252 | hsa-miR-548b-5p | aaaaguaauuguggpuuuuggcc | 1 | 1 | 1.00 | 3.29E-01 |
| SEQ ID NO: 253 | 253 | hsa-miR-549 | ugacaacuauggaugagcucu | 1 | 1 | 1.00 | 3.29E-01 |
| SEQ ID NO: 254 | 254 | hsa-miR-576-5p | auucuaauuucuccacgucuuu | 1 | 4 | 0.24 | 3.29E-01 |
| SEQ ID NO: 255 | 255 | hsa-miR-577 | uagauaaaauauugguaccug | 1 | 1 | 1.00 | 3.29E-01 |
| SEQ ID NO: 256 | 256 | hsa-miR-583 | caaagaggaaggucccauuac | 50 | 55 | 0.90 | 3.29E-01 |
| SEQ ID NO: 257 | 257 | hsa-miR-587 | uuuccauaggugaugagucac | 1 | 2 | 0.64 | 3.29E-01 |
| SEQ ID NO: 258 | 258 | hsa-miR-624 | cacaagguauugguauuaccu | 1 | 1 | 1.00 | 3.29E-01 |
| SEQ ID NO: 259 | 259 | hsa-miR-646 | aagcagcugccucugaggc | 1 | 1 | 1.00 | 3.29E-01 |
| SEQ ID NO: 260 | 260 | hsa-miR-655 | auaauacaugguuaaccucuuu | 1 | 1 | 1.00 | 3.29E-01 |
| SEQ ID NO: 261 | 261 | hsa-miR-885-5p | uccauuacacuacccugccucu | 6 | 28 | 0.20 | 3.29E-01 |
| SEQ ID NO: 262 | 262 | hsa-miR-194* | ccaguggggcugcuguuaucug | 7 | 5 | 1.33 | 3.29E-01 |
| SEQ ID NO: 263 | 263 | hsa-miR-299-5p | ugguuuaccgucccacauacau | 1 | 1 | 1.00 | 3.29E-01 |
| SEQ ID NO: 264 | 264 | hsa-miR-337-3p | cuccuauaugaugccuuucuuc | 1 | 4 | 0.23 | 3.29E-01 |
| SEQ ID NO: 265 | 265 | hsa-miR-493 | ugaaggucuacugugugccagg | 1 | 1 | 1.00 | 3.29E-01 |
| SEQ ID NO: 266 | 266 | hsa-miR-497* | caaaccacacugugguguuaga | 1 | 1 | 1.00 | 3.29E-01 |
| SEQ ID NO: 267 | 267 | hsa-miR-519a | aaagugcauccuuuuagagugu | 1 | 1 | 1.00 | 3.29E-01 |
| SEQ ID NO: 268 | 268 | hsa-miR-99a* | caagcucgcuucuaugggucug | 1 | 1 | 1.00 | 3.29E-01 |
| SEQ ID NO: 269 | 269 | hsa-miR-1280 | ucccaccgcugccaccc | 237 | 159 | 1.49 | 3.29E-01 |
| SEQ ID NO: 270 | 270 | hsa-miR-523* | cucuagagggaagcgcuuucug | 7 | 19 | 0.36 | 3.29E-01 |
| SEQ ID NO: 271 | 271 | hsa-miR-198 | gguccagaggggagauagguuc | 428 | 382 | 1.12 | 3.29E-01 |
| SEQ ID NO: 272 | 272 | hsa-miR-934 | ugucuacuacuggagacacugg | 1 | 1 | 1.00 | 3.29E-01 |
| SEQ ID NO: 273 | 273 | hsa-miR-30d* | cuuucagucagauguuugcugc | 1 | 1 | 1.00 | 3.31E-01 |
| SEQ ID NO: 274 | 274 | hsa-miR-452* | cucaucugcaaagaaguaagug | 1 | 1 | 1.00 | 3.31E-01 |
| SEQ ID NO: 275 | 275 | hsa-miR-548b-3p | caagaaccucaguugcuuuugu | 1 | 1 | 1.00 | 3.31E-01 |
| SEQ ID NO: 276 | 276 | hsa-miR-586 | uaugcauuguauuuuuaggucc | 1 | 1 | 1.00 | 3.31E-01 |
| SEQ ID NO: 277 | 277 | hsa-miR-92b | uauugcacucgucccggccucc | 4260 | 5531 | 0.77 | 3.31E-01 |

Figure 10B (cont'd)

| | | | | | | | |
|---|---|---|---|---|---|---|---|
| SEQ ID NO: 278 | 278 | hsa-miR-517b | ucgugcaucccuuuagaguguu | 1 | 1 | 1.00 | 3.31E-01 |
| SEQ ID NO: 279 | 279 | hsa-miR-548a-3p | caaaacuggcaauuacuuuugc | 1 | 1 | 1.00 | 3.31E-01 |
| SEQ ID NO: 280 | 280 | hsa-miR-875-5p | uauaccucaguuuuaucaggug | 1 | 1 | 1.00 | 3.35E-01 |
| SEQ ID NO: 281 | 281 | hsa-miR-431* | caggucgucuugcagggcuucu | 1 | 1 | 1.00 | 3.36E-01 |
| SEQ ID NO: 282 | 282 | hsa-miR-384 | auuccuagaaauuguucaua | 1 | 1 | 1.00 | 3.36E-01 |
| SEQ ID NO: 283 | 283 | hsa-miR-644 | aguguggcuuucuuagagc | 1 | 1 | 1.00 | 3.38E-01 |
| SEQ ID NO: 284 | 284 | hsa-miR-1185 | agaggauacccuuuguauguu | 1 | 1 | 1.00 | 3.41E-01 |
| SEQ ID NO: 285 | 285 | hsa-miR-29b-2* | cugguuucacaugguggcuuag | 34 | 47 | 0.73 | 3.41E-01 |
| SEQ ID NO: 286 | 286 | hsa-miR-489 | gugacaucacauauacggcagc | 1 | 1 | 1.00 | 3.41E-01 |
| SEQ ID NO: 287 | 287 | hsa-miR-566 | gggcgccugugaucccaac | 1 | 1 | 1.00 | 3.41E-01 |
| SEQ ID NO: 288 | 288 | hsa-miR-1538 | cggcccgggcugcugcuguuccu | 48 | 19 | 2.56 | 3.41E-01 |
| SEQ ID NO: 289 | 289 | hsa-miR-26-3p | cacuagauugugagcuccugga | 29 | 21 | 1.38 | 3.43E-01 |
| SEQ ID NO: 290 | 290 | hsa-let-7f-2* | cuauacagucuacugucuuucc | 1 | 1 | 1.00 | 3.43E-01 |
| SEQ ID NO: 291 | 291 | hsa-miR-1322 | gaugaugcugcugaugcug | 2 | 7 | 0.24 | 3.43E-01 |
| SEQ ID NO: 292 | 292 | hsa-miR-1827 | ugaggcaguagauugaau | 10 | 4 | 2.15 | 3.43E-01 |
| SEQ ID NO: 293 | 293 | hsa-miR-192* | cugccaauuccauaggucacag | 1 | 1 | 1.00 | 3.43E-01 |
| SEQ ID NO: 294 | 294 | hsa-miR-302e | uaagugcuuccaugcuu | 1 | 1 | 1.00 | 3.43E-01 |
| SEQ ID NO: 295 | 295 | hsa-miR-411* | uauguaacacgguccacuaacc | 1 | 2 | 0.64 | 3.43E-01 |
| SEQ ID NO: 296 | 296 | hsa-miR-424 | cagcagcaauucauguuuugaa | 53 | 41 | 1.30 | 3.43E-01 |
| SEQ ID NO: 297 | 297 | hsa-miR-582-3p | uaacugguugaacaacugaacc | 4 | 4 | 0.95 | 3.43E-01 |
| SEQ ID NO: 298 | 298 | hsa-miR-629* | guucucccaacguaagcccagc | 32 | 34 | 0.94 | 3.43E-01 |
| SEQ ID NO: 299 | 299 | hsa-miR-491-3p | cuuaugcaagauucccuucuac | 1 | 1 | 1.00 | 3.43E-01 |
| SEQ ID NO: 300 | 300 | hsa-miR-519b-3p | aaagugcauccuuuuagagguu | 1 | 1 | 1.00 | 3.43E-01 |
| SEQ ID NO: 301 | 301 | hsa-miR-1197 | uaggacacauggucuacuucu | 1 | 2 | 0.64 | 3.43E-01 |
| SEQ ID NO: 302 | 302 | hsa-miR-127-5p | cugaagcucagagggcucugau | 6 | 22 | 0.26 | 3.43E-01 |
| SEQ ID NO: 303 | 303 | hsa-miR-1286 | ugcaggaccaagaugagcccu | 12 | 12 | 1.04 | 3.43E-01 |
| SEQ ID NO: 304 | 304 | hsa-miR-132* | accguggcuuucgauuguuacu | 1 | 1 | 1.00 | 3.43E-01 |
| SEQ ID NO: 305 | 305 | hsa-miR-33b | gugcauugcuguugcauugc | 1 | 2 | 0.64 | 3.43E-01 |
| SEQ ID NO: 306 | 306 | hsa-miR-553 | aaaacggugagauuuuguuuu | 1 | 1 | 1.00 | 3.43E-01 |
| SEQ ID NO: 307 | 307 | hsa-miR-620 | auggagauagauauagaaau | 1 | 2 | 0.64 | 3.43E-01 |
| SEQ ID NO: 308 | 308 | hsa-miR-708 | aaggagcuuacaaucuagcuggg | 1 | 1 | 1.00 | 3.43E-01 |

Figure 10B (cont'd)

| | | | | | | | |
|---|---|---|---|---|---|---|---|
| SEQ ID NO: 309 | 309 | hsa-miR-892b | cacuggcucccuuucuggguaga | 1 | 1 | 1.00 | 3.43E-01 |
| SEQ ID NO: 310 | 310 | hsa-miR-520h | acaaagugcuucccuuuagagu | 1 | 1 | 1.00 | 3.43E-01 |
| SEQ ID NO: 311 | 311 | hsa-miR-500* | augcaccugggcaaggauucug | 254 | 8 | 30.51 | 3.43E-01 |
| SEQ ID NO: 312 | 312 | hsa-miR-551b* | gaaaucaagcgugggugagacc | 97 | 88 | 1.11 | 3.43E-01 |
| SEQ ID NO: 313 | 313 | hsa-miR-186 | caaagaauucuccuuuugggcu | 40 | 19 | 2.12 | 3.43E-01 |
| SEQ ID NO: 314 | 314 | hsa-miR-558 | ugagcugcuguaccaaaau | 1 | 1 | 1.00 | 3.45E-01 |
| SEQ ID NO: 315 | 315 | hsa-miR-26a | uucaaguaauccaggauaggcu | 8970 | 11137 | 0.81 | 3.45E-01 |
| SEQ ID NO: 316 | 316 | hsa-miR-1263 | augguacccuggcauacugagu | 1 | 1 | 1.00 | 3.45E-01 |
| SEQ ID NO: 317 | 317 | hsa-miR-211 | uucccuuugucauccuucgccu | 1 | 4 | 0.27 | 3.45E-01 |
| SEQ ID NO: 318 | 318 | hsa-miR-1304 | uuugaggcuacagugagaugug | 21 | 28 | 0.73 | 3.45E-01 |
| SEQ ID NO: 319 | 319 | hsa-miR-220b | ccaccaccgugucugacacuu | 3 | 1 | 2.67 | 3.45E-01 |
| SEQ ID NO: 320 | 320 | hsa-miR-891a | ugcaacgaaccugagccacuga | 7 | 7 | 1.03 | 3.45E-01 |
| SEQ ID NO: 321 | 321 | hsa-miR-1253 | agagaagaagaucagccugca | 1 | 1 | 1.00 | 3.45E-01 |
| SEQ ID NO: 322 | 322 | hsa-miR-1205 | ucugcaggguuugcuuugag | 1 | 1 | 1.00 | 3.45E-01 |
| SEQ ID NO: 323 | 323 | hsa-miR-137 | uuauugcuuaagaauacgcguag | 1 | 1 | 1.00 | 3.45E-01 |
| SEQ ID NO: 324 | 324 | hsa-miR-154* | aaucauacacgguugaccuauu | 1 | 1 | 1.00 | 3.45E-01 |
| SEQ ID NO: 325 | 325 | hsa-miR-555 | aggguaagcugaaccucugau | 1 | 1 | 1.00 | 3.45E-01 |
| SEQ ID NO: 326 | 326 | hsa-miR-887 | gugaacgggcgccaucccgagg | 23 | 31 | 0.72 | 3.45E-01 |
| SEQ ID NO: 327 | 327 | hsa-miR-363 | aauugcacgguauccaucugua | 2791 | 3304 | 0.84 | 3.45E-01 |
| SEQ ID NO: 328 | 328 | hsa-miR-1537 | aaaaccgucuaguuacaguugu | 1 | 1 | 1.00 | 3.45E-01 |
| SEQ ID NO: 329 | 329 | hsa-miR-219-1-3p | agaguugagucuggacgucccg | 1 | 1 | 1.00 | 3.45E-01 |
| SEQ ID NO: 330 | 330 | hsa-miR-220a | ccacaccguaucugacacuuu | 1 | 1 | 1.00 | 3.45E-01 |
| SEQ ID NO: 331 | 331 | hsa-miR-222* | cucaguagccaguguagauccu | 1 | 1 | 1.00 | 3.45E-01 |
| SEQ ID NO: 332 | 332 | hsa-miR-323-3p | cacauuacacggucgaccucu | 1 | 1 | 1.00 | 3.45E-01 |
| SEQ ID NO: 333 | 333 | hsa-miR-376b | aucauagaggaaaauccauguu | 1 | 7 | 0.15 | 3.45E-01 |
| SEQ ID NO: 334 | 334 | hsa-miR-490-5p | ccauggaucuccaggugggu | 1 | 4 | 0.24 | 3.45E-01 |
| SEQ ID NO: 335 | 335 | hsa-miR-523 | gaacgcgcuucccuauagagggu | 1 | 1 | 1.00 | 3.45E-01 |
| SEQ ID NO: 336 | 336 | hsa-miR-302a* | acuuaaacguggauguacuugcu | 1 | 1 | 1.00 | 3.45E-01 |
| SEQ ID NO: 337 | 337 | hsa-miR-27b* | agagcuuagcugauuggugaac | 8 | 4 | 2.00 | 3.45E-01 |
| SEQ ID NO: 338 | 338 | hsa-miR-591 | agaccauggguucucauugu | 1 | 1 | 1.00 | 3.45E-01 |
| SEQ ID NO: 339 | 339 | hsa-miR-888 | uacucaaaaagcugucaguca | 1 | 1 | 1.00 | 3.45E-01 |

Figure 10B (cont'd)

| | | | | | | | |
|---|---|---|---|---|---|---|---|
| SEQ ID NO: 340 | 340 | hsa-miR-376a* | guagauucuccuucuaugagua | 1 | 1 | 1.00 | 3.45E-01 |
| SEQ ID NO: 341 | 341 | hsa-miR-618 | aaacucuacuuguccuucugagu | 1 | 1 | 1.00 | 3.46E-01 |
| SEQ ID NO: 342 | 342 | hsa-miR-1182 | gagggucuugggagggaugugac | 708 | 675 | 1.05 | 3.48E-01 |
| SEQ ID NO: 343 | 343 | hsa-miR-532-3p | ccucccacacccaaggcuugca | 88 | 115 | 0.77 | 3.48E-01 |
| SEQ ID NO: 344 | 344 | hsa-miR-181b | aacauucauugcugucggugggu | 61 | 28 | 2.20 | 3.48E-01 |
| SEQ ID NO: 345 | 345 | hsa-miR-521 | aacgcacuucccuuuagagugu | 1 | 4 | 0.23 | 3.48E-01 |
| SEQ ID NO: 346 | 346 | hsa-miR-545* | ucaguaaauguuuauuagauga | 1 | 1 | 1.00 | 3.48E-01 |
| SEQ ID NO: 347 | 347 | hsa-miR-9* | auaaagcuagauaaccgaaagu | 1 | 1 | 1.00 | 3.48E-01 |
| SEQ ID NO: 348 | 348 | hsa-miR-920 | ggggagcuguggaagcagua | 51 | 80 | 0.63 | 3.48E-01 |
| SEQ ID NO: 349 | 349 | hsa-miR-571 | ugaguuggccaucugagugag | 1 | 1 | 1.00 | 3.48E-01 |
| SEQ ID NO: 350 | 350 | hsa-miR-635 | acuugggcacugaaacaaugucc | 1 | 1 | 1.00 | 3.48E-01 |
| SEQ ID NO: 351 | 351 | hsa-miR-200b | uaauacugccugguaaugauga | 1 | 1 | 1.00 | 3.49E-01 |
| SEQ ID NO: 352 | 352 | hsa-miR-455-5p | uaugugccuuuggacuacaucg | 1 | 1 | 1.00 | 3.49E-01 |
| SEQ ID NO: 353 | 353 | hsa-miR-876-3p | ugguggguuuacaaaguaauuca | 1 | 1 | 1.00 | 3.49E-01 |
| SEQ ID NO: 354 | 354 | hsa-miR-373* | acucaaaaugggggcgcuuucc | 80 | 116 | 0.68 | 3.49E-01 |
| SEQ ID NO: 355 | 355 | hsa-miR-146a* | ccucugaaauucaguucuucag | 1 | 1 | 1.00 | 3.50E-01 |
| SEQ ID NO: 356 | 356 | hsa-miR-122* | aacgccauuaucacacuaaaua | 1 | 1 | 1.00 | 3.50E-01 |
| SEQ ID NO: 357 | 357 | hsa-miR-450b-3p | uugggaucauuuugcauccaua | 1 | 1 | 1.00 | 3.50E-01 |
| SEQ ID NO: 358 | 358 | hsa-miR-24 | uggcucaguucagcaggaacag | 512 | 331 | 1.55 | 3.52E-01 |
| SEQ ID NO: 359 | 359 | hsa-miR-484 | ucaggcucaguccccucccgau | 3779 | 2576 | 1.47 | 3.52E-01 |
| SEQ ID NO: 360 | 360 | hsa-miR-103-as | ucauagcccuguacaaugcugcu | 1 | 1 | 1.00 | 3.52E-01 |
| SEQ ID NO: 361 | 361 | hsa-miR-380 | uauguaauaugguccacaucuu | 1 | 1 | 1.00 | 3.52E-01 |
| SEQ ID NO: 362 | 362 | hsa-miR-513a-5p | uucacagggaggugucau | 451 | 348 | 1.29 | 3.52E-01 |
| SEQ ID NO: 363 | 363 | hsa-miR-509-3-5p | uacugcagacguggcaaucaug | 1 | 1 | 1.00 | 3.52E-01 |
| SEQ ID NO: 364 | 364 | hsa-miR-873 | gcaggaacuugugagucuccu | 1 | 5 | 0.20 | 3.52E-01 |
| SEQ ID NO: 365 | 365 | hsa-miR-556-5p | gaugagcucauuguaauaugag | 1 | 1 | 1.00 | 3.53E-01 |
| SEQ ID NO: 366 | 366 | hsa-miR-369-5p | agaucgaccguguuauauucgc | 1 | 1 | 1.00 | 3.54E-01 |
| SEQ ID NO: 367 | 367 | hsa-miR-653 | guguugaaacaaucucuacug | 1 | 1 | 1.00 | 3.54E-01 |
| SEQ ID NO: 368 | 368 | hsa-miR-767-3p | ucugcucauaccccaugguuucu | 17 | 19 | 0.90 | 3.54E-01 |
| SEQ ID NO: 369 | 369 | hsa-miR-516a-3p | ugcuuccuuucagagggu | 1 | 1 | 1.00 | 3.54E-01 |
| SEQ ID NO: 370 | 370 | hsa-miR-520c-3p | aaagugcuuccuuuuagagggu | 1 | 1 | 1.00 | 3.54E-01 |

Figure 10B (cont'd)

| | | | | | | | |
|---|---|---|---|---|---|---|---|
| SEQ ID NO: 371 | 371 | hsa-miR-708* | caacuagacugugagcuucuag | 1 | 1 | 1.00 | 3.54E-01 |
| SEQ ID NO: 372 | 372 | hsa-miR-924 | agagucuugugaugucuugc | 1 | 1 | 1.00 | 3.54E-01 |
| SEQ ID NO: 373 | 373 | hsa-miR-520d-5p | cuacaaagggaagcccuuuc | 38 | 45 | 0.84 | 3.54E-01 |
| SEQ ID NO: 374 | 374 | hsa-miR-512-5p | cacucagccuugagggcacuuuc | 1 | 4 | 0.24 | 3.54E-01 |
| SEQ ID NO: 375 | 375 | hsa-miR-374a* | cuuaucagauuguauuguaauu | 1 | 1 | 1.00 | 3.55E-01 |
| SEQ ID NO: 376 | 376 | hsa-miR-921 | cuagugagggacagaaccaggauuc | 260 | 207 | 1.26 | 3.57E-01 |
| SEQ ID NO: 377 | 377 | hsa-miR-1206 | uguucauguagauguuuaagc | 1 | 10 | 0.10 | 3.57E-01 |
| SEQ ID NO: 378 | 378 | hsa-miR-1259 | auauaugaugacuuagcuuuu | 112 | 106 | 1.06 | 3.57E-01 |
| SEQ ID NO: 379 | 379 | hsa-miR-525-5p | cuccagagggaugcacuuucu | 2 | 4 | 0.45 | 3.57E-01 |
| SEQ ID NO: 380 | 380 | hsa-miR-200a* | caucuuaccggacagugcugga | 1 | 1 | 1.00 | 3.57E-01 |
| SEQ ID NO: 381 | 381 | hsa-miR-1293 | uggguggucuggagauuugugc | 51 | 21 | 2.39 | 3.57E-01 |
| SEQ ID NO: 382 | 382 | hsa-miR-372 | aaagugcugcgacauuugagcgu | 1 | 1 | 1.00 | 3.57E-01 |
| SEQ ID NO: 383 | 383 | hsa-miR-548a-5p | aaaaguaauugcgaguuuuacc | 1 | 1 | 1.00 | 3.57E-01 |
| SEQ ID NO: 384 | 384 | hsa-miR-548k | aaaaguacuugcggauuuugcu | 1 | 1 | 1.00 | 3.57E-01 |
| SEQ ID NO: 385 | 385 | hsa-miR-1300 | uugagaaggaggcugcug | 327 | 193 | 1.70 | 3.57E-01 |
| SEQ ID NO: 386 | 386 | hsa-miR-1264 | caagucuuauuugagcaccuguu | 1 | 1 | 1.00 | 3.57E-01 |
| SEQ ID NO: 387 | 387 | hsa-miR-551a | gcgacccacucuugguuucca | 1 | 1 | 1.00 | 3.57E-01 |
| SEQ ID NO: 388 | 388 | hsa-miR-196b | uagguaguuuccuguuguuggg | 1 | 22 | 0.05 | 3.57E-01 |
| SEQ ID NO: 389 | 389 | hsa-miR-32* | caauuuagugugugugauauuu | 1 | 1 | 1.00 | 3.57E-01 |
| SEQ ID NO: 390 | 390 | hsa-miR-33a | gugcauuguaguugcauugca | 1 | 1 | 1.00 | 3.57E-01 |
| SEQ ID NO: 391 | 391 | hsa-miR-548d-5p | aaaaguaauuguggguuuugcc | 1 | 1 | 1.00 | 3.57E-01 |
| SEQ ID NO: 392 | 392 | hsa-miR-616 | agucauuggaggguuugagcag | 27 | 30 | 0.89 | 3.57E-01 |
| SEQ ID NO: 393 | 393 | hsa-miR-876-5p | uggauuucuuugugaaucacca | 1 | 1 | 1.00 | 3.57E-01 |
| SEQ ID NO: 394 | 394 | hsa-miR-508-3p | ugauuguagccuuuuggaguaga | 1 | 1 | 1.00 | 3.57E-01 |
| SEQ ID NO: 395 | 395 | hsa-miR-26a-2* | ccuauucuugauuacuuguuuc | 1 | 1 | 1.00 | 3.57E-01 |
| SEQ ID NO: 396 | 396 | hsa-miR-187 | ucgugucuuguguugcagccgg | 1 | 4 | 0.23 | 3.57E-01 |
| SEQ ID NO: 397 | 397 | hsa-miR-199a-3p | acaguagucugcacauugguua | 1 | 20 | 0.05 | 3.57E-01 |
| SEQ ID NO: 398 | 398 | hsa-miR-96* | aaucaugugcagugccaauaug | 1 | 1 | 1.00 | 3.58E-01 |
| SEQ ID NO: 399 | 399 | hsa-miR-18b | uaaggugcaucuagugcaguuag | 137 | 234 | 0.59 | 3.59E-01 |
| SEQ ID NO: 400 | 400 | hsa-miR-432* | cuggauggcuccuccaugucu | 1 | 1 | 1.00 | 3.59E-01 |
| SEQ ID NO: 401 | 401 | hsa-miR-509-3p | ugauugguacgucuguggguag | 2 | 2 | 1.21 | 3.59E-01 |

Figure 10B (cont'd)

| | | | | | | | |
|---|---|---|---|---|---|---|---|
| SEQ ID NO: 402 | 402 | hsa-miR-1183 | cacuguaggugaugguggagaguggggca | 120 | 83 | 1.45 | 3.59E-01 |
| SEQ ID NO: 403 | 403 | hsa-miR-626 | agcugucugaaaaugucuu | 1 | 1 | 1.00 | 3.59E-01 |
| SEQ ID NO: 404 | 404 | hsa-miR-513b | uucacaaggaggugucauuuau | 91 | 72 | 1.26 | 3.59E-01 |
| SEQ ID NO: 405 | 405 | hsa-miR-617 | agacuucccauuugaagguggc | 3 | 4 | 0.60 | 3.62E-01 |
| SEQ ID NO: 406 | 406 | hsa-miR-9 | ucuuugguuaucuagcuguauga | 1 | 1 | 1.00 | 3.62E-01 |
| SEQ ID NO: 407 | 407 | hsa-miR-519e | aagugccuccuuuuagaguguu | 1 | 1 | 1.00 | 3.62E-01 |
| SEQ ID NO: 408 | 408 | hsa-miR-204 | uucccuuugucauccuaugccu | 1 | 1 | 1.00 | 3.62E-01 |
| SEQ ID NO: 409 | 409 | hsa-miR-29c | uagcaccauuugaaaucgguua | 341 | 36 | 9.44 | 3.63E-01 |
| SEQ ID NO: 410 | 410 | hsa-miR-1268 | cgggcgugguggugggg | 902 | 1056 | 0.85 | 3.63E-01 |
| SEQ ID NO: 411 | 411 | hsa-miR-122 | uggagugugacaaugguguuug | 17 | 21 | 0.81 | 3.63E-01 |
| SEQ ID NO: 412 | 412 | hsa-miR-7-2* | caacaaaucccagucuaccuaa | 13 | 12 | 1.07 | 3.63E-01 |
| SEQ ID NO: 413 | 413 | hsa-miR-15a* | caggccauauugugcugccuca | 1 | 1 | 1.00 | 3.63E-01 |
| SEQ ID NO: 414 | 414 | hsa-miR-181d | aacauucauuguugucgguggu | 3 | 3 | 1.00 | 3.63E-01 |
| SEQ ID NO: 415 | 415 | hsa-miR-219-5p | ugauuguccaaacgcaauucu | 1 | 1 | 1.00 | 3.63E-01 |
| SEQ ID NO: 416 | 416 | hsa-miR-302d | uaagugcuuccauguuugagugu | 1 | 1 | 1.00 | 3.63E-01 |
| SEQ ID NO: 417 | 417 | hsa-miR-34a | uggcagugucuuagcugguugu | 1 | 1 | 1.00 | 3.63E-01 |
| SEQ ID NO: 418 | 418 | hsa-miR-410 | aauauaacacagauggccugu | 1 | 1 | 1.00 | 3.63E-01 |
| SEQ ID NO: 419 | 419 | hsa-miR-33a* | caauguuuccacagugcaucac | 1 | 1 | 1.00 | 3.63E-01 |
| SEQ ID NO: 420 | 420 | hsa-miR-502-3p | aaugcaccugggcaaggauuca | 364 | 15 | 24.46 | 3.63E-01 |
| SEQ ID NO: 421 | 421 | hsa-miR-379 | ugguagacuauggaacguagg | 26 | 39 | 0.65 | 3.63E-01 |
| SEQ ID NO: 422 | 422 | hsa-miR-498 | uuucaagccagggggcguuuuuc | 101 | 59 | 1.72 | 3.63E-01 |
| SEQ ID NO: 423 | 423 | hsa-miR-518d-5p | cucuagagggaagcacuuucug | 37 | 20 | 1.86 | 3.63E-01 |
| SEQ ID NO: 424 | 424 | hsa-miR-556-3p | auauuaccauuagcucaucuuu | 1 | 1 | 1.00 | 3.63E-01 |
| SEQ ID NO: 425 | 425 | hsa-miR-502-5p | auccuugcuaucugggugcua | 7 | 1 | 6.78 | 3.63E-01 |
| SEQ ID NO: 426 | 426 | hsa-miR-31 | aggcaagaugcuggcauagcu | 8 | 4 | 2.30 | 3.63E-01 |
| SEQ ID NO: 427 | 427 | hsa-miR-100 | aacccguagauccgaacuugug | 212 | 99 | 2.15 | 3.63E-01 |
| SEQ ID NO: 428 | 428 | hsa-miR-296-3p | gaggguugggguggaggcucucc | 606 | 408 | 1.48 | 3.63E-01 |
| SEQ ID NO: 429 | 429 | hsa-miR-615-5p | ggggguccccggugcucggauc | 34 | 12 | 2.81 | 3.63E-01 |
| SEQ ID NO: 430 | 430 | hsa-miR-21* | caacaccagucgaugggcugu | 1 | 1 | 1.00 | 3.64E-01 |
| SEQ ID NO: 431 | 431 | hsa-miR-657 | ggcagguucucacccucucuagg | 1 | 1 | 1.00 | 3.64E-01 |
| SEQ ID NO: 432 | 432 | hsa-miR-651 | uuuaggauaagcuugacuuuug | 1 | 1 | 1.00 | 3.64E-01 |

Figure 10B (cont'd)

| | | | | | | | |
|---|---|---|---|---|---|---|---|
| SEQ ID NO: 433 | 433 | hsa-miR-765 | uggaggagaaggaaggugaug | 1085 | 1102 | 0.98 | 3.64E-01 |
| SEQ ID NO: 434 | 434 | hsa-miR-548m | caaagguauuugugguuuuug | 1 | 1 | 1.00 | 3.64E-01 |
| SEQ ID NO: 435 | 435 | hsa-miR-219-2-3p | agaauuguggcuggacaucugu | 4 | 1 | 4.00 | 3.64E-01 |
| SEQ ID NO: 436 | 436 | hsa-miR-501-3p | aaugcacccgggcaaggauucu | 286 | 22 | 13.27 | 3.64E-01 |
| SEQ ID NO: 437 | 437 | hsa-miR-302a | uaagugcuuccauguuuugguga | 1 | 1 | 1.00 | 3.65E-01 |
| SEQ ID NO: 438 | 438 | hsa-miR-202* | uuccuaugcauauacuucuuug | 1 | 1 | 1.00 | 3.65E-01 |
| SEQ ID NO: 439 | 439 | hsa-miR-206 | uggaauguaaggaagugugugg | 16 | 28 | 0.55 | 3.65E-01 |
| SEQ ID NO: 440 | 440 | hsa-miR-520d-3p | aaagugcuucucuuugguggu | 1 | 1 | 1.00 | 3.65E-01 |
| SEQ ID NO: 441 | 441 | hsa-miR-548i | aaaaguaauugcggauuuugcc | 1 | 1 | 1.00 | 3.67E-01 |
| SEQ ID NO: 442 | 442 | hsa-miR-511 | gugucuuuugcucugcaguca | 1 | 1 | 1.00 | 3.68E-01 |
| SEQ ID NO: 443 | 443 | hsa-miR-30a | uguaaacauccucgacuggaag | 1175 | 1056 | 1.11 | 3.68E-01 |
| SEQ ID NO: 444 | 444 | hsa-miR-1224-3p | ccccaccuccucucuccucag | 26 | 67 | 0.38 | 3.68E-01 |
| SEQ ID NO: 445 | 445 | hsa-miR-525-3p | gaaggcgcuucccuuuagagcg | 1 | 1 | 1.00 | 3.68E-01 |
| SEQ ID NO: 446 | 446 | hsa-miR-1225-5p | guggguacggcccaguggggg | 143 | 194 | 0.74 | 3.70E-01 |
| SEQ ID NO: 447 | 447 | hsa-miR-223* | cguguauuugacaagcugaguu | 1 | 4 | 0.23 | 3.70E-01 |
| SEQ ID NO: 448 | 448 | hsa-miR-615-3p | uccgagccugggucucccucuu | 1 | 1 | 1.00 | 3.72E-01 |
| SEQ ID NO: 449 | 449 | hsa-miR-570 | cgaaaacagcaauuaccuuugc | 1 | 1 | 1.00 | 3.73E-01 |
| SEQ ID NO: 450 | 450 | hsa-miR-320a | aaaagcugggguugagagggcga | 10048 | 8310 | 1.21 | 3.73E-01 |
| SEQ ID NO: 451 | 451 | hsa-miR-770-5p | uccaguaccacgugucagggcca | 9 | 11 | 0.80 | 3.73E-01 |
| SEQ ID NO: 452 | 452 | hsa-miR-582-5p | uuacaguuguucaaccaguuacu | 1 | 3 | 0.32 | 3.75E-01 |
| SEQ ID NO: 453 | 453 | hsa-miR-590-5p | gagcuuauucauaaaagugcag | 1 | 1 | 1.00 | 3.76E-01 |
| SEQ ID NO: 454 | 454 | hsa-miR-659 | cuugguucagggagggucccca | 151 | 133 | 1.13 | 3.77E-01 |
| SEQ ID NO: 455 | 455 | hsa-miR-1251 | acucuagcugccaaaggcgcu | 1 | 1 | 1.00 | 3.77E-01 |
| SEQ ID NO: 456 | 456 | hsa-miR-664 | uauucauuuauccccagccuaca | 8 | 11 | 0.75 | 3.77E-01 |
| SEQ ID NO: 457 | 457 | hsa-miR-488* | cccagauaauggcacucucaa | 1 | 1 | 1.00 | 3.77E-01 |
| SEQ ID NO: 458 | 458 | hsa-miR-548g | aaaacuguaauuacuuuuguac | 1 | 1 | 1.00 | 3.77E-01 |
| SEQ ID NO: 459 | 459 | hsa-miR-802 | caguaacaaagauucauccuugu | 1 | 1 | 1.00 | 3.77E-01 |
| SEQ ID NO: 460 | 460 | hsa-miR-542-5p | ucggggaucaucaugucacgaga | 7 | 1 | 6.78 | 3.77E-01 |
| SEQ ID NO: 461 | 461 | hsa-miR-190 | ugauauguuugauauauuaggu | 1 | 1 | 1.00 | 3.77E-01 |
| SEQ ID NO: 462 | 462 | hsa-miR-218-1* | augguuccgucaagcaccaugg | 1 | 1 | 1.00 | 3.77E-01 |
| SEQ ID NO: 463 | 463 | hsa-miR-367* | acuguugcuaauaugcaacucu | 1 | 1 | 1.00 | 3.77E-01 |

Figure 10B (cont'd)

| | | | | | | | |
|---|---|---|---|---|---|---|---|
| SEQ ID NO: 464 | 464 | hsa-miR-450a | uuuugcgauguguuccuaauau | 1 | 1 | 1.00 | 3.77E-01 |
| SEQ ID NO: 465 | 465 | hsa-miR-367 | aauugcacuuuagcaauggua | 1 | 1 | 1.00 | 3.78E-01 |
| SEQ ID NO: 466 | 466 | hsa-miR-124 | uaaggcacgcggugaaugcc | 21 | 11 | 1.81 | 3.80E-01 |
| SEQ ID NO: 467 | 467 | hsa-miR-767-5p | ugcaccaugguugucugagcaug | 1 | 1 | 1.00 | 3.80E-01 |
| SEQ ID NO: 468 | 468 | hsa-miR-200c | uaauacugccggguaaugaugga | 7 | 10 | 0.71 | 3.82E-01 |
| SEQ ID NO: 469 | 469 | hsa-miR-572 | guccgcucggcgguggccca | 7 | 4 | 1.53 | 3.84E-01 |
| SEQ ID NO: 470 | 470 | hsa-miR-526a | cucuagagggaagcacuuucug | 27 | 56 | 0.48 | 3.85E-01 |
| SEQ ID NO: 471 | 471 | hsa-miR-936 | acaguagagggaggaaucgcag | 684 | 660 | 1.04 | 3.86E-01 |
| SEQ ID NO: 472 | 472 | hsa-miR-548n | caaaaguaauuguggauuuugu | 1 | 1 | 1.00 | 3.86E-01 |
| SEQ ID NO: 473 | 473 | hsa-miR-21 | uagcuuaucagacugauguuga | 708 | 857 | 0.83 | 3.87E-01 |
| SEQ ID NO: 474 | 474 | hsa-miR-182* | ugguucuagacuugccaacua | 1 | 1 | 1.00 | 3.87E-01 |
| SEQ ID NO: 475 | 475 | hsa-miR-34c-5p | aggcaguguaguuagcugauugc | 1 | 1 | 1.00 | 3.87E-01 |
| SEQ ID NO: 476 | 476 | hsa-miR-429 | uaauacugucugguaaaaccgu | 1 | 1 | 1.00 | 3.87E-01 |
| SEQ ID NO: 477 | 477 | hsa-miR-628-5p | augcugacauauuuacuagagg | 1 | 1 | 1.00 | 3.87E-01 |
| SEQ ID NO: 478 | 478 | hsa-miR-29a* | acugauuucuuuugguguucag | 2 | 1 | 2.22 | 3.87E-01 |
| SEQ ID NO: 479 | 479 | hsa-miR-370 | gccugcugggguggaaccuggu | 194 | 157 | 1.24 | 3.87E-01 |
| SEQ ID NO: 480 | 480 | hsa-let-7a* | cuauacaaucuacugucuuuc | 5 | 4 | 1.13 | 3.87E-01 |
| SEQ ID NO: 481 | 481 | hsa-miR-101* | caguuaucacagugcugaugcu | 1 | 1 | 1.00 | 3.87E-01 |
| SEQ ID NO: 482 | 482 | hsa-miR-559 | uaaaguaaauaugcaccaaaa | 1 | 1 | 1.00 | 3.87E-01 |
| SEQ ID NO: 483 | 483 | hsa-miR-217 | uacugcaucaggaacugauugga | 1 | 1 | 1.00 | 3.89E-01 |
| SEQ ID NO: 484 | 484 | hsa-miR-519b-5p | cucuagagggaagcgcuuucug | 2 | 4 | 0.35 | 3.89E-01 |
| SEQ ID NO: 485 | 485 | hsa-miR-30e* | cuuucagucggauguuuacagc | 21 | 8 | 2.47 | 3.90E-01 |
| SEQ ID NO: 486 | 486 | hsa-miR-147 | guguguggaaaugcuucugc | 4 | 1 | 4.00 | 3.94E-01 |
| SEQ ID NO: 487 | 487 | hsa-miR-487b | aaucguacagggucauccacuu | 21 | 12 | 1.70 | 3.94E-01 |
| SEQ ID NO: 488 | 488 | hsa-miR-888* | gacugacaccucuuugggugaa | 1 | 7 | 0.15 | 3.94E-01 |
| SEQ ID NO: 489 | 489 | hsa-miR-205 | uccuucauuccaccggagucug | 1 | 1 | 1.00 | 3.95E-01 |
| SEQ ID NO: 490 | 490 | hsa-miR-1257 | agugaaugaugggguucugacc | 3 | 2 | 1.71 | 3.95E-01 |
| SEQ ID NO: 491 | 491 | hsa-miR-7 | uggaagacuagugauuuuguugu | 256 | 1 | 256.44 | 3.96E-01 |
| SEQ ID NO: 492 | 492 | hsa-miR-296-5p | agggcccccccucaauccugu | 48 | 59 | 0.82 | 3.97E-01 |
| SEQ ID NO: 493 | 493 | hsa-miR-1255a | aggaugagcaaagaaaguagauu | 46 | 28 | 1.63 | 3.99E-01 |
| SEQ ID NO: 494 | 494 | hsa-miR-380* | ugguugaccauagaacaugcgc | 1 | 1 | 1.00 | 3.99E-01 |

Figure 10B (cont'd)

| | | | | | | | |
|---|---|---|---|---|---|---|---|
| SEQ ID NO: 495 | 495 | hsa-miR-1275 | gugggggagaggcuguc | 1147 | 902 | 1.27 | 3.99E-01 |
| SEQ ID NO: 496 | 496 | hsa-miR-330-5p | ucucugggccugugucuuaggc | 1 | 1 | 1.00 | 3.99E-01 |
| SEQ ID NO: 497 | 497 | hsa-miR-1243 | aacuggaucaauuauaggagug | 1 | 1 | 1.00 | 3.99E-01 |
| SEQ ID NO: 498 | 498 | hsa-miR-136* | caucaucgucucaaaugagucu | 1 | 1 | 1.00 | 3.99E-01 |
| SEQ ID NO: 499 | 499 | hsa-miR-141* | caucuuccaguacaguguugga | 1 | 1 | 1.00 | 3.99E-01 |
| SEQ ID NO: 500 | 500 | hsa-miR-517c | aucgugcauccuuuuagagugu | 1 | 1 | 1.00 | 3.99E-01 |
| SEQ ID NO: 501 | 501 | hsa-miR-621 | ggcuagcaacagcgcuuaccu | 1 | 1 | 1.00 | 3.99E-01 |
| SEQ ID NO: 502 | 502 | hsa-miR-1915* | accuugccuugcugcccgggcc | 1 | 11 | 0.09 | 3.99E-01 |
| SEQ ID NO: 503 | 503 | hsa-miR-541 | uggugggcacagaaucuggacu | 17 | 28 | 0.59 | 3.99E-01 |
| SEQ ID NO: 504 | 504 | hsa-miR-543 | aaacauucgcggugcacuucuu | 1 | 1 | 1.00 | 3.99E-01 |
| SEQ ID NO: 505 | 505 | hsa-miR-942 | ucuucucuguuuuggccaugug | 52 | 18 | 2.87 | 4.00E-01 |
| SEQ ID NO: 506 | 506 | hsa-miR-26a-1* | ccuauucuugguuacuugcacg | 1 | 1 | 1.00 | 4.01E-01 |
| SEQ ID NO: 507 | 507 | hsa-miR-567 | aguauguucuuccaggacagaac | 1 | 1 | 1.00 | 4.01E-01 |
| SEQ ID NO: 508 | 508 | hsa-miR-184 | uggacggagaacugauaagggu | 95 | 57 | 1.67 | 4.01E-01 |
| SEQ ID NO: 509 | 509 | hsa-miR-376a | aucauagaggaaaauccacgu | 1 | 3 | 0.32 | 4.02E-01 |
| SEQ ID NO: 510 | 510 | hsa-miR-124* | cguguucacagcggaccuugau | 3 | 1 | 2.67 | 4.03E-01 |
| SEQ ID NO: 511 | 511 | hsa-miR-1254 | agccuggaagcuggagccugcagu | 245 | 724 | 0.34 | 4.05E-01 |
| SEQ ID NO: 512 | 512 | hsa-miR-1207-5p | uggcagggaggcugggagggg | 5382 | 4319 | 1.25 | 4.05E-01 |
| SEQ ID NO: 513 | 513 | hsa-miR-580 | uugagaaugaugaaucauuagg | 1 | 1 | 1.00 | 4.05E-01 |
| SEQ ID NO: 514 | 514 | hsa-let-7b* | cuauacaaccuacugccuuccc | 22 | 14 | 1.62 | 4.05E-01 |
| SEQ ID NO: 515 | 515 | hsa-miR-539 | ggagaaauuauccuuggugugu | 1 | 1 | 1.00 | 4.07E-01 |
| SEQ ID NO: 516 | 516 | hsa-miR-520a-3p | aaagugcuucccuuuggacugu | 1 | 1 | 1.00 | 4.09E-01 |
| SEQ ID NO: 517 | 517 | hsa-miR-585 | ugggcguaucuguaugcua | 1 | 1 | 1.00 | 4.09E-01 |
| SEQ ID NO: 518 | 518 | hsa-miR-675b | cuguaugcccucaccgcuca | 4 | 4 | 0.90 | 4.09E-01 |
| SEQ ID NO: 519 | 519 | hsa-miR-943 | cugacuguugccguccuccag | 1 | 1 | 1.00 | 4.09E-01 |
| SEQ ID NO: 520 | 520 | hsa-miR-573 | cugaagugauguguaacugaucag | 1 | 1 | 1.00 | 4.09E-01 |
| SEQ ID NO: 521 | 521 | hsa-miR-93 | caaagugcuguucgugcagguag | 4779 | 5660 | 0.84 | 4.09E-01 |
| SEQ ID NO: 522 | 522 | hsa-miR-27a* | agggcuuagcugcuugugagca | 1 | 1 | 1.00 | 4.13E-01 |
| SEQ ID NO: 523 | 523 | hsa-miR-613 | aggaauguucc uucuuugcc | 1 | 1 | 1.00 | 4.13E-01 |
| SEQ ID NO: 524 | 524 | hsa-miR-220c | acacagggcuguugugaagacu | 1 | 3 | 0.32 | 4.14E-01 |
| SEQ ID NO: 525 | 525 | hsa-miR-524-3p | gaaggcgcuucccuuuggagu | 1 | 1 | 1.00 | 4.16E-01 |

Figure 10B (cont'd)

| | | | | | | | |
|---|---|---|---|---|---|---|---|
| SEQ ID NO: 526 | 526 | hsa-miR-500 | uaauccuugcuaccugggugaga | 136 | 59 | 2.32 | 4.16E-01 |
| SEQ ID NO: 527 | 527 | hsa-miR-1201 | agccugauuaaacacaugcucuga | 38 | 18 | 2.09 | 4.16E-01 |
| SEQ ID NO: 528 | 528 | hsa-miR-20a* | acugcauuaugagcacuuaaag | 1 | 1 | 1.00 | 4.16E-01 |
| SEQ ID NO: 529 | 529 | hsa-miR-1914* | ggaggggucccgcacugggagg | 249 | 153 | 1.63 | 4.18E-01 |
| SEQ ID NO: 530 | 530 | hsa-miR-425* | aucgggaaugucguguccgccc | 98 | 34 | 2.90 | 4.18E-01 |
| SEQ ID NO: 531 | 531 | hsa-miR-515-3p | gagugccuucuuuuggagcguu | 1 | 1 | 1.00 | 4.18E-01 |
| SEQ ID NO: 532 | 532 | hsa-miR-377* | agagguugcccuuggugaauuc | 1 | 1 | 1.00 | 4.18E-01 |
| SEQ ID NO: 533 | 533 | hsa-miR-504 | agacccuggucugcacucuauc | 1 | 1 | 1.00 | 4.18E-01 |
| SEQ ID NO: 534 | 534 | hsa-miR-548c-3p | caaaaaucucaauuacuuuugc | 1 | 1 | 1.00 | 4.18E-01 |
| SEQ ID NO: 535 | 535 | hsa-miR-1276 | uaaagagcccuguggagaca | 25 | 30 | 0.81 | 4.18E-01 |
| SEQ ID NO: 536 | 536 | hsa-miR-138 | agcugguguugugaaucaggccg | 8 | 1 | 8.44 | 4.18E-01 |
| SEQ ID NO: 537 | 537 | hsa-miR-431 | ugucuugcaggccgucaugca | 1 | 4 | 0.27 | 4.18E-01 |
| SEQ ID NO: 538 | 538 | hsa-miR-494 | ugaaacauacacgggaaaccuc | 20350 | 20350 | 1.00 | 4.18E-01 |
| SEQ ID NO: 539 | 539 | hsa-miR-448 | uugcauauguaggaugucccau | 1 | 1 | 1.00 | 4.18E-01 |
| SEQ ID NO: 540 | 540 | hsa-miR-633 | cuaauaguaucuaccacaauaaa | 1 | 1 | 1.00 | 4.18E-01 |
| SEQ ID NO: 541 | 541 | hsa-miR-487a | aaucauacagggacauccaguu | 2 | 2 | 1.00 | 4.18E-01 |
| SEQ ID NO: 542 | 542 | hsa-miR-149 | ucuggcucegugucuucacuccc | 10 | 11 | 0.84 | 4.18E-01 |
| SEQ ID NO: 543 | 543 | hsa-miR-300 | uauacaagggcagacucucucu | 1 | 1 | 1.00 | 4.18E-01 |
| SEQ ID NO: 544 | 544 | hsa-miR-1826 | auugaucaucgacacuucgaacgcaau | 35853 | 35853 | 1.00 | 4.18E-01 |
| SEQ ID NO: 545 | 545 | hsa-miR-127-3p | ucggauccgucugagcuuggcu | 1 | 1 | 1.00 | 4.18E-01 |
| SEQ ID NO: 546 | 546 | hsa-miR-486-5p | uccuguacugagcugccccgag | 42197 | 42197 | 1.00 | 4.18E-01 |
| SEQ ID NO: 547 | 547 | hsa-miR-146a | ucagugcacuacagaacuuugu | 382 | 902 | 0.42 | 4.19E-01 |
| SEQ ID NO: 548 | 548 | hsa-miR-1294 | ugugagguuggcauuguugucu | 29 | 19 | 1.55 | 4.19E-01 |
| SEQ ID NO: 549 | 549 | hsa-miR-548l | aaaaguauuugcggguuuuguc | 1 | 1 | 1.00 | 4.22E-01 |
| SEQ ID NO: 550 | 550 | hsa-miR-142-5p | cauaaaguagaaagcacuacu | 29 | 10 | 2.79 | 4.24E-01 |
| SEQ ID NO: 551 | 551 | hsa-miR-889 | uuaauaucggacaaccauugu | 1 | 1 | 1.00 | 4.31E-01 |
| SEQ ID NO: 552 | 552 | hsa-miR-365 | uaaugccccuaaaaauccuuau | 24 | 43 | 0.56 | 4.31E-01 |
| SEQ ID NO: 553 | 553 | hsa-miR-99b | cacccguagaaccgaccuugcg | 73 | 34 | 2.19 | 4.37E-01 |
| SEQ ID NO: 554 | 554 | hsa-miR-200b* | caucuuacugggcagcauugga | 7 | 4 | 1.76 | 4.37E-01 |
| SEQ ID NO: 555 | 555 | hsa-miR-200a | uaacacugucugguaacgaugu | 1 | 1 | 1.00 | 4.37E-01 |
| SEQ ID NO: 556 | 556 | hsa-miR-518e | aaagcgcuucccuucagagug | 1 | 1 | 1.00 | 4.37E-01 |

Figure 10B (cont'd)

| | | | | | | | |
|---|---|---|---|---|---|---|---|
| SEQ ID NO: 557 | 557 | hsa-miR-612 | gcugggcagggcuucugagcuccuu | 25 | 33 | 0.73 | 4.39E-01 |
| SEQ ID NO: 558 | 558 | hsa-miR-183* | gugaauuaccgaagggccauaa | 82 | 72 | 1.14 | 4.39E-01 |
| SEQ ID NO: 559 | 559 | hsa-miR-148b | ucagugcaucacagaacuuugu | 364 | 1 | 364.22 | 4.40E-01 |
| SEQ ID NO: 560 | 560 | hsa-miR-103 | agcagcauuguacagggcuauga | 3869 | 5382 | 0.72 | 4.41E-01 |
| SEQ ID NO: 561 | 561 | hsa-miR-548o | ccaaaacugcaguuacuuuugc | 1 | 1 | 1.00 | 4.41E-01 |
| SEQ ID NO: 562 | 562 | hsa-miR-1203 | cccggagccaggaugcagcuc | 43 | 28 | 1.54 | 4.41E-01 |
| SEQ ID NO: 563 | 563 | hsa-miR-135a* | uauagggauuggagccguggcg | 645 | 480 | 1.34 | 4.41E-01 |
| SEQ ID NO: 564 | 564 | hsa-miR-383 | agaucagaaggugauuguggcu | 15 | 19 | 0.82 | 4.41E-01 |
| SEQ ID NO: 565 | 565 | hsa-miR-1913 | ucugcccccuccgcugcugcca | 34 | 52 | 0.66 | 4.41E-01 |
| SEQ ID NO: 566 | 566 | hsa-miR-373 | gaagugcuucgauuuuggggugu | 1 | 2 | 0.64 | 4.42E-01 |
| SEQ ID NO: 567 | 567 | hsa-miR-371-5p | acucaaacugugggggcacu | 98 | 93 | 1.05 | 4.44E-01 |
| SEQ ID NO: 568 | 568 | hsa-miR-298 | agcagaagcagggagguucuccca | 72 | 53 | 1.34 | 4.46E-01 |
| SEQ ID NO: 569 | 569 | hsa-miR-758 | uuugugaccugguccacuaacc | 9 | 15 | 0.61 | 4.46E-01 |
| SEQ ID NO: 570 | 570 | hsa-miR-412 | acuucaccugguccacuagccgu | 4 | 2 | 2.57 | 4.46E-01 |
| SEQ ID NO: 571 | 571 | hsa-miR-518c | caaagcgcuucucuuuagagugu | 1 | 1 | 1.00 | 4.46E-01 |
| SEQ ID NO: 572 | 572 | hsa-miR-589* | ucagaacaaaugccgguucccaga | 23 | 21 | 1.10 | 4.46E-01 |
| SEQ ID NO: 573 | 573 | hsa-miR-643 | acuuguaugcuagcucagguag | 1 | 1 | 1.00 | 4.46E-01 |
| SEQ ID NO: 574 | 574 | hsa-miR-592 | uugugucaauaugcgaugaugu | 1 | 1 | 1.00 | 4.46E-01 |
| SEQ ID NO: 575 | 575 | hsa-miR-892a | cacuguguccuuucugcguag | 8 | 15 | 0.53 | 4.46E-01 |
| SEQ ID NO: 576 | 576 | hsa-miR-944 | aaauuauuguacaucggaugag | 1 | 1 | 1.00 | 4.47E-01 |
| SEQ ID NO: 577 | 577 | hsa-miR-576-3p | aagauguggaaaaauuggaauc | 1 | 11 | 0.09 | 4.47E-01 |
| SEQ ID NO: 578 | 578 | hsa-miR-581 | ucuuguguucucuagaucagu | 1 | 1 | 1.00 | 4.48E-01 |
| SEQ ID NO: 579 | 579 | hsa-miR-625* | gacuauagaacuuucccccuca | 52 | 22 | 2.38 | 4.51E-01 |
| SEQ ID NO: 580 | 580 | hsa-miR-1260 | aucccaccucugccacca | 84 | 51 | 1.64 | 4.52E-01 |
| SEQ ID NO: 581 | 581 | hsa-miR-1261 | ucgccucccucucucc | 8 | 36 | 0.24 | 4.52E-01 |
| SEQ ID NO: 582 | 582 | hsa-miR-337-5p | gaacggcuucauacaggaguu | 3 | 8 | 0.32 | 4.54E-01 |
| SEQ ID NO: 583 | 583 | hsa-miR-133b | uuugguccccuucaaccagcua | 24 | 20 | 1.21 | 4.56E-01 |
| SEQ ID NO: 584 | 584 | hsa-miR-92a-2* | ggguggggauuuguugcauuac | 148 | 67 | 2.20 | 4.56E-01 |
| SEQ ID NO: 585 | 585 | hsa-miR-100* | caagcuuguaucuauagguaug | 1 | 1 | 1.00 | 4.59E-01 |
| SEQ ID NO: 586 | 586 | hsa-miR-589 | ugagaaccacgucugcucugag | 7 | 1 | 6.78 | 4.64E-01 |
| SEQ ID NO: 587 | 587 | hsa-miR-218 | uugugcuugaucuaaccaugu | 1 | 1 | 1.00 | 4.64E-01 |

Figure 10B (cont'd)

| | | | | | | | |
|---|---|---|---|---|---|---|---|
| SEQ ID NO: 588 | 586 | hsa-miR-224 | caagucacuagugguuccguu | 1 | 1 | 1.00 | 4.68E-01 |
| SEQ ID NO: 589 | 589 | hsa-miR-16-2* | ccaauauuacugugcugcuuua | 41 | 30 | 1.34 | 4.69E-01 |
| SEQ ID NO: 590 | 590 | hsa-miR-301b | cagugcaaugauauugucaaagc | 1 | 1 | 1.00 | 4.72E-01 |
| SEQ ID NO: 591 | 591 | hsa-miR-190b | ugauauguuugauauuggguu | 1 | 1 | 1.00 | 4.72E-01 |
| SEQ ID NO: 592 | 592 | hsa-miR-375 | uuuguucguucggcucgcguga | 1 | 1 | 1.00 | 4.73E-01 |
| SEQ ID NO: 593 | 593 | hsa-miR-548p | uagcaaaaacugcaguuacuuu | 1 | 1 | 1.00 | 4.74E-01 |
| SEQ ID NO: 594 | 594 | hsa-miR-185* | aggggcuggcuuuccucugguc | 56 | 47 | 1.18 | 4.74E-01 |
| SEQ ID NO: 595 | 595 | hsa-miR-519d | caaagugccucccuuuagagug | 1 | 1 | 1.00 | 4.77E-01 |
| SEQ ID NO: 596 | 596 | hsa-miR-605 | uaaaucccaugguguccuucuccu | 7 | 4 | 1.85 | 4.79E-01 |
| SEQ ID NO: 597 | 597 | hsa-miR-877 | guagaggagauggcgcaggg | 364 | 451 | 0.81 | 4.81E-01 |
| SEQ ID NO: 598 | 598 | hsa-miR-125a-3p | acaggugagguucuugggagcc | 58 | 39 | 1.49 | 4.81E-01 |
| SEQ ID NO: 599 | 599 | hsa-miR-744* | cuguugccacuaaccucaaccu | 15 | 11 | 1.35 | 4.81E-01 |
| SEQ ID NO: 600 | 600 | hsa-miR-520c-5p | cucuagagggaagcacuuucug | 32 | 30 | 1.04 | 4.81E-01 |
| SEQ ID NO: 601 | 601 | hsa-miR-148a* | aaaguucugagacacuccgacu | 1 | 1 | 1.00 | 4.91E-01 |
| SEQ ID NO: 602 | 602 | hsa-miR-212 | uaacagucuccagucacggcc | 7 | 4 | 1.68 | 4.92E-01 |
| SEQ ID NO: 603 | 603 | hsa-miR-505 | cgucaacacuugcugguuuccu | 53 | 11 | 4.68 | 4.92E-01 |
| SEQ ID NO: 604 | 604 | hsa-miR-496 | ugaguauuacauggccaaucuc | 15 | 4 | 3.45 | 4.94E-01 |
| SEQ ID NO: 605 | 605 | hsa-miR-1323 | ucaaaacugaggggcauuuucu | 68 | 44 | 1.55 | 4.97E-01 |
| SEQ ID NO: 606 | 606 | hsa-miR-548e | aaaaacugagacuacuuuugca | 1 | 1 | 1.00 | 4.97E-01 |
| SEQ ID NO: 607 | 607 | hsa-miR-628-3p | ucuaguaagaguggcagucga | 50 | 34 | 1.44 | 5.00E-01 |
| SEQ ID NO: 608 | 608 | hsa-miR-1914 | cccugugcccggcccacuucug | 7 | 15 | 0.46 | 5.01E-01 |
| SEQ ID NO: 609 | 609 | hsa-miR-584 | uuaugguuugccugggacugag | 120 | 115 | 1.05 | 5.03E-01 |
| SEQ ID NO: 610 | 610 | hsa-miR-135b* | auguagggcuaaaagccauggg | 34 | 12 | 2.83 | 5.05E-01 |
| SEQ ID NO: 611 | 611 | hsa-miR-1295 | uuaggccgcagaucuggguga | 8 | 11 | 0.75 | 5.05E-01 |
| SEQ ID NO: 612 | 612 | hsa-miR-95 | uucaacggguauuuauugagca | 1 | 1 | 1.00 | 5.05E-01 |
| SEQ ID NO: 613 | 613 | hsa-miR-133a | uuugguccccuucaaccagcug | 34 | 21 | 1.62 | 5.05E-01 |
| SEQ ID NO: 614 | 614 | hsa-miR-485-3p | gucauacacggcucuccucucu | 1 | 2 | 0.64 | 5.07E-01 |
| SEQ ID NO: 615 | 615 | hsa-miR-541* | aaaggauucugcugucggucccacu | 1 | 1 | 1.00 | 5.12E-01 |
| SEQ ID NO: 616 | 616 | hsa-miR-374b | auauaauacaaccugcuaagug | 126 | 22 | 5.87 | 5.12E-01 |
| SEQ ID NO: 617 | 617 | hsa-miR-329 | aacacaccugguuaaccucuuu | 1 | 2 | 0.64 | 5.15E-01 |
| SEQ ID NO: 618 | 618 | hsa-miR-483-5p | aagacgggaggaaagaagggag | 4542 | 3573 | 1.27 | 5.15E-01 |

Figure 10B (cont'd)

| | | | | | | | |
|---|---|---|---|---|---|---|---|
| SEQ ID NO: 619 | 619 | hsa-miR-885-3p | aggcagcgggguguaguggaua | 463 | 1040 | 0.45 | 5.16E-01 |
| SEQ ID NO: 620 | 620 | hsa-let-7i* | cugcgcaagcuacugccuugcu | 5 | 1 | 5.22 | 5.16E-01 |
| SEQ ID NO: 621 | 621 | hsa-miR-935 | ccaguuaccgcuuccgcuaccgc | 1 | 1 | 1.00 | 5.16E-01 |
| SEQ ID NO: 622 | 622 | hsa-miR-130b | cagugcaaugaugaaagggcau | 388 | 185 | 2.09 | 5.23E-01 |
| SEQ ID NO: 623 | 623 | hsa-miR-1274a | gucccuguucaggcgcca | 94 | 12 | 7.82 | 5.23E-01 |
| SEQ ID NO: 624 | 624 | hsa-miR-1226 | ucaccagcccuguguucccuag | 1 | 4 | 0.23 | 5.28E-01 |
| SEQ ID NO: 625 | 625 | hsa-miR-518e* | cucuagagggaagcgcuuucug | 2 | 3 | 0.83 | 5.30E-01 |
| SEQ ID NO: 626 | 626 | hsa-miR-1225-3p | ugagccccugugccgcccccag | 40 | 43 | 0.93 | 5.30E-01 |
| SEQ ID NO: 627 | 627 | hsa-miR-923 | gucagcggaggaaaagaaacu | 24784 | 20350 | 1.22 | 5.31E-01 |
| SEQ ID NO: 628 | 628 | hsa-miR-196a* | cggcaacaagaaacugccugag | 15 | 19 | 0.82 | 5.31E-01 |
| SEQ ID NO: 629 | 629 | hsa-miR-1270 | cuggagauauggaagagcugugu | 32 | 30 | 1.04 | 5.32E-01 |
| SEQ ID NO: 630 | 630 | hsa-miR-1271 | cuuggcaccuagcaagcacuca | 16 | 2 | 10.14 | 5.32E-01 |
| SEQ ID NO: 631 | 631 | hsa-miR-610 | ugagcuaaaugugugcuggga | 24 | 36 | 0.66 | 5.32E-01 |
| SEQ ID NO: 632 | 632 | hsa-miR-574-3p | cacgcucaugcacacacccaca | 48 | 59 | 0.82 | 5.33E-01 |
| SEQ ID NO: 633 | 633 | hsa-miR-1282 | ucguuugccuuuuucugcuu | 29 | 2 | 18.93 | 5.34E-01 |
| SEQ ID NO: 634 | 634 | hsa-miR-10b* | acagauucgauucuaggggaau | 1 | 1 | 1.00 | 5.34E-01 |
| SEQ ID NO: 635 | 635 | hsa-miR-216a | uaaucucagcuggcaacuguga | 1 | 1 | 1.00 | 5.34E-01 |
| SEQ ID NO: 636 | 636 | hsa-miR-144* | ggauaucaucauauacuguaag | 341 | 451 | 0.76 | 5.34E-01 |
| SEQ ID NO: 637 | 637 | hsa-miR-23a* | gggguuccuggggaugggauuu | 74 | 122 | 0.60 | 5.36E-01 |
| SEQ ID NO: 638 | 638 | hsa-miR-499-5p | uuaagacuugcagugauguuu | 1 | 1 | 1.00 | 5.40E-01 |
| SEQ ID NO: 639 | 639 | hsa-miR-183 | uauggcacugguagaauucacu | 90 | 27 | 3.39 | 5.41E-01 |
| SEQ ID NO: 640 | 640 | hsa-miR-490-3p | caaccuggaggacuccaugcug | 1 | 1 | 1.00 | 5.46E-01 |
| SEQ ID NO: 641 | 641 | hsa-miR-330-3p | gcaaagcacacggccugcagaga | 15 | 11 | 1.38 | 5.48E-01 |
| SEQ ID NO: 642 | 642 | hsa-let-7g* | cuguacaggccacugccuugc | 1 | 1 | 1.00 | 5.48E-01 |
| SEQ ID NO: 643 | 643 | hsa-miR-483-3p | ucacuccucuccucccgucuu | 13 | 30 | 0.43 | 5.51E-01 |
| SEQ ID NO: 644 | 644 | hsa-miR-214 | acagcaggcacagacaggcagu | 29 | 3 | 9.36 | 5.55E-01 |
| SEQ ID NO: 645 | 645 | hsa-miR-34b* | uaggcagugucauuagcugauug | 1 | 1 | 1.00 | 5.55E-01 |
| SEQ ID NO: 646 | 646 | hsa-miR-302d* | acuuuaacauggaggcacuugc | 1 | 11 | 0.09 | 5.58E-01 |
| SEQ ID NO: 647 | 647 | hsa-miR-382 | gaaguuguucgugguggauucg | 10 | 2 | 6.14 | 5.61E-01 |
| SEQ ID NO: 648 | 648 | hsa-miR-454* | acccuaucaauauugucucugc | 27 | 21 | 1.28 | 5.61E-01 |
| SEQ ID NO: 649 | 649 | hsa-miR-1202 | gugccagcugcaguggggggag | 72 | 87 | 0.83 | 5.61E-01 |

Figure 10B (cont'd)

| | | | | | | | |
|---|---|---|---|---|---|---|---|
| SEQ ID NO: 650 | 650 | hsa-miR-202 | agagguauagggcaugggaa | 112 | 61 | 1.83 | 5.64E-01 |
| SEQ ID NO: 651 | 651 | hsa-miR-544 | auucugcauuuuuagcaaguuc | 1 | 1 | 1.00 | 5.64E-01 |
| SEQ ID NO: 652 | 652 | hsa-miR-593 | ugucucugcuggggguuucu | 30 | 46 | 0.66 | 5.64E-01 |
| SEQ ID NO: 653 | 653 | hsa-miR-760 | cggcucugggucugugggga | 35 | 53 | 0.65 | 5.64E-01 |
| SEQ ID NO: 654 | 654 | hsa-miR-940 | aaggcagggcccccgcuccccc | 112 | 67 | 1.67 | 5.65E-01 |
| SEQ ID NO: 655 | 655 | hsa-let-7e* | cuauacggccuccuagcuuucc | 1 | 1 | 1.00 | 5.68E-01 |
| SEQ ID NO: 656 | 656 | hsa-miR-1237 | uccuucugcuccguccccccag | 38 | 30 | 1.24 | 5.70E-01 |
| SEQ ID NO: 657 | 657 | hsa-miR-18b* | ugcccuaaaugccccuucuggc | 25 | 18 | 1.36 | 5.76E-01 |
| SEQ ID NO: 658 | 658 | hsa-miR-630 | aguauucuguaccagggaaggu | 4 | 7 | 0.61 | 5.76E-01 |
| SEQ ID NO: 659 | 659 | hsa-miR-519e* | uucuccaaaagggagcacuuuc | 17 | 20 | 0.87 | 5.80E-01 |
| SEQ ID NO: 660 | 660 | hsa-miR-452 | aacuguuugcagaggaaacuga | 3 | 1 | 2.67 | 5.81E-01 |
| SEQ ID NO: 661 | 661 | hsa-miR-26b* | ccuguucuccauuacuuggcuc | 1 | 4 | 0.24 | 5.81E-01 |
| SEQ ID NO: 662 | 662 | hsa-miR-516b | aucuggagguaagaagcacuuu | 52 | 56 | 0.92 | 5.81E-01 |
| SEQ ID NO: 663 | 663 | hsa-miR-299-3p | uaugugggaugguaaaccgcuu | 59 | 55 | 1.06 | 5.82E-01 |
| SEQ ID NO: 664 | 664 | hsa-miR-381 | uauacaagggcaagcucucugu | 7 | 1 | 7.44 | 5.82E-01 |
| SEQ ID NO: 665 | 665 | hsa-miR-340 | uuauaaagcaaugagacugauu | 80 | 22 | 3.70 | 5.82E-01 |
| SEQ ID NO: 666 | 666 | hsa-miR-132 | uaacagucuacagccauggucg | 25 | 4 | 5.62 | 5.82E-01 |
| SEQ ID NO: 667 | 667 | hsa-miR-142-3p | uguaguguuuccuacuuuaugga | 1 | 1 | 1.00 | 5.82E-01 |
| SEQ ID NO: 668 | 668 | hsa-miR-125b-1* | acggguuaggcucuugggagcu | 60 | 56 | 0.88 | 5.87E-01 |
| SEQ ID NO: 669 | 669 | hsa-miR-30c-2* | cugggagaaggcuguuuacucu | 69 | 57 | 1.21 | 5.87E-01 |
| SEQ ID NO: 670 | 670 | hsa-miR-627 | gugagucucuaagaaaagagga | 1 | 1 | 1.00 | 5.87E-01 |
| SEQ ID NO: 671 | 671 | hsa-miR-1908 | cggcggggacggcgauugguc | 5945 | 6598 | 0.90 | 5.90E-01 |
| SEQ ID NO: 672 | 672 | hsa-miR-1267 | ccuguugaaguguaaucccca | 10 | 2 | 6.14 | 5.90E-01 |
| SEQ ID NO: 673 | 673 | hsa-miR-507 | uuuugcaccuuuuggagugaa | 1 | 1 | 1.00 | 5.90E-01 |
| SEQ ID NO: 674 | 674 | hsa-miR-188-5p | caucccuugcaugguggaggg | 21 | 22 | 0.97 | 5.93E-01 |
| SEQ ID NO: 675 | 675 | hsa-miR-486-3p | cggggcagcucaguacaggau | 38 | 19 | 2.02 | 5.93E-01 |
| SEQ ID NO: 676 | 676 | hsa-miR-596 | aagccugcccggcuccucggg | 1 | 3 | 0.32 | 5.96E-01 |
| SEQ ID NO: 677 | 677 | hsa-miR-193a-5p | ugggucuuugcgggcgagauga | 47 | 30 | 1.54 | 6.00E-01 |
| SEQ ID NO: 678 | 678 | hsa-miR-671-3p | uccgguucucagggcuccacc | 21 | 14 | 1.54 | 6.02E-01 |
| SEQ ID NO: 679 | 679 | hsa-miR-24-1* | ugccuacugagcugauaucagu | 1 | 1 | 1.00 | 6.03E-01 |
| SEQ ID NO: 680 | 680 | hsa-miR-19b-2* | aguuuugcagguuugcauuuca | 1 | 1 | 1.00 | 6.09E-01 |

Figure 10B (cont'd)

| | | | | | | | |
|---|---|---|---|---|---|---|---|
| SEQ ID NO: 681 | 681 | hsa-miR-1308 | gcaugggugguucagugg | 15422 | 9313 | 1.66 | 6.12E-01 |
| SEQ ID NO: 682 | 682 | hsa-miR-208a | auaagacgagcaaaaagcuugu | 20 | 15 | 1.34 | 6.12E-01 |
| SEQ ID NO: 683 | 683 | hsa-miR-135a | uauggcuuuuuauuccuauguga | 1 | 1 | 1.00 | 6.14E-01 |
| SEQ ID NO: 684 | 684 | hsa-miR-331-5p | cuagguaugguccagggaucc | 22 | 21 | 1.05 | 6.14E-01 |
| SEQ ID NO: 685 | 685 | hsa-miR-181c | aacauucaaccugucggugagu | 130 | 22 | 5.99 | 6.19E-01 |
| SEQ ID NO: 686 | 686 | hsa-miR-640 | augauccaggaaccugccucu | 4 | 4 | 0.90 | 6.24E-01 |
| SEQ ID NO: 687 | 687 | hsa-miR-1909 | cgcaggggccgggugcucaccg | 154 | 133 | 1.16 | 6.29E-01 |
| SEQ ID NO: 688 | 688 | hsa-miR-629 | uggguuuacguugggagaacu | 106 | 63 | 1.68 | 6.29E-01 |
| SEQ ID NO: 689 | 689 | hsa-miR-10a | uacccuguagauccgaauuugug | 34 | 30 | 1.12 | 6.29E-01 |
| SEQ ID NO: 690 | 690 | hsa-miR-491-5p | aguggggaacccuuccaugagg | 101 | 97 | 1.04 | 6.29E-01 |
| SEQ ID NO: 691 | 691 | hsa-miR-492 | aggaccugcgggacaagauucuu | 89 | 88 | 1.01 | 6.29E-01 |
| SEQ ID NO: 692 | 692 | hsa-miR-516a-5p | uucucgaggaaagaagcacuuuc | 40 | 59 | 0.67 | 6.29E-01 |
| SEQ ID NO: 693 | 693 | hsa-miR-510 | uacucaggagaguggcaaucac | 27 | 8 | 3.21 | 6.29E-01 |
| SEQ ID NO: 694 | 694 | hsa-miR-1915 | ccccagggcgacgcggcggg | 2224 | 3080 | 0.72 | 6.29E-01 |
| SEQ ID NO: 695 | 695 | hsa-miR-518c* | ucucuggagggaagcacuuucug | 110 | 64 | 1.72 | 6.29E-01 |
| SEQ ID NO: 696 | 696 | hsa-miR-1273 | gggcgacaaagcaagacucuuucuu | 26 | 31 | 0.84 | 6.29E-01 |
| SEQ ID NO: 697 | 697 | hsa-miR-25* | aggcggagacuugggcaauug | 112 | 68 | 1.63 | 6.29E-01 |
| SEQ ID NO: 698 | 698 | hsa-miR-744 | ugcggggcuagggcuaacagca | 364 | 388 | 0.94 | 6.29E-01 |
| SEQ ID NO: 699 | 699 | hsa-miR-550 | agugccugagggaguaagagccc | 136 | 91 | 1.50 | 6.29E-01 |
| SEQ ID NO: 700 | 700 | hsa-miR-890 | uacuuggaaaggcaucaguug | 21 | 12 | 1.78 | 6.31E-01 |
| SEQ ID NO: 701 | 701 | hsa-miR-1303 | uuuagagacggggucuugcucu | 42 | 31 | 1.34 | 6.32E-01 |
| SEQ ID NO: 702 | 702 | hsa-miR-650 | aggaggcagcgcucucaggac | 15 | 12 | 1.20 | 6.32E-01 |
| SEQ ID NO: 703 | 703 | hsa-miR-1227 | cgugccacccuuuuccccag | 32 | 30 | 1.07 | 6.32E-01 |
| SEQ ID NO: 704 | 704 | hsa-miR-595 | gaagugugccgugguguguc u | 12 | 11 | 1.06 | 6.32E-01 |
| SEQ ID NO: 705 | 705 | hsa-miR-1255b | cggaugagcaaagaaagugguu | 88 | 77 | 1.15 | 6.32E-01 |
| SEQ ID NO: 706 | 706 | hsa-miR-1252 | agaaggaaauugaauucauuua | 1 | 1 | 1.00 | 6.32E-01 |
| SEQ ID NO: 707 | 707 | hsa-miR-455-3p | gcaguccaugggcauauacac | 1 | 1 | 1.00 | 6.34E-01 |
| SEQ ID NO: 708 | 708 | hsa-miR-345 | gcugacuccuaguccagggcuc | 168 | 34 | 4.88 | 6.34E-01 |
| SEQ ID NO: 709 | 709 | hsa-miR-96 | uuuggcacuagcacauuuuugcu | 107 | 36 | 2.96 | 6.34E-01 |
| SEQ ID NO: 710 | 710 | hsa-miR-1321 | cagggaggugaaugugau | 74 | 59 | 1.26 | 6.35E-01 |
| SEQ ID NO: 711 | 711 | hsa-miR-513c | uucucaaggaggugucguuuau | 69 | 45 | 1.52 | 6.36E-01 |

Figure 10B (cont'd)

| | | | | | | | |
|---|---|---|---|---|---|---|---|
| SEQ ID NO: 712 | 712 | hsa-miR-548c-5p | aaaaguaauugcgguuuuugcc | 1 | 1 | 1.00 | 6.39E-01 |
| SEQ ID NO: 713 | 713 | hsa-miR-663 | aggcggggcgccgcgggaccgc | 716 | 1175 | 0.61 | 6.42E-01 |
| SEQ ID NO: 714 | 714 | hsa-miR-320c | aaaagcuggguugagagggu | 5382 | 6142 | 0.88 | 6.44E-01 |
| SEQ ID NO: 715 | 715 | hsa-miR-320b | aaaagcuggguugagagggcaa | 6349 | 6349 | 1.00 | 6.44E-01 |
| SEQ ID NO: 716 | 716 | hsa-miR-654-5p | uggugggccgcagaacaugugc | 124 | 99 | 1.26 | 6.46E-01 |
| SEQ ID NO: 717 | 717 | hsa-miR-326 | ccucugggcccuuccuccag | 21 | 20 | 1.04 | 6.46E-01 |
| SEQ ID NO: 718 | 718 | hsa-miR-1825 | uccagugcccuccucucc | 21 | 30 | 0.69 | 6.46E-01 |
| SEQ ID NO: 719 | 719 | hsa-miR-328 | cuggcccucucugcccuuccgu | 72 | 68 | 1.06 | 6.49E-01 |
| SEQ ID NO: 720 | 720 | hsa-miR-146b-5p | ugagaacugaauuccauaggcu | 93 | 67 | 1.37 | 6.49E-01 |
| SEQ ID NO: 721 | 721 | hsa-miR-886-3p | cgcgggugcuuacugacccuu | 12 | 1 | 12.33 | 6.60E-01 |
| SEQ ID NO: 722 | 722 | hsa-miR-1909* | ugagugccggugccugcccug | 21 | 16 | 1.26 | 6.65E-01 |
| SEQ ID NO: 723 | 723 | hsa-miR-1469 | cucggcgcggggcgcgggcucc | 962 | 1298 | 0.74 | 6.70E-01 |
| SEQ ID NO: 724 | 724 | hsa-miR-338-3p | uccagcaucagugauuuuguug | 14 | 1 | 13.72 | 6.72E-01 |
| SEQ ID NO: 725 | 725 | hsa-miR-886-5p | cgggucggaguuagcucaagcgg | 126 | 88 | 1.44 | 6.79E-01 |
| SEQ ID NO: 726 | 726 | hsa-miR-601 | uggucuaggauuguuggaggag | 21 | 22 | 0.94 | 6.79E-01 |
| SEQ ID NO: 727 | 727 | hsa-miR-1298 | uucauucggcuguccagaugua | 1 | 1 | 1.00 | 6.80E-01 |
| SEQ ID NO: 728 | 728 | hsa-miR-1910 | ccaguccugugccugccgccu | 7 | 12 | 0.64 | 6.81E-01 |
| SEQ ID NO: 729 | 729 | hsa-miR-1226* | gugagggcaugcaggccuggauggggg | 99 | 97 | 1.02 | 6.88E-01 |
| SEQ ID NO: 730 | 730 | hsa-miR-421 | aucaacagacauuaauugggcgc | 218 | 1 | 217.67 | 6.93E-01 |
| SEQ ID NO: 731 | 731 | hsa-miR-1471 | gcccgcguguggagccaggugu | 38 | 34 | 1.12 | 6.95E-01 |
| SEQ ID NO: 732 | 732 | hsa-miR-150* | cugguacaggccugggggacag | 101 | 102 | 0.99 | 7.00E-01 |
| SEQ ID NO: 733 | 733 | hsa-miR-1229 | cucucaccacugcccucccacag | 28 | 34 | 0.83 | 7.00E-01 |
| SEQ ID NO: 734 | 734 | hsa-miR-17* | acugcagugaaggcacuuguag | 194 | 91 | 2.14 | 7.03E-01 |
| SEQ ID NO: 735 | 735 | hsa-miR-320d | aaaagcuggguugagagga | 4319 | 4391 | 0.98 | 7.03E-01 |
| SEQ ID NO: 736 | 736 | hsa-miR-10b | uacccuguagaaccgaauuugug | 22 | 8 | 2.67 | 7.06E-01 |
| SEQ ID NO: 737 | 737 | hsa-miR-766 | acuccagccccacagccucagc | 106 | 71 | 1.50 | 7.17E-01 |
| SEQ ID NO: 738 | 738 | hsa-miR-600 | acuuacagacaagagccuugcuc | 1 | 1 | 1.00 | 7.24E-01 |
| SEQ ID NO: 739 | 739 | hsa-miR-641 | aaagacauaggauagagucaccuc | 34 | 22 | 1.58 | 7.29E-01 |
| SEQ ID NO: 740 | 740 | hsa-miR-340* | uccgucucaguuacuuuauagc | 4 | 1 | 4.00 | 7.30E-01 |
| SEQ ID NO: 741 | 741 | hsa-miR-616* | acucaaaacccuucagugacuu | 1 | 2 | 0.64 | 7.30E-01 |
| SEQ ID NO: 742 | 742 | hsa-miR-520a-5p | cuccagagggaaguacuuucu | 15 | 19 | 0.82 | 7.34E-01 |

Figure 10B (cont'd)

| | | | | | | | |
|---|---|---|---|---|---|---|---|
| SEQ ID NO: 743 | 743 | hsa-miR-1179 | aagcauucuuucauugguugg | 1 | 1 | 1.00 | 7.34E-01 |
| SEQ ID NO: 744 | 744 | hsa-miR-1178 | uugcucacuguucuucccuag | 1 | 1 | 1.00 | 7.34E-01 |
| SEQ ID NO: 745 | 745 | hsa-miR-30b* | cugggagguggauguuuacuuc | 89 | 99 | 0.90 | 7.35E-01 |
| SEQ ID NO: 746 | 746 | hsa-miR-155* | cuccuacauauuagcauuaaca | 1 | 1 | 1.00 | 7.35E-01 |
| SEQ ID NO: 747 | 747 | hsa-miR-138-1* | gcuacuucacaacaccagggcc | 20 | 4 | 4.71 | 7.37E-01 |
| SEQ ID NO: 748 | 748 | hsa-miR-501-5p | aauccuuugucccuggguugaga | 5 | 3 | 1.54 | 7.37E-01 |
| SEQ ID NO: 749 | 749 | hsa-miR-191 | caacggaaucccaaaagcagcug | 31578 | 27467 | 1.15 | 7.40E-01 |
| SEQ ID NO: 750 | 750 | hsa-miR-107 | agcagcauuguacagggcuauca | 4106 | 4916 | 0.84 | 7.43E-01 |
| SEQ ID NO: 751 | 751 | hsa-miR-639 | aucgcugcgguugcgagcgcugu | 1 | 1 | 1.00 | 7.43E-01 |
| SEQ ID NO: 752 | 752 | hsa-miR-518d-3p | caaagcgcuucccuuuggagc | 1 | 1 | 1.00 | 7.47E-01 |
| SEQ ID NO: 753 | 753 | hsa-miR-106b | uaaagugcugacagugcagau | 3080 | 2320 | 1.33 | 7.47E-01 |
| SEQ ID NO: 754 | 754 | hsa-miR-129-3p | aagcccuuaccccaaaaagcau | 4 | 28 | 0.14 | 7.48E-01 |
| SEQ ID NO: 755 | 755 | hsa-miR-1306 | acguuggcucugguggug | 7 | 4 | 1.61 | 7.48E-01 |
| SEQ ID NO: 756 | 756 | hsa-miR-187* | ggcuacaacacaggacccgggc | 89 | 68 | 1.29 | 7.54E-01 |
| SEQ ID NO: 757 | 757 | hsa-miR-125b | ucccugagacccuaacuuguga | 66 | 38 | 1.71 | 7.63E-01 |
| SEQ ID NO: 758 | 758 | hsa-miR-642 | gucccucuccaaaugugucuug | 1 | 1 | 1.00 | 7.68E-01 |
| SEQ ID NO: 759 | 759 | hsa-miR-30a* | cuuucagucggauguuugcagc | 1 | 1 | 1.00 | 7.68E-01 |
| SEQ ID NO: 760 | 760 | hsa-miR-139-5p | ucuacagugcacgugucuccag | 2 | 4 | 0.37 | 7.66E-01 |
| SEQ ID NO: 761 | 761 | hsa-miR-1307 | acucggcguggcgucggucgug | 82 | 71 | 1.16 | 7.72E-01 |
| SEQ ID NO: 762 | 762 | hsa-miR-769-3p | cugggaucuccggggucuugguu | 26 | 16 | 1.64 | 7.72E-01 |
| SEQ ID NO: 763 | 763 | hsa-miR-532-5p | caugccuugaguguaggaccgu | 121 | 93 | 1.31 | 7.76E-01 |
| SEQ ID NO: 764 | 764 | hsa-miR-7-1* | caacaaaucacagucugccaua | 16 | 28 | 0.56 | 7.79E-01 |
| SEQ ID NO: 765 | 765 | hsa-miR-196a | uagguaguuucauguuguuggg | 4 | 1 | 4.00 | 7.81E-01 |
| SEQ ID NO: 766 | 766 | hsa-miR-1296 | uuagggcccuggcuccaucucc | 15 | 4 | 3.45 | 7.82E-01 |
| SEQ ID NO: 767 | 767 | hsa-miR-191* | gcugcgcuuggauuucgucccc | 53 | 47 | 1.13 | 7.86E-01 |
| SEQ ID NO: 768 | 768 | hsa-miR-221 | agcuacauugucugcuggguuuc | 382 | 540 | 0.71 | 7.86E-01 |
| SEQ ID NO: 769 | 769 | hsa-miR-92a-1* | agguugggaucgguugcaaugcu | 21 | 22 | 0.95 | 7.92E-01 |
| SEQ ID NO: 770 | 770 | hsa-miR-1285 | ucugggcaacaaagugagaccu | 301 | 53 | 5.67 | 7.98E-01 |
| SEQ ID NO: 771 | 771 | hsa-miR-518f* | cucuagagggaagcacuuucuc | 25 | 59 | 0.43 | 7.98E-01 |
| SEQ ID NO: 772 | 772 | hsa-miR-1233 | ugagcccuguccucccgcag | 8 | 12 | 0.68 | 7.98E-01 |
| SEQ ID NO: 773 | 773 | hsa-miR-1290 | uggauuuuuggaucaggga | 40 | 28 | 1.40 | 7.98E-01 |

Figure 10B (cont'd)

| | | | | | | | |
|---|---|---|---|---|---|---|---|
| SEQ ID NO: 774 | 774 | hsa-miR-598 | uacgucaucguugucaucguca | 12 | 1 | 12.22 | 8.02E-01 |
| SEQ ID NO: 775 | 775 | hsa-miR-769-5p | ugagaccucuggguucugagcu | 15 | 4 | 4.18 | 8.02E-01 |
| SEQ ID NO: 776 | 776 | hsa-miR-614 | gaacgccuguucuugccaggugg | 9 | 4 | 2.16 | 8.02E-01 |
| SEQ ID NO: 777 | 777 | hsa-miR-578 | cuucuugugcucuaggauugu | 1 | 1 | 1.00 | 8.02E-01 |
| SEQ ID NO: 778 | 778 | hsa-miR-1301 | uugcagcugccugggagugacuuc | 23 | 16 | 1.25 | 8.04E-01 |
| SEQ ID NO: 779 | 779 | hsa-miR-515-5p | uucuccaaaagaaagcacuuucug | 1 | 1 | 1.00 | 8.09E-01 |
| SEQ ID NO: 780 | 780 | hsa-miR-564 | aggcacggugucagcaggc | 57 | 47 | 1.21 | 8.14E-01 |
| SEQ ID NO: 781 | 781 | hsa-miR-634 | aaccagcaccccaacuuuggac | 37 | 49 | 0.75 | 8.15E-01 |
| SEQ ID NO: 782 | 782 | hsa-miR-518b | caaagcgcucccciuuuagaggu | 21 | 4 | 4.63 | 8.15E-01 |
| SEQ ID NO: 783 | 783 | hsa-miR-941 | cacccggcugugugcacaugugc | 40 | 4 | 9.39 | 8.23E-01 |
| SEQ ID NO: 784 | 784 | hsa-miR-376c | aacauagaggaaauuccacgu | 1 | 1 | 1.00 | 8.28E-01 |
| SEQ ID NO: 785 | 785 | hsa-miR-195* | ccaauauuggcugugcugcucc | 1 | 1 | 1.00 | 8.28E-01 |
| SEQ ID NO: 786 | 786 | hsa-miR-518a-5p | cugcaaagggaagcccuuuc | 55 | 34 | 1.63 | 8.29E-01 |
| SEQ ID NO: 787 | 787 | hsa-miR-557 | guuugcacggugggccuugucu | 115 | 132 | 0.87 | 8.33E-01 |
| SEQ ID NO: 788 | 788 | hsa-miR-1228* | gugggcgggggcaggugugug | 5946 | 5803 | 1.02 | 8.33E-01 |
| SEQ ID NO: 789 | 789 | hsa-miR-22* | aguucuucaguggcaagcuuua | 70 | 36 | 1.93 | 8.33E-01 |
| SEQ ID NO: 790 | 790 | hsa-miR-1234 | ucggccugaccacccaccccac | 54 | 82 | 0.65 | 8.33E-01 |
| SEQ ID NO: 791 | 791 | hsa-miR-149* | agggagggacgggggcugugc | 18004 | 13308 | 1.35 | 8.37E-01 |
| SEQ ID NO: 792 | 792 | hsa-miR-30c-1* | cugggagaggguuguuuacucc | 101 | 101 | 1.00 | 8.37E-01 |
| SEQ ID NO: 793 | 793 | hsa-miR-200c* | cgucuuacccagcaguguuugg | 1 | 1 | 1.00 | 8.37E-01 |
| SEQ ID NO: 794 | 794 | hsa-miR-1181 | ccgucgccgccacccgagccg | 21 | 28 | 0.75 | 8.37E-01 |
| SEQ ID NO: 795 | 795 | hsa-miR-323-5p | aggugguccguggcgcguucgc | 58 | 67 | 0.86 | 8.40E-01 |
| SEQ ID NO: 796 | 796 | hsa-miR-1231 | gugucugggcggacagcugc | 43 | 30 | 1.42 | 8.40E-01 |
| SEQ ID NO: 797 | 797 | hsa-miR-203 | gugaaauguuuaggaccacuag | 1 | 1 | 1.00 | 8.42E-01 |
| SEQ ID NO: 798 | 798 | hsa-miR-302c* | uuuaacaugggggguaccugcug | 69 | 19 | 3.67 | 8.42E-01 |
| SEQ ID NO: 799 | 799 | hsa-miR-99a | aacccguagauccgaucuugug | 93 | 22 | 4.17 | 8.42E-01 |
| SEQ ID NO: 800 | 800 | hsa-miR-146a | ugagaacugaauuccauggguu | 136 | 129 | 1.05 | 8.42E-01 |
| SEQ ID NO: 801 | 801 | hsa-miR-656 | aauauuauacagucaaccucu | 1 | 1 | 1.00 | 8.42E-01 |
| SEQ ID NO: 802 | 802 | hsa-miR-526b* | gaaagugcuuccuuuuagaggc | 1 | 1 | 1.00 | 8.43E-01 |
| SEQ ID NO: 803 | 803 | hsa-miR-148b* | aaguucuguuauacacucaggc | 1 | 1 | 1.00 | 8.44E-01 |
| SEQ ID NO: 804 | 804 | hsa-miR-181a | aacauucaacgcugucggugagu | 587 | 133 | 4.41 | 8.48E-01 |

Figure 10B (cont'd)

| | | | | | | | |
|---|---|---|---|---|---|---|---|
| SEQ ID NO: 805 | 805 | hsa-miR-622 | acagucugcugagguuggagc | 7 | 3 | 2.18 | 8.53E-01 |
| SEQ ID NO: 806 | 806 | hsa-miR-125a-5p | ucccugagacccuuuaaccuguga | 83 | 22 | 3.85 | 8.53E-01 |
| SEQ ID NO: 807 | 807 | hsa-miR-152 | ucagugcaugacagaacuugg | 17 | 12 | 1.39 | 8.59E-01 |
| SEQ ID NO: 808 | 808 | hsa-miR-197 | uucaccaccuucuccacccagc | 144 | 112 | 1.29 | 8.59E-01 |
| SEQ ID NO: 809 | 809 | hsa-miR-27b | uucacaguggcuaaguucugc | 73 | 34 | 2.17 | 8.65E-01 |
| SEQ ID NO: 810 | 810 | hsa-miR-1236 | ccucuuccccuugucucuccag | 40 | 44 | 0.90 | 8.65E-01 |
| SEQ ID NO: 811 | 811 | hsa-miR-495 | aaacaaacauggugcacuucuu | 3 | 4 | 0.73 | 8.68E-01 |
| SEQ ID NO: 812 | 812 | hsa-miR-143 | ugagaugaagcacuguagcuc | 21 | 12 | 1.71 | 8.69E-01 |
| SEQ ID NO: 813 | 813 | hsa-miR-362-3p | aacacaccuauucaaggauuca | 16 | 15 | 1.10 | 8.78E-01 |
| SEQ ID NO: 814 | 814 | hsa-miR-675 | uggugcggagagggcccacagug | 185 | 172 | 1.07 | 8.78E-01 |
| SEQ ID NO: 815 | 815 | hsa-miR-1274b | ucccuguucgggcgcca | 177 | 64 | 2.78 | 8.84E-01 |
| SEQ ID NO: 816 | 816 | hsa-miR-139-3p | ggagacgcggcccuguuggagu | 43 | 34 | 1.28 | 8.86E-01 |
| SEQ ID NO: 817 | 817 | hsa-miR-130b* | acucuuucccuguugcacuac | 3 | 1 | 2.67 | 8.86E-01 |
| SEQ ID NO: 818 | 818 | hsa-miR-1228 | ucacaccugccucgcccccc | 40 | 141 | 0.28 | 8.89E-01 |
| SEQ ID NO: 819 | 819 | hsa-miR-1180 | uuuccggcucgcgugggugugu | 61 | 21 | 2.89 | 8.94E-01 |
| SEQ ID NO: 820 | 820 | hsa-miR-575 | gagccaguuggacaggagc | 59 | 71 | 0.83 | 8.94E-01 |
| SEQ ID NO: 821 | 821 | hsa-miR-134 | ugugacugguugaccagagggg | 56 | 34 | 1.64 | 8.94E-01 |
| SEQ ID NO: 822 | 822 | hsa-miR-875-3p | ccuggaaacacugagguugug | 7 | 1 | 6.78 | 8.94E-01 |
| SEQ ID NO: 823 | 823 | hsa-miR-92b* | agggacgggacgcggugcagug | 1344 | 2426 | 0.55 | 8.95E-01 |
| SEQ ID NO: 824 | 824 | hsa-miR-660 | uacccauugcauaucggaguug | 130 | 57 | 2.29 | 8.99E-01 |
| SEQ ID NO: 825 | 825 | hsa-miR-526b | cucuugagggaagcacuuucugu | 68 | 34 | 2.01 | 8.99E-01 |
| SEQ ID NO: 826 | 826 | hsa-miR-422a | acuggacuuagggucagaaggc | 166 | 1 | 166.44 | 9.00E-01 |
| SEQ ID NO: 827 | 827 | hsa-miR-1250 | acggugcuggauguggccuuu | 38 | 41 | 0.92 | 9.01E-01 |
| SEQ ID NO: 828 | 828 | hsa-miR-938 | ugcccuuaaaggugaacccagu | 2 | 1 | 2.22 | 9.05E-01 |
| SEQ ID NO: 829 | 829 | hsa-miR-608 | agggguugguguugggacagcuccgu | 107 | 97 | 1.10 | 9.08E-01 |
| SEQ ID NO: 830 | 830 | hsa-miR-1279 | ucauauugcuucuuucu | 1 | 1 | 1.00 | 9.08E-01 |
| SEQ ID NO: 831 | 831 | hsa-miR-1249 | acgcccuucccccccuucuuca | 25 | 30 | 0.81 | 9.08E-01 |
| SEQ ID NO: 832 | 832 | hsa-miR-661 | ugccugggucucuggccugcgcgu | 4 | 1 | 4.00 | 9.22E-01 |
| SEQ ID NO: 833 | 833 | hsa-miR-1208 | ucacuguucagacaggcgga | 27 | 19 | 1.44 | 9.22E-01 |
| SEQ ID NO: 834 | 834 | hsa-miR-130a | cagugcaauguuaaaagggcau | 746 | 875 | 0.85 | 9.25E-01 |
| SEQ ID NO: 835 | 835 | hsa-miR-450b-5p | uuuugcaauauguuccugaaua | 1 | 1 | 1.00 | 9.25E-01 |

Figure 10B (cont'd)

| | | | | | | | |
|---|---|---|---|---|---|---|---|
| SEQ ID NO: 836 | 836 | hsa-miR-432 | ucuuggaguaggucauugggugg | 42 | 39 | 1.07 | 9.27E-01 |
| SEQ ID NO: 837 | 837 | hsa-miR-409-3p | gaauguugcucggugaaccccu | 97 | 68 | 1.42 | 9.30E-01 |
| SEQ ID NO: 838 | 838 | hsa-miR-527 | cugcaaagggaagcccuuuc | 75 | 68 | 1.09 | 9.41E-01 |
| SEQ ID NO: 839 | 839 | hsa-miR-877* | uccucuucucccuccucccag | 21 | 21 | 0.99 | 9.47E-01 |
| SEQ ID NO: 840 | 840 | hsa-miR-1238 | cuuccucgucugucugcccc | 52 | 59 | 0.88 | 9.54E-01 |
| SEQ ID NO: 841 | 841 | hsa-miR-517* | ccucuagauggaagcacugucu | 17 | 12 | 1.39 | 9.61E-01 |
| SEQ ID NO: 842 | 842 | hsa-miR-193b* | cgggguuuugagggcgagauga | 81 | 109 | 0.75 | 9.66E-01 |
| SEQ ID NO: 843 | 843 | hsa-miR-524-5p | cuacaaagggaagcacuuucuc | 31 | 29 | 1.06 | 9.67E-01 |
| SEQ ID NO: 844 | 844 | hsa-miR-1258 | aguuaggauuaggucguggaa | 16 | 12 | 1.27 | 9.67E-01 |
| SEQ ID NO: 845 | 845 | hsa-miR-154 | uagguuauccguguugccuucg | 1 | 1 | 1.00 | 9.70E-01 |
| SEQ ID NO: 846 | 846 | hsa-miR-637 | acugggggcuuucgggcucugcgu | 90 | 71 | 1.27 | 9.72E-01 |
| SEQ ID NO: 847 | 847 | hsa-miR-568 | auguauaaauguauacacac | 2 | 2 | 1.00 | 9.76E-01 |
| SEQ ID NO: 848 | 848 | hsa-miR-155 | uuaaugcuaaucgugauaggggu | 128 | 15 | 8.63 | 9.83E-01 |
| SEQ ID NO: 849 | 849 | hsa-miR-664* | acuggcuagggaaaaugauuggau | 62 | 39 | 1.56 | 9.88E-01 |
| SEQ ID NO: 850 | 850 | hsa-miR-1470 | gcccuccgcccgugcaccccg | 21 | 12 | 1.70 | 9.88E-01 |
| SEQ ID NO: 851 | 851 | hsa-miR-105* | acggauguuugagcaugugcua | 3 | 1 | 2.67 | 9.88E-01 |
| SEQ ID NO: 852 | 852 | hsa-miR-324-5p | cgcauccccuagggcauuggugu | 233 | 56 | 4.14 | 9.94E-01 |
| SEQ ID NO: 853 | 853 | hsa-miR-129* | aagcccuuaccccaaaaaguau | 8 | 1 | 8.44 | 9.94E-01 |
| SEQ ID NO: 854 | 854 | hsa-miR-625 | agggggaaaguucuauagucc | 182 | 110 | 1.66 | 9.94E-01 |
| SEQ ID NO: 855 | 855 | hsa-miR-519a* | cucuagagggaagcgcuuucug | 1 | 4 | 0.23 | 9.94E-01 |
| SEQ ID NO: 856 | 856 | hsa-miR-181a-2* | accacugaccguugacuguacc | 115 | 67 | 1.71 | 9.94E-01 |
| SEQ ID NO: 857 | 857 | hsa-miR-199b-5p | cccaguguuuagacuaucuguuc | 4 | 1 | 4.00 | 9.94E-01 |
| SEQ ID NO: 858 | 858 | hsa-miR-27a | uucacaguggcuaaguuccgc | 151 | 55 | 2.73 | 9.94E-01 |
| SEQ ID NO: 859 | 859 | hsa-miR-518a-3p | gaaagcgcuucccuuugcugga | 1 | 1 | 1.00 | 9.94E-01 |
| SEQ ID NO: 860 | 860 | hsa-miR-1265 | caggauguggucaaguguuguu | 7 | 2 | 4.36 | 9.94E-01 |
| SEQ ID NO: 861 | 861 | hsa-miR-92a | uauugcacuugucccggccugu | 22686 | 18004 | 1.26 | 9.95E-01 |
| SEQ ID NO: 862 | 862 | hsa-miR-29b-1* | gcugguuucauauggugguuuaga | 1 | 1 | 1.00 | 9.95E-01 |
| SEQ ID NO: 863 | 863 | hsa-miR-150 | ucucccaacccuuguaccagug | 600 | 840 | 0.72 | 9.96E-01 |
| SEQ ID NO: 864 | 864 | hsa-miR-335 | ucaagagcaauaacgaaaaaugu | 115 | 67 | 1.71 | 9.97E-01 |
| SEQ ID NO: 865 | 865 | hsa-miR-638 | agggaucgcgggcggguggcggccu | 4916 | 5945 | 0.83 | 9.99E-01 |

Figure 10B (cont'd)

| SEQ ID NO | microRNA | Sequence | median g1 | median g2 | qmedian | logqmedian | ttest_rawp | ttest_adjp | AUC | limma_rawp | limma_adjp |
|---|---|---|---|---|---|---|---|---|---|---|---|
| SEQ ID NO: 526 | hsa-miR-500 | uaauccuugcuaccugggugaga | 213 | 445 | 0.478 | -0.739 | 2.02E-03 | 5.62E-02 | 0.294 | 1.13E-03 | 4.89E-02 |
| SEQ ID NO: 735 | hsa-miR-320d | aaaagcuggguugagagga | 908 | 466 | 1.947 | 0.666 | 4.44E-05 | 1.28E-02 | 0.694 | 8.05E-04 | 4.13E-02 |
| SEQ ID NO: 699 | hsa-miR-550 | agugccugagggaguaagagccc | 114 | 169 | 0.673 | -0.396 | 1.55E-04 | 1.67E-02 | 0.260 | 2.93E-03 | 8.24E-02 |
| SEQ ID NO: 714 | hsa-miR-320c | aaaagcuggguugagagggu | 783 | 466 | 1.679 | 0.518 | 3.07E-04 | 2.25E-02 | 0.677 | 1.40E-03 | 5.26E-02 |
| SEQ ID NO: 623 | hsa-miR-1274a | gucccuguucaggcgcca | 142 | 275 | 0.518 | -0.659 | 1.08E-03 | 4.24E-02 | 0.295 | 3.78E-03 | 8.56E-02 |
| SEQ ID NO: 565 | hsa-miR-1913 | ucugcccccuccgcugcugcca | 359 | 258 | 1.391 | 0.330 | 1.79E-03 | 5.62E-02 | 0.649 | 2.62E-02 | 2.15E-01 |
| SEQ ID NO: 780 | hsa-miR-564 | aggcacggugucagcaggc | 157 | 126 | 1.246 | 0.220 | 3.92E-03 | 6.27E-02 | 0.638 | 7.28E-02 | 3.46E-01 |
| SEQ ID NO: 815 | hsa-miR-1274b | ucccuguucgggcgcca | 770 | 1244 | 0.619 | -0.480 | 6.78E-03 | 8.73E-02 | 0.338 | 2.05E-02 | 1.86E-01 |
| SEQ ID NO: 544 | hsa-miR-1826 | auugaucaucgacacuucgaacgcaau | 196 | 139 | 1.406 | 0.341 | 7.29E-03 | 8.80E-02 | 0.670 | 1.97E-01 | 5.35E-01 |
| SEQ ID NO: 74 | hsa-let-7d* | cuauacgaccugcugccuuucu | 59 | 166 | 0.353 | -1.042 | 7.04E-04 | 3.51E-02 | 0.264 | 6.30E-04 | 4.13E-02 |
| SEQ ID NO: 854 | hsa-miR-625 | agggggaaaguucuauagucc | 59 | 165 | 0.356 | -1.032 | 8.59E-04 | 3.90E-02 | 0.289 | 4.32E-03 | 9.10E-02 |
| SEQ ID NO: 134 | hsa-miR-378* | cuccugacuccagguccugugu | 51 | 123 | 0.417 | -0.876 | 7.84E-03 | 9.14E-02 | 0.365 | 2.16E-01 | 5.64E-01 |
| SEQ ID NO: 558 | hsa-miR-183* | gugaauuaccgaagggccauaa | 85 | 146 | 0.577 | -0.549 | 1.25E-04 | 1.54E-02 | 0.233 | 7.70E-04 | 4.13E-02 |
| SEQ ID NO: 430 | hsa-miR-21* | caacaccagucgaugggcugu | 102 | 79 | 1.300 | 0.263 | 4.45E-04 | 2.40E-02 | 0.690 | 2.63E-02 | 2.24E-01 |
| SEQ ID NO: 597 | hsa-miR-877 | guagaggagauggcgcaggg | 60 | 102 | 0.587 | -0.532 | 2.50E-03 | 5.64E-02 | 0.298 | 5.71E-03 | 9.77E-02 |
| SEQ ID NO: 22 | hsa-miR-1283 | ucuacaaaggaaagcgcuuucu | 109 | 71 | 1.548 | 0.437 | 2.68E-03 | 5.64E-02 | 0.685 | 3.02E-04 | 2.74E-02 |
| SEQ ID NO: 303 | hsa-miR-1286 | ugcaggaccaagaugagcccu | 120 | 92 | 1.296 | 0.259 | 2.81E-03 | 5.64E-02 | 0.661 | 3.13E-01 | 6.60E-01 |

Figure 11A

| | | | | | | | | | | |
|---|---|---|---|---|---|---|---|---|---|---|
| SEQ ID NO: 771 | hsa-miR-518f* | cucuagagggaagcacuuucuc | 123 | 83 | 1.476 | 0.390 | 3.78E-03 | 6.19E-02 | 0.671 | 8.61E-04 | 4.13E-02 |
| SEQ ID NO: 454 | hsa-miR-659 | cuugguucagggagggucccca | 65 | 109 | 0.697 | -0.515 | 5.40E-03 | 8.02E-02 | 0.320 | 3.35E-02 | 2.43E-01 |
| SEQ ID NO: 81 | hsa-miR-922 | gcagcagagaauaggacuacguc | 136 | 83 | 1.521 | 0.419 | 5.58E-03 | 8.02E-02 | 0.629 | 1.42E-02 | 1.61E-01 |
| SEQ ID NO: 202 | hsa-miR-508-5p | uacuccagagggcgucacucaug | 114 | 94 | 1.207 | 0.188 | 6.26E-03 | 8.58E-02 | 0.631 | 6.29E-03 | 1.01E-01 |
| SEQ ID NO: 474 | hsa-miR-182* | ugguucuagacuugccaacua | 47 | 20 | 2.311 | 0.838 | 8.53E-05 | 1.28E-02 | 0.723 | 1.64E-03 | 5.42E-02 |
| SEQ ID NO: 42 | hsa-miR-29c* | ugaccgauuucuccugguguuc | 1 | 24 | 0.052 | -2.955 | 1.61E-03 | 5.57E-02 | 0.361 | 2.68E-02 | 2.18E-01 |
| SEQ ID NO: 505 | hsa-miR-942 | ucuucucuguuuuggccaugug | 16 | 73 | 0.219 | -1.520 | 1.85E-03 | 5.62E-02 | 0.305 | 5.64E-03 | 9.77E-02 |
| SEQ ID NO: 368 | hsa-miR-767-3p | ucugcucauaccccaugguuucu | 44 | 18 | 2.502 | 0.917 | 2.60E-03 | 5.64E-02 | 0.683 | 1.97E-02 | 1.83E-01 |
| SEQ ID NO: 110 | hsa-miR-1256 | aggcauugacuucucacuagcu | 67 | 26 | 2.582 | 0.949 | 2.72E-03 | 5.64E-02 | 0.678 | 3.29E-04 | 2.74E-02 |
| SEQ ID NO: 366 | hsa-miR-369-5p | agaucgaccguguuauauucgc | 31 | 14 | 2.160 | 0.770 | 3.55E-03 | 6.12E-02 | 0.628 | 1.79E-01 | 5.15E-01 |
| SEQ ID NO: 718 | hsa-miR-1825 | uccagugcccuccucucc | 46 | 93 | 0.496 | -0.698 | 3.67E-03 | 6.19E-02 | 0.300 | 1.39E-02 | 1.61E-01 |
| SEQ ID NO: 659 | hsa-miR-519e* | uucuccaaaagggagcacuuuc | 60 | 20 | 2.981 | 1.092 | 4.73E-03 | 7.29E-02 | 0.711 | 5.65E-05 | 9.76E-03 |
| SEQ ID NO: 377 | hsa-miR-1206 | uguucauguagauguuuaagc | 59 | 22 | 2.616 | 0.962 | 5.72E-03 | 8.10E-02 | 0.674 | 3.09E-03 | 8.24E-02 |
| SEQ ID NO: 643 | hsa-miR-483-3p | ucacuccucuccucccgucuu | 21 | 51 | 0.415 | -0.879 | 7.35E-03 | 8.80E-02 | 0.344 | 2.48E-02 | 2.12E-01 |
| SEQ ID NO: 171 | hsa-miR-214* | ugccugucuacacuugcugugc | 58 | 34 | 1.736 | 0.551 | 3.90E-05 | 1.28E-02 | 0.744 | 4.99E-05 | 9.76E-03 |
| SEQ ID NO: 701 | hsa-miR-1303 | uuuagagacggggucuugcucu | 29 | 56 | 0.522 | -0.650 | 3.51E-04 | 2.25E-02 | 0.268 | 8.27E-04 | 4.13E-02 |
| SEQ ID NO: 181 | hsa-miR-891b | ugcaacuuaccugagucauuga | 95 | 68 | 1.409 | 0.343 | 7.32E-04 | 3.51E-02 | 0.693 | 3.25E-03 | 8.24E-02 |
| SEQ ID NO: 485 | hsa-miR-30e* | cuuucagucggauguuuacagc | 39 | 63 | 0.621 | -0.476 | 9.23E-04 | 3.98E-02 | 0.290 | 1.70E-03 | 5.42E-02 |

Figure 11A (cont'd)

| | | | | | | | | | | |
|---|---|---|---|---|---|---|---|---|---|---|
| SEQ ID NO: 746 | hsa-miR-155* | cuccuacauauuagcauuaaca | 59 | 39 | 1.490 | 0.399 | 1.49E-03 | 5.36E-02 | 0.677 | 1.79E-02 | 1.80E-01 |
| SEQ ID NO: 39 | hsa-miR-668 | ugucacucggcucggcccacuac | 38 | 59 | 0.647 | -0.436 | 1.93E-03 | 5.62E-02 | 0.280 | 1.35E-03 | 5.26E-02 |
| SEQ ID NO: 624 | hsa-miR-1226 | ucaccagcccuguguucccuag | 49 | 85 | 0.584 | -0.538 | 1.70E-03 | 5.62E-02 | 0.261 | 1.90E-02 | 1.80E-01 |
| SEQ ID NO: 108 | hsa-miR-34a* | caaucagcaaguauacugcccu | 90 | 68 | 1.327 | 0.283 | 2.35E-03 | 5.64E-02 | 0.687 | 3.75E-03 | 8.58E-02 |
| SEQ ID NO: 149 | hsa-miR-647 | guggcugcacucacuuccuuc | 68 | 41 | 1.673 | 0.615 | 2.78E-03 | 5.64E-02 | 0.704 | 4.91E-06 | 2.12E-03 |
| SEQ ID NO: 631 | hsa-miR-610 | ugagcuaaaugugugcuggga | 50 | 33 | 1.521 | 0.419 | 3.03E-03 | 5.73E-02 | 0.640 | 8.59E-02 | 3.80E-01 |
| SEQ ID NO: 499 | hsa-miR-141* | caucuuccaguacaguguugga | 88 | 68 | 1.288 | 0.253 | 4.10E-03 | 6.43E-02 | 0.690 | 3.49E-04 | 2.74E-02 |
| SEQ ID NO: 79 | hsa-miR-297 | auguaugugugcaugugcaug | 50 | 74 | 0.682 | -0.382 | 5.52E-03 | 8.02E-02 | 0.295 | 8.24E-03 | 1.23E-01 |
| SEQ ID NO: 621 | hsa-miR-935 | ccaguuaccgcuuccgcuaccgc | 29 | 15 | 1.872 | 0.627 | 5.95E-03 | 8.20E-02 | 0.627 | 9.63E-02 | 3.90E-01 |
| SEQ ID NO: 431 | hsa-miR-657 | ggcagguucucacccucucuagg | 59 | 37 | 1.570 | 0.451 | 6.77E-03 | 8.73E-02 | 0.660 | 7.04E-02 | 3.43E-01 |
| SEQ ID NO: 279 | hsa-miR-548a-3p | caaaacuggcaauuacuuuugc | 70 | 60 | 1.151 | 0.140 | 6.58E-03 | 8.73E-02 | 0.615 | 1.63E-01 | 4.96E-01 |
| SEQ ID NO: 459 | hsa-miR-802 | caguaacaaagauucauccuugu | 60 | 39 | 1.544 | 0.434 | 7.24E-03 | 8.80E-02 | 0.647 | 7.96E-02 | 3.65E-01 |
| SEQ ID NO: 185 | hsa-miR-208b | auaagacgaacaaaagguuugu | 60 | 33 | 1.830 | 0.604 | 7.26E-03 | 8.80E-02 | 0.687 | 5.73E-03 | 9.77E-02 |
| SEQ ID NO: 188 | hsa-miR-146b-3p | ugcccuguggacucaguucugg | 55 | 34 | 1.611 | 0.477 | 8.01E-03 | 9.22E-02 | 0.656 | 1.12E-02 | 1.45E-01 |
| SEQ ID NO: 75 | hsa-miR-199a-5p | cccaguguucagacuaccuguuc | 236 | 673 | 0.411 | -0.889 | 5.30E-06 | 4.57E-03 | 0.188 | 2.45E-07 | 2.12E-04 |
| SEQ ID NO: 806 | hsa-miR-125a-5p | ucccugagacccuuuaaccuguga | 151 | 418 | 0.362 | -1.017 | 3.65E-04 | 2.25E-02 | 0.277 | 2.87E-04 | 2.74E-02 |
| SEQ ID NO: 622 | hsa-miR-130b | cagugcaaugaugaaagggcau | 1463 | 946 | 1.547 | 0.436 | 1.78E-04 | 1.70E-02 | 0.708 | 1.33E-02 | 1.61E-01 |
| SEQ ID NO: 28 | hsa-miR-423-3p | agcucggucugaggccccucagu | 1105 | 1587 | 0.696 | -0.362 | 3.23E-04 | 2.25E-02 | 0.253 | 2.72E-04 | 2.74E-02 |

Figure 11A (cont'd)

| | | | | | | | | | | |
|---|---|---|---|---|---|---|---|---|---|---|
| SEQ ID NO: 852 | hsa-miR-324-5p | cgcauccccuagggcauuggugu | 332 | 496 | 0.669 | -0.402 | 1.01E-03 | 4.15E-02 | 0.286 | 1.46E-03 | 6.31E-02 |
| SEQ ID NO: 21 | hsa-miR-361-5p | uuaucagaaucuccagggguac | 418 | 629 | 0.664 | -0.410 | 2.62E-03 | 5.64E-02 | 0.320 | 2.59E-03 | 7.70E-02 |
| SEQ ID NO: 420 | hsa-miR-502-3p | aaugcaccugggcaaggauuca | 662 | 926 | 0.714 | -0.336 | 2.36E-03 | 5.64E-02 | 0.317 | 4.96E-03 | 9.73E-02 |
| SEQ ID NO: 31 | hsa-miR-19b | ugugcaaauccaugcaaaacuga | 10422 | 12496 | 0.834 | -0.181 | 3.06E-03 | 5.73E-02 | 0.338 | 1.86E-02 | 1.80E-01 |
| SEQ ID NO: 97 | hsa-miR-331-3p | gccccugggccuauccuagaa | 970 | 1621 | 0.596 | -0.613 | 3.43E-03 | 6.05E-02 | 0.299 | 3.09E-03 | 8.24E-02 |
| SEQ ID NO: 101 | hsa-miR-30b | uguaaacauccuacacucagcu | 7318 | 6233 | 1.174 | 0.160 | 3.37E-03 | 6.05E-02 | 0.639 | 2.89E-02 | 2.25E-01 |
| SEQ ID NO: 550 | hsa-miR-142-5p | cauaaaguagaaagcacuacu | 752 | 520 | 1.446 | 0.369 | 3.80E-03 | 6.19E-02 | 0.640 | 1.32E-01 | 4.40E-01 |
| SEQ ID NO: 719 | hsa-miR-328 | cuggcccucucugcccuuccgu | 57 | 123 | 0.466 | -0.764 | 4.39E-04 | 2.40E-02 | 0.266 | 1.57E-03 | 6.41E-02 |
| SEQ ID NO: 677 | hsa-miR-193a-5p | ugggucuuugcgggcgagauga | 55 | 126 | 0.441 | -0.819 | 1.35E-03 | 5.08E-02 | 0.250 | 6.11E-04 | 4.13E-02 |
| SEQ ID NO: 614 | hsa-miR-485-3p | gucauacacggcucuccucucu | 52 | 103 | 0.509 | -0.675 | 1.96E-03 | 5.62E-02 | 0.273 | 1.40E-03 | 5.26E-02 |
| SEQ ID NO: 667 | hsa-miR-142-3p | uguaguguuuccuacuuuaugga | 18 | 93 | 0.195 | -1.632 | 2.13E-03 | 5.64E-02 | 0.300 | 2.59E-03 | 7.70E-02 |
| SEQ ID NO: 404 | hsa-miR-513b | uucacaaggaggugucauuuau | 46 | 18 | 2.480 | 0.908 | 2.99E-03 | 5.73E-02 | 0.654 | 3.76E-02 | 2.54E-01 |
| SEQ ID NO: 330 | hsa-miR-220a | ccacaccguaucugacacuuu | 61 | 29 | 2.064 | 0.726 | 3.17E-03 | 5.83E-02 | 0.685 | 4.87E-03 | 9.73E-02 |
| SEQ ID NO: 313 | hsa-miR-186 | caaagaauucuccuuuugggcu | 34 | 99 | 0.340 | -1.078 | 6.67E-03 | 8.73E-02 | 0.298 | 3.50E-03 | 8.58E-02 |
| SEQ ID NO: 595 | hsa-miR-200a | uaacacugucugguaacgaugu | 90 | 74 | 1.218 | 0.197 | 7.67E-03 | 9.07E-02 | 0.636 | 8.84E-02 | 3.84E-01 |
| SEQ ID NO: 99 | hsa-miR-145 | guccaguuuucccaggaaucccu | 131 | 268 | 0.488 | -0.717 | 2.34E-03 | 5.64E-02 | 0.310 | 7.15E-03 | 1.10E-01 |
| SEQ ID NO: 560 | hsa-miR-103 | agcagcauuguacagggcuauga | 6845 | 3626 | 1.887 | 0.635 | 8.87E-05 | 1.28E-02 | 0.711 | 1.65E-02 | 1.76E-01 |
| SEQ ID NO: 547 | hsa-miR-148a | ucagugcacuacagaacuuugu | 950 | 682 | 1.393 | 0.331 | 6.12E-05 | 1.28E-02 | 0.685 | 6.43E-02 | 3.32E-01 |

Figure 11A (cont'd)

| | | | | | | | | | | | |
|---|---|---|---|---|---|---|---|---|---|---|---|
| SEQ ID NO: 750 | hsa-miR-107 | agcagcauuguacagggcuauca | 1306 | 774 | 1.686 | 0.523 | 2.19E-04 | 1.89E-02 | 0.685 | 1.93E-02 | 1.81E-01 |
| SEQ ID NO: 636 | hsa-miR-144* | ggauaucaucauauacuguaag | 636 | 386 | 1.649 | 0.499 | 2.17E-03 | 5.64E-02 | 0.626 | 4.31E-01 | 7.56E-01 |
| SEQ ID NO: 11 | hsa-miR-20b | caaagugcucauagugcagguag | 2820 | 2010 | 1.403 | 0.339 | 7.08E-03 | 8.80E-02 | 0.636 | 6.40E-01 | 8.75E-01 |
| SEQ ID NO: 334 | hsa-miR-490-5p | ccauggaucuccaggugggu | 130 | 94 | 1.381 | 0.323 | 5.55E-03 | 8.02E-02 | 0.657 | 8.83E-03 | 1.25E-01 |

Figure 11A (cont'd)

| Signature | SEQ ID Nos | miRNAs | Acc | Spec | Sens | Acc | Spec | Sens |
|---|---|---|---|---|---|---|---|---|
| L-1 | SEQ ID NO: 735, SEQ ID NO: 699, SEQ ID NO: 714 | hsa-miR-320d, hsa-miR-550, hsa-miR-320c | | | | 66.6% | 64.8% | 68.5% |
| L-2 | SEQ ID NO: 714, SEQ ID NO: 623, SEQ ID NO: 74 | hsa-miR-320c, hsa-miR-1274a, hsa-let-7d* | | | | 68.9% | 79.4% | 58.4% |
| L-3 | SEQ ID NO: 74, SEQ ID NO: 854, SEQ ID NO: 558 | hsa-let-7d*, hsa-miR-625, hsa-miR-183* | | | | 69.8% | 79.3% | 60.2% |
| L-4 | SEQ ID NO: 558, SEQ ID NO: 430, SEQ ID NO: 474 | hsa-miR-183*, hsa-miR-21*, hsa-miR-182* | | | | 77.3% | 83.8% | 70.7% |
| L-5 | SEQ ID NO: 474, SEQ ID NO: 171, SEQ ID NO: 701 | hsa-miR-182*, hsa-miR-214*, hsa-miR-1303 | | | | 71.8% | 75.5% | 68.1% |
| L-6 | SEQ ID NO: 701, SEQ ID NO: 181, SEQ ID NO: 485 | hsa-miR-1303, hsa-miR-891b, hsa-miR-30e* | | | | 66.5% | 77.7% | 55.3% |
| L-7 | SEQ ID NO: 485, SEQ ID NO: 75, SEQ ID NO: 806 | hsa-miR-30e*, hsa-miR-199a-5p, hsa-miR-125a-5p | | | | 77.0% | 87.4% | 66.5% |
| L-8 | SEQ ID NO: 806, SEQ ID NO: 622, SEQ ID NO: 26 | hsa-miR-125a-5p, hsa-miR-130b, hsa-miR-423-3p | | | | 75.7% | 81.6% | 69.8% |
| L-9 | SEQ ID NO: 26, SEQ ID NO: 852, SEQ ID NO: 719 | hsa-miR-423-3p, hsa-miR-324-5p, hsa-miR-328 | | | | 71.0% | 76.2% | 65.8% |
| L-10 | SEQ ID NO: 719, SEQ ID NO: 560, SEQ ID NO: 547 | hsa-miR-328, hsa-miR-103, hsa-miR-148a | | | | 74.1% | 76.5% | 71.8% |
| L-11 | SEQ ID NO: 547, SEQ ID NO: 750 | hsa-miR-148a, hsa-miR-107 | | | | 69.9% | 63.5% | 76.3% |
| L-12 | SEQ ID NO: 735, SEQ ID NO: 699, SEQ ID NO: 714, SEQ ID NO: 623, SEQ ID NO: 74 | hsa-miR-320d, hsa-miR-550, hsa-miR-320c, hsa-miR-1274a, hsa-let-7d* | | | | 69.2% | 83.0% | 55.4% |
| L-13 | SEQ ID NO: 714, SEQ ID NO: 623, SEQ ID NO: 74, SEQ ID NO: 854, SEQ ID NO: 558 | hsa-miR-320c, hsa-miR-1274a, hsa-let-7d*, hsa-miR-625, hsa-miR-183* | | | | 72.9% | 81.1% | 64.6% |
| L-14 | SEQ ID NO: 74, SEQ ID NO: 854, SEQ ID NO: 558, SEQ ID NO: 430, SEQ ID NO: 474 | hsa-let-7d*, hsa-miR-625, hsa-miR-183*, hsa-miR-21*, hsa-miR-182* | | | | 75.4% | 76.7% | 74.2% |

Figure 11B

| | | | | | | | | |
|---|---|---|---|---|---|---|---|---|
| L-15 | SEQ ID NO: 854, SEQ ID NO: 558, SEQ ID NO: 430, SEQ ID NO: 474, SEQ ID NO: 171 | hsa-miR-625, hsa-miR-183*, hsa-miR-21*, hsa-miR-182*, hsa-miR-214* | | | | 71.7% | 75.4% | 68.0% |
| L-16 | SEQ ID NO: 430, SEQ ID NO: 474, SEQ ID NO: 171, SEQ ID NO: 701, SEQ ID NO: 181 | hsa-miR-21*, hsa-miR-182*, hsa-miR-214*, hsa-miR-1303, hsa-miR-891b | | | | 69.9% | 71.3% | 68.6% |
| L-17 | SEQ ID NO: 171, SEQ ID NO: 701, SEQ ID NO: 181, SEQ ID NO: 485, SEQ ID NO: 75 | hsa-miR-214*, hsa-miR-1303, hsa-miR-891b, hsa-miR-30e*, hsa-miR-199a-5p | | | | 73.0% | 79.8% | 66.2% |
| L-18 | SEQ ID NO: 701, SEQ ID NO: 181, SEQ ID NO: 485, SEQ ID NO: 75, SEQ ID NO: 806, SEQ ID NO: 622 | hsa-miR-1303, hsa-miR-891b, hsa-miR-30e*, hsa-miR-199a-5p, hsa-miR-125a-5p, hsa-miR-130b | | | | 77.3% | 83.0% | 71.7% |
| L-19 | SEQ ID NO: 75, SEQ ID NO: 806, SEQ ID NO: 622, SEQ ID NO: 26, SEQ ID NO: 852, SEQ ID NO: 719 | hsa-miR-199a-5p, hsa-miR-125a-5p, hsa-miR-130b, hsa-miR-423-3p, hsa-miR-324-5p, hsa-miR-328 | | | | 76.3% | 83.5% | 69.1% |
| L-20 | SEQ ID NO: 26, SEQ ID NO: 852, SEQ ID NO: 719, SEQ ID NO: 560, SEQ ID NO: 547, SEQ ID NO: 750 | hsa-miR-423-3p, hsa-miR-324-5p, hsa-miR-328, hsa-miR-103, hsa-miR-148a, hsa-miR-107 | | | | 75.4% | 78.4% | 72.5% |
| L-21 | SEQ ID NO: 735, SEQ ID NO: 699, SEQ ID NO: 714, SEQ ID NO: 623, SEQ ID NO: 74, SEQ ID NO: 854, SEQ ID NO: 558, SEQ ID NO: 430, SEQ ID NO: 474, SEQ ID NO: 171 | hsa-miR-320d, hsa-miR-550, hsa-miR-320c, hsa-miR-1274a, hsa-let-7d*, hsa-miR-625, hsa-miR-183*, hsa-miR-21*, hsa-miR-182*, hsa-miR-214* | | | | 75.9% | 80.7% | 71.2% |
| L-22 | SEQ ID NO: 854, SEQ ID NO: 558, SEQ ID NO: 430, SEQ ID NO: 474, SEQ ID NO: 171, SEQ ID NO: 701, SEQ ID NO: 181, SEQ ID NO: 485, SEQ ID NO: 75, SEQ ID NO: 806, SEQ ID NO: 622 | hsa-miR-625, hsa-miR-183*, hsa-miR-21*, hsa-miR-182*, hsa-miR-214*, hsa-miR-1303, hsa-miR-891b, hsa-miR-30e*, hsa-miR-199a-5p, hsa-miR-125a-5p, hsa-miR-130b | | | | 76.3% | 80.1% | 72.6% |
| L-23 | SEQ ID NO: 181, SEQ ID NO: 485, SEQ ID NO: 75, SEQ ID NO: 806, SEQ ID NO: 622, SEQ ID NO: 26, SEQ ID NO: 852, SEQ ID NO: 719, SEQ ID NO: 560, SEQ ID NO: 547 | hsa-miR-891b, hsa-miR-30e*, hsa-miR-199a-5p, hsa-miR-125a-5p, hsa-miR-130b, hsa-miR-423-3p, hsa-miR-324-5p, hsa-miR-328, hsa-miR-103, hsa-miR-148a | | | | 75.5% | 79.7% | 71.3% |

Figure 11B (cont'd)

| | | | | | | | | |
|---|---|---|---|---|---|---|---|---|
| L-24 | SEQ ID NO: 26, SEQ ID NO: 852, SEQ ID NO: 719, SEQ ID NO: 560, SEQ ID NO: 547, SEQ ID NO: 750 | hsa-miR-423-3p, hsa-miR-324-5p, hsa-miR-328, hsa-miR-103, hsa-miR-148a, hsa-miR-107 | | | | 75.9% | 80.5% | 71.3% |
| L-25 | SEQ ID NO: 735, SEQ ID NO: 714, SEQ ID NO: 74, SEQ ID NO: 558, SEQ ID NO: 474 | hsa-miR-320d, hsa-miR-320c, hsa-let-7d*, hsa-miR-183*, hsa-miR-182* | | | | 73.9% | 82.4% | 65.5% |
| L-26 | SEQ ID NO: 623, SEQ ID NO: 854, SEQ ID NO: 430, SEQ ID NO: 171, SEQ ID NO: 181 | hsa-miR-1274a, hsa-miR-625, hsa-miR-21*, hsa-miR-214*, hsa-miR-891b | | | | 66.1% | 64.8% | 67.4% |
| L-27 | SEQ ID NO: 430, SEQ ID NO: 171, SEQ ID NO: 181, SEQ ID NO: 75, SEQ ID NO: 622 | hsa-miR-21*, hsa-miR-214*, hsa-miR-891b, hsa-miR-199a-5p, hsa-miR-130b | | | | 70.0% | 77.1% | 62.9% |
| L-28 | SEQ ID NO: 735, SEQ ID NO: 699, SEQ ID NO: 714 | hsa-miR-320d, hsa-miR-550, hsa-miR-320c | | | | 66.7% | 65.4% | 68.0% |
| L-29 | SEQ ID NO: 714, SEQ ID NO: 623, SEQ ID NO: 74 | hsa-miR-320c, hsa-miR-1274a, hsa-let-7d* | | | | 71.4% | 81.8% | 60.9% |
| L-30 | SEQ ID NO: 74, SEQ ID NO: 854, SEQ ID NO: 558 | hsa-let-7d*, hsa-miR-625, hsa-miR-183* | | | | 69.3% | 79.7% | 58.9% |
| L-31 | SEQ ID NO: 558, SEQ ID NO: 430, SEQ ID NO: 474 | hsa-miR-183*, hsa-miR-21*, hsa-miR-182* | | | | 75.8% | 82.3% | 69.4% |
| L-32 | SEQ ID NO: 474, SEQ ID NO: 171, SEQ ID NO: 701 | hsa-miR-182*, hsa-miR-214*, hsa-miR-1303 | | | | 71.8% | 76.8% | 66.9% |
| L-33 | SEQ ID NO: 701, SEQ ID NO: 181, SEQ ID NO: 485 | hsa-miR-1303, hsa-miR-891b, hsa-miR-30e* | | | | 68.1% | 79.4% | 56.7% |
| L-34 | SEQ ID NO: 485, SEQ ID NO: 75, SEQ ID NO: 806 | hsa-miR-30e*, hsa-miR-199a-5p, hsa-miR-125a-5p | | | | 77.8% | 88.6% | 67.1% |
| L-35 | SEQ ID NO: 806, SEQ ID NO: 560, SEQ ID NO: 547 | hsa-miR-125a-5p, hsa-miR-103, hsa-miR-148a | | | | 69.8% | 71.2% | 68.3% |
| L-36 | SEQ ID NO: 547, SEQ ID NO: 622, SEQ ID NO: 750 | hsa-miR-148a, hsa-miR-130b, hsa-miR-107 | | | | 73.1% | 70.9% | 75.4% |
| L-37 | SEQ ID NO: 750, SEQ ID NO: 26, SEQ ID NO: 852 | hsa-miR-107, hsa-miR-423-3p, hsa-miR-324-5p | | | | 72.5% | 76.7% | 68.2% |
| L-38 | SEQ ID NO: 852, SEQ ID NO: 719 | hsa-miR-324-5p, hsa-miR-328 | | | | 71.9% | 82.2% | 61.6% |
| L-39 | SEQ ID NO: 735, SEQ ID NO: 699, SEQ ID NO: 714, SEQ ID NO: 623, SEQ ID NO: 74 | hsa-miR-320d, hsa-miR-550, hsa-miR-320c, hsa-miR-1274a, hsa-let-7d* | | | | 69.3% | 83.4% | 55.2% |

Figure 11B (cont'd)

| | | | | | | | | |
|---|---|---|---|---|---|---|---|---|
| L-40 | SEQ ID NO: 714, SEQ ID NO: 623, SEQ ID NO: 74, SEQ ID NO: 854, SEQ ID NO: 558 | hsa-miR-320c, hsa-miR-1274a, hsa-let-7d*, hsa-miR-625, hsa-miR-183* | | | | 73.8% | 83.5% | 64.1% |
| L-41 | SEQ ID NO: 74, SEQ ID NO: 854, SEQ ID NO: 558, SEQ ID NO: 430, SEQ ID NO: 474 | hsa-let-7d*, hsa-miR-625, hsa-miR-183*, hsa-miR-21*, hsa-miR-182* | | | | 74.9% | 75.7% | 74.2% |
| L-42 | SEQ ID NO: 854, SEQ ID NO: 558, SEQ ID NO: 430, SEQ ID NO: 474, SEQ ID NO: 171 | hsa-miR-625, hsa-miR-183*, hsa-miR-21*, hsa-miR-182*, hsa-miR-214* | | | | 72.2% | 75.9% | 68.5% |
| L-43 | SEQ ID NO: 430, SEQ ID NO: 474, SEQ ID NO: 171, SEQ ID NO: 701, SEQ ID NO: 181 | hsa-miR-21*, hsa-miR-182*, hsa-miR-214*, hsa-miR-1303, hsa-miR-891b | | | | 69.6% | 71.7% | 67.5% |
| L-44 | SEQ ID NO: 171, SEQ ID NO: 701, SEQ ID NO: 181, SEQ ID NO: 485, SEQ ID NO: 75 | hsa-miR-214*, hsa-miR-1303, hsa-miR-891b, hsa-miR-30e*, hsa-miR-199a-5p | | | | 74.6% | 81.4% | 67.8% |
| L-45 | SEQ ID NO: 701, SEQ ID NO: 181, SEQ ID NO: 485, SEQ ID NO: 75, SEQ ID NO: 806, SEQ ID NO: 560 | hsa-miR-1303, hsa-miR-891b, hsa-miR-30e*, hsa-miR-199a-5p, hsa-miR-125a-5p, hsa-miR-103 | | | | 76.4% | 84.5% | 68.3% |
| L-46 | SEQ ID NO: 75, SEQ ID NO: 806, SEQ ID NO: 560, SEQ ID NO: 547, SEQ ID NO: 622, SEQ ID NO: 750 | hsa-miR-199a-5p, hsa-miR-125a-5p, hsa-miR-103, hsa-miR-148a, hsa-miR-130b, hsa-miR-107 | | | | 76.7% | 84.0% | 69.4% |
| L-47 | SEQ ID NO: 547, SEQ ID NO: 622, SEQ ID NO: 750, SEQ ID NO: 26, SEQ ID NO: 852, SEQ ID NO: 719 | hsa-miR-148a, hsa-miR-130b, hsa-miR-107, hsa-miR-423-3p, hsa-miR-324-5p, hsa-miR-328 | | | | 76.0% | 81.4% | 70.6% |
| L-48 | SEQ ID NO: 735, SEQ ID NO: 699, SEQ ID NO: 714, SEQ ID NO: 623, SEQ ID NO: 74, SEQ ID NO: 854, SEQ ID NO: 558, SEQ ID NO: 430, SEQ ID NO: 474, SEQ ID NO: 171 | hsa-miR-320d, hsa-miR-550, hsa-miR-320c, hsa-miR-1274a, hsa-let-7d*, hsa-miR-625, hsa-miR-183*, hsa-miR-21*, hsa-miR-182*, hsa-miR-214* | | | | 77.1% | 83.5% | 70.7% |
| L-49 | SEQ ID NO: 854, SEQ ID NO: 558, SEQ ID NO: 430, SEQ ID NO: 474, SEQ ID NO: 171, SEQ ID NO: 701, SEQ ID NO: 181, SEQ ID NO: 485, SEQ ID NO: 75, SEQ ID NO: 806, SEQ ID NO: 560 | hsa-miR-625, hsa-miR-183*, hsa-miR-21*, hsa-miR-182*, hsa-miR-214*, hsa-miR-1303, hsa-miR-891b, hsa-miR-30e*, hsa-miR-199a-5p, hsa-miR-125a-5p, hsa-miR-103 | | | | 77.4% | 77.3% | 77.6% |

Figure 11B (cont'd)

| | | | | | | | | |
|---|---|---|---|---|---|---|---|---|
| L-50 | SEQ ID NO: 181, SEQ ID NO: 485, SEQ ID NO: 75, SEQ ID NO: 806, SEQ ID NO: 560, SEQ ID NO: 547, SEQ ID NO: 622, SEQ ID NO: 750, SEQ ID NO: 26, SEQ ID NO: 852 | hsa-miR-891b, hsa-miR-30e*, hsa-miR-199a-5p, hsa-miR-125a-5p, hsa-miR-103, hsa-miR-148a, hsa-miR-130b, hsa-miR-107, hsa-miR-423-3p, hsa-miR-324-5p | | | | 75.0% | 80.2% | 69.8% |
| L-51 | SEQ ID NO: 547, SEQ ID NO: 622, SEQ ID NO: 750, SEQ ID NO: 26, SEQ ID NO: 852, SEQ ID NO: 719 | hsa-miR-148a, hsa-miR-130b, hsa-miR-107, hsa-miR-423-3p, hsa-miR-324-5p, hsa-miR-328 | | | | 75.8% | 80.5% | 71.1% |
| L-52 | SEQ ID NO: 735, SEQ ID NO: 714, SEQ ID NO: 74, SEQ ID NO: 558, SEQ ID NO: 474 | hsa-miR-320d, hsa-miR-320c, hsa-let-7d*, hsa-miR-183*, hsa-miR-182* | | | | 75.5% | 82.7% | 68.2% |
| L-53 | SEQ ID NO: 623, SEQ ID NO: 854, SEQ ID NO: 430, SEQ ID NO: 171, SEQ ID NO: 181 | hsa-miR-1274a, hsa-miR-625, hsa-miR-21*, hsa-miR-214*, hsa-miR-891b | | | | 64.5% | 63.1% | 65.8% |
| L-54 | SEQ ID NO: 430, SEQ ID NO: 171, SEQ ID NO: 181, SEQ ID NO: 75, SEQ ID NO: 560 | hsa-miR-21*, hsa-miR-214*, hsa-miR-891b, hsa-miR-199a-5p, hsa-miR-103 | | | | 69.5% | 73.5% | 65.6% |
| L-55 | SEQ ID NO: 75, SEQ ID NO: 806, SEQ ID NO: 735 | hsa-miR-199a-5p, hsa-miR-125a-5p, hsa-miR-320d | | | | 79.3% | 91.3% | 67.3% |
| L-56 | SEQ ID NO: 735, SEQ ID NO: 699, SEQ ID NO: 714 | hsa-miR-320d, hsa-miR-550, hsa-miR-320c | | | | 65.4% | 63.0% | 67.9% |
| L-57 | SEQ ID NO: 714, SEQ ID NO: 623, SEQ ID NO: 622 | hsa-miR-320c, hsa-miR-1274a, hsa-miR-130b | | | | 70.4% | 74.2% | 66.6% |
| L-58 | SEQ ID NO: 622, SEQ ID NO: 26, SEQ ID NO: 852 | hsa-miR-130b, hsa-miR-423-3p, hsa-miR-324-5p | | | | 65.8% | 63.0% | 68.7% |
| L-59 | SEQ ID NO: 852, SEQ ID NO: 74, SEQ ID NO: 854 | hsa-miR-324-5p, hsa-let-7d*, hsa-miR-625 | | | | 72.6% | 80.7% | 64.5% |
| L-60 | SEQ ID NO: 854, SEQ ID NO: 719, SEQ ID NO: 558 | hsa-miR-625, hsa-miR-328, hsa-miR-183* | | | | 67.7% | 75.0% | 60.3% |
| L-61 | SEQ ID NO: 558, SEQ ID NO: 430, SEQ ID NO: 474 | hsa-miR-183*, hsa-miR-21*, hsa-miR-182* | | | | 76.6% | 84.3% | 68.9% |
| L-62 | SEQ ID NO: 474, SEQ ID NO: 171, SEQ ID NO: 701 | hsa-miR-182*, hsa-miR-214*, hsa-miR-1303 | | | | 71.0% | 76.1% | 65.9% |
| L-63 | SEQ ID NO: 701, SEQ ID NO: 181, SEQ ID NO: 485 | hsa-miR-1303, hsa-miR-891b, hsa-miR-30e* | | | | 66.8% | 78.7% | 54.9% |

Figure 11B (cont'd)

| | | | | | | | | |
|---|---|---|---|---|---|---|---|---|
| L-64 | SEQ ID NO: 485, SEQ ID NO: 560, SEQ ID NO: 547 | hsa-miR-30e*, hsa-miR-103, hsa-miR-148a | | | | 70.5% | 68.3% | 72.7% |
| L-65 | SEQ ID NO: 547, SEQ ID NO: 750 | hsa-miR-148a, hsa-miR-107 | | | | 72.1% | 68.1% | 76.1% |
| L-66 | SEQ ID NO: 75, SEQ ID NO: 806, SEQ ID NO: 735, SEQ ID NO: 699, SEQ ID NO: 714 | hsa-miR-199a-5p, hsa-miR-125a-5p, hsa-miR-320d, hsa-miR-550, hsa-miR-320c | | | | 78.0% | 92.3% | 63.7% |
| L-67 | SEQ ID NO: 735, SEQ ID NO: 699, SEQ ID NO: 714, SEQ ID NO: 623, SEQ ID NO: 622 | hsa-miR-320d, hsa-miR-550, hsa-miR-320c, hsa-miR-1274a, hsa-miR-130b | | | | 70.2% | 74.9% | 65.6% |
| L-68 | SEQ ID NO: 714, SEQ ID NO: 623, SEQ ID NO: 622, SEQ ID NO: 26, SEQ ID NO: 852 | hsa-miR-320c, hsa-miR-1274a, hsa-miR-130b, hsa-miR-423-3p, hsa-miR-324-5p | | | | 77.5% | 78.1% | 77.0% |
| L-69 | SEQ ID NO: 623, SEQ ID NO: 622, SEQ ID NO: 26, SEQ ID NO: 852, SEQ ID NO: 74 | hsa-miR-1274a, hsa-miR-130b, hsa-miR-423-3p, hsa-miR-324-5p, hsa-let-7d* | | | | 74.0% | 76.2% | 71.8% |
| L-70 | SEQ ID NO: 26, SEQ ID NO: 852, SEQ ID NO: 74, SEQ ID NO: 854, SEQ ID NO: 719 | hsa-miR-423-3p, hsa-miR-324-5p, hsa-let-7d*, hsa-miR-625, hsa-miR-328 | | | | 74.5% | 78.9% | 70.2% |
| L-71 | SEQ ID NO: 74, SEQ ID NO: 854, SEQ ID NO: 719, SEQ ID NO: 558, SEQ ID NO: 430 | hsa-let-7d*, hsa-miR-625, hsa-miR-328, hsa-miR-183*, hsa-miR-21* | | | | 69.8% | 78.4% | 61.1% |
| L-72 | SEQ ID NO: 854, SEQ ID NO: 719, SEQ ID NO: 558, SEQ ID NO: 430, SEQ ID NO: 474, SEQ ID NO: 171 | hsa-miR-625, hsa-miR-328, hsa-miR-183*, hsa-miR-21*, hsa-miR-182*, hsa-miR-214* | | | | 70.8% | 75.0% | 66.6% |
| L-73 | SEQ ID NO: 430, SEQ ID NO: 474, SEQ ID NO: 171, SEQ ID NO: 701, SEQ ID NO: 181, SEQ ID NO: 485 | hsa-miR-21*, hsa-miR-182*, hsa-miR-214*, hsa-miR-1303, hsa-miR-891b, hsa-miR-30e* | | | | 68.7% | 67.2% | 70.3% |
| L-74 | SEQ ID NO: 701, SEQ ID NO: 181, SEQ ID NO: 485, SEQ ID NO: 560, SEQ ID NO: 547, SEQ ID NO: 750 | hsa-miR-1303, hsa-miR-891b, hsa-miR-30e*, hsa-miR-103, hsa-miR-148a, hsa-miR-107 | | | | 73.4% | 61.6% | 85.3% |
| L-75 | SEQ ID NO: 75, SEQ ID NO: 806, SEQ ID NO: 735, SEQ ID NO: 699, SEQ ID NO: 714, SEQ ID NO: 623, SEQ ID NO: 622, SEQ ID NO: 26, SEQ ID NO: 852, SEQ ID NO: 74 | hsa-miR-199a-5p, hsa-miR-125a-5p, hsa-miR-320d, hsa-miR-550, hsa-miR-320c, hsa-miR-1274a, hsa-miR-130b, hsa-miR-423-3p, hsa-miR-324-5p, hsa-let-7d* | | | | 73.8% | 81.5% | 66.1% |

Figure 11B (cont'd)

| | | | | | | | | |
|---|---|---|---|---|---|---|---|---|
| L-76 | SEQ ID NO: 623, SEQ ID NO: 622, SEQ ID NO: 26, SEQ ID NO: 852, SEQ ID NO: 74, SEQ ID NO: 854, SEQ ID NO: 719, SEQ ID NO: 558, SEQ ID NO: 430, SEQ ID NO: 474, SEQ ID NO: 171 | hsa-miR-1274a, hsa-miR-130b, hsa-miR-423-3p, hsa-miR-324-5p, hsa-let-7d*, hsa-miR-625, hsa-miR-328, hsa-miR-183*, hsa-miR-21*, hsa-miR-182*, hsa-miR-214* | | | | 76.9% | 77.7% | 76.1% |
| L-77 | SEQ ID NO: 719, SEQ ID NO: 558, SEQ ID NO: 430, SEQ ID NO: 474, SEQ ID NO: 171, SEQ ID NO: 701, SEQ ID NO: 181, SEQ ID NO: 485, SEQ ID NO: 560, SEQ ID NO: 547 | hsa-miR-328, hsa-miR-183*, hsa-miR-21*, hsa-miR-182*, hsa-miR-214*, hsa-miR-1303, hsa-miR-891b, hsa-miR-30e*, hsa-miR-103, hsa-miR-148a | | | | 81.3% | 82.9% | 79.7% |
| L-78 | SEQ ID NO: 701, SEQ ID NO: 181, SEQ ID NO: 485, SEQ ID NO: 560, SEQ ID NO: 547, SEQ ID NO: 750 | hsa-miR-1303, hsa-miR-891b, hsa-miR-30e*, hsa-miR-103, hsa-miR-148a, hsa-miR-107 | | | | 72.3% | 58.9% | 85.7% |
| L-79 | SEQ ID NO: 75, SEQ ID NO: 735, SEQ ID NO: 714, SEQ ID NO: 622, SEQ ID NO: 852 | hsa-miR-199a-5p, hsa-miR-320d, hsa-miR-320c, hsa-miR-130b, hsa-miR-324-5p | | | | 74.5% | 82.1% | 67.0% |
| L-80 | SEQ ID NO: 699, SEQ ID NO: 623, SEQ ID NO: 26, SEQ ID NO: 74, SEQ ID NO: 719 | hsa-miR-550, hsa-miR-1274a, hsa-miR-423-3p, hsa-let-7d*, hsa-miR-328 | | | | 76.0% | 79.2% | 72.8% |
| L-81 | SEQ ID NO: 26, SEQ ID NO: 74, SEQ ID NO: 719, SEQ ID NO: 430, SEQ ID NO: 171 | hsa-miR-423-3p, hsa-let-7d*, hsa-miR-328, hsa-miR-21*, hsa-miR-214* | | | | 74.4% | 77.1% | 71.7% |
| L-82 | SEQ ID NO: 75, SEQ ID NO: 806, SEQ ID NO: 526 | hsa-miR-199a-5p, hsa-miR-125a-5p, hsa-miR-500 | | | | 77.8% | 91.1% | 64.6% |
| L-83 | SEQ ID NO: 526, SEQ ID NO: 735, SEQ ID NO: 699 | hsa-miR-500, hsa-miR-320d, hsa-miR-550 | | | | 68.2% | 75.7% | 60.8% |
| L-84 | SEQ ID NO: 699, SEQ ID NO: 622, SEQ ID NO: 714 | hsa-miR-550, hsa-miR-130b, hsa-miR-320c | | | | 72.1% | 74.1% | 70.1% |
| L-85 | SEQ ID NO: 714, SEQ ID NO: 26, SEQ ID NO: 852 | hsa-miR-320c, hsa-miR-423-3p, hsa-miR-324-5p | | | | 65.6% | 68.3% | 62.9% |
| L-86 | SEQ ID NO: 852, SEQ ID NO: 623, SEQ ID NO: 565 | hsa-miR-324-5p, hsa-miR-1274a, hsa-miR-1913 | | | | 75.7% | 81.7% | 69.7% |
| L-87 | SEQ ID NO: 565, SEQ ID NO: 21, SEQ ID NO: 420 | hsa-miR-1913, hsa-miR-361-5p, hsa-miR-502-3p | | | | 64.2% | 69.7% | 58.7% |

Figure 11B (cont'd)

| | | | | | | | | |
|---|---|---|---|---|---|---|---|---|
| L-88 | SEQ ID NO: 420, SEQ ID NO: 31, SEQ ID NO: 97 | hsa-miR-502-3p, hsa-miR-19b, hsa-miR-331-3p | | | | 68.9% | 68.5% | 69.3% |
| L-89 | SEQ ID NO: 97, SEQ ID NO: 101, SEQ ID NO: 550 | hsa-miR-331-3p, hsa-miR-30b, hsa-miR-142-5p | | | | 71.8% | 76.5% | 67.1% |
| L-90 | SEQ ID NO: 550, SEQ ID NO: 780, SEQ ID NO: 815 | hsa-miR-142-5p, hsa-miR-564, hsa-miR-1274b | | | | 71.0% | 73.8% | 68.2% |
| L-91 | SEQ ID NO: 815, SEQ ID NO: 544, SEQ ID NO: 719 | hsa-miR-1274b, hsa-miR-1826, hsa-miR-328 | | | | 68.7% | 80.2% | 57.1% |
| L-92 | SEQ ID NO: 719, SEQ ID NO: 74, SEQ ID NO: 854 | hsa-miR-328, hsa-let-7d*, hsa-miR-625 | | | | 69.0% | 79.8% | 58.2% |
| L-93 | SEQ ID NO: 854, SEQ ID NO: 677, SEQ ID NO: 134 | hsa-miR-625, hsa-miR-193a-5p, hsa-miR-378* | | | | 69.3% | 87.0% | 51.5% |
| L-94 | SEQ ID NO: 134, SEQ ID NO: 430, SEQ ID NO: 597 | hsa-miR-378*, hsa-miR-21*, hsa-miR-877 | | | | 66.1% | 75.0% | 57.3% |
| L-95 | SEQ ID NO: 430, SEQ ID NO: 614, SEQ ID NO: 597 | hsa-miR-21*, hsa-miR-485-3p, hsa-miR-877 | | | | 66.0% | 72.9% | 59.1% |
| L-96 | SEQ ID NO: 597, SEQ ID NO: 22, SEQ ID NO: 303 | hsa-miR-877, hsa-miR-1283, hsa-miR-1286 | | | | 65.0% | 70.2% | 59.8% |
| L-97 | SEQ ID NO: 75, SEQ ID NO: 806, SEQ ID NO: 526, SEQ ID NO: 735, SEQ ID NO: 699 | hsa-miR-199a-5p, hsa-miR-125a-5p, hsa-miR-500, hsa-miR-320d, hsa-miR-550 | | | | 75.7% | 87.7% | 63.7% |
| L-98 | SEQ ID NO: 526, SEQ ID NO: 735, SEQ ID NO: 699, SEQ ID NO: 622, SEQ ID NO: 714 | hsa-miR-500, hsa-miR-320d, hsa-miR-550, hsa-miR-130b, hsa-miR-320c | | | | 69.8% | 75.9% | 63.8% |
| L-99 | SEQ ID NO: 699, SEQ ID NO: 622, SEQ ID NO: 714, SEQ ID NO: 26, SEQ ID NO: 852 | hsa-miR-550, hsa-miR-130b, hsa-miR-320c, hsa-miR-423-3p, hsa-miR-324-5p | | | | 74.2% | 78.5% | 69.9% |
| L-100 | SEQ ID NO: 622, SEQ ID NO: 714, SEQ ID NO: 26, SEQ ID NO: 852, SEQ ID NO: 623 | hsa-miR-130b, hsa-miR-320c, hsa-miR-423-3p, hsa-miR-324-5p, hsa-miR-1274a | | | | 76.5% | 75.3% | 77.7% |
| L-101 | SEQ ID NO: 26, SEQ ID NO: 852, SEQ ID NO: 623, SEQ ID NO: 565, SEQ ID NO: 21 | hsa-miR-423-3p, hsa-miR-324-5p, hsa-miR-1274a, hsa-miR-1913, hsa-miR-361-5p | | | | 80.3% | 81.3% | 79.3% |
| L-102 | SEQ ID NO: 623, SEQ ID NO: 565, SEQ ID NO: 21, SEQ ID NO: 420, SEQ ID NO: 31 | hsa-miR-1274a, hsa-miR-1913, hsa-miR-361-5p, hsa-miR-502-3p, hsa-miR-19b | | | | 77.3% | 76.5% | 78.2% |

Figure 11B (cont'd)

| | | | | | | | | |
|---|---|---|---|---|---|---|---|---|
| L-103 | SEQ ID NO: 565, SEQ ID NO: 21, SEQ ID NO: 420, SEQ ID NO: 31, SEQ ID NO: 97, SEQ ID NO: 101 | hsa-miR-1913, hsa-miR-361-5p, hsa-miR-502-3p, hsa-miR-19b, hsa-miR-331-3p, hsa-miR-30b | | | | 71.1% | 69.0% | 73.1% |
| L-104 | SEQ ID NO: 31, SEQ ID NO: 97, SEQ ID NO: 101, SEQ ID NO: 550, SEQ ID NO: 780, SEQ ID NO: 815 | hsa-miR-19b, hsa-miR-331-3p, hsa-miR-30b, hsa-miR-142-5p, hsa-miR-564, hsa-miR-1274b | | | | 76.0% | 77.8% | 74.2% |
| L-105 | SEQ ID NO: 550, SEQ ID NO: 780, SEQ ID NO: 815, SEQ ID NO: 544, SEQ ID NO: 719, SEQ ID NO: 74 | hsa-miR-142-5p, hsa-miR-564, hsa-miR-1274b, hsa-miR-1826, hsa-miR-328, hsa-let-7d* | | | | 74.1% | 79.2% | 69.0% |
| L-106 | SEQ ID NO: 544, SEQ ID NO: 719, SEQ ID NO: 74, SEQ ID NO: 854, SEQ ID NO: 677, SEQ ID NO: 134 | hsa-miR-1826, hsa-miR-328, hsa-let-7d*, hsa-miR-625, hsa-miR-193a-5p, hsa-miR-378* | | | | 68.2% | 84.2% | 52.1% |
| L-107 | SEQ ID NO: 854, SEQ ID NO: 677, SEQ ID NO: 134, SEQ ID NO: 558, SEQ ID NO: 430, SEQ ID NO: 614 | hsa-miR-625, hsa-miR-193a-5p, hsa-miR-378*, hsa-miR-183*, hsa-miR-21*, hsa-miR-485-3p | | | | 72.4% | 78.3% | 66.5% |
| L-108 | SEQ ID NO: 558, SEQ ID NO: 430, SEQ ID NO: 614, SEQ ID NO: 597, SEQ ID NO: 22, SEQ ID NO: 303 | hsa-miR-183*, hsa-miR-21*, hsa-miR-485-3p, hsa-miR-877, hsa-miR-1283, hsa-miR-1286 | | | | 69.0% | 74.1% | 64.0% |
| L-109 | SEQ ID NO: 597, SEQ ID NO: 22, SEQ ID NO: 303, SEQ ID NO: 771, SEQ ID NO: 454, SEQ ID NO: 81 | hsa-miR-877, hsa-miR-1283, hsa-miR-1286, hsa-miR-518f*, hsa-miR-659, hsa-miR-922 | | | | 65.9% | 73.7% | 58.1% |
| L-110 | SEQ ID NO: 771, SEQ ID NO: 454, SEQ ID NO: 81, SEQ ID NO: 202, SEQ ID NO: 474, SEQ ID NO: 42 | hsa-miR-518f*, hsa-miR-659, hsa-miR-922, hsa-miR-508-5p, hsa-miR-182*, hsa-miR-29c* | | | | 69.5% | 77.7% | 61.4% |
| L-111 | SEQ ID NO: 202, SEQ ID NO: 474, SEQ ID NO: 42, SEQ ID NO: 505, SEQ ID NO: 368, SEQ ID NO: 667 | hsa-miR-508-5p, hsa-miR-182*, hsa-miR-29c*, hsa-miR-942, hsa-miR-767-3p, hsa-miR-142-3p | | | | 68.7% | 73.1% | 64.2% |
| L-112 | SEQ ID NO: 75, SEQ ID NO: 806, SEQ ID NO: 526, SEQ ID NO: 735, SEQ ID NO: 699, SEQ ID NO: 622, SEQ ID NO: 714, SEQ ID NO: 26, SEQ ID NO: 852, SEQ ID NO: 623 | hsa-miR-199a-5p, hsa-miR-125a-5p, hsa-miR-500, hsa-miR-320d, hsa-miR-550, hsa-miR-130b, hsa-miR-320c, hsa-miR-423-3p, hsa-miR-324-5p, hsa-miR-1274a | | | | 75.4% | 80.9% | 69.9% |

Figure 11B (cont'd)

| | | | | | | | | |
|---|---|---|---|---|---|---|---|---|
| L-113 | SEQ ID NO: 622, SEQ ID NO: 714, SEQ ID NO: 26, SEQ ID NO: 852, SEQ ID NO: 623, SEQ ID NO: 565, SEQ ID NO: 21, SEQ ID NO: 420, SEQ ID NO: 31, SEQ ID NO: 97, SEQ ID NO: 101 | hsa-miR-130b, hsa-miR-320c, hsa-miR-423-3p, hsa-miR-324-5p, hsa-miR-1274a, hsa-miR-1913, hsa-miR-361-5p, hsa-miR-502-3p, hsa-miR-19b, hsa-miR-331-3p, hsa-miR-30b | | | | 80.6% | 79.3% | 81.9% |
| L-114 | SEQ ID NO: 21, SEQ ID NO: 420, SEQ ID NO: 31, SEQ ID NO: 97, SEQ ID NO: 101, SEQ ID NO: 550, SEQ ID NO: 780, SEQ ID NO: 815, SEQ ID NO: 544, SEQ ID NO: 719 | hsa-miR-361-5p, hsa-miR-502-3p, hsa-miR-19b, hsa-miR-331-3p, hsa-miR-30b, hsa-miR-142-5p, hsa-miR-564, hsa-miR-1274b, hsa-miR-1826, hsa-miR-328 | | | | 74.6% | 75.1% | 74.2% |
| L-115 | SEQ ID NO: 550, SEQ ID NO: 780, SEQ ID NO: 815, SEQ ID NO: 544, SEQ ID NO: 719, SEQ ID NO: 74, SEQ ID NO: 854, SEQ ID NO: 677, SEQ ID NO: 134, SEQ ID NO: 558 | hsa-miR-142-5p, hsa-miR-564, hsa-miR-1274b, hsa-miR-1826, hsa-miR-328, hsa-let-7d*, hsa-miR-625, hsa-miR-193a-5p, hsa-miR-378*, hsa-miR-183* | | | | 72.7% | 82.4% | 63.0% |
| L-116 | SEQ ID NO: 74, SEQ ID NO: 854, SEQ ID NO: 677, SEQ ID NO: 134, SEQ ID NO: 558, SEQ ID NO: 430, SEQ ID NO: 614, SEQ ID NO: 597, SEQ ID NO: 22, SEQ ID NO: 303 | hsa-let-7d*, hsa-miR-625, hsa-miR-193a-5p, hsa-miR-378*, hsa-miR-183*, hsa-miR-21*, hsa-miR-485-3p, hsa-miR-877, hsa-miR-1283, hsa-miR-1286 | | | | 70.6% | 76.9% | 64.3% |
| L-117 | SEQ ID NO: 430, SEQ ID NO: 614, SEQ ID NO: 597, SEQ ID NO: 22, SEQ ID NO: 303, SEQ ID NO: 771, SEQ ID NO: 454, SEQ ID NO: 81, SEQ ID NO: 202, SEQ ID NO: 474 | hsa-miR-21*, hsa-miR-485-3p, hsa-miR-877, hsa-miR-1283, hsa-miR-1286, hsa-miR-518f*, hsa-miR-659, hsa-miR-922, hsa-miR-508-5p, hsa-miR-182* | | | | 69.5% | 77.4% | 61.7% |
| L-118 | SEQ ID NO: 771, SEQ ID NO: 454, SEQ ID NO: 81, SEQ ID NO: 202, SEQ ID NO: 474, SEQ ID NO: 42, SEQ ID NO: 505, SEQ ID NO: 368, SEQ ID NO: 667, SEQ ID NO: 110 | hsa-miR-518f*, hsa-miR-659, hsa-miR-922, hsa-miR-508-5p, hsa-miR-182*, hsa-miR-29c*, hsa-miR-942, hsa-miR-767-3p, hsa-miR-142-3p, hsa-miR-1256 | | | | 67.7% | 73.1% | 62.2% |

Figure 11B (cont'd)

| | | | | | | | | |
|---|---|---|---|---|---|---|---|---|
| L-119 | SEQ ID NO: 42, SEQ ID NO: 505, SEQ ID NO: 368, SEQ ID NO: 667, SEQ ID NO: 110, SEQ ID NO: 404, SEQ ID NO: 330, SEQ ID NO: 366, SEQ ID NO: 718, SEQ ID NO: 659 | hsa-miR-29c*, hsa-miR-942, hsa-miR-767-3p, hsa-miR-142-3p, hsa-miR-1256, hsa-miR-513b, hsa-miR-220a, hsa-miR-369-5p, hsa-miR-1825, hsa-miR-519e* | | | | 64.3% | 78.6% | 50.1% |
| L-120 | SEQ ID NO: 404, SEQ ID NO: 330, SEQ ID NO: 366, SEQ ID NO: 718, SEQ ID NO: 659, SEQ ID NO: 377, SEQ ID NO: 313, SEQ ID NO: 643, SEQ ID NO: 171, SEQ ID NO: 701 | hsa-miR-513b, hsa-miR-220a, hsa-miR-369-5p, hsa-miR-1825, hsa-miR-519e*, hsa-miR-1206, hsa-miR-186, hsa-miR-483-3p, hsa-miR-214*, hsa-miR-1303 | | | | 63.2% | 73.3% | 53.1% |
| L-121 | SEQ ID NO: 75, SEQ ID NO: 526, SEQ ID NO: 699, SEQ ID NO: 714, SEQ ID NO: 852 | hsa-miR-199a-5p, hsa-miR-500, hsa-miR-550, hsa-miR-320c, hsa-miR-324-5p | | | | 73.9% | 84.0% | 63.8% |
| L-122 | SEQ ID NO: 735, SEQ ID NO: 622, SEQ ID NO: 26, SEQ ID NO: 623, SEQ ID NO: 21 | hsa-miR-320d, hsa-miR-130b, hsa-miR-423-3p, hsa-miR-1274a, hsa-miR-361-5p | | | | 77.0% | 76.1% | 77.9% |
| L-123 | SEQ ID NO: 26, SEQ ID NO: 623, SEQ ID NO: 21, SEQ ID NO: 31, SEQ ID NO: 101 | hsa-miR-423-3p, hsa-miR-1274a, hsa-miR-361-5p, hsa-miR-19b, hsa-miR-30b | | | | 75.5% | 72.7% | 78.4% |
| L-124 | SEQ ID NO: 526, SEQ ID NO: 735, SEQ ID NO: 699 | hsa-miR-500, hsa-miR-320d, hsa-miR-550 | | | | 69.1% | 76.3% | 61.9% |
| L-125 | SEQ ID NO: 699, SEQ ID NO: 714, SEQ ID NO: 623 | hsa-miR-550, hsa-miR-320c, hsa-miR-1274a | | | | 65.5% | 67.2% | 63.8% |
| L-126 | SEQ ID NO: 623, SEQ ID NO: 565, SEQ ID NO: 780 | hsa-miR-1274a, hsa-miR-1913, hsa-miR-564 | | | | 66.4% | 75.4% | 57.4% |
| L-127 | SEQ ID NO: 780, SEQ ID NO: 815, SEQ ID NO: 544 | hsa-miR-564, hsa-miR-1274b, hsa-miR-1826 | | | | 61.1% | 60.3% | 61.8% |
| L-128 | SEQ ID NO: 544, SEQ ID NO: 74, SEQ ID NO: 854 | hsa-miR-1826, hsa-let-7d*, hsa-miR-625 | | | | 66.3% | 79.7% | 53.0% |
| L-129 | SEQ ID NO: 854, SEQ ID NO: 134, SEQ ID NO: 558 | hsa-miR-625, hsa-miR-378*, hsa-miR-183* | | | | 71.1% | 85.6% | 56.6% |
| L-130 | SEQ ID NO: 558, SEQ ID NO: 430, SEQ ID NO: 597 | hsa-miR-183*, hsa-miR-21*, hsa-miR-877 | | | | 70.6% | 68.3% | 72.9% |
| L-131 | SEQ ID NO: 597, SEQ ID NO: 22, SEQ ID NO: 303 | hsa-miR-877, hsa-miR-1283, hsa-miR-1286 | | | | 64.4% | 67.9% | 60.9% |

Figure 11B (cont'd)

| | | | | | | | | |
|---|---|---|---|---|---|---|---|---|
| L-132 | SEQ ID NO: 303, SEQ ID NO: 771, SEQ ID NO: 454 | hsa-miR-1286, hsa-miR-518f*, hsa-miR-659 | | | | 55.2% | 64.7% | 45.7% |
| L-133 | SEQ ID NO: 454, SEQ ID NO: 81, SEQ ID NO: 202 | hsa-miR-659, hsa-miR-922, hsa-miR-508-5p | | | | 52.9% | 59.4% | 46.4% |
| L-134 | SEQ ID NO: 202, SEQ ID NO: 474, SEQ ID NO: 42 | hsa-miR-508-5p, hsa-miR-182*, hsa-miR-29c* | | | | 71.6% | 81.6% | 61.6% |
| L-135 | SEQ ID NO: 42, SEQ ID NO: 505, SEQ ID NO: 368 | hsa-miR-29c*, hsa-miR-942, hsa-miR-767-3p | | | | 70.1% | 75.2% | 64.9% |
| L-136 | SEQ ID NO: 368, SEQ ID NO: 366, SEQ ID NO: 659 | hsa-miR-767-3p, hsa-miR-369-5p, hsa-miR-519e* | | | | 66.9% | 78.6% | 55.1% |
| L-137 | SEQ ID NO: 366, SEQ ID NO: 718, SEQ ID NO: 659 | hsa-miR-369-5p, hsa-miR-1825, hsa-miR-519e* | | | | 65.7% | 81.4% | 50.1% |
| L-138 | SEQ ID NO: 659, SEQ ID NO: 377, SEQ ID NO: 643 | hsa-miR-519e*, hsa-miR-1206, hsa-miR-483-3p | | | | 60.1% | 69.0% | 51.1% |
| L-139 | SEQ ID NO: 526, SEQ ID NO: 735, SEQ ID NO: 699, SEQ ID NO: 714, SEQ ID NO: 623 | hsa-miR-500, hsa-miR-320d, hsa-miR-550, hsa-miR-320c, hsa-miR-1274a | | | | 74.1% | 79.1% | 69.0% |
| L-140 | SEQ ID NO: 699, SEQ ID NO: 714, SEQ ID NO: 623, SEQ ID NO: 565, SEQ ID NO: 780 | hsa-miR-550, hsa-miR-320c, hsa-miR-1274a, hsa-miR-1913, hsa-miR-564 | | | | 68.0% | 76.8% | 59.2% |
| L-141 | SEQ ID NO: 623, SEQ ID NO: 565, SEQ ID NO: 780, SEQ ID NO: 815, SEQ ID NO: 544 | hsa-miR-1274a, hsa-miR-1913, hsa-miR-564, hsa-miR-1274b, hsa-miR-1826 | | | | 66.2% | 68.3% | 64.1% |
| L-142 | SEQ ID NO: 565, SEQ ID NO: 780, SEQ ID NO: 815, SEQ ID NO: 544, SEQ ID NO: 74 | hsa-miR-1913, hsa-miR-564, hsa-miR-1274b, hsa-miR-1826, hsa-let-7d* | | | | 68.3% | 76.8% | 59.9% |
| L-143 | SEQ ID NO: 815, SEQ ID NO: 544, SEQ ID NO: 74, SEQ ID NO: 854, SEQ ID NO: 134 | hsa-miR-1274b, hsa-miR-1826, hsa-let-7d*, hsa-miR-625, hsa-miR-378* | | | | 72.7% | 86.6% | 58.7% |
| L-144 | SEQ ID NO: 74, SEQ ID NO: 854, SEQ ID NO: 134, SEQ ID NO: 558, SEQ ID NO: 430 | hsa-let-7d*, hsa-miR-625, hsa-miR-378*, hsa-miR-183*, hsa-miR-21* | | | | 70.9% | 78.3% | 63.5% |
| L-145 | SEQ ID NO: 854, SEQ ID NO: 134, SEQ ID NO: 558, SEQ ID NO: 430, SEQ ID NO: 597, SEQ ID NO: 22 | hsa-miR-625, hsa-miR-378*, hsa-miR-183*, hsa-miR-21*, hsa-miR-877, hsa-miR-1283 | | | | 68.3% | 74.3% | 62.4% |

Figure 11B (cont'd)

| | | | | | | | | |
|---|---|---|---|---|---|---|---|---|
| L-146 | SEQ ID NO: 430, SEQ ID NO: 597, SEQ ID NO: 22, SEQ ID NO: 303, SEQ ID NO: 771, SEQ ID NO: 454 | hsa-miR-21*, hsa-miR-877, hsa-miR-1283, hsa-miR-1286, hsa-miR-518f*, hsa-miR-659 | | | | 66.1% | 72.8% | 59.4% |
| L-147 | SEQ ID NO: 303, SEQ ID NO: 771, SEQ ID NO: 454, SEQ ID NO: 81, SEQ ID NO: 202, SEQ ID NO: 474 | hsa-miR-1286, hsa-miR-518f*, hsa-miR-659, hsa-miR-922, hsa-miR-508-5p, hsa-miR-182* | | | | 67.0% | 73.4% | 60.7% |
| L-148 | SEQ ID NO: 81, SEQ ID NO: 202, SEQ ID NO: 474, SEQ ID NO: 42, SEQ ID NO: 505, SEQ ID NO: 368 | hsa-miR-922, hsa-miR-508-5p, hsa-miR-182*, hsa-miR-29c*, hsa-miR-942, hsa-miR-767-3p | | | | 71.8% | 75.3% | 68.2% |
| L-149 | SEQ ID NO: 42, SEQ ID NO: 505, SEQ ID NO: 368, SEQ ID NO: 110, SEQ ID NO: 366, SEQ ID NO: 718 | hsa-miR-29c*, hsa-miR-942, hsa-miR-767-3p, hsa-miR-1256, hsa-miR-369-5p, hsa-miR-1825 | | | | 65.1% | 74.3% | 56.0% |
| L-150 | SEQ ID NO: 110, SEQ ID NO: 366, SEQ ID NO: 718, SEQ ID NO: 659, SEQ ID NO: 377, SEQ ID NO: 643 | hsa-miR-1256, hsa-miR-369-5p, hsa-miR-1825, hsa-miR-519e*, hsa-miR-1206, hsa-miR-483-3p | | | | 68.7% | 86.6% | 50.9% |
| L-151 | SEQ ID NO: 659, SEQ ID NO: 377, SEQ ID NO: 643, SEQ ID NO: 171, SEQ ID NO: 701, SEQ ID NO: 181 | hsa-miR-519e*, hsa-miR-1206, hsa-miR-483-3p, hsa-miR-214*, hsa-miR-1303, hsa-miR-891b | | | | 67.7% | 76.7% | 58.7% |
| L-152 | SEQ ID NO: 171, SEQ ID NO: 701, SEQ ID NO: 181, SEQ ID NO: 485, SEQ ID NO: 746, SEQ ID NO: 39 | hsa-miR-214*, hsa-miR-1303, hsa-miR-891b, hsa-miR-30e*, hsa-miR-155*, hsa-miR-668 | | | | 67.4% | 68.8% | 65.9% |
| L-153 | SEQ ID NO: 485, SEQ ID NO: 746, SEQ ID NO: 39, SEQ ID NO: 624, SEQ ID NO: 108, SEQ ID NO: 149 | hsa-miR-30e*, hsa-miR-155*, hsa-miR-668, hsa-miR-1226, hsa-miR-34a*, hsa-miR-647 | | | | 59.7% | 57.1% | 62.3% |
| L-154 | SEQ ID NO: 526, SEQ ID NO: 735, SEQ ID NO: 699, SEQ ID NO: 714, SEQ ID NO: 623, SEQ ID NO: 565, SEQ ID NO: 780, SEQ ID NO: 815, SEQ ID NO: 544, SEQ ID NO: 74 | hsa-miR-500, hsa-miR-320d, hsa-miR-550, hsa-miR-320c, hsa-miR-1274a, hsa-miR-1913, hsa-miR-564, hsa-miR-1274b, hsa-miR-1826, hsa-let-7d* | | | | 73.8% | 83.0% | 64.6% |

Figure 11B (cont'd)

| | | | | | | | | |
|---|---|---|---|---|---|---|---|---|
| L-155 | SEQ ID NO: 565, SEQ ID NO: 780, SEQ ID NO: 815, SEQ ID NO: 544, SEQ ID NO: 74, SEQ ID NO: 854, SEQ ID NO: 134, SEQ ID NO: 558, SEQ ID NO: 430, SEQ ID NO: 597, SEQ ID NO: 22 | hsa-miR-1913, hsa-miR-564, hsa-miR-1274b, hsa-miR-1826, hsa-let-7d*, hsa-miR-625, hsa-miR-378*, hsa-miR-183*, hsa-miR-21*, hsa-miR-877, hsa-miR-1283 | | | | 72.5% | 83.0% | 61.9% |
| L-156 | SEQ ID NO: 134, SEQ ID NO: 558, SEQ ID NO: 430, SEQ ID NO: 597, SEQ ID NO: 22, SEQ ID NO: 303, SEQ ID NO: 771, SEQ ID NO: 454, SEQ ID NO: 81, SEQ ID NO: 202 | hsa-miR-378*, hsa-miR-183*, hsa-miR-21*, hsa-miR-877, hsa-miR-1283, hsa-miR-1286, hsa-miR-518f*, hsa-miR-659, hsa-miR-922, hsa-miR-508-5p | | | | 67.3% | 74.3% | 60.2% |
| L-157 | SEQ ID NO: 303, SEQ ID NO: 771, SEQ ID NO: 454, SEQ ID NO: 81, SEQ ID NO: 202, SEQ ID NO: 474, SEQ ID NO: 42, SEQ ID NO: 505, SEQ ID NO: 368, SEQ ID NO: 110 | hsa-miR-1286, hsa-miR-518f*, hsa-miR-659, hsa-miR-922, hsa-miR-508-5p, hsa-miR-182*, hsa-miR-29c*, hsa-miR-942, hsa-miR-767-3p, hsa-miR-1256 | | | | 68.9% | 76.6% | 61.1% |
| L-158 | SEQ ID NO: 474, SEQ ID NO: 42, SEQ ID NO: 505, SEQ ID NO: 368, SEQ ID NO: 110, SEQ ID NO: 366, SEQ ID NO: 718, SEQ ID NO: 659, SEQ ID NO: 377, SEQ ID NO: 643 | hsa-miR-182*, hsa-miR-29c*, hsa-miR-942, hsa-miR-767-3p, hsa-miR-1256, hsa-miR-369-5p, hsa-miR-1825, hsa-miR-519e*, hsa-miR-1206, hsa-miR-483-3p | | | | 72.1% | 84.1% | 60.1% |
| L-159 | SEQ ID NO: 366, SEQ ID NO: 718, SEQ ID NO: 659, SEQ ID NO: 377, SEQ ID NO: 643, SEQ ID NO: 171, SEQ ID NO: 701, SEQ ID NO: 181, SEQ ID NO: 485, SEQ ID NO: 746 | hsa-miR-369-5p, hsa-miR-1825, hsa-miR-519e*, hsa-miR-1206, hsa-miR-483-3p, hsa-miR-214*, hsa-miR-1303, hsa-miR-891b, hsa-miR-30e*, hsa-miR-155* | | | | 64.3% | 73.7% | 55.0% |
| L-160 | SEQ ID NO: 171, SEQ ID NO: 701, SEQ ID NO: 181, SEQ ID NO: 485, SEQ ID NO: 746, SEQ ID NO: 39, SEQ ID NO: 624, SEQ ID NO: 108, SEQ ID NO: 149, SEQ ID NO: 631 | hsa-miR-214*, hsa-miR-1303, hsa-miR-891b, hsa-miR-30e*, hsa-miR-155*, hsa-miR-668, hsa-miR-1226, hsa-miR-34a*, hsa-miR-647, hsa-miR-610 | | | | 62.2% | 66.5% | 57.8% |

Figure 11B (cont'd)

| | | | | | | | | |
|---|---|---|---|---|---|---|---|---|
| L-161 | SEQ ID NO: 39, SEQ ID NO: 624, SEQ ID NO: 108, SEQ ID NO: 149, SEQ ID NO: 631, SEQ ID NO: 499, SEQ ID NO: 79, SEQ ID NO: 621, SEQ ID NO: 431, SEQ ID NO: 279 | hsa-miR-668, hsa-miR-1226, hsa-miR-34a*, hsa-miR-647, hsa-miR-610, hsa-miR-141*, hsa-miR-297, hsa-miR-935, hsa-miR-657, hsa-miR-548a-3p | | | | 62.5% | 68.7% | 56.3% |
| L-162 | SEQ ID NO: 499, SEQ ID NO: 79, SEQ ID NO: 621, SEQ ID NO: 431, SEQ ID NO: 279, SEQ ID NO: 459, SEQ ID NO: 185, SEQ ID NO: 188, SEQ ID NO: 75, SEQ ID NO: 806 | hsa-miR-141*, hsa-miR-297, hsa-miR-935, hsa-miR-657, hsa-miR-548a-3p, hsa-miR-802, hsa-miR-208b, hsa-miR-146b-3p, hsa-miR-199a-5p, hsa-miR-125a-5p | | | | 71.7% | 78.6% | 64.7% |
| L-163 | SEQ ID NO: 526, SEQ ID NO: 699, SEQ ID NO: 623, SEQ ID NO: 780, SEQ ID NO: 544 | hsa-miR-500, hsa-miR-550, hsa-miR-1274a, hsa-miR-564, hsa-miR-1826 | | | | 66.7% | 72.8% | 60.6% |
| L-164 | SEQ ID NO: 714, SEQ ID NO: 565, SEQ ID NO: 815, SEQ ID NO: 74, SEQ ID NO: 134 | hsa-miR-320c, hsa-miR-1913, hsa-miR-1274b, hsa-let-7d*, hsa-miR-378* | | | | 70.3% | 85.1% | 55.5% |
| L-165 | SEQ ID NO: 815, SEQ ID NO: 74, SEQ ID NO: 134, SEQ ID NO: 430, SEQ ID NO: 22 | hsa-miR-1274b, hsa-let-7d*, hsa-miR-378*, hsa-miR-21*, hsa-miR-1283 | | | | 68.9% | 75.3% | 62.4% |
| L-166 | SEQ ID NO: 1, SEQ ID NO: 2, SEQ ID NO: 3 | hsa-miR-126, hsa-miR-423-5p, hsa-let-7i | | | | 70.3% | 66.6% | 73.9% |
| L-167 | SEQ ID NO: 3, SEQ ID NO: 4, SEQ ID NO: 5 | hsa-let-7i, hsa-let-7d, hsa-miR-22 | | | | 57.5% | 50.1% | 65.0% |
| L-168 | SEQ ID NO: 5, SEQ ID NO: 6, SEQ ID NO: 7 | hsa-miR-22, hsa-miR-15a, hsa-miR-98 | | | | 53.7% | 49.0% | 58.4% |
| L-169 | SEQ ID NO: 7, SEQ ID NO: 8, SEQ ID NO: 9 | hsa-miR-98, hsa-miR-19a, hsa-miR-574-5p | | | | 56.2% | 74.5% | 37.9% |
| L-170 | SEQ ID NO: 9, SEQ ID NO: 10, SEQ ID NO: 11 | hsa-miR-574-5p, hsa-miR-324-3p, hsa-miR-20b | | | | 64.5% | 53.0% | 76.0% |
| L-171 | SEQ ID NO: 11, SEQ ID NO: 12, SEQ ID NO: 13 | hsa-miR-20b, hsa-miR-25, hsa-miR-195 | | | | 61.1% | 58.9% | 63.4% |
| L-172 | SEQ ID NO: 13, SEQ ID NO: 14, SEQ ID NO: 15 | hsa-miR-195, hsa-let-7e, hsa-let-7c | | | | 53.8% | 54.7% | 52.9% |
| L-173 | SEQ ID NO: 15, SEQ ID NO: 16, SEQ ID NO: 17 | hsa-let-7c, hsa-let-7f, hsa-let-7a | | | | 50.9% | 40.8% | 60.9% |

Figure 11B (cont'd)

| | | | | | | | | |
|---|---|---|---|---|---|---|---|---|
| L-174 | SEQ ID NO: 17, SEQ ID NO: 18, SEQ ID NO: 19 | hsa-let-7a, hsa-let-7g, hsa-miR-140-3p | | | | 42.2% | 46.5% | 37.9% |
| L-175 | SEQ ID NO: 19, SEQ ID NO: 20, SEQ ID NO: 21 | hsa-miR-140-3p, hsa-miR-339-5p, hsa-miR-361-5p | | | | 67.4% | 68.9% | 65.8% |
| L-176 | SEQ ID NO: 21, SEQ ID NO: 22, SEQ ID NO: 23 | hsa-miR-361-5p, hsa-miR-1283, hsa-miR-18a* | | | | 67.9% | 72.1% | 63.7% |
| L-177 | SEQ ID NO: 23, SEQ ID NO: 24, SEQ ID NO: 25 | hsa-miR-18a*, hsa-miR-26b, hsa-miR-604 | | | | 60.2% | 55.2% | 65.3% |
| L-178 | SEQ ID NO: 25, SEQ ID NO: 27, SEQ ID NO: 29 | hsa-miR-604, hsa-miR-93*, hsa-miR-1248 | | | | 53.8% | 57.3% | 50.4% |
| L-179 | SEQ ID NO: 27, SEQ ID NO: 28, SEQ ID NO: 29 | hsa-miR-93*, hsa-miR-29a, hsa-miR-1248 | | | | 57.5% | 62.5% | 52.5% |
| L-180 | SEQ ID NO: 29, SEQ ID NO: 30, SEQ ID NO: 31 | hsa-miR-1248, hsa-miR-210, hsa-miR-19b | | | | 63.4% | 77.5% | 49.4% |
| L-181 | SEQ ID NO: 1, SEQ ID NO: 2, SEQ ID NO: 3, SEQ ID NO: 4, SEQ ID NO: 5 | hsa-miR-126, hsa-miR-423-5p, hsa-let-7i, hsa-let-7d, hsa-miR-22 | | | | 70.5% | 67.7% | 73.4% |
| L-182 | SEQ ID NO: 3, SEQ ID NO: 4, SEQ ID NO: 5, SEQ ID NO: 6, SEQ ID NO: 7 | hsa-let-7i, hsa-let-7d, hsa-miR-22, hsa-miR-15a, hsa-miR-98 | | | | 54.7% | 50.9% | 58.5% |
| L-183 | SEQ ID NO: 5, SEQ ID NO: 6, SEQ ID NO: 7, SEQ ID NO: 8, SEQ ID NO: 9 | hsa-miR-22, hsa-miR-15a, hsa-miR-98, hsa-miR-19a, hsa-miR-574-5p | | | | 59.1% | 69.1% | 49.0% |
| L-184 | SEQ ID NO: 6, SEQ ID NO: 7, SEQ ID NO: 8, SEQ ID NO: 9, SEQ ID NO: 10 | hsa-miR-15a, hsa-miR-98, hsa-miR-19a, hsa-miR-574-5p, hsa-miR-324-3p | | | | 60.3% | 69.5% | 51.2% |
| L-185 | SEQ ID NO: 8, SEQ ID NO: 9, SEQ ID NO: 10, SEQ ID NO: 11, SEQ ID NO: 12 | hsa-miR-19a, hsa-miR-574-5p, hsa-miR-324-3p, hsa-miR-20b, hsa-miR-25 | | | | 59.2% | 57.0% | 61.4% |
| L-186 | SEQ ID NO: 10, SEQ ID NO: 11, SEQ ID NO: 12, SEQ ID NO: 13, SEQ ID NO: 14 | hsa-miR-324-3p, hsa-miR-20b, hsa-miR-25, hsa-miR-195, hsa-let-7e | | | | 64.2% | 60.9% | 67.4% |
| L-187 | SEQ ID NO: 11, SEQ ID NO: 12, SEQ ID NO: 13, SEQ ID NO: 14, SEQ ID NO: 15, SEQ ID NO: 16 | hsa-miR-20b, hsa-miR-25, hsa-miR-195, hsa-let-7e, hsa-let-7c, hsa-let-7f | | | | 59.4% | 54.3% | 64.6% |
| L-188 | SEQ ID NO: 14, SEQ ID NO: 15, SEQ ID NO: 16, SEQ ID NO: 17, SEQ ID NO: 18, SEQ ID NO: 19 | hsa-let-7e, hsa-let-7c, hsa-let-7f, hsa-let-7a, hsa-let-7g, hsa-miR-140-3p | | | | 49.4% | 48.0% | 50.9% |

Figure 11B (cont'd)

| | | | | | | | | |
|---|---|---|---|---|---|---|---|---|
| L-189 | SEQ ID NO: 17, SEQ ID NO: 18, SEQ ID NO: 19, SEQ ID NO: 20, SEQ ID NO: 21, SEQ ID NO: 22 | hsa-let-7a, hsa-let-7g, hsa-miR-140-3p, hsa-miR-339-5p, hsa-miR-361-5p, hsa-miR-1283 | | | | 68.4% | 70.4% | 66.4% |
| L-190 | SEQ ID NO: 20, SEQ ID NO: 21, SEQ ID NO: 22, SEQ ID NO: 23, SEQ ID NO: 24, SEQ ID NO: 25 | hsa-miR-339-5p, hsa-miR-361-5p, hsa-miR-1283, hsa-miR-18a*, hsa-miR-26b, hsa-miR-604 | | | | 64.2% | 61.5% | 66.9% |
| L-191 | SEQ ID NO: 23, SEQ ID NO: 24, SEQ ID NO: 25, SEQ ID NO: 26, SEQ ID NO: 27, SEQ ID NO: 28 | hsa-miR-18a*, hsa-miR-26b, hsa-miR-604, hsa-miR-423-3p, hsa-miR-93*, hsa-miR-29a | | | | 63.9% | 55.9% | 71.9% |
| L-192 | SEQ ID NO: 26, SEQ ID NO: 27, SEQ ID NO: 28, SEQ ID NO: 29, SEQ ID NO: 30, SEQ ID NO: 31 | hsa-miR-423-3p, hsa-miR-93*, hsa-miR-29a, hsa-miR-1248, hsa-miR-210, hsa-miR-19b | | | | 70.7% | 70.3% | 71.1% |
| L-193 | SEQ ID NO: 29, SEQ ID NO: 30, SEQ ID NO: 31, SEQ ID NO: 32, SEQ ID NO: 33, SEQ ID NO: 34 | hsa-miR-1248, hsa-miR-210, hsa-miR-19b, hsa-miR-453, hsa-miR-126*, hsa-miR-188-3p | | | | 59.9% | 67.7% | 52.2% |
| L-194 | SEQ ID NO: 32, SEQ ID NO: 33, SEQ ID NO: 34, SEQ ID NO: 35, SEQ ID NO: 36, SEQ ID NO: 37 | hsa-miR-453, hsa-miR-126*, hsa-miR-188-3p, hsa-miR-624*, hsa-miR-505*, hsa-miR-425 | | | | 65.5% | 75.3% | 55.8% |
| L-195 | SEQ ID NO: 35, SEQ ID NO: 36, SEQ ID NO: 37, SEQ ID NO: 38, SEQ ID NO: 39, SEQ ID NO: 40 | hsa-miR-624*, hsa-miR-505*, hsa-miR-425, hsa-miR-339-3p, hsa-miR-668, hsa-miR-363* | | | | 70.6% | 75.4% | 65.8% |
| L-196 | SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 | hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p | | | | 69.8% | 69.9% | 69.7% |
| L-197 | SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 | hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f | | | | 66.7% | 62.7% | 70.7% |

Figure 11B (cont'd)

| | | | | | | | | |
|---|---|---|---|---|---|---|---|---|
| L-198 | SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 | hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p | | | | 66.1% | 69.1% | 63.0% |
| L-199 | SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 | hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p | | | | 66.1% | 60.5% | 71.7% |
| L-200 | SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 | hsa-miR-1283, hsa-miR-18a*, hsa-miR-26b, hsa-miR-604, hsa-miR-423-3p, hsa-miR-93*, hsa-miR-29a, hsa-miR-1248, hsa-miR-210, hsa-miR-19b | | | | 67.8% | 59.2% | 76.3% |
| L-201 | SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 | hsa-miR-93*, hsa-miR-29a, hsa-miR-1248, hsa-miR-210, hsa-miR-19b, hsa-miR-453, hsa-miR-126*, hsa-miR-188-3p, hsa-miR-624*, hsa-miR-505* | | | | 74.6% | 75.1% | 74.2% |
| L-202 | SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41 | hsa-miR-453, hsa-miR-126*, hsa-miR-188-3p, hsa-miR-624*, hsa-miR-505*, hsa-miR-425, hsa-miR-339-3p, hsa-miR-668, hsa-miR-363*, hsa-miR-15b* | | | | 69.7% | 78.4% | 61.0% |
| L-203 | SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 | hsa-miR-425, hsa-miR-339-3p, hsa-miR-668, hsa-miR-363*, hsa-miR-15b*, hsa-miR-29c*, hsa-miR-550*, hsa-miR-34c-3p, hsa-miR-20a, hsa-miR-374a | | | | 69.1% | 75.9% | 62.3% |
| L-204 | SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51 | hsa-miR-29c*, hsa-miR-550*, hsa-miR-34c-3p, hsa-miR-20a, hsa-miR-374a, hsa-miR-145*, hsa-miR-302b, hsa-miR-106a, hsa-miR-30e, hsa-miR-223 | | | | 67.2% | 70.6% | 63.8% |
| L-205 | SEQ ID NO: 1, SEQ ID NO: 3, SEQ ID NO: 5, SEQ ID NO: 7, SEQ ID NO: 9 | hsa-miR-126, hsa-let-7i, hsa-miR-22, hsa-miR-98, hsa-miR-574-5p | | | | 67.4% | 67.8% | 67.1% |
| L-206 | SEQ ID NO: 4, SEQ ID NO: 6, SEQ ID NO: 8, SEQ ID NO: 10, SEQ ID NO: 12 | hsa-let-7d, hsa-miR-15a, hsa-miR-19a, hsa-miR-324-3p, hsa-miR-25 | | | | 56.2% | 56.3% | 56.1% |

Figure 11B (cont'd)

| | | | | | | | | |
|---|---|---|---|---|---|---|---|---|
| L-207 | SEQ ID NO: 8, SEQ ID NO: 10, SEQ ID NO: 12, SEQ ID NO: 14, SEQ ID NO: 16 | hsa-miR-19a, hsa-miR-324-3p, hsa-miR-25, hsa-let-7e, hsa-let-7f | | | | 59.1% | 60.3% | 57.8% |
| L-208 | SEQ ID NO: 21, SEQ ID NO: 118, SEQ ID NO: 1 | hsa-miR-361-5p, hsa-miR-23b, hsa-miR-126 | | | | 65.4% | 73.6% | 57.3% |
| L-209 | SEQ ID NO: 1, SEQ ID NO: 838, SEQ ID NO: 28 | hsa-miR-126, hsa-miR-527, hsa-miR-29a | | | | 69.5% | 63.1% | 75.9% |
| L-210 | SEQ ID NO: 28, SEQ ID NO: 3, SEQ ID NO: 8 | hsa-miR-29a, hsa-let-7i, hsa-miR-19a | | | | 53.8% | 63.8% | 43.9% |
| L-211 | SEQ ID NO: 8, SEQ ID NO: 146, SEQ ID NO: 594 | hsa-miR-19a, hsa-miR-28-5p, hsa-miR-185* | | | | 49.3% | 55.9% | 42.7% |
| L-212 | SEQ ID NO: 594, SEQ ID NO: 147, SEQ ID NO: 529 | hsa-miR-185*, hsa-miR-23a, hsa-miR-1914* | | | | 58.9% | 58.4% | 59.3% |
| L-213 | SEQ ID NO: 529, SEQ ID NO: 409, SEQ ID NO: 36 | hsa-miR-1914*, hsa-miR-29c, hsa-miR-505* | | | | 51.3% | 42.4% | 60.1% |
| L-214 | SEQ ID NO: 36, SEQ ID NO: 4, SEQ ID NO: 139 | hsa-miR-505*, hsa-let-7d, hsa-miR-378 | | | | 55.2% | 46.7% | 63.7% |
| L-215 | SEQ ID NO: 139, SEQ ID NO: 156, SEQ ID NO: 25 | hsa-miR-378, hsa-miR-29b, hsa-miR-604 | | | | 51.3% | 40.0% | 62.6% |
| L-216 | SEQ ID NO: 25, SEQ ID NO: 5, SEQ ID NO: 53 | hsa-miR-604, hsa-miR-22, hsa-let-7b | | | | 46.3% | 39.4% | 53.3% |
| L-217 | SEQ ID NO: 53, SEQ ID NO: 663, SEQ ID NO: 26 | hsa-let-7b, hsa-miR-299-3p, hsa-miR-423-3p | | | | 63.4% | 63.8% | 63.1% |
| L-218 | SEQ ID NO: 26, SEQ ID NO: 23, SEQ ID NO: 687 | hsa-miR-423-3p, hsa-miR-18a*, hsa-miR-1909 | | | | 72.2% | 68.5% | 76.0% |
| L-219 | SEQ ID NO: 687, SEQ ID NO: 15, SEQ ID NO: 6 | hsa-miR-1909, hsa-let-7c, hsa-miR-15a | | | | 57.7% | 54.6% | 60.7% |
| L-220 | SEQ ID NO: 6, SEQ ID NO: 27, SEQ ID NO: 50 | hsa-miR-15a, hsa-miR-93*, hsa-miR-30e | | | | 59.3% | 63.0% | 55.5% |
| L-221 | SEQ ID NO: 27, SEQ ID NO: 157, SEQ ID NO: 50 | hsa-miR-93*, hsa-miR-665, hsa-miR-30e | | | | 58.1% | 65.1% | 51.0% |
| L-222 | SEQ ID NO: 50, SEQ ID NO: 38, SEQ ID NO: 761 | hsa-miR-30e, hsa-miR-339-3p, hsa-miR-1307 | | | | 52.6% | 55.9% | 49.4% |

Figure 11B (cont'd)

| | | | | | | | | |
|---|---|---|---|---|---|---|---|---|
| L-223 | SEQ ID NO: 21, SEQ ID NO: 118, SEQ ID NO: 1, SEQ ID NO: 838, SEQ ID NO: 28 | hsa-miR-361-5p, hsa-miR-23b, hsa-miR-126, hsa-miR-527, hsa-miR-29a | | | | 64.1% | 65.4% | 62.9% |
| L-224 | SEQ ID NO: 1, SEQ ID NO: 838, SEQ ID NO: 28, SEQ ID NO: 3, SEQ ID NO: 8 | hsa-miR-126, hsa-miR-527, hsa-miR-29a, hsa-let-7i, hsa-miR-19a | | | | 68.7% | 64.2% | 73.1% |
| L-225 | SEQ ID NO: 28, SEQ ID NO: 3, SEQ ID NO: 8, SEQ ID NO: 146, SEQ ID NO: 594 | hsa-miR-29a, hsa-let-7i, hsa-miR-19a, hsa-miR-28-5p, hsa-miR-185* | | | | 49.6% | 52.8% | 46.4% |
| L-226 | SEQ ID NO: 3, SEQ ID NO: 8, SEQ ID NO: 146, SEQ ID NO: 594, SEQ ID NO: 147 | hsa-let-7i, hsa-miR-19a, hsa-miR-28-5p, hsa-miR-185*, hsa-miR-23a | | | | 55.1% | 63.5% | 46.7% |
| L-227 | SEQ ID NO: 146, SEQ ID NO: 594, SEQ ID NO: 147, SEQ ID NO: 529, SEQ ID NO: 409 | hsa-miR-28-5p, hsa-miR-185*, hsa-miR-23a, hsa-miR-1914*, hsa-miR-29c | | | | 55.4% | 58.6% | 52.2% |
| L-228 | SEQ ID NO: 147, SEQ ID NO: 529, SEQ ID NO: 409, SEQ ID NO: 36, SEQ ID NO: 4 | hsa-miR-23a, hsa-miR-1914*, hsa-miR-29c, hsa-miR-505*, hsa-let-7d | | | | 54.9% | 56.3% | 53.4% |
| L-229 | SEQ ID NO: 529, SEQ ID NO: 409, SEQ ID NO: 36, SEQ ID NO: 4, SEQ ID NO: 139, SEQ ID NO: 156 | hsa-miR-1914*, hsa-miR-29c, hsa-miR-505*, hsa-let-7d, hsa-miR-378, hsa-miR-29b | | | | 52.4% | 46.6% | 58.2% |
| L-230 | SEQ ID NO: 4, SEQ ID NO: 139, SEQ ID NO: 156, SEQ ID NO: 25, SEQ ID NO: 5, SEQ ID NO: 53 | hsa-let-7d, hsa-miR-378, hsa-miR-29b, hsa-miR-604, hsa-miR-22, hsa-let-7b | | | | 58.6% | 50.7% | 66.5% |
| L-231 | SEQ ID NO: 25, SEQ ID NO: 5, SEQ ID NO: 53, SEQ ID NO: 663, SEQ ID NO: 26, SEQ ID NO: 23 | hsa-miR-604, hsa-miR-22, hsa-let-7b, hsa-miR-299-3p, hsa-miR-423-3p, hsa-miR-18a* | | | | 64.4% | 66.9% | 61.9% |
| L-232 | SEQ ID NO: 663, SEQ ID NO: 26, SEQ ID NO: 23, SEQ ID NO: 687, SEQ ID NO: 15, SEQ ID NO: 6 | hsa-miR-299-3p, hsa-miR-423-3p, hsa-miR-18a*, hsa-miR-1909, hsa-let-7c, hsa-miR-15a | | | | 67.8% | 71.2% | 64.5% |
| L-233 | SEQ ID NO: 687, SEQ ID NO: 15, SEQ ID NO: 6, SEQ ID NO: 37, SEQ ID NO: 27, SEQ ID NO: 157 | hsa-miR-1909, hsa-let-7c, hsa-miR-15a, hsa-miR-425, hsa-miR-93*, hsa-miR-665 | | | | 64.6% | 66.4% | 62.9% |
| L-234 | SEQ ID NO: 37, SEQ ID NO: 27, SEQ ID NO: 157, SEQ ID NO: 50, SEQ ID NO: 38, SEQ ID NO: 761 | hsa-miR-425, hsa-miR-93*, hsa-miR-665, hsa-miR-30e, hsa-miR-339-3p, hsa-miR-1307 | | | | 56.7% | 62.3% | 51.2% |

Figure 11B (cont'd)

| | | | | | | | | |
|---|---|---|---|---|---|---|---|---|
| L-235 | SEQ ID NO: 50, SEQ ID NO: 38, SEQ ID NO: 761, SEQ ID NO: 579, SEQ ID NO: 677, SEQ ID NO: 622 | hsa-miR-30e, hsa-miR-339-3p, hsa-miR-1307, hsa-miR-625*, hsa-miR-193a-5p, hsa-miR-130b | | | | 65.8% | 71.1% | 60.5% |
| L-236 | SEQ ID NO: 579, SEQ ID NO: 677, SEQ ID NO: 622, SEQ ID NO: 734, SEQ ID NO: 9, SEQ ID NO: 10 | hsa-miR-625*, hsa-miR-193a-5p, hsa-miR-130b, hsa-miR-17*, hsa-miR-574-5p, hsa-miR-324-3p | | | | 72.6% | 75.9% | 69.3% |
| L-237 | SEQ ID NO: 734, SEQ ID NO: 9, SEQ ID NO: 10, SEQ ID NO: 358, SEQ ID NO: 688, SEQ ID NO: 605 | hsa-miR-17*, hsa-miR-574-5p, hsa-miR-324-3p, hsa-miR-24, hsa-miR-629, hsa-miR-1323 | | | | 64.3% | 67.7% | 60.9% |
| L-238 | SEQ ID NO: 21, SEQ ID NO: 118, SEQ ID NO: 1, SEQ ID NO: 838, SEQ ID NO: 28, SEQ ID NO: 3, SEQ ID NO: 8, SEQ ID NO: 146, SEQ ID NO: 594, SEQ ID NO: 147 | hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a | | | | 67.8% | 72.2% | 63.4% |
| L-239 | SEQ ID NO: 3, SEQ ID NO: 8, SEQ ID NO: 146, SEQ ID NO: 594, SEQ ID NO: 147, SEQ ID NO: 529, SEQ ID NO: 409, SEQ ID NO: 36, SEQ ID NO: 4, SEQ ID NO: 139, SEQ ID NO: 156 | hsa-let-7i, hsa-miR-19a, hsa-miR-28-5p, hsa-miR-185*, hsa-miR-23a, hsa-miR-1914*, hsa-miR-29c, hsa-miR-505*, hsa-let-7d, hsa-miR-378, hsa-miR-29b | | | | 59.5% | 59.8% | 59.3% |
| L-240 | SEQ ID NO: 409, SEQ ID NO: 36, SEQ ID NO: 4, SEQ ID NO: 139, SEQ ID NO: 156, SEQ ID NO: 25, SEQ ID NO: 5, SEQ ID NO: 53, SEQ ID NO: 663, SEQ ID NO: 26 | hsa-miR-29c, hsa-miR-505*, hsa-let-7d, hsa-miR-378, hsa-miR-29b, hsa-miR-604, hsa-miR-22, hsa-let-7b, hsa-miR-299-3p, hsa-miR-423-3p | | | | 62.3% | 64.0% | 60.6% |
| L-241 | SEQ ID NO: 25, SEQ ID NO: 5, SEQ ID NO: 53, SEQ ID NO: 663, SEQ ID NO: 26, SEQ ID NO: 23, SEQ ID NO: 687, SEQ ID NO: 15, SEQ ID NO: 6, SEQ ID NO: 37 | hsa-miR-604, hsa-miR-22, hsa-let-7b, hsa-miR-299-3p, hsa-miR-423-3p, hsa-miR-18a*, hsa-miR-1909, hsa-let-7c, hsa-miR-15a, hsa-miR-425 | | | | 67.5% | 69.8% | 65.1% |
| L-242 | SEQ ID NO: 23, SEQ ID NO: 687, SEQ ID NO: 15, SEQ ID NO: 6, SEQ ID NO: 37, SEQ ID NO: 27, SEQ ID NO: 157, SEQ ID NO: 50, SEQ ID NO: 38, SEQ ID NO: 761 | hsa-miR-18a*, hsa-miR-1909, hsa-let-7c, hsa-miR-15a, hsa-miR-425, hsa-miR-93*, hsa-miR-665, hsa-miR-30e, hsa-miR-339-3p, hsa-miR-1307 | | | | 65.5% | 70.2% | 60.8% |

Figure 11B (cont'd)

| | | | | | | | | |
|---|---|---|---|---|---|---|---|---|
| L-243 | SEQ ID NO: 27, SEQ ID NO: 157, SEQ ID NO: 50, SEQ ID NO: 38, SEQ ID NO: 761, SEQ ID NO: 579, SEQ ID NO: 677, SEQ ID NO: 622, SEQ ID NO: 734, SEQ ID NO: 9 | hsa-miR-93*, hsa-miR-665, hsa-miR-30e, hsa-miR-339-3p, hsa-miR-1307, hsa-miR-625*, hsa-miR-193a-5p, hsa-miR-130b, hsa-miR-17*, hsa-miR-574-5p | | | | 71.3% | 75.1% | 67.5% |
| L-244 | SEQ ID NO: 579, SEQ ID NO: 677, SEQ ID NO: 622, SEQ ID NO: 734, SEQ ID NO: 9, SEQ ID NO: 10, SEQ ID NO: 358, SEQ ID NO: 688, SEQ ID NO: 605, SEQ ID NO: 18 | hsa-miR-625*, hsa-miR-193a-5p, hsa-miR-130b, hsa-miR-17*, hsa-miR-574-5p, hsa-miR-324-3p, hsa-miR-24, hsa-miR-629, hsa-miR-1323, hsa-let-7g | | | | 73.8% | 79.9% | 67.8% |
| L-245 | SEQ ID NO: 10, SEQ ID NO: 358, SEQ ID NO: 688, SEQ ID NO: 605, SEQ ID NO: 18, SEQ ID NO: 77, SEQ ID NO: 131, SEQ ID NO: 196, SEQ ID NO: 731, SEQ ID NO: 109 | hsa-miR-324-3p, hsa-miR-24, hsa-miR-629, hsa-miR-1323, hsa-let-7g, hsa-miR-1246, hsa-miR-215, hsa-miR-151-3p, hsa-miR-1471, hsa-miR-652 | | | | 64.2% | 66.1% | 62.4% |
| L-246 | SEQ ID NO: 77, SEQ ID NO: 131, SEQ ID NO: 196, SEQ ID NO: 731, SEQ ID NO: 109, SEQ ID NO: 41, SEQ ID NO: 30, SEQ ID NO: 20, SEQ ID NO: 11, SEQ ID NO: 716 | hsa-miR-1246, hsa-miR-215, hsa-miR-151-3p, hsa-miR-1471, hsa-miR-652, hsa-miR-15b*, hsa-miR-210, hsa-miR-339-5p, hsa-miR-20b, hsa-miR-654-5p | | | | 66.7% | 71.0% | 62.4% |
| L-247 | SEQ ID NO: 21, SEQ ID NO: 1, SEQ ID NO: 28, SEQ ID NO: 8, SEQ ID NO: 594 | hsa-miR-361-5p, hsa-miR-126, hsa-miR-29a, hsa-miR-19a, hsa-miR-185* | | | | 66.3% | 60.7% | 71.9% |
| L-248 | SEQ ID NO: 838, SEQ ID NO: 3, SEQ ID NO: 146, SEQ ID NO: 147, SEQ ID NO: 409 | hsa-miR-527, hsa-let-7i, hsa-miR-28-5p, hsa-miR-23a, hsa-miR-29c | | | | 56.1% | 61.5% | 50.7% |
| L-249 | SEQ ID NO: 146, SEQ ID NO: 147, SEQ ID NO: 409, SEQ ID NO: 4, SEQ ID NO: 156 | hsa-miR-28-5p, hsa-miR-23a, hsa-miR-29c, hsa-let-7d, hsa-miR-29b | | | | 55.0% | 54.6% | 55.3% |
| L-250 | SEQ ID NO: 75, SEQ ID NO: 26, SEQ ID NO: 21, SEQ ID NO: 31, SEQ ID NO: 97, SEQ ID NO: 74 | hsa-miR-199a-5p, hsa-miR-423-3p, hsa-miR-361-5p, hsa-miR-361-5p, hsa-miR-19b, hsa-miR-331-3p, hsa-let-7d* | | | | 72.3% | 72.8% | 71.9% |
| L-251 | SEQ ID NO: 622, SEQ ID NO: 26, SEQ ID NO: 21, SEQ ID NO: 719, SEQ ID NO: 677, SEQ ID NO: 134 | hsa-miR-130b, hsa-miR-423-3p, hsa-miR-361-5p, hsa-miR-328, hsa-miR-193a-5p, hsa-miR-378* | | | | 74.0% | 75.8% | 72.2% |

Figure 11B (cont'd)

SEQUENCE LISTING

<160> NUMBER OF SEQ ID NOS: 866

<210> SEQ ID NO 1
<211> LENGTH: 22
<212> TYPE: RNA
<213> ORGANISM: Homo sapiens

<400> SEQUENCE: 1 ucguaccgugaguaauaaugcg 22

<210> SEQ ID NO 2
<211> LENGTH: 23
<212> TYPE: RNA

-continued

<213> ORGANISM: Homo sapiens

<400> SEQUENCE: 2 ugaggggcagagagcgagacuuu 23

<210> SEQ ID NO 3
<211> LENGTH: 22
<212> TYPE: RNA
<213> ORGANISM: Homo sapiens

<400> SEQUENCE: 3 ugagguaguaguuugugcuguu 22

<210> SEQ ID NO 4
<211> LENGTH: 22
<212> TYPE: RNA
<213> ORGANISM: Homo sapiens

<400> SEQUENCE: 4 agagguaguagguugcauaguu 22

<210> SEQ ID NO 5
<211> LENGTH: 22
<212> TYPE: RNA
<213> ORGANISM: Homo sapiens

<400> SEQUENCE: 5 aagcugccaguugaagaacugu 22

<210> SEQ ID NO 6
<211> LENGTH: 22
<212> TYPE: RNA
<213> ORGANISM: Homo sapiens

<400> SEQUENCE: 6 uagcagcacauaaugguuugug 22

<210> SEQ ID NO 7
<211> LENGTH: 22
<212> TYPE: RNA
<213> ORGANISM: Homo sapiens

<400> SEQUENCE: 7 ugagguaguaaguuguauuguu 22

<210> SEQ ID NO 8
<211> LENGTH: 23
<212> TYPE: RNA
<213> ORGANISM: Homo sapiens

<400> SEQUENCE: 8 ugugcaaaucuaugcaaaacuga 23

<210> SEQ ID NO 9
<211> LENGTH: 23
<212> TYPE: RNA
<213> ORGANISM: Homo sapiens

<400> SEQUENCE: 9 ugagugugugugugugagugugu 23

<210> SEQ ID NO 10
<211> LENGTH: 20

<212> TYPE: RNA
<213> ORGANISM: Homo sapiens

<400> SEQUENCE: 10 acugccccaggugcugcugg 20

<210> SEQ ID NO 11
<211> LENGTH: 23
<212> TYPE: RNA
<213> ORGANISM: Homo sapiens

<400> SEQUENCE: 11 caaagugcucauagugcagguag 23

<210> SEQ ID NO 12
<211> LENGTH: 22
<212> TYPE: RNA
<213> ORGANISM: Homo sapiens

<400> SEQUENCE: 12 cauugcacuugucucggucuga 22

<210> SEQ ID NO 13
<211> LENGTH: 21
<212> TYPE: RNA
<213> ORGANISM: Homo sapiens

<400> SEQUENCE: 13 uagcagcacagaaauauuggc 21

<210> SEQ ID NO 14
<211> LENGTH: 22
<212> TYPE: RNA
<213> ORGANISM: Homo sapiens

<400> SEQUENCE: 14 ugagguaggagguuguauaguu 22

<210> SEQ ID NO 15
<211> LENGTH: 22
<212> TYPE: RNA
<213> ORGANISM: Homo sapiens

<400> SEQUENCE: 15 ugagguaguagguuguaugguu 22

<210> SEQ ID NO 16
<211> LENGTH: 22
<212> TYPE: RNA
<213> ORGANISM: Homo sapiens

<400> SEQUENCE: 16 ugagguaguagauuguauaguu 22

<210> SEQ ID NO 17
<211> LENGTH: 22
<212> TYPE: RNA
<213> ORGANISM: Homo sapiens

<400> SEQUENCE: 17 ugagguaguagguuguauaguu 22

<210> SEQ ID NO 18

-continued

<211> LENGTH: 22
<212> TYPE: RNA
<213> ORGANISM: Homo sapiens

<400> SEQUENCE: 18 ugagguaguaguuuguacaguu 22

<210> SEQ ID NO 19
<211> LENGTH: 21
<212> TYPE: RNA
<213> ORGANISM: Homo sapiens

<400> SEQUENCE: 19 uaccacaggguagaaccacgg 21

<210> SEQ ID NO 20
<211> LENGTH: 23
<212> TYPE: RNA
<213> ORGANISM: Homo sapiens

<400> SEQUENCE: 20 ucccuguccuccaggagcucacg 23

<210> SEQ ID NO 21
<211> LENGTH: 22
<212> TYPE: RNA
<213> ORGANISM: Homo sapiens

<400> SEQUENCE: 21 uuaucagaaucuccagggguac 22

<210> SEQ ID NO 22
<211> LENGTH: 22
<212> TYPE: RNA
<213> ORGANISM: Homo sapiens

<400> SEQUENCE: 22 ucuacaaaggaaagcgcuuucu 22

<210> SEQ ID NO 23
<211> LENGTH: 23
<212> TYPE: RNA
<213> ORGANISM: Homo sapiens

<400> SEQUENCE: 23 acugcccuaagugcuccuucugg 23

<210> SEQ ID NO 24
<211> LENGTH: 21
<212> TYPE: RNA
<213> ORGANISM: Homo sapiens

<400> SEQUENCE: 24 uucaaguaauucaggauaggu 21

<210> SEQ ID NO 25
<211> LENGTH: 19
<212> TYPE: RNA
<213> ORGANISM: Homo sapiens

<400> SEQUENCE: 25 aggcugcggaauucaggac 19

-continued

<210> SEQ ID NO 26
<211> LENGTH: 23
<212> TYPE: RNA
<213> ORGANISM: Homo sapiens

<400> SEQUENCE: 26 agcucggucugaggccccucagu 23

<210> SEQ ID NO 27
<211> LENGTH: 22
<212> TYPE: RNA
<213> ORGANISM: Homo sapiens

<400> SEQUENCE: 27 acugcugagcuagcacuucccg 22

<210> SEQ ID NO 28
<211> LENGTH: 22
<212> TYPE: RNA
<213> ORGANISM: Homo sapiens

<400> SEQUENCE: 28 uagcaccaucugaaaucgguua 22

<210> SEQ ID NO 29
<211> LENGTH: 27
<212> TYPE: RNA
<213> ORGANISM: Homo sapiens

<400> SEQUENCE: 29 accuucuuguauaagcacugugcuaaa 27

<210> SEQ ID NO 30
<211> LENGTH: 22
<212> TYPE: RNA
<213> ORGANISM: Homo sapiens

<400> SEQUENCE: 30 cugugcgugugacagcggcuga 22

<210> SEQ ID NO 31
<211> LENGTH: 23
<212> TYPE: RNA
<213> ORGANISM: Homo sapiens

<400> SEQUENCE: 31 ugugcaaauccaugcaaaacuga 23

<210> SEQ ID NO 32
<211> LENGTH: 23
<212> TYPE: RNA
<213> ORGANISM: Homo sapiens

<400> SEQUENCE: 32 agguuguccguggugaguucgca 23

<210> SEQ ID NO 33
<211> LENGTH: 21
<212> TYPE: RNA
<213> ORGANISM: Homo sapiens

<400> SEQUENCE: 33 cauuauuacuuuugguacgcg 21

<210> SEQ ID NO 34
<211> LENGTH: 21
<212> TYPE: RNA
<213> ORGANISM: Homo sapiens

<400> SEQUENCE: 34 cucccacaugcaggguuugca 21

<210> SEQ ID NO 35
<211> LENGTH: 22
<212> TYPE: RNA
<213> ORGANISM: Homo sapiens

<400> SEQUENCE: 35 uaguaccaguaccuuguguuca 22

<210> SEQ ID NO 36
<211> LENGTH: 22
<212> TYPE: RNA
<213> ORGANISM: Homo sapiens

<400> SEQUENCE: 36 gggagccaggaaguauugaugu 22

<210> SEQ ID NO 37
<211> LENGTH: 23
<212> TYPE: RNA
<213> ORGANISM: Homo sapiens

<400> SEQUENCE: 37 aaugacacgaucacucccguuga 23

<210> SEQ ID NO 38
<211> LENGTH: 23
<212> TYPE: RNA
<213> ORGANISM: Homo sapiens

<400> SEQUENCE: 38 ugagcgccucgacgacagagccg 23

<210> SEQ ID NO 39
<211> LENGTH: 23
<212> TYPE: RNA
<213> ORGANISM: Homo sapiens

<400> SEQUENCE: 39 ugucacucggcucggcccacuac 23

<210> SEQ ID NO 40
<211> LENGTH: 22
<212> TYPE: RNA
<213> ORGANISM: Homo sapiens

<400> SEQUENCE: 40 cggguggaucacgaugcaauuu 22

<210> SEQ ID NO 41
<211> LENGTH: 22
<212> TYPE: RNA
<213> ORGANISM: Homo sapiens

<400> SEQUENCE: 41 cgaaucauuauuugcugcucua 22

<210> SEQ ID NO 42
<211> LENGTH: 22
<212> TYPE: RNA
<213> ORGANISM: Homo sapiens

<400> SEQUENCE: 42 ugaccgauuucuccugguguuc 22

<210> SEQ ID NO 43
<211> LENGTH: 22
<212> TYPE: RNA
<213> ORGANISM: Homo sapiens

<400> SEQUENCE: 43 ugucuuacucccucaggcacau 22

<210> SEQ ID NO 44
<211> LENGTH: 22
<212> TYPE: RNA
<213> ORGANISM: Homo sapiens

<400> SEQUENCE: 44 aaucacuaaccacacggccagg 22

<210> SEQ ID NO 45
<211> LENGTH: 23
<212> TYPE: RNA
<213> ORGANISM: Homo sapiens

<400> SEQUENCE: 45 uaaagugcuuauagugcagguag 23

<210> SEQ ID NO 46
<211> LENGTH: 22
<212> TYPE: RNA
<213> ORGANISM: Homo sapiens

<400> SEQUENCE: 46 uuauaauacaaccugauaagug 22

<210> SEQ ID NO 47
<211> LENGTH: 22
<212> TYPE: RNA
<213> ORGANISM: Homo sapiens

<400> SEQUENCE: 47 ggauuccuggaaauacuguucu 22

<210> SEQ ID NO 48
<211> LENGTH: 23
<212> TYPE: RNA
<213> ORGANISM: Homo sapiens

<400> SEQUENCE: 48 uaagugcuuccauguuuuaguag 23

<210> SEQ ID NO 49
<211> LENGTH: 23
<212> TYPE: RNA
<213> ORGANISM: Homo sapiens

<400> SEQUENCE: 49 aaaagugcuuacagugcagguag 23

<210> SEQ ID NO 50
<211> LENGTH: 22
<212> TYPE: RNA
<213> ORGANISM: Homo sapiens

<400> SEQUENCE: 50 uguaaacauccuugacuggaag 22

<210> SEQ ID NO 51
<211> LENGTH: 22
<212> TYPE: RNA
<213> ORGANISM: Homo sapiens

<400> SEQUENCE: 51 ugucaguuugucaaauacccca 22

<210> SEQ ID NO 52
<211> LENGTH: 22
<212> TYPE: RNA
<213> ORGANISM: Homo sapiens

<400> SEQUENCE: 52 cuggacugagccgugcuacugg 22

<210> SEQ ID NO 53
<211> LENGTH: 22
<212> TYPE: RNA
<213> ORGANISM: Homo sapiens

<400> SEQUENCE: 53 ugagguaguagguugugugguu 22

<210> SEQ ID NO 54
<211> LENGTH: 22
<212> TYPE: RNA
<213> ORGANISM: Homo sapiens

<400> SEQUENCE: 54 ugugacagauugauaacugaaa 22

<210> SEQ ID NO 55
<211> LENGTH: 18
<212> TYPE: RNA
<213> ORGANISM: Homo sapiens

<400> SEQUENCE: 55 ugcuuccuuucagagggu 18

<210> SEQ ID NO 56
<211> LENGTH: 22
<212> TYPE: RNA
<213> ORGANISM: Homo sapiens

<400> SEQUENCE: 56 aaaccguuaccauuacugaguu 22

<210> SEQ ID NO 57
<211> LENGTH: 22
<212> TYPE: RNA
<213> ORGANISM: Homo sapiens

<400> SEQUENCE: 57

-continued aaagugcaucuuuuuagaggau 22

<210> SEQ ID NO 58
<211> LENGTH: 26
<212> TYPE: RNA
<213> ORGANISM: Homo sapiens

<400> SEQUENCE: 58 aaguaguugguuuguaugagaugguu 26

<210> SEQ ID NO 59
<211> LENGTH: 23
<212> TYPE: RNA
<213> ORGANISM: Homo sapiens

<400> SEQUENCE: 59 gacacgggcgacagcugcggccc 23

<210> SEQ ID NO 60
<211> LENGTH: 23
<212> TYPE: RNA
<213> ORGANISM: Homo sapiens

<400> SEQUENCE: 60 ucccccaggugugauucugauuu 23

<210> SEQ ID NO 61
<211> LENGTH: 22
<212> TYPE: RNA
<213> ORGANISM: Homo sapiens

<400> SEQUENCE: 61 aguuuugcauaguugcacuaca 22

<210> SEQ ID NO 62
<211> LENGTH: 22
<212> TYPE: RNA
<213> ORGANISM: Homo sapiens

<400> SEQUENCE: 62 aucaugaugggcuccucggugu 22

<210> SEQ ID NO 63
<211> LENGTH: 22
<212> TYPE: RNA
<213> ORGANISM: Homo sapiens

<400> SEQUENCE: 63 cuccugagccauucugagccuc 22

<210> SEQ ID NO 64
<211> LENGTH: 22
<212> TYPE: RNA
<213> ORGANISM: Homo sapiens

<400> SEQUENCE: 64 aaaaugguucccuuuagagugu 22

<210> SEQ ID NO 65
<211> LENGTH: 22
<212> TYPE: RNA
<213> ORGANISM: Homo sapiens

<400> SEQUENCE: 65 aagugcuuccuuuuagaggguu 22

<210> SEQ ID NO 66
<211> LENGTH: 22
<212> TYPE: RNA
<213> ORGANISM: Homo sapiens

<400> SEQUENCE: 66 cucuagagggaagcgcuuucug 22

<210> SEQ ID NO 67
<211> LENGTH: 21
<212> TYPE: RNA
<213> ORGANISM: Homo sapiens

<400> SEQUENCE: 67 cugaccuaugaauugacagcc 21

<210> SEQ ID NO 68
<211> LENGTH: 21
<212> TYPE: RNA
<213> ORGANISM: Homo sapiens

<400> SEQUENCE: 68 aagugaucuaaaggccuacau 21

<210> SEQ ID NO 69
<211> LENGTH: 21
<212> TYPE: RNA
<213> ORGANISM: Homo sapiens

<400> SEQUENCE: 69 ucgaggagcucacagucuagu 21

<210> SEQ ID NO 70
<211> LENGTH: 21
<212> TYPE: RNA
<213> ORGANISM: Homo sapiens

<400> SEQUENCE: 70 uggacugcccugaucuggaga 21

<210> SEQ ID NO 71
<211> LENGTH: 23
<212> TYPE: RNA
<213> ORGANISM: Homo sapiens

<400> SEQUENCE: 71 uagcagcgggaacaguucugcag 23

<210> SEQ ID NO 72
<211> LENGTH: 19
<212> TYPE: RNA
<213> ORGANISM: Homo sapiens

<400> SEQUENCE: 72 agguugacauacguuuccc 19

<210> SEQ ID NO 73
<211> LENGTH: 22
<212> TYPE: RNA
<213> ORGANISM: Homo sapiens

```
<400> SEQUENCE: 73

gguggcccggccgugccugagg                                                  22

<210> SEQ ID NO 74
<211> LENGTH: 22
<212> TYPE: RNA
<213> ORGANISM: Homo sapiens

<400> SEQUENCE: 74

cuauacgaccugcugccuuucu                                                  22

<210> SEQ ID NO 75
<211> LENGTH: 23
<212> TYPE: RNA
<213> ORGANISM: Homo sapiens

<400> SEQUENCE: 75

cccaguguucagacuaccuguuc                                                 23

<210> SEQ ID NO 76
<211> LENGTH: 17
<212> TYPE: RNA
<213> ORGANISM: Homo sapiens

<400> SEQUENCE: 76

ucucgcuggggccucca                                                       17

<210> SEQ ID NO 77
<211> LENGTH: 19
<212> TYPE: RNA
<213> ORGANISM: Homo sapiens

<400> SEQUENCE: 77

aauggauuuuuggagcagg                                                     19

<210> SEQ ID NO 78
<211> LENGTH: 22
<212> TYPE: RNA
<213> ORGANISM: Homo sapiens

<400> SEQUENCE: 78

aacaauauccuggugcugagug                                                  22

<210> SEQ ID NO 79
<211> LENGTH: 21
<212> TYPE: RNA
<213> ORGANISM: Homo sapiens

<400> SEQUENCE: 79

auguaugugugcaugugcaug                                                   21

<210> SEQ ID NO 80
<211> LENGTH: 19
<212> TYPE: RNA
<213> ORGANISM: Homo sapiens

<400> SEQUENCE: 80

auggauaaggcuuuggcuu                                                     19

<210> SEQ ID NO 81
<211> LENGTH: 23
<212> TYPE: RNA
```

<213> ORGANISM: Homo sapiens

<400> SEQUENCE: 81 gcagcagagaauaggacuacguc 23

<210> SEQ ID NO 82
<211> LENGTH: 22
<212> TYPE: RNA
<213> ORGANISM: Homo sapiens

<400> SEQUENCE: 82 uggagagaaaggcaguuccuga 22

<210> SEQ ID NO 83
<211> LENGTH: 23
<212> TYPE: RNA
<213> ORGANISM: Homo sapiens

<400> SEQUENCE: 83 gcgaggaccccucggggucugac 23

<210> SEQ ID NO 84
<211> LENGTH: 26
<212> TYPE: RNA
<213> ORGANISM: Homo sapiens

<400> SEQUENCE: 84 gaugaugauggcagcaaauucugaaa 26

<210> SEQ ID NO 85
<211> LENGTH: 22
<212> TYPE: RNA
<213> ORGANISM: Homo sapiens

<400> SEQUENCE: 85 uucuggaauucugugugaggga 22

<210> SEQ ID NO 86
<211> LENGTH: 22
<212> TYPE: RNA
<213> ORGANISM: Homo sapiens

<400> SEQUENCE: 86 uuuuucauuauugcuccugacc 22

<210> SEQ ID NO 87
<211> LENGTH: 21
<212> TYPE: RNA
<213> ORGANISM: Homo sapiens

<400> SEQUENCE: 87 cagcagcacacugugguuugu 21

<210> SEQ ID NO 88
<211> LENGTH: 18
<212> TYPE: RNA
<213> ORGANISM: Homo sapiens

<400> SEQUENCE: 88 ucagcuggcccucauuuc 18

<210> SEQ ID NO 89
<211> LENGTH: 22

<212> TYPE: RNA
<213> ORGANISM: Homo sapiens

<400> SEQUENCE: 89 uagcagcacguaaauauuggcg 22

<210> SEQ ID NO 90
<211> LENGTH: 22
<212> TYPE: RNA
<213> ORGANISM: Homo sapiens

<400> SEQUENCE: 90 uggaauguaaagaaguauguau 22

<210> SEQ ID NO 91
<211> LENGTH: 24
<212> TYPE: RNA
<213> ORGANISM: Homo sapiens

<400> SEQUENCE: 91 uggcccugacugaagaccagcagu 24

<210> SEQ ID NO 92
<211> LENGTH: 22
<212> TYPE: RNA
<213> ORGANISM: Homo sapiens

<400> SEQUENCE: 92 gcuauuucacgacaccaggguu 22

<210> SEQ ID NO 93
<211> LENGTH: 23
<212> TYPE: RNA
<213> ORGANISM: Homo sapiens

<400> SEQUENCE: 93 acuccauuuguuuugaugaugga 23

<210> SEQ ID NO 94
<211> LENGTH: 22
<212> TYPE: RNA
<213> ORGANISM: Homo sapiens

<400> SEQUENCE: 94 caaaaaccacaguuucuuuugc 22

<210> SEQ ID NO 95
<211> LENGTH: 22
<212> TYPE: RNA
<213> ORGANISM: Homo sapiens

<400> SEQUENCE: 95 caaaguuuaagauccuugaagu 22

<210> SEQ ID NO 96
<211> LENGTH: 22
<212> TYPE: RNA
<213> ORGANISM: Homo sapiens

<400> SEQUENCE: 96 aaaaguaaucgcgguuuuuguc 22

<210> SEQ ID NO 97

<211> LENGTH: 21
<212> TYPE: RNA
<213> ORGANISM: Homo sapiens

<400> SEQUENCE: 97 gccccugggccuauccuagaa 21

<210> SEQ ID NO 98
<211> LENGTH: 22
<212> TYPE: RNA
<213> ORGANISM: Homo sapiens

<400> SEQUENCE: 98 gcccaaaggugaauuuuuuggg 22

<210> SEQ ID NO 99
<211> LENGTH: 23
<212> TYPE: RNA
<213> ORGANISM: Homo sapiens

<400> SEQUENCE: 99 guccaguuuucccaggaaucccu 23

<210> SEQ ID NO 100
<211> LENGTH: 23
<212> TYPE: RNA
<213> ORGANISM: Homo sapiens

<400> SEQUENCE: 100 caaagugcuuacagugcagguag 23

<210> SEQ ID NO 101
<211> LENGTH: 22
<212> TYPE: RNA
<213> ORGANISM: Homo sapiens

<400> SEQUENCE: 101 uguaaacauccuacacucagcu 22

<210> SEQ ID NO 102
<211> LENGTH: 22
<212> TYPE: RNA
<213> ORGANISM: Homo sapiens

<400> SEQUENCE: 102 cuauacaaucuauugccuuccc 22

<210> SEQ ID NO 103
<211> LENGTH: 22
<212> TYPE: RNA
<213> ORGANISM: Homo sapiens

<400> SEQUENCE: 103 uuucaacucuaaugggagaga 22

<210> SEQ ID NO 104
<211> LENGTH: 21
<212> TYPE: RNA
<213> ORGANISM: Homo sapiens

<400> SEQUENCE: 104 cuuuuugcggucugggcuugc 21

<210> SEQ ID NO 105
<211> LENGTH: 21
<212> TYPE: RNA
<213> ORGANISM: Homo sapiens

<400> SEQUENCE: 105 ucguggccuggucuccauuau 21

<210> SEQ ID NO 106
<211> LENGTH: 22
<212> TYPE: RNA
<213> ORGANISM: Homo sapiens

<400> SEQUENCE: 106 ccgcacuguggguacuugcugc 22

<210> SEQ ID NO 107
<211> LENGTH: 24
<212> TYPE: RNA
<213> ORGANISM: Homo sapiens

<400> SEQUENCE: 107 gaccuggacauguuugugcccagu 24

<210> SEQ ID NO 108
<211> LENGTH: 22
<212> TYPE: RNA
<213> ORGANISM: Homo sapiens

<400> SEQUENCE: 108 caaucagcaaguauacugcccu 22

<210> SEQ ID NO 109
<211> LENGTH: 21
<212> TYPE: RNA
<213> ORGANISM: Homo sapiens

<400> SEQUENCE: 109 aauggcgccacuaggguugug 21

<210> SEQ ID NO 110
<211> LENGTH: 22
<212> TYPE: RNA
<213> ORGANISM: Homo sapiens

<400> SEQUENCE: 110 aggcauugacuucucacuagcu 22

<210> SEQ ID NO 111
<211> LENGTH: 22
<212> TYPE: RNA
<213> ORGANISM: Homo sapiens

<400> SEQUENCE: 111 acuguaguaugggcacuuccag 22

<210> SEQ ID NO 112
<211> LENGTH: 21
<212> TYPE: RNA
<213> ORGANISM: Homo sapiens

<400> SEQUENCE: 112 caaaacgugaggcgcugcuau 21

<210> SEQ ID NO 113
<211> LENGTH: 22
<212> TYPE: RNA
<213> ORGANISM: Homo sapiens

<400> SEQUENCE: 113 aucgugcaucccuuuagagugu 22

<210> SEQ ID NO 114
<211> LENGTH: 22
<212> TYPE: RNA
<213> ORGANISM: Homo sapiens

<400> SEQUENCE: 114 ucuauacagacccuggcuuuuc 22

<210> SEQ ID NO 115
<211> LENGTH: 22
<212> TYPE: RNA
<213> ORGANISM: Homo sapiens

<400> SEQUENCE: 115 acaguagucugcacauugguua 22

<210> SEQ ID NO 116
<211> LENGTH: 20
<212> TYPE: RNA
<213> ORGANISM: Homo sapiens

<400> SEQUENCE: 116 guugugucaguuuaucaaac 20

<210> SEQ ID NO 117
<211> LENGTH: 21
<212> TYPE: RNA
<213> ORGANISM: Homo sapiens

<400> SEQUENCE: 117 uaguagaccguauagcguacg 21

<210> SEQ ID NO 118
<211> LENGTH: 21
<212> TYPE: RNA
<213> ORGANISM: Homo sapiens

<400> SEQUENCE: 118 aucacauugccagggauuacc 21

<210> SEQ ID NO 119
<211> LENGTH: 21
<212> TYPE: RNA
<213> ORGANISM: Homo sapiens

<400> SEQUENCE: 119 uugggacauacuuaugcuaaa 21

<210> SEQ ID NO 120
<211> LENGTH: 22
<212> TYPE: RNA
<213> ORGANISM: Homo sapiens

<400> SEQUENCE: 120 uggcaguguauuguuagcuggu 22

<210> SEQ ID NO 121
<211> LENGTH: 19
<212> TYPE: RNA
<213> ORGANISM: Homo sapiens

<400> SEQUENCE: 121 aaaaacuguaauuacuuuu 19

<210> SEQ ID NO 122
<211> LENGTH: 22
<212> TYPE: RNA
<213> ORGANISM: Homo sapiens

<400> SEQUENCE: 122 ugugucacucgaugaccacugu 22

<210> SEQ ID NO 123
<211> LENGTH: 22
<212> TYPE: RNA
<213> ORGANISM: Homo sapiens

<400> SEQUENCE: 123 cacacacugcaauuacuuuugc 22

<210> SEQ ID NO 124
<211> LENGTH: 22
<212> TYPE: RNA
<213> ORGANISM: Homo sapiens

<400> SEQUENCE: 124 acccgucccguucguccccgga 22

<210> SEQ ID NO 125
<211> LENGTH: 21
<212> TYPE: RNA
<213> ORGANISM: Homo sapiens

<400> SEQUENCE: 125 uccugcgcgucccagaugccc 21

<210> SEQ ID NO 126
<211> LENGTH: 23
<212> TYPE: RNA
<213> ORGANISM: Homo sapiens

<400> SEQUENCE: 126 ugaguaccgccaugucuguuggg 23

<210> SEQ ID NO 127
<211> LENGTH: 23
<212> TYPE: RNA
<213> ORGANISM: Homo sapiens

<400> SEQUENCE: 127 ccuaguagguguccaguaagugu 23

<210> SEQ ID NO 128
<211> LENGTH: 23
<212> TYPE: RNA
<213> ORGANISM: Homo sapiens

<400> SEQUENCE: 128 agguuacccgagcaacuuugcau 23

<210> SEQ ID NO 129
<211> LENGTH: 24
<212> TYPE: RNA
<213> ORGANISM: Homo sapiens

<400> SEQUENCE: 129 uuuggcaaugguagaacucacacu 24

<210> SEQ ID NO 130
<211> LENGTH: 25
<212> TYPE: RNA
<213> ORGANISM: Homo sapiens

<400> SEQUENCE: 130 ggcggagggaaguagguccguuggu 25

<210> SEQ ID NO 131
<211> LENGTH: 21
<212> TYPE: RNA
<213> ORGANISM: Homo sapiens

<400> SEQUENCE: 131 augaccuaugaauugacagac 21

<210> SEQ ID NO 132
<211> LENGTH: 22
<212> TYPE: RNA
<213> ORGANISM: Homo sapiens

<400> SEQUENCE: 132 gugugcggaaaugcuucugcua 22

<210> SEQ ID NO 133
<211> LENGTH: 22
<212> TYPE: RNA
<213> ORGANISM: Homo sapiens

<400> SEQUENCE: 133 uguaaacauccccgacuggaag 22

<210> SEQ ID NO 134
<211> LENGTH: 22
<212> TYPE: RNA
<213> ORGANISM: Homo sapiens

<400> SEQUENCE: 134 cuccugacuccagguccugugu 22

<210> SEQ ID NO 135
<211> LENGTH: 22
<212> TYPE: RNA
<213> ORGANISM: Homo sapiens

<400> SEQUENCE: 135 accuggcauacaauguagauuu 22

<210> SEQ ID NO 136
<211> LENGTH: 22
<212> TYPE: RNA
<213> ORGANISM: Homo sapiens

<400> SEQUENCE: 136 caaucacuaacuccacugccau 22

<210> SEQ ID NO 137
<211> LENGTH: 25
<212> TYPE: RNA
<213> ORGANISM: Homo sapiens

<400> SEQUENCE: 137 aggcaccagccaggcauugcucagc 25

<210> SEQ ID NO 138
<211> LENGTH: 21
<212> TYPE: RNA
<213> ORGANISM: Homo sapiens

<400> SEQUENCE: 138 aacaggugacugguuagacaa 21

<210> SEQ ID NO 139
<211> LENGTH: 21
<212> TYPE: RNA
<213> ORGANISM: Homo sapiens

<400> SEQUENCE: 139 acuggacuuggagucagaagg 21

<210> SEQ ID NO 140
<211> LENGTH: 22
<212> TYPE: RNA
<213> ORGANISM: Homo sapiens

<400> SEQUENCE: 140 ggugcagugcugcaucucuggu 22

<210> SEQ ID NO 141
<211> LENGTH: 23
<212> TYPE: RNA
<213> ORGANISM: Homo sapiens

<400> SEQUENCE: 141 ccucagggcuguagaacagggcu 23

<210> SEQ ID NO 142
<211> LENGTH: 21
<212> TYPE: RNA
<213> ORGANISM: Homo sapiens

<400> SEQUENCE: 142 gcuaguccugacucagccagu 21

<210> SEQ ID NO 143
<211> LENGTH: 21
<212> TYPE: RNA
<213> ORGANISM: Homo sapiens

<400> SEQUENCE: 143 agaccuggcccagaccucagc 21

<210> SEQ ID NO 144
<211> LENGTH: 20
<212> TYPE: RNA
<213> ORGANISM: Homo sapiens

<400> SEQUENCE: 144 agggguguuucucucaucucu 20

<210> SEQ ID NO 145
<211> LENGTH: 23
<212> TYPE: RNA
<213> ORGANISM: Homo sapiens

<400> SEQUENCE: 145 uguaaacauccuacacucucagc 23

<210> SEQ ID NO 146
<211> LENGTH: 22
<212> TYPE: RNA
<213> ORGANISM: Homo sapiens

<400> SEQUENCE: 146 aaggagcucacagucuauugag 22

<210> SEQ ID NO 147
<211> LENGTH: 21
<212> TYPE: RNA
<213> ORGANISM: Homo sapiens

<400> SEQUENCE: 147 aucacauugccagggauuucc 21

<210> SEQ ID NO 148
<211> LENGTH: 19
<212> TYPE: RNA
<213> ORGANISM: Homo sapiens

<400> SEQUENCE: 148 ucuaggcugguacugcuga 19

<210> SEQ ID NO 149
<211> LENGTH: 21
<212> TYPE: RNA
<213> ORGANISM: Homo sapiens

<400> SEQUENCE: 149 guggcugcacucacuuccuuc 21

<210> SEQ ID NO 150
<211> LENGTH: 22
<212> TYPE: RNA
<213> ORGANISM: Homo sapiens

<400> SEQUENCE: 150 acuuuaacauggaagugcuuuc 22

<210> SEQ ID NO 151
<211> LENGTH: 21
<212> TYPE: RNA
<213> ORGANISM: Homo sapiens

<400> SEQUENCE: 151 guucaaauccagaucuauaac 21

<210> SEQ ID NO 152
<211> LENGTH: 23
<212> TYPE: RNA
<213> ORGANISM: Homo sapiens

<400> SEQUENCE: 152 uggaguccaggaaucugcauuuu 23

<210> SEQ ID NO 153
<211> LENGTH: 24
<212> TYPE: RNA
<213> ORGANISM: Homo sapiens

<400> SEQUENCE: 153 ccagacagaauucuaugcacuuuc 24

<210> SEQ ID NO 154
<211> LENGTH: 23
<212> TYPE: RNA
<213> ORGANISM: Homo sapiens

<400> SEQUENCE: 154 uaaauuucaccuuucugagaagg 23

<210> SEQ ID NO 155
<211> LENGTH: 24
<212> TYPE: RNA
<213> ORGANISM: Homo sapiens

<400> SEQUENCE: 155 uggggagcugaggcucugggggug 24

<210> SEQ ID NO 156
<211> LENGTH: 23
<212> TYPE: RNA
<213> ORGANISM: Homo sapiens

<400> SEQUENCE: 156 uagcaccauuugaaaucaguguu 23

<210> SEQ ID NO 157
<211> LENGTH: 20
<212> TYPE: RNA
<213> ORGANISM: Homo sapiens

<400> SEQUENCE: 157 accaggaggcugaggccccu 20

<210> SEQ ID NO 158
<211> LENGTH: 23
<212> TYPE: RNA
<213> ORGANISM: Homo sapiens

<400> SEQUENCE: 158 uaaggugcaucuagugcagauag 23

<210> SEQ ID NO 159
<211> LENGTH: 19
<212> TYPE: RNA
<213> ORGANISM: Homo sapiens

<400> SEQUENCE: 159 gugaggacucgggaggugg 19

<210> SEQ ID NO 160
<211> LENGTH: 22
<212> TYPE: RNA

<213> ORGANISM: Homo sapiens

<400> SEQUENCE: 160 caaauucguaucuaggggaaua 22

<210> SEQ ID NO 161
<211> LENGTH: 22
<212> TYPE: RNA
<213> ORGANISM: Homo sapiens

<400> SEQUENCE: 161 accaucgaccguugauuguacc 22

<210> SEQ ID NO 162
<211> LENGTH: 22
<212> TYPE: RNA
<213> ORGANISM: Homo sapiens

<400> SEQUENCE: 162 caugguucugucaagcaccgcg 22

<210> SEQ ID NO 163
<211> LENGTH: 23
<212> TYPE: RNA
<213> ORGANISM: Homo sapiens

<400> SEQUENCE: 163 aagugccgccaucuuuugagugu 23

<210> SEQ ID NO 164
<211> LENGTH: 22
<212> TYPE: RNA
<213> ORGANISM: Homo sapiens

<400> SEQUENCE: 164 aucacacaaaggcaacuuuugu 22

<210> SEQ ID NO 165
<211> LENGTH: 22
<212> TYPE: RNA
<213> ORGANISM: Homo sapiens

<400> SEQUENCE: 165 cagugguuuuacccuaugguag 22

<210> SEQ ID NO 166
<211> LENGTH: 23
<212> TYPE: RNA
<213> ORGANISM: Homo sapiens

<400> SEQUENCE: 166 cagugcaauaguauugucaaagc 23

<210> SEQ ID NO 167
<211> LENGTH: 22
<212> TYPE: RNA
<213> ORGANISM: Homo sapiens

<400> SEQUENCE: 167 uacguagauauauauguauuuu 22

<210> SEQ ID NO 168
<211> LENGTH: 22

-continued

<212> TYPE: RNA
<213> ORGANISM: Homo sapiens

<400> SEQUENCE: 168 uucacauugugcuacugucugc 22

<210> SEQ ID NO 169
<211> LENGTH: 22
<212> TYPE: RNA
<213> ORGANISM: Homo sapiens

<400> SEQUENCE: 169 uacccagagcaugcagugugaa 22

<210> SEQ ID NO 170
<211> LENGTH: 22
<212> TYPE: RNA
<213> ORGANISM: Homo sapiens

<400> SEQUENCE: 170 aacuggcccucaaagucccgcu 22

<210> SEQ ID NO 171
<211> LENGTH: 22
<212> TYPE: RNA
<213> ORGANISM: Homo sapiens

<400> SEQUENCE: 171 ugccugucuacacuugcugugc 22

<210> SEQ ID NO 172
<211> LENGTH: 22
<212> TYPE: RNA
<213> ORGANISM: Homo sapiens

<400> SEQUENCE: 172 aaaucucugcaggcaaauguga 22

<210> SEQ ID NO 173
<211> LENGTH: 17
<212> TYPE: RNA
<213> ORGANISM: Homo sapiens

<400> SEQUENCE: 173 uaauugcuuccauguuu 17

<210> SEQ ID NO 174
<211> LENGTH: 22
<212> TYPE: RNA
<213> ORGANISM: Homo sapiens

<400> SEQUENCE: 174 cucuagagggaagcgcuuucug 22

<210> SEQ ID NO 175
<211> LENGTH: 22
<212> TYPE: RNA
<213> ORGANISM: Homo sapiens

<400> SEQUENCE: 175 aaaaguaauugcggucuuuggu 22

<210> SEQ ID NO 176

<211> LENGTH: 20
<212> TYPE: RNA
<213> ORGANISM: Homo sapiens

<400> SEQUENCE: 176 auguauaaauguauacacac 20

<210> SEQ ID NO 177
<211> LENGTH: 19
<212> TYPE: RNA
<213> ORGANISM: Homo sapiens

<400> SEQUENCE: 177 aagugugcagggcacuggu 19

<210> SEQ ID NO 178
<211> LENGTH: 21
<212> TYPE: RNA
<213> ORGANISM: Homo sapiens

<400> SEQUENCE: 178 ucccacguuguggcccagcag 21

<210> SEQ ID NO 179
<211> LENGTH: 21
<212> TYPE: RNA
<213> ORGANISM: Homo sapiens

<400> SEQUENCE: 179 agcuacaucuggcuacugggu 21

<210> SEQ ID NO 180
<211> LENGTH: 22
<212> TYPE: RNA
<213> ORGANISM: Homo sapiens

<400> SEQUENCE: 180 ugcuggaucagugguucgaguc 22

<210> SEQ ID NO 181
<211> LENGTH: 22
<212> TYPE: RNA
<213> ORGANISM: Homo sapiens

<400> SEQUENCE: 181 ugcaacuuaccugagucauuga 22

<210> SEQ ID NO 182
<211> LENGTH: 23
<212> TYPE: RNA
<213> ORGANISM: Homo sapiens

<400> SEQUENCE: 182 ucucacacagaaaucgcacccgu 23

<210> SEQ ID NO 183
<211> LENGTH: 22
<212> TYPE: RNA
<213> ORGANISM: Homo sapiens

<400> SEQUENCE: 183 aagugcugucauagcugagguc 22

-continued

<210> SEQ ID NO 184
<211> LENGTH: 23
<212> TYPE: RNA
<213> ORGANISM: Homo sapiens

<400> SEQUENCE: 184 aucccuugcaggggcuguugggu 23

<210> SEQ ID NO 185
<211> LENGTH: 22
<212> TYPE: RNA
<213> ORGANISM: Homo sapiens

<400> SEQUENCE: 185 auaagacgaacaaaagguuugu 22

<210> SEQ ID NO 186
<211> LENGTH: 22
<212> TYPE: RNA
<213> ORGANISM: Homo sapiens

<400> SEQUENCE: 186 ccaguauuaacugugcugcuga 22

<210> SEQ ID NO 187
<211> LENGTH: 21
<212> TYPE: RNA
<213> ORGANISM: Homo sapiens

<400> SEQUENCE: 187 gcgacccauacuugguuucag 21

<210> SEQ ID NO 188
<211> LENGTH: 22
<212> TYPE: RNA
<213> ORGANISM: Homo sapiens

<400> SEQUENCE: 188 ugcccuguggacucaguucugg 22

<210> SEQ ID NO 189
<211> LENGTH: 21
<212> TYPE: RNA
<213> ORGANISM: Homo sapiens

<400> SEQUENCE: 189 aaagugcuuccuuuuagaggg 21

<210> SEQ ID NO 190
<211> LENGTH: 22
<212> TYPE: RNA
<213> ORGANISM: Homo sapiens

<400> SEQUENCE: 190 aggcaguguauuguuagcuggc 22

<210> SEQ ID NO 191
<211> LENGTH: 24
<212> TYPE: RNA
<213> ORGANISM: Homo sapiens

<400> SEQUENCE: 191 acaaagugcuucccuuuagagugu 24

<210> SEQ ID NO 192
<211> LENGTH: 22
<212> TYPE: RNA
<213> ORGANISM: Homo sapiens

<400> SEQUENCE: 192 ugccuacugagcugaaacacag 22

<210> SEQ ID NO 193
<211> LENGTH: 21
<212> TYPE: RNA
<213> ORGANISM: Homo sapiens

<400> SEQUENCE: 193 gaaagcgcuucucuuuagagg 21

<210> SEQ ID NO 194
<211> LENGTH: 22
<212> TYPE: RNA
<213> ORGANISM: Homo sapiens

<400> SEQUENCE: 194 aaaccuguguuguucaagaguc 22

<210> SEQ ID NO 195
<211> LENGTH: 22
<212> TYPE: RNA
<213> ORGANISM: Homo sapiens

<400> SEQUENCE: 195 uauugcacauuacuaaguugca 22

<210> SEQ ID NO 196
<211> LENGTH: 21
<212> TYPE: RNA
<213> ORGANISM: Homo sapiens

<400> SEQUENCE: 196 cuagacugaagcuccuugagg 21

<210> SEQ ID NO 197
<211> LENGTH: 23
<212> TYPE: RNA
<213> ORGANISM: Homo sapiens

<400> SEQUENCE: 197 uagugcaauauugcuuauagggu 23

<210> SEQ ID NO 198
<211> LENGTH: 21
<212> TYPE: RNA
<213> ORGANISM: Homo sapiens

<400> SEQUENCE: 198 uacaguacugugauaacugaa 21

<210> SEQ ID NO 199
<211> LENGTH: 23
<212> TYPE: RNA
<213> ORGANISM: Homo sapiens

<400> SEQUENCE: 199 aguuuugcagguuugcauccagc 23

<210> SEQ ID NO 200
<211> LENGTH: 21
<212> TYPE: RNA
<213> ORGANISM: Homo sapiens

<400> SEQUENCE: 200 uacugcagacaguggcaauca 21

<210> SEQ ID NO 201
<211> LENGTH: 20
<212> TYPE: RNA
<213> ORGANISM: Homo sapiens

<400> SEQUENCE: 201 uacaguauagaugauguacu 20

<210> SEQ ID NO 202
<211> LENGTH: 23
<212> TYPE: RNA
<213> ORGANISM: Homo sapiens

<400> SEQUENCE: 202 uacuccagagggcgucacucaug 23

<210> SEQ ID NO 203
<211> LENGTH: 21
<212> TYPE: RNA
<213> ORGANISM: Homo sapiens

<400> SEQUENCE: 203 aguuaaugaauccuggaaagu 21

<210> SEQ ID NO 204
<211> LENGTH: 23
<212> TYPE: RNA
<213> ORGANISM: Homo sapiens

<400> SEQUENCE: 204 ugugcuugcucgucccgcccgca 23

<210> SEQ ID NO 205
<211> LENGTH: 22
<212> TYPE: RNA
<213> ORGANISM: Homo sapiens

<400> SEQUENCE: 205 auccgcgcucugacucucugcc 22

<210> SEQ ID NO 206
<211> LENGTH: 23
<212> TYPE: RNA
<213> ORGANISM: Homo sapiens

<400> SEQUENCE: 206 ugucugcccgcaugccugccucu 23

<210> SEQ ID NO 207
<211> LENGTH: 21
<212> TYPE: RNA
<213> ORGANISM: Homo sapiens

<400> SEQUENCE: 207

-continued uaaggcacccuucugaguaga 21

<210> SEQ ID NO 208
<211> LENGTH: 22
<212> TYPE: RNA
<213> ORGANISM: Homo sapiens

<400> SEQUENCE: 208 uauguaacaugguccacuaacu 22

<210> SEQ ID NO 209
<211> LENGTH: 23
<212> TYPE: RNA
<213> ORGANISM: Homo sapiens

<400> SEQUENCE: 209 ccugcagcgacuugauggcuucc 23

<210> SEQ ID NO 210
<211> LENGTH: 23
<212> TYPE: RNA
<213> ORGANISM: Homo sapiens

<400> SEQUENCE: 210 uucauuugguauaaaccgcgauu 23

<210> SEQ ID NO 211
<211> LENGTH: 22
<212> TYPE: RNA
<213> ORGANISM: Homo sapiens

<400> SEQUENCE: 211 uggguuccuggcaugcugauuu 22

<210> SEQ ID NO 212
<211> LENGTH: 22
<212> TYPE: RNA
<213> ORGANISM: Homo sapiens

<400> SEQUENCE: 212 augggugaauuuguagaaggau 22

<210> SEQ ID NO 213
<211> LENGTH: 22
<212> TYPE: RNA
<213> ORGANISM: Homo sapiens

<400> SEQUENCE: 213 uugcauagucacaaaagugauc 22

<210> SEQ ID NO 214
<211> LENGTH: 21
<212> TYPE: RNA
<213> ORGANISM: Homo sapiens

<400> SEQUENCE: 214 aaagugcuuccuuuuugaggg 21

<210> SEQ ID NO 215
<211> LENGTH: 19
<212> TYPE: RNA
<213> ORGANISM: Homo sapiens

<400> SEQUENCE: 215

-continued gugucugcuuccuguggga 19

<210> SEQ ID NO 216
<211> LENGTH: 22
<212> TYPE: RNA
<213> ORGANISM: Homo sapiens

<400> SEQUENCE: 216 cugcaauguaagcacuucuuac 22

<210> SEQ ID NO 217
<211> LENGTH: 22
<212> TYPE: RNA
<213> ORGANISM: Homo sapiens

<400> SEQUENCE: 217 ugcuaugccaacauauugccau 22

<210> SEQ ID NO 218
<211> LENGTH: 22
<212> TYPE: RNA
<213> ORGANISM: Homo sapiens

<400> SEQUENCE: 218 cagugccucggcagugcagccc 22

<210> SEQ ID NO 219
<211> LENGTH: 22
<212> TYPE: RNA
<213> ORGANISM: Homo sapiens

<400> SEQUENCE: 219 uaugucugcugaccaucaccuu 22

<210> SEQ ID NO 220
<211> LENGTH: 22
<212> TYPE: RNA
<213> ORGANISM: Homo sapiens

<400> SEQUENCE: 220 caagcucgugucuguggguccg 22

<210> SEQ ID NO 221
<211> LENGTH: 22
<212> TYPE: RNA
<213> ORGANISM: Homo sapiens

<400> SEQUENCE: 221 uaguacugugcauaucaucuau 22

<210> SEQ ID NO 222
<211> LENGTH: 23
<212> TYPE: RNA
<213> ORGANISM: Homo sapiens

<400> SEQUENCE: 222 uauggcuuuucauuccuauguga 23

<210> SEQ ID NO 223
<211> LENGTH: 22
<212> TYPE: RNA
<213> ORGANISM: Homo sapiens

<400> SEQUENCE: 223 uagaguuacacccugggaguua 22

<210> SEQ ID NO 224
<211> LENGTH: 21
<212> TYPE: RNA
<213> ORGANISM: Homo sapiens

<400> SEQUENCE: 224 cuccguuugccuguuucgcug 21

<210> SEQ ID NO 225
<211> LENGTH: 22
<212> TYPE: RNA
<213> ORGANISM: Homo sapiens

<400> SEQUENCE: 225 cuuagcagguuguauuaucauu 22

<210> SEQ ID NO 226
<211> LENGTH: 21
<212> TYPE: RNA
<213> ORGANISM: Homo sapiens

<400> SEQUENCE: 226 auugacacuucugugaguaga 21

<210> SEQ ID NO 227
<211> LENGTH: 21
<212> TYPE: RNA
<213> ORGANISM: Homo sapiens

<400> SEQUENCE: 227 uaauuuuauguauaagcuagu 21

<210> SEQ ID NO 228
<211> LENGTH: 21
<212> TYPE: RNA
<213> ORGANISM: Homo sapiens

<400> SEQUENCE: 228 aaacuacugaaaaucaaagau 21

<210> SEQ ID NO 229
<211> LENGTH: 21
<212> TYPE: RNA
<213> ORGANISM: Homo sapiens

<400> SEQUENCE: 229 aauaauacaugguugaucuuu 21

<210> SEQ ID NO 230
<211> LENGTH: 21
<212> TYPE: RNA
<213> ORGANISM: Homo sapiens

<400> SEQUENCE: 230 uugaaaggcuauuucuugguc 21

<210> SEQ ID NO 231
<211> LENGTH: 21
<212> TYPE: RNA
<213> ORGANISM: Homo sapiens

<400> SEQUENCE: 231 ucacagugaaccggucucuuu 21

<210> SEQ ID NO 232
<211> LENGTH: 24
<212> TYPE: RNA
<213> ORGANISM: Homo sapiens

<400> SEQUENCE: 232 aauccuuggaaccuaggugugagu 24

<210> SEQ ID NO 233
<211> LENGTH: 23
<212> TYPE: RNA
<213> ORGANISM: Homo sapiens

<400> SEQUENCE: 233 aggaagcccuggaggggcuggag 23

<210> SEQ ID NO 234
<211> LENGTH: 22
<212> TYPE: RNA
<213> ORGANISM: Homo sapiens

<400> SEQUENCE: 234 cugcccuggcccgagggaccga 22

<210> SEQ ID NO 235
<211> LENGTH: 20
<212> TYPE: RNA
<213> ORGANISM: Homo sapiens

<400> SEQUENCE: 235 caccaggcauuguggucucc 20

<210> SEQ ID NO 236
<211> LENGTH: 25
<212> TYPE: RNA
<213> ORGANISM: Homo sapiens

<400> SEQUENCE: 236 ugggaacggguuccggcagacgcug 25

<210> SEQ ID NO 237
<211> LENGTH: 22
<212> TYPE: RNA
<213> ORGANISM: Homo sapiens

<400> SEQUENCE: 237 uguaacagcaacuccaugugga 22

<210> SEQ ID NO 238
<211> LENGTH: 22
<212> TYPE: RNA
<213> ORGANISM: Homo sapiens

<400> SEQUENCE: 238 uagcagcacaucaugguuuaca 22

<210> SEQ ID NO 239
<211> LENGTH: 21
<212> TYPE: RNA

<213> ORGANISM: Homo sapiens

<400> SEQUENCE: 239 aggggugcuaucugugauuga 21

<210> SEQ ID NO 240
<211> LENGTH: 22
<212> TYPE: RNA
<213> ORGANISM: Homo sapiens

<400> SEQUENCE: 240 ucacaagucaggcucuugggac 22

<210> SEQ ID NO 241
<211> LENGTH: 17
<212> TYPE: RNA
<213> ORGANISM: Homo sapiens

<400> SEQUENCE: 241 uucaaguaauucaggug 17

<210> SEQ ID NO 242
<211> LENGTH: 22
<212> TYPE: RNA
<213> ORGANISM: Homo sapiens

<400> SEQUENCE: 242 ugugcgcagggagaccucuccc 22

<210> SEQ ID NO 243
<211> LENGTH: 22
<212> TYPE: RNA
<213> ORGANISM: Homo sapiens

<400> SEQUENCE: 243 uuguacaugguaggcuuucauu 22

<210> SEQ ID NO 244
<211> LENGTH: 23
<212> TYPE: RNA
<213> ORGANISM: Homo sapiens

<400> SEQUENCE: 244 ucaaaugcucagacuccugugguu 23

<210> SEQ ID NO 245
<211> LENGTH: 22
<212> TYPE: RNA
<213> ORGANISM: Homo sapiens

<400> SEQUENCE: 245 uaacacugucugguaaagaugg 22

<210> SEQ ID NO 246
<211> LENGTH: 22
<212> TYPE: RNA
<213> ORGANISM: Homo sapiens

<400> SEQUENCE: 246 aaccaucgaccguugaguggac 22

<210> SEQ ID NO 247
<211> LENGTH: 22

-continued

<212> TYPE: RNA
<213> ORGANISM: Homo sapiens

<400> SEQUENCE: 247 aacuggccuacaaagucccagu 22

<210> SEQ ID NO 248
<211> LENGTH: 23
<212> TYPE: RNA
<213> ORGANISM: Homo sapiens

<400> SEQUENCE: 248 uaagugcuuccauguuucagugg 23

<210> SEQ ID NO 249
<211> LENGTH: 22
<212> TYPE: RNA
<213> ORGANISM: Homo sapiens

<400> SEQUENCE: 249 agaggcuggccgugaugaauuc 22

<210> SEQ ID NO 250
<211> LENGTH: 22
<212> TYPE: RNA
<213> ORGANISM: Homo sapiens

<400> SEQUENCE: 250 aacaucacagcaagucugugcu 22

<210> SEQ ID NO 251
<211> LENGTH: 22
<212> TYPE: RNA
<213> ORGANISM: Homo sapiens

<400> SEQUENCE: 251 ucagcaaacauuuauugugugc 22

<210> SEQ ID NO 252
<211> LENGTH: 22
<212> TYPE: RNA
<213> ORGANISM: Homo sapiens

<400> SEQUENCE: 252 aaaaguaauugugguuuuggcc 22

<210> SEQ ID NO 253
<211> LENGTH: 21
<212> TYPE: RNA
<213> ORGANISM: Homo sapiens

<400> SEQUENCE: 253 ugacaacuauggaugagcucu 21

<210> SEQ ID NO 254
<211> LENGTH: 22
<212> TYPE: RNA
<213> ORGANISM: Homo sapiens

<400> SEQUENCE: 254 auucuaauuucuccacgucuuu 22

<210> SEQ ID NO 255

<211> LENGTH: 21
<212> TYPE: RNA
<213> ORGANISM: Homo sapiens

<400> SEQUENCE: 255 uagauaaaauauugguaccug 21

<210> SEQ ID NO 256
<211> LENGTH: 21
<212> TYPE: RNA
<213> ORGANISM: Homo sapiens

<400> SEQUENCE: 256 caaagaggaaggucccauuac 21

<210> SEQ ID NO 257
<211> LENGTH: 21
<212> TYPE: RNA
<213> ORGANISM: Homo sapiens

<400> SEQUENCE: 257 uuuccauaggugaugagucac 21

<210> SEQ ID NO 258
<211> LENGTH: 21
<212> TYPE: RNA
<213> ORGANISM: Homo sapiens

<400> SEQUENCE: 258 cacaagguauugguauuaccu 21

<210> SEQ ID NO 259
<211> LENGTH: 19
<212> TYPE: RNA
<213> ORGANISM: Homo sapiens

<400> SEQUENCE: 259 aagcagcugccucugaggc 19

<210> SEQ ID NO 260
<211> LENGTH: 22
<212> TYPE: RNA
<213> ORGANISM: Homo sapiens

<400> SEQUENCE: 260 auaauacaugguuaaccucuuu 22

<210> SEQ ID NO 261
<211> LENGTH: 22
<212> TYPE: RNA
<213> ORGANISM: Homo sapiens

<400> SEQUENCE: 261 uccauuacacuacccugccucu 22

<210> SEQ ID NO 262
<211> LENGTH: 22
<212> TYPE: RNA
<213> ORGANISM: Homo sapiens

<400> SEQUENCE: 262 ccaguggggcugcuguuaucug 22

-continued

<210> SEQ ID NO 263
<211> LENGTH: 22
<212> TYPE: RNA
<213> ORGANISM: Homo sapiens

<400> SEQUENCE: 263 ugguuuaccgucccacauacau 22

<210> SEQ ID NO 264
<211> LENGTH: 22
<212> TYPE: RNA
<213> ORGANISM: Homo sapiens

<400> SEQUENCE: 264 cuccuauaugaugccuuucuuc 22

<210> SEQ ID NO 265
<211> LENGTH: 22
<212> TYPE: RNA
<213> ORGANISM: Homo sapiens

<400> SEQUENCE: 265 ugaaggucuacugugugccagg 22

<210> SEQ ID NO 266
<211> LENGTH: 22
<212> TYPE: RNA
<213> ORGANISM: Homo sapiens

<400> SEQUENCE: 266 caaaccacacugugguguuaga 22

<210> SEQ ID NO 267
<211> LENGTH: 22
<212> TYPE: RNA
<213> ORGANISM: Homo sapiens

<400> SEQUENCE: 267 aaagugcauccuuuuagagugu 22

<210> SEQ ID NO 268
<211> LENGTH: 22
<212> TYPE: RNA
<213> ORGANISM: Homo sapiens

<400> SEQUENCE: 268 caagcucgcuucuaugggucug 22

<210> SEQ ID NO 269
<211> LENGTH: 17
<212> TYPE: RNA
<213> ORGANISM: Homo sapiens

<400> SEQUENCE: 269 ucccaccgcugccaccc 17

<210> SEQ ID NO 270
<211> LENGTH: 22
<212> TYPE: RNA
<213> ORGANISM: Homo sapiens

<400> SEQUENCE: 270 cucuagagggaagcgcuuucug 22

```
<210> SEQ ID NO 271
<211> LENGTH: 22
<212> TYPE: RNA
<213> ORGANISM: Homo sapiens

<400> SEQUENCE: 271

gguccagaggggagauagguuc                                                      22

<210> SEQ ID NO 272
<211> LENGTH: 22
<212> TYPE: RNA
<213> ORGANISM: Homo sapiens

<400> SEQUENCE: 272

ugucuacuacuggagacacugg                                                      22

<210> SEQ ID NO 273
<211> LENGTH: 22
<212> TYPE: RNA
<213> ORGANISM: Homo sapiens

<400> SEQUENCE: 273

cuuucagucagauguuugcugc                                                      22

<210> SEQ ID NO 274
<211> LENGTH: 22
<212> TYPE: RNA
<213> ORGANISM: Homo sapiens

<400> SEQUENCE: 274

cucaucugcaaagaaguaagug                                                      22

<210> SEQ ID NO 275
<211> LENGTH: 22
<212> TYPE: RNA
<213> ORGANISM: Homo sapiens

<400> SEQUENCE: 275

caagaaccucaguugcuuuugu                                                      22

<210> SEQ ID NO 276
<211> LENGTH: 22
<212> TYPE: RNA
<213> ORGANISM: Homo sapiens

<400> SEQUENCE: 276

uaugcauuguauuuuuaggucc                                                      22

<210> SEQ ID NO 277
<211> LENGTH: 22
<212> TYPE: RNA
<213> ORGANISM: Homo sapiens

<400> SEQUENCE: 277

uauugcacucgucccggccucc                                                      22

<210> SEQ ID NO 278
<211> LENGTH: 22
<212> TYPE: RNA
<213> ORGANISM: Homo sapiens

<400> SEQUENCE: 278

ucgugcauccccuuuagaguguu                                                     22
```

<210> SEQ ID NO 279
<211> LENGTH: 22
<212> TYPE: RNA
<213> ORGANISM: Homo sapiens

<400> SEQUENCE: 279 caaaacuggcaauuacuuuugc 22

<210> SEQ ID NO 280
<211> LENGTH: 22
<212> TYPE: RNA
<213> ORGANISM: Homo sapiens

<400> SEQUENCE: 280 uauaccucaguuuuaucaggug 22

<210> SEQ ID NO 281
<211> LENGTH: 22
<212> TYPE: RNA
<213> ORGANISM: Homo sapiens

<400> SEQUENCE: 281 caggucgucuugcagggcuucu 22

<210> SEQ ID NO 282
<211> LENGTH: 20
<212> TYPE: RNA
<213> ORGANISM: Homo sapiens

<400> SEQUENCE: 282 auuccuagaaauuguucaua 20

<210> SEQ ID NO 283
<211> LENGTH: 19
<212> TYPE: RNA
<213> ORGANISM: Homo sapiens

<400> SEQUENCE: 283 aguguggcuuucuuagagc 19

<210> SEQ ID NO 284
<211> LENGTH: 21
<212> TYPE: RNA
<213> ORGANISM: Homo sapiens

<400> SEQUENCE: 284 agaggauacccuuuguauguu 21

<210> SEQ ID NO 285
<211> LENGTH: 22
<212> TYPE: RNA
<213> ORGANISM: Homo sapiens

<400> SEQUENCE: 285 cugguuucacaugguggcuuag 22

<210> SEQ ID NO 286
<211> LENGTH: 22
<212> TYPE: RNA
<213> ORGANISM: Homo sapiens

<400> SEQUENCE: 286 gugacaucacauauacggcagc 22

<210> SEQ ID NO 287
<211> LENGTH: 19
<212> TYPE: RNA
<213> ORGANISM: Homo sapiens

<400> SEQUENCE: 287 gggcgccugugaucccaac 19

<210> SEQ ID NO 288
<211> LENGTH: 23
<212> TYPE: RNA
<213> ORGANISM: Homo sapiens

<400> SEQUENCE: 288 cggcccgggcugcugcuguuccu 23

<210> SEQ ID NO 289
<211> LENGTH: 22
<212> TYPE: RNA
<213> ORGANISM: Homo sapiens

<400> SEQUENCE: 289 cacuagauugugagcuccugga 22

<210> SEQ ID NO 290
<211> LENGTH: 22
<212> TYPE: RNA
<213> ORGANISM: Homo sapiens

<400> SEQUENCE: 290 cuauacagucuacugucuuucc 22

<210> SEQ ID NO 291
<211> LENGTH: 19
<212> TYPE: RNA
<213> ORGANISM: Homo sapiens

<400> SEQUENCE: 291 gaugaugcugcugaugcug 19

<210> SEQ ID NO 292
<211> LENGTH: 18
<212> TYPE: RNA
<213> ORGANISM: Homo sapiens

<400> SEQUENCE: 292 ugaggcaguagauugaau 18

<210> SEQ ID NO 293
<211> LENGTH: 22
<212> TYPE: RNA
<213> ORGANISM: Homo sapiens

<400> SEQUENCE: 293 cugccaauuccauaggucacag 22

<210> SEQ ID NO 294
<211> LENGTH: 17
<212> TYPE: RNA
<213> ORGANISM: Homo sapiens

<400> SEQUENCE: 294 uaagugcuuccaugcuu 17

<210> SEQ ID NO 295
<211> LENGTH: 22
<212> TYPE: RNA
<213> ORGANISM: Homo sapiens

<400> SEQUENCE: 295 uauguaacacgguccacuaacc 22

<210> SEQ ID NO 296
<211> LENGTH: 22
<212> TYPE: RNA
<213> ORGANISM: Homo sapiens

<400> SEQUENCE: 296 cagcagcaauucauguuuugaa 22

<210> SEQ ID NO 297
<211> LENGTH: 22
<212> TYPE: RNA
<213> ORGANISM: Homo sapiens

<400> SEQUENCE: 297 uaacugguugaacaacugaacc 22

<210> SEQ ID NO 298
<211> LENGTH: 22
<212> TYPE: RNA
<213> ORGANISM: Homo sapiens

<400> SEQUENCE: 298 guucucccaacguaagcccagc 22

<210> SEQ ID NO 299
<211> LENGTH: 22
<212> TYPE: RNA
<213> ORGANISM: Homo sapiens

<400> SEQUENCE: 299 cuuaugcaagauucccuucuac 22

<210> SEQ ID NO 300
<211> LENGTH: 22
<212> TYPE: RNA
<213> ORGANISM: Homo sapiens

<400> SEQUENCE: 300 aaagugcauccuuuuagagguu 22

<210> SEQ ID NO 301
<211> LENGTH: 21
<212> TYPE: RNA
<213> ORGANISM: Homo sapiens

<400> SEQUENCE: 301 uaggacacauggucuacuucu 21

<210> SEQ ID NO 302
<211> LENGTH: 22
<212> TYPE: RNA
<213> ORGANISM: Homo sapiens

```
<400> SEQUENCE: 302

cugaagcucagagggcucugau                                          22

<210> SEQ ID NO 303
<211> LENGTH: 21
<212> TYPE: RNA
<213> ORGANISM: Homo sapiens

<400> SEQUENCE: 303

ugcaggaccaagaugagcccu                                           21

<210> SEQ ID NO 304
<211> LENGTH: 22
<212> TYPE: RNA
<213> ORGANISM: Homo sapiens

<400> SEQUENCE: 304

accguggcuuucgauuguuacu                                          22

<210> SEQ ID NO 305
<211> LENGTH: 20
<212> TYPE: RNA
<213> ORGANISM: Homo sapiens

<400> SEQUENCE: 305

gugcauugcuguugcauugc                                            20

<210> SEQ ID NO 306
<211> LENGTH: 21
<212> TYPE: RNA
<213> ORGANISM: Homo sapiens

<400> SEQUENCE: 306

aaaacggugagauuuuguuuu                                           21

<210> SEQ ID NO 307
<211> LENGTH: 20
<212> TYPE: RNA
<213> ORGANISM: Homo sapiens

<400> SEQUENCE: 307

auggagauagauauagaaau                                            20

<210> SEQ ID NO 308
<211> LENGTH: 23
<212> TYPE: RNA
<213> ORGANISM: Homo sapiens

<400> SEQUENCE: 308

aaggagcuuacaaucuagcuggg                                         23

<210> SEQ ID NO 309
<211> LENGTH: 22
<212> TYPE: RNA
<213> ORGANISM: Homo sapiens

<400> SEQUENCE: 309

cacuggcuccuuucuggguaga                                          22

<210> SEQ ID NO 310
<211> LENGTH: 22
<212> TYPE: RNA
<213> ORGANISM: Homo sapiens
```

<400> SEQUENCE: 310 acaaagugcuucccuuuagagu 22

<210> SEQ ID NO 311
<211> LENGTH: 22
<212> TYPE: RNA
<213> ORGANISM: Homo sapiens

<400> SEQUENCE: 311 augcaccugggcaaggauucug 22

<210> SEQ ID NO 312
<211> LENGTH: 22
<212> TYPE: RNA
<213> ORGANISM: Homo sapiens

<400> SEQUENCE: 312 gaaaucaagcgugggugagacc 22

<210> SEQ ID NO 313
<211> LENGTH: 22
<212> TYPE: RNA
<213> ORGANISM: Homo sapiens

<400> SEQUENCE: 313 caaagaauucuccuuuugggcu 22

<210> SEQ ID NO 314
<211> LENGTH: 19
<212> TYPE: RNA
<213> ORGANISM: Homo sapiens

<400> SEQUENCE: 314 ugagcugcuguaccaaaau 19

<210> SEQ ID NO 315
<211> LENGTH: 22
<212> TYPE: RNA
<213> ORGANISM: Homo sapiens

<400> SEQUENCE: 315 uucaaguaauccaggauaggcu 22

<210> SEQ ID NO 316
<211> LENGTH: 22
<212> TYPE: RNA
<213> ORGANISM: Homo sapiens

<400> SEQUENCE: 316 augguacccuggcauacugagu 22

<210> SEQ ID NO 317
<211> LENGTH: 22
<212> TYPE: RNA
<213> ORGANISM: Homo sapiens

<400> SEQUENCE: 317 uucccuuugucauccuucgccu 22

<210> SEQ ID NO 318
<211> LENGTH: 22
<212> TYPE: RNA

<213> ORGANISM: Homo sapiens

<400> SEQUENCE: 318 uuugaggcuacagugagaugug 22

<210> SEQ ID NO 319
<211> LENGTH: 21
<212> TYPE: RNA
<213> ORGANISM: Homo sapiens

<400> SEQUENCE: 319 ccaccaccgugucugacacuu 21

<210> SEQ ID NO 320
<211> LENGTH: 22
<212> TYPE: RNA
<213> ORGANISM: Homo sapiens

<400> SEQUENCE: 320 ugcaacgaaccugagccacuga 22

<210> SEQ ID NO 321
<211> LENGTH: 21
<212> TYPE: RNA
<213> ORGANISM: Homo sapiens

<400> SEQUENCE: 321 agagaagaagaucagccugca 21

<210> SEQ ID NO 322
<211> LENGTH: 20
<212> TYPE: RNA
<213> ORGANISM: Homo sapiens

<400> SEQUENCE: 322 ucugcaggguuugcuuugag 20

<210> SEQ ID NO 323
<211> LENGTH: 23
<212> TYPE: RNA
<213> ORGANISM: Homo sapiens

<400> SEQUENCE: 323 uuauugcuuaagaauacgcguag 23

<210> SEQ ID NO 324
<211> LENGTH: 22
<212> TYPE: RNA
<213> ORGANISM: Homo sapiens

<400> SEQUENCE: 324 aaucauacacgguugaccuauu 22

<210> SEQ ID NO 325
<211> LENGTH: 21
<212> TYPE: RNA
<213> ORGANISM: Homo sapiens

<400> SEQUENCE: 325 aggguaagcugaaccucugau 21

<210> SEQ ID NO 326
<211> LENGTH: 22

<212> TYPE: RNA
<213> ORGANISM: Homo sapiens

<400> SEQUENCE: 326 gugaacgggcgccaucccgagg 22

<210> SEQ ID NO 327
<211> LENGTH: 22
<212> TYPE: RNA
<213> ORGANISM: Homo sapiens

<400> SEQUENCE: 327 aauugcacgguauccaucugua 22

<210> SEQ ID NO 328
<211> LENGTH: 22
<212> TYPE: RNA
<213> ORGANISM: Homo sapiens

<400> SEQUENCE: 328 aaaaccgucuaguuacaguugu 22

<210> SEQ ID NO 329
<211> LENGTH: 22
<212> TYPE: RNA
<213> ORGANISM: Homo sapiens

<400> SEQUENCE: 329 agaguugagucuggacgucccg 22

<210> SEQ ID NO 330
<211> LENGTH: 21
<212> TYPE: RNA
<213> ORGANISM: Homo sapiens

<400> SEQUENCE: 330 ccacaccguaucugacacuuu 21

<210> SEQ ID NO 331
<211> LENGTH: 22
<212> TYPE: RNA
<213> ORGANISM: Homo sapiens

<400> SEQUENCE: 331 cucaguagccaguguagauccu 22

<210> SEQ ID NO 332
<211> LENGTH: 21
<212> TYPE: RNA
<213> ORGANISM: Homo sapiens

<400> SEQUENCE: 332 cacauuacacggucgaccucu 21

<210> SEQ ID NO 333
<211> LENGTH: 22
<212> TYPE: RNA
<213> ORGANISM: Homo sapiens

<400> SEQUENCE: 333 aucauagaggaaaauccauguu 22

<210> SEQ ID NO 334

<211> LENGTH: 20
<212> TYPE: RNA
<213> ORGANISM: Homo sapiens

<400> SEQUENCE: 334 ccauggaucuccaggugggu 20

<210> SEQ ID NO 335
<211> LENGTH: 23
<212> TYPE: RNA
<213> ORGANISM: Homo sapiens

<400> SEQUENCE: 335 gaacgcgcuucccuauagagggu 23

<210> SEQ ID NO 336
<211> LENGTH: 23
<212> TYPE: RNA
<213> ORGANISM: Homo sapiens

<400> SEQUENCE: 336 acuuaaacguggauguacuugcu 23

<210> SEQ ID NO 337
<211> LENGTH: 22
<212> TYPE: RNA
<213> ORGANISM: Homo sapiens

<400> SEQUENCE: 337 agagcuuagcugauuggugaac 22

<210> SEQ ID NO 338
<211> LENGTH: 20
<212> TYPE: RNA
<213> ORGANISM: Homo sapiens

<400> SEQUENCE: 338 agaccaugggguucucauugu 20

<210> SEQ ID NO 339
<211> LENGTH: 21
<212> TYPE: RNA
<213> ORGANISM: Homo sapiens

<400> SEQUENCE: 339 uacucaaaaagcugucaguca 21

<210> SEQ ID NO 340
<211> LENGTH: 22
<212> TYPE: RNA
<213> ORGANISM: Homo sapiens

<400> SEQUENCE: 340 guagauucuccuucuaugagua 22

<210> SEQ ID NO 341
<211> LENGTH: 23
<212> TYPE: RNA
<213> ORGANISM: Homo sapiens

<400> SEQUENCE: 341 aaacucuacuuguccuucugagu 23

<210> SEQ ID NO 342
<211> LENGTH: 23
<212> TYPE: RNA
<213> ORGANISM: Homo sapiens

<400> SEQUENCE: 342 gagggucuugggagggaugugac 23

<210> SEQ ID NO 343
<211> LENGTH: 22
<212> TYPE: RNA
<213> ORGANISM: Homo sapiens

<400> SEQUENCE: 343 ccucccacacccaaggcuugca 22

<210> SEQ ID NO 344
<211> LENGTH: 23
<212> TYPE: RNA
<213> ORGANISM: Homo sapiens

<400> SEQUENCE: 344 aacauucauugcugucggugggu 23

<210> SEQ ID NO 345
<211> LENGTH: 22
<212> TYPE: RNA
<213> ORGANISM: Homo sapiens

<400> SEQUENCE: 345 aacgcacuucccuuuagagugu 22

<210> SEQ ID NO 346
<211> LENGTH: 22
<212> TYPE: RNA
<213> ORGANISM: Homo sapiens

<400> SEQUENCE: 346 ucaguaaauguuuauuagauga 22

<210> SEQ ID NO 347
<211> LENGTH: 22
<212> TYPE: RNA
<213> ORGANISM: Homo sapiens

<400> SEQUENCE: 347 auaaagcuagauaaccgaaagu 22

<210> SEQ ID NO 348
<211> LENGTH: 20
<212> TYPE: RNA
<213> ORGANISM: Homo sapiens

<400> SEQUENCE: 348 ggggagcuguggaagcagua 20

<210> SEQ ID NO 349
<211> LENGTH: 21
<212> TYPE: RNA
<213> ORGANISM: Homo sapiens

<400> SEQUENCE: 349 ugaguuggccaucugagugag 21

<210> SEQ ID NO 350
<211> LENGTH: 23
<212> TYPE: RNA
<213> ORGANISM: Homo sapiens

<400> SEQUENCE: 350 acuugggcacugaaacaaugucc 23

<210> SEQ ID NO 351
<211> LENGTH: 22
<212> TYPE: RNA
<213> ORGANISM: Homo sapiens

<400> SEQUENCE: 351 uaauacugccugguaaugauga 22

<210> SEQ ID NO 352
<211> LENGTH: 22
<212> TYPE: RNA
<213> ORGANISM: Homo sapiens

<400> SEQUENCE: 352 uaugugccuuuggacuacaucg 22

<210> SEQ ID NO 353
<211> LENGTH: 22
<212> TYPE: RNA
<213> ORGANISM: Homo sapiens

<400> SEQUENCE: 353 uggugguuuacaaaguaauuca 22

<210> SEQ ID NO 354
<211> LENGTH: 22
<212> TYPE: RNA
<213> ORGANISM: Homo sapiens

<400> SEQUENCE: 354 acucaaaaugggggcgcuuucc 22

<210> SEQ ID NO 355
<211> LENGTH: 22
<212> TYPE: RNA
<213> ORGANISM: Homo sapiens

<400> SEQUENCE: 355 ccucugaaauucaguucuucag 22

<210> SEQ ID NO 356
<211> LENGTH: 22
<212> TYPE: RNA
<213> ORGANISM: Homo sapiens

<400> SEQUENCE: 356 aacgccauuaucacacuaaaua 22

<210> SEQ ID NO 357
<211> LENGTH: 22
<212> TYPE: RNA
<213> ORGANISM: Homo sapiens

<400> SEQUENCE: 357 uugggaucauuuugcauccaua 22

<210> SEQ ID NO 358
<211> LENGTH: 22
<212> TYPE: RNA
<213> ORGANISM: Homo sapiens

<400> SEQUENCE: 358 uggcucaguucagcaggaacag 22

<210> SEQ ID NO 359
<211> LENGTH: 22
<212> TYPE: RNA
<213> ORGANISM: Homo sapiens

<400> SEQUENCE: 359 ucaggcucaguccccucccgau 22

<210> SEQ ID NO 360
<211> LENGTH: 23
<212> TYPE: RNA
<213> ORGANISM: Homo sapiens

<400> SEQUENCE: 360 ucauagcccuguacaaugcugcu 23

<210> SEQ ID NO 361
<211> LENGTH: 22
<212> TYPE: RNA
<213> ORGANISM: Homo sapiens

<400> SEQUENCE: 361 uauguaauaugguccacaucuu 22

<210> SEQ ID NO 362
<211> LENGTH: 18
<212> TYPE: RNA
<213> ORGANISM: Homo sapiens

<400> SEQUENCE: 362 uucacagggaggugucau 18

<210> SEQ ID NO 363
<211> LENGTH: 22
<212> TYPE: RNA
<213> ORGANISM: Homo sapiens

<400> SEQUENCE: 363 uacugcagacguggcaaucaug 22

<210> SEQ ID NO 364
<211> LENGTH: 21
<212> TYPE: RNA
<213> ORGANISM: Homo sapiens

<400> SEQUENCE: 364 gcaggaacuugugagucuccu 21

<210> SEQ ID NO 365
<211> LENGTH: 22
<212> TYPE: RNA
<213> ORGANISM: Homo sapiens

<400> SEQUENCE: 365

| | |
|---|---|
| gaugagcucauuguaauaugag | 22 |

<210> SEQ ID NO 366
<211> LENGTH: 22
<212> TYPE: RNA
<213> ORGANISM: Homo sapiens

<400> SEQUENCE: 366

| | |
|---|---|
| agaucgaccguguuauauucgc | 22 |

<210> SEQ ID NO 367
<211> LENGTH: 21
<212> TYPE: RNA
<213> ORGANISM: Homo sapiens

<400> SEQUENCE: 367

| | |
|---|---|
| guguugaaacaaucucuacug | 21 |

<210> SEQ ID NO 368
<211> LENGTH: 23
<212> TYPE: RNA
<213> ORGANISM: Homo sapiens

<400> SEQUENCE: 368

| | |
|---|---|
| ucugcucauaccccaugguuucu | 23 |

<210> SEQ ID NO 369
<211> LENGTH: 18
<212> TYPE: RNA
<213> ORGANISM: Homo sapiens

<400> SEQUENCE: 369

| | |
|---|---|
| ugcuuccuuucagagggu | 18 |

<210> SEQ ID NO 370
<211> LENGTH: 22
<212> TYPE: RNA
<213> ORGANISM: Homo sapiens

<400> SEQUENCE: 370

| | |
|---|---|
| aaagugcuuccuuuuagagggu | 22 |

<210> SEQ ID NO 371
<211> LENGTH: 22
<212> TYPE: RNA
<213> ORGANISM: Homo sapiens

<400> SEQUENCE: 371

| | |
|---|---|
| caacuagacugugagcuucuag | 22 |

<210> SEQ ID NO 372
<211> LENGTH: 20
<212> TYPE: RNA
<213> ORGANISM: Homo sapiens

<400> SEQUENCE: 372

| | |
|---|---|
| agagucuugugaugucuugc | 20 |

<210> SEQ ID NO 373
<211> LENGTH: 20
<212> TYPE: RNA
<213> ORGANISM: Homo sapiens

<400> SEQUENCE: 373 cuacaaagggaagcccuuuc 20

<210> SEQ ID NO 374
<211> LENGTH: 23
<212> TYPE: RNA
<213> ORGANISM: Homo sapiens

<400> SEQUENCE: 374 cacucagccuugagggcacuuuc 23

<210> SEQ ID NO 375
<211> LENGTH: 22
<212> TYPE: RNA
<213> ORGANISM: Homo sapiens

<400> SEQUENCE: 375 cuuaucagauuguauuguaauu 22

<210> SEQ ID NO 376
<211> LENGTH: 25
<212> TYPE: RNA
<213> ORGANISM: Homo sapiens

<400> SEQUENCE: 376 cuagugagggacagaaccaggauuc 25

<210> SEQ ID NO 377
<211> LENGTH: 21
<212> TYPE: RNA
<213> ORGANISM: Homo sapiens

<400> SEQUENCE: 377 uguucauguagauguuuaagc 21

<210> SEQ ID NO 378
<211> LENGTH: 21
<212> TYPE: RNA
<213> ORGANISM: Homo sapiens

<400> SEQUENCE: 378 auauaugaugacuuagcuuuu 21

<210> SEQ ID NO 379
<211> LENGTH: 21
<212> TYPE: RNA
<213> ORGANISM: Homo sapiens

<400> SEQUENCE: 379 cuccagagggaugcacuuucu 21

<210> SEQ ID NO 380
<211> LENGTH: 22
<212> TYPE: RNA
<213> ORGANISM: Homo sapiens

<400> SEQUENCE: 380 caucuuaccggacagugcugga 22

<210> SEQ ID NO 381
<211> LENGTH: 22
<212> TYPE: RNA
<213> ORGANISM: Homo sapiens

<400> SEQUENCE: 381 uggguggucuggagauuugugc 22

<210> SEQ ID NO 382
<211> LENGTH: 23
<212> TYPE: RNA
<213> ORGANISM: Homo sapiens

<400> SEQUENCE: 382 aaagugcugcgacauuugagcgu 23

<210> SEQ ID NO 383
<211> LENGTH: 22
<212> TYPE: RNA
<213> ORGANISM: Homo sapiens

<400> SEQUENCE: 383 aaaaguaauugcgaguuuuacc 22

<210> SEQ ID NO 384
<211> LENGTH: 22
<212> TYPE: RNA
<213> ORGANISM: Homo sapiens

<400> SEQUENCE: 384 aaaaguacuugcggauuuugcu 22

<210> SEQ ID NO 385
<211> LENGTH: 18
<212> TYPE: RNA
<213> ORGANISM: Homo sapiens

<400> SEQUENCE: 385 uugagaaggaggcugcug 18

<210> SEQ ID NO 386
<211> LENGTH: 23
<212> TYPE: RNA
<213> ORGANISM: Homo sapiens

<400> SEQUENCE: 386 caagucuuauuugagcaccuguu 23

<210> SEQ ID NO 387
<211> LENGTH: 21
<212> TYPE: RNA
<213> ORGANISM: Homo sapiens

<400> SEQUENCE: 387 gcgacccacucuugguuucca 21

<210> SEQ ID NO 388
<211> LENGTH: 22
<212> TYPE: RNA
<213> ORGANISM: Homo sapiens

<400> SEQUENCE: 388 uagguaguuuccuguuguuggg 22

<210> SEQ ID NO 389
<211> LENGTH: 22
<212> TYPE: RNA
<213> ORGANISM: Homo sapiens

<400> SEQUENCE: 389 caauuuagugugugugauauuu 22

<210> SEQ ID NO 390
<211> LENGTH: 21
<212> TYPE: RNA
<213> ORGANISM: Homo sapiens

<400> SEQUENCE: 390 gugcauuguaguugcauugca 21

<210> SEQ ID NO 391
<211> LENGTH: 22
<212> TYPE: RNA
<213> ORGANISM: Homo sapiens

<400> SEQUENCE: 391 aaaaguaauugugguuuuugcc 22

<210> SEQ ID NO 392
<211> LENGTH: 22
<212> TYPE: RNA
<213> ORGANISM: Homo sapiens

<400> SEQUENCE: 392 agucauuggagguuugagcag 22

<210> SEQ ID NO 393
<211> LENGTH: 22
<212> TYPE: RNA
<213> ORGANISM: Homo sapiens

<400> SEQUENCE: 393 uggauuucuuugugaaucacca 22

<210> SEQ ID NO 394
<211> LENGTH: 23
<212> TYPE: RNA
<213> ORGANISM: Homo sapiens

<400> SEQUENCE: 394 ugauuguagccuuuuggaguaga 23

<210> SEQ ID NO 395
<211> LENGTH: 22
<212> TYPE: RNA
<213> ORGANISM: Homo sapiens

<400> SEQUENCE: 395 ccuauucuugauuacuuguuuc 22

<210> SEQ ID NO 396
<211> LENGTH: 22
<212> TYPE: RNA
<213> ORGANISM: Homo sapiens

<400> SEQUENCE: 396 ucgugucuuguguugcagccgg 22

<210> SEQ ID NO 397
<211> LENGTH: 22
<212> TYPE: RNA

<213> ORGANISM: Homo sapiens

<400> SEQUENCE: 397 acaguagucugcacauugguua 22

<210> SEQ ID NO 398
<211> LENGTH: 22
<212> TYPE: RNA
<213> ORGANISM: Homo sapiens

<400> SEQUENCE: 398 aaucaugugcagugccaauaug 22

<210> SEQ ID NO 399
<211> LENGTH: 23
<212> TYPE: RNA
<213> ORGANISM: Homo sapiens

<400> SEQUENCE: 399 uaaggugcaucuagugcaguuag 23

<210> SEQ ID NO 400
<211> LENGTH: 21
<212> TYPE: RNA
<213> ORGANISM: Homo sapiens

<400> SEQUENCE: 400 cuggauggcuccuccaugucu 21

<210> SEQ ID NO 401
<211> LENGTH: 22
<212> TYPE: RNA
<213> ORGANISM: Homo sapiens

<400> SEQUENCE: 401 ugauugguacgucugugggguag 22

<210> SEQ ID NO 402
<211> LENGTH: 27
<212> TYPE: RNA
<213> ORGANISM: Homo sapiens

<400> SEQUENCE: 402 cacuguaggugauggugagagugggca 27

<210> SEQ ID NO 403
<211> LENGTH: 19
<212> TYPE: RNA
<213> ORGANISM: Homo sapiens

<400> SEQUENCE: 403 agcugucugaaaaugucuu 19

<210> SEQ ID NO 404
<211> LENGTH: 22
<212> TYPE: RNA
<213> ORGANISM: Homo sapiens

<400> SEQUENCE: 404 uucacaaggaggugucauuuau 22

<210> SEQ ID NO 405
<211> LENGTH: 22

-continued

<212> TYPE: RNA
<213> ORGANISM: Homo sapiens

<400> SEQUENCE: 405 agacuucccauuugaagguggc 22

<210> SEQ ID NO 406
<211> LENGTH: 23
<212> TYPE: RNA
<213> ORGANISM: Homo sapiens

<400> SEQUENCE: 406 ucuuugguuaucuagcuguauga 23

<210> SEQ ID NO 407
<211> LENGTH: 22
<212> TYPE: RNA
<213> ORGANISM: Homo sapiens

<400> SEQUENCE: 407 aagugccuccuuuuagaguguu 22

<210> SEQ ID NO 408
<211> LENGTH: 22
<212> TYPE: RNA
<213> ORGANISM: Homo sapiens

<400> SEQUENCE: 408 uucccuuugucauccuaugccu 22

<210> SEQ ID NO 409
<211> LENGTH: 22
<212> TYPE: RNA
<213> ORGANISM: Homo sapiens

<400> SEQUENCE: 409 uagcaccauuugaaaucgguua 22

<210> SEQ ID NO 410
<211> LENGTH: 18
<212> TYPE: RNA
<213> ORGANISM: Homo sapiens

<400> SEQUENCE: 410 cgggcgugguggugggg 18

<210> SEQ ID NO 411
<211> LENGTH: 22
<212> TYPE: RNA
<213> ORGANISM: Homo sapiens

<400> SEQUENCE: 411 uggagugugacaaugguguuug 22

<210> SEQ ID NO 412
<211> LENGTH: 22
<212> TYPE: RNA
<213> ORGANISM: Homo sapiens

<400> SEQUENCE: 412 caacaaaucccagucuaccuaa 22

<210> SEQ ID NO 413

-continued

<211> LENGTH: 22
<212> TYPE: RNA
<213> ORGANISM: Homo sapiens

<400> SEQUENCE: 413 caggccauauugugcugccuca 22

<210> SEQ ID NO 414
<211> LENGTH: 23
<212> TYPE: RNA
<213> ORGANISM: Homo sapiens

<400> SEQUENCE: 414 aacauucauuguugucggugggu 23

<210> SEQ ID NO 415
<211> LENGTH: 21
<212> TYPE: RNA
<213> ORGANISM: Homo sapiens

<400> SEQUENCE: 415 ugauuguccaaacgcaauucu 21

<210> SEQ ID NO 416
<211> LENGTH: 23
<212> TYPE: RNA
<213> ORGANISM: Homo sapiens

<400> SEQUENCE: 416 uaagugcuuccauguuugagugu 23

<210> SEQ ID NO 417
<211> LENGTH: 22
<212> TYPE: RNA
<213> ORGANISM: Homo sapiens

<400> SEQUENCE: 417 uggcagugucuuagcugguugu 22

<210> SEQ ID NO 418
<211> LENGTH: 21
<212> TYPE: RNA
<213> ORGANISM: Homo sapiens

<400> SEQUENCE: 418 aauauaacacagauggccugu 21

<210> SEQ ID NO 419
<211> LENGTH: 22
<212> TYPE: RNA
<213> ORGANISM: Homo sapiens

<400> SEQUENCE: 419 caauguuuccacagugcaucac 22

<210> SEQ ID NO 420
<211> LENGTH: 22
<212> TYPE: RNA
<213> ORGANISM: Homo sapiens

<400> SEQUENCE: 420 aaugcaccugggcaaggauuca 22

<210> SEQ ID NO 421
<211> LENGTH: 21
<212> TYPE: RNA
<213> ORGANISM: Homo sapiens

<400> SEQUENCE: 421 ugguagacuauggaacguagg 21

<210> SEQ ID NO 422
<211> LENGTH: 23
<212> TYPE: RNA
<213> ORGANISM: Homo sapiens

<400> SEQUENCE: 422 uuucaagccagggggcguuuuuc 23

<210> SEQ ID NO 423
<211> LENGTH: 22
<212> TYPE: RNA
<213> ORGANISM: Homo sapiens

<400> SEQUENCE: 423 cucuagagggaagcacuuucug 22

<210> SEQ ID NO 424
<211> LENGTH: 22
<212> TYPE: RNA
<213> ORGANISM: Homo sapiens

<400> SEQUENCE: 424 auauuaccauuagcucaucuuu 22

<210> SEQ ID NO 425
<211> LENGTH: 21
<212> TYPE: RNA
<213> ORGANISM: Homo sapiens

<400> SEQUENCE: 425 auccuugcuaucugggugcua 21

<210> SEQ ID NO 426
<211> LENGTH: 21
<212> TYPE: RNA
<213> ORGANISM: Homo sapiens

<400> SEQUENCE: 426 aggcaagaugcuggcauagcu 21

<210> SEQ ID NO 427
<211> LENGTH: 22
<212> TYPE: RNA
<213> ORGANISM: Homo sapiens

<400> SEQUENCE: 427 aacccguagauccgaacuugug 22

<210> SEQ ID NO 428
<211> LENGTH: 22
<212> TYPE: RNA
<213> ORGANISM: Homo sapiens

<400> SEQUENCE: 428 gaggguugggguggaggcucucc 22

<210> SEQ ID NO 429
<211> LENGTH: 22
<212> TYPE: RNA
<213> ORGANISM: Homo sapiens

<400> SEQUENCE: 429 gggggucccggugcucggauc 22

<210> SEQ ID NO 430
<211> LENGTH: 21
<212> TYPE: RNA
<213> ORGANISM: Homo sapiens

<400> SEQUENCE: 430 caacaccagucgaugggcugu 21

<210> SEQ ID NO 431
<211> LENGTH: 23
<212> TYPE: RNA
<213> ORGANISM: Homo sapiens

<400> SEQUENCE: 431 ggcagguucucacccucucuagg 23

<210> SEQ ID NO 432
<211> LENGTH: 22
<212> TYPE: RNA
<213> ORGANISM: Homo sapiens

<400> SEQUENCE: 432 uuuaggauaagcuugacuuuug 22

<210> SEQ ID NO 433
<211> LENGTH: 21
<212> TYPE: RNA
<213> ORGANISM: Homo sapiens

<400> SEQUENCE: 433 uggaggagaaggaaggugaug 21

<210> SEQ ID NO 434
<211> LENGTH: 21
<212> TYPE: RNA
<213> ORGANISM: Homo sapiens

<400> SEQUENCE: 434 caaagguauuugugguuuuug 21

<210> SEQ ID NO 435
<211> LENGTH: 22
<212> TYPE: RNA
<213> ORGANISM: Homo sapiens

<400> SEQUENCE: 435 agaauuguggcuggacaucugu 22

<210> SEQ ID NO 436
<211> LENGTH: 22
<212> TYPE: RNA
<213> ORGANISM: Homo sapiens

<400> SEQUENCE: 436 aaugcacccgggcaaggauucu 22

<210> SEQ ID NO 437
<211> LENGTH: 23
<212> TYPE: RNA
<213> ORGANISM: Homo sapiens

<400> SEQUENCE: 437 uaagugcuuccauguuuugguga 23

<210> SEQ ID NO 438
<211> LENGTH: 22
<212> TYPE: RNA
<213> ORGANISM: Homo sapiens

<400> SEQUENCE: 438 uuccuaugcauauacuucuuug 22

<210> SEQ ID NO 439
<211> LENGTH: 22
<212> TYPE: RNA
<213> ORGANISM: Homo sapiens

<400> SEQUENCE: 439 uggaauguaaggaagugugugg 22

<210> SEQ ID NO 440
<211> LENGTH: 22
<212> TYPE: RNA
<213> ORGANISM: Homo sapiens

<400> SEQUENCE: 440 aaagugcuucucuuuggugggu 22

<210> SEQ ID NO 441
<211> LENGTH: 22
<212> TYPE: RNA
<213> ORGANISM: Homo sapiens

<400> SEQUENCE: 441 aaaaguaauugcggauuuugcc 22

<210> SEQ ID NO 442
<211> LENGTH: 21
<212> TYPE: RNA
<213> ORGANISM: Homo sapiens

<400> SEQUENCE: 442 gugucuuuugcucugcaguca 21

<210> SEQ ID NO 443
<211> LENGTH: 22
<212> TYPE: RNA
<213> ORGANISM: Homo sapiens

<400> SEQUENCE: 443 uguaaacauccucgacuggaag 22

<210> SEQ ID NO 444
<211> LENGTH: 21
<212> TYPE: RNA
<213> ORGANISM: Homo sapiens

<400> SEQUENCE: 444 ccccaccuccucucuccucag 21

<210> SEQ ID NO 445
<211> LENGTH: 22
<212> TYPE: RNA
<213> ORGANISM: Homo sapiens

<400> SEQUENCE: 445 gaaggcgcuucccuuuagagcg 22

<210> SEQ ID NO 446
<211> LENGTH: 22
<212> TYPE: RNA
<213> ORGANISM: Homo sapiens

<400> SEQUENCE: 446 guggguacggcccagugggggg 22

<210> SEQ ID NO 447
<211> LENGTH: 22
<212> TYPE: RNA
<213> ORGANISM: Homo sapiens

<400> SEQUENCE: 447 cguguauuugacaagcugaguu 22

<210> SEQ ID NO 448
<211> LENGTH: 22
<212> TYPE: RNA
<213> ORGANISM: Homo sapiens

<400> SEQUENCE: 448 uccgagccugggucucccucuu 22

<210> SEQ ID NO 449
<211> LENGTH: 22
<212> TYPE: RNA
<213> ORGANISM: Homo sapiens

<400> SEQUENCE: 449 cgaaaacagcaauuaccuuugc 22

<210> SEQ ID NO 450
<211> LENGTH: 22
<212> TYPE: RNA
<213> ORGANISM: Homo sapiens

<400> SEQUENCE: 450 aaaagcugguugagagggcga 22

<210> SEQ ID NO 451
<211> LENGTH: 23
<212> TYPE: RNA
<213> ORGANISM: Homo sapiens

<400> SEQUENCE: 451 uccaguaccacgugucagggcca 23

<210> SEQ ID NO 452
<211> LENGTH: 23
<212> TYPE: RNA
<213> ORGANISM: Homo sapiens

<400> SEQUENCE: 452

-continued uuacaguuguucaaccaguuacu 23

<210> SEQ ID NO 453
<211> LENGTH: 22
<212> TYPE: RNA
<213> ORGANISM: Homo sapiens

<400> SEQUENCE: 453 gagcuuauucauaaaagugcag 22

<210> SEQ ID NO 454
<211> LENGTH: 22
<212> TYPE: RNA
<213> ORGANISM: Homo sapiens

<400> SEQUENCE: 454 cuugguucagggagggucccca 22

<210> SEQ ID NO 455
<211> LENGTH: 21
<212> TYPE: RNA
<213> ORGANISM: Homo sapiens

<400> SEQUENCE: 455 acucuagcugccaaaggcgcu 21

<210> SEQ ID NO 456
<211> LENGTH: 23
<212> TYPE: RNA
<213> ORGANISM: Homo sapiens

<400> SEQUENCE: 456 uauucauuuauccccagccuaca 23

<210> SEQ ID NO 457
<211> LENGTH: 21
<212> TYPE: RNA
<213> ORGANISM: Homo sapiens

<400> SEQUENCE: 457 cccagauaauggcacucucaa 21

<210> SEQ ID NO 458
<211> LENGTH: 22
<212> TYPE: RNA
<213> ORGANISM: Homo sapiens

<400> SEQUENCE: 458 aaaacuguaauuacuuuuguac 22

<210> SEQ ID NO 459
<211> LENGTH: 23
<212> TYPE: RNA
<213> ORGANISM: Homo sapiens

<400> SEQUENCE: 459 caguaacaaagauucauccuugu 23

<210> SEQ ID NO 460
<211> LENGTH: 23
<212> TYPE: RNA
<213> ORGANISM: Homo sapiens

```
<400> SEQUENCE: 460

ucggggaucaucaugucacgaga                                          23

<210> SEQ ID NO 461
<211> LENGTH: 22
<212> TYPE: RNA
<213> ORGANISM: Homo sapiens

<400> SEQUENCE: 461

ugauauguuugauauauuaggu                                           22

<210> SEQ ID NO 462
<211> LENGTH: 22
<212> TYPE: RNA
<213> ORGANISM: Homo sapiens

<400> SEQUENCE: 462

augguuccgucaagcaccaugg                                           22

<210> SEQ ID NO 463
<211> LENGTH: 22
<212> TYPE: RNA
<213> ORGANISM: Homo sapiens

<400> SEQUENCE: 463

acuguugcuaauaugcaacucu                                           22

<210> SEQ ID NO 464
<211> LENGTH: 22
<212> TYPE: RNA
<213> ORGANISM: Homo sapiens

<400> SEQUENCE: 464

uuuugcgauguguuccuaauau                                           22

<210> SEQ ID NO 465
<211> LENGTH: 22
<212> TYPE: RNA
<213> ORGANISM: Homo sapiens

<400> SEQUENCE: 465

aauugcacuuuagcaaugguga                                           22

<210> SEQ ID NO 466
<211> LENGTH: 20
<212> TYPE: RNA
<213> ORGANISM: Homo sapiens

<400> SEQUENCE: 466

uaaggcacgcggugaaugcc                                             20

<210> SEQ ID NO 467
<211> LENGTH: 23
<212> TYPE: RNA
<213> ORGANISM: Homo sapiens

<400> SEQUENCE: 467

ugcaccaugguugucugagcaug                                          23

<210> SEQ ID NO 468
<211> LENGTH: 23
<212> TYPE: RNA
<213> ORGANISM: Homo sapiens
```

<400> SEQUENCE: 468 uaauacugccggguaaugaugga 23

<210> SEQ ID NO 469
<211> LENGTH: 20
<212> TYPE: RNA
<213> ORGANISM: Homo sapiens

<400> SEQUENCE: 469 guccgcucggcgguggccca 20

<210> SEQ ID NO 470
<211> LENGTH: 22
<212> TYPE: RNA
<213> ORGANISM: Homo sapiens

<400> SEQUENCE: 470 cucuagagggaagcacuuucug 22

<210> SEQ ID NO 471
<211> LENGTH: 22
<212> TYPE: RNA
<213> ORGANISM: Homo sapiens

<400> SEQUENCE: 471 acaguagagggaggaaucgcag 22

<210> SEQ ID NO 472
<211> LENGTH: 22
<212> TYPE: RNA
<213> ORGANISM: Homo sapiens

<400> SEQUENCE: 472 caaaaguaauuguggauuuugu 22

<210> SEQ ID NO 473
<211> LENGTH: 22
<212> TYPE: RNA
<213> ORGANISM: Homo sapiens

<400> SEQUENCE: 473 uagcuuaucagacugauguuga 22

<210> SEQ ID NO 474
<211> LENGTH: 21
<212> TYPE: RNA
<213> ORGANISM: Homo sapiens

<400> SEQUENCE: 474 ugguucuagacuugccaacua 21

<210> SEQ ID NO 475
<211> LENGTH: 23
<212> TYPE: RNA
<213> ORGANISM: Homo sapiens

<400> SEQUENCE: 475 aggcaguguaguuagcugauugc 23

<210> SEQ ID NO 476
<211> LENGTH: 22
<212> TYPE: RNA

<213> ORGANISM: Homo sapiens

<400> SEQUENCE: 476 uaauacugucugguaaaaccgu 22

<210> SEQ ID NO 477
<211> LENGTH: 22
<212> TYPE: RNA
<213> ORGANISM: Homo sapiens

<400> SEQUENCE: 477 augcugacauauuuacuagagg 22

<210> SEQ ID NO 478
<211> LENGTH: 22
<212> TYPE: RNA
<213> ORGANISM: Homo sapiens

<400> SEQUENCE: 478 acugauuucuuuugguguucag 22

<210> SEQ ID NO 479
<211> LENGTH: 22
<212> TYPE: RNA
<213> ORGANISM: Homo sapiens

<400> SEQUENCE: 479 gccugcuggggugggaaccuggu 22

<210> SEQ ID NO 480
<211> LENGTH: 21
<212> TYPE: RNA
<213> ORGANISM: Homo sapiens

<400> SEQUENCE: 480 cuauacaaucuacugucuuuc 21

<210> SEQ ID NO 481
<211> LENGTH: 22
<212> TYPE: RNA
<213> ORGANISM: Homo sapiens

<400> SEQUENCE: 481 caguuaucacagugcugaugcu 22

<210> SEQ ID NO 482
<211> LENGTH: 21
<212> TYPE: RNA
<213> ORGANISM: Homo sapiens

<400> SEQUENCE: 482 uaaaguaaauaugcaccaaaa 21

<210> SEQ ID NO 483
<211> LENGTH: 23
<212> TYPE: RNA
<213> ORGANISM: Homo sapiens

<400> SEQUENCE: 483 uacugcaucaggaacugauugga 23

<210> SEQ ID NO 484
<211> LENGTH: 22

<212> TYPE: RNA
<213> ORGANISM: Homo sapiens

<400> SEQUENCE: 484 cucuagagggaagcgcuuucug 22

<210> SEQ ID NO 485
<211> LENGTH: 22
<212> TYPE: RNA
<213> ORGANISM: Homo sapiens

<400> SEQUENCE: 485 cuuucagucggauguuuacagc 22

<210> SEQ ID NO 486
<211> LENGTH: 20
<212> TYPE: RNA
<213> ORGANISM: Homo sapiens

<400> SEQUENCE: 486 guguguggaaaugcuucugc 20

<210> SEQ ID NO 487
<211> LENGTH: 22
<212> TYPE: RNA
<213> ORGANISM: Homo sapiens

<400> SEQUENCE: 487 aaucguacagggucauccacuu 22

<210> SEQ ID NO 488
<211> LENGTH: 22
<212> TYPE: RNA
<213> ORGANISM: Homo sapiens

<400> SEQUENCE: 488 gacugacaccucuuugggugaa 22

<210> SEQ ID NO 489
<211> LENGTH: 22
<212> TYPE: RNA
<213> ORGANISM: Homo sapiens

<400> SEQUENCE: 489 uccuucauuccaccggagucug 22

<210> SEQ ID NO 490
<211> LENGTH: 21
<212> TYPE: RNA
<213> ORGANISM: Homo sapiens

<400> SEQUENCE: 490 agugaaugaugggguucugacc 21

<210> SEQ ID NO 491
<211> LENGTH: 23
<212> TYPE: RNA
<213> ORGANISM: Homo sapiens

<400> SEQUENCE: 491 uggaagacuagugauuuuguugu 23

<210> SEQ ID NO 492

<211> LENGTH: 21
<212> TYPE: RNA
<213> ORGANISM: Homo sapiens

<400> SEQUENCE: 492 agggccccccucaauccugu 21

<210> SEQ ID NO 493
<211> LENGTH: 23
<212> TYPE: RNA
<213> ORGANISM: Homo sapiens

<400> SEQUENCE: 493 aggaugagcaaagaaaguagauu 23

<210> SEQ ID NO 494
<211> LENGTH: 22
<212> TYPE: RNA
<213> ORGANISM: Homo sapiens

<400> SEQUENCE: 494 ugguugaccauagaacaugcgc 22

<210> SEQ ID NO 495
<211> LENGTH: 17
<212> TYPE: RNA
<213> ORGANISM: Homo sapiens

<400> SEQUENCE: 495 gugggggagaggcuguc 17

<210> SEQ ID NO 496
<211> LENGTH: 22
<212> TYPE: RNA
<213> ORGANISM: Homo sapiens

<400> SEQUENCE: 496 ucucugggccugugucuuaggc 22

<210> SEQ ID NO 497
<211> LENGTH: 22
<212> TYPE: RNA
<213> ORGANISM: Homo sapiens

<400> SEQUENCE: 497 aacuggaucaauuauaggagug 22

<210> SEQ ID NO 498
<211> LENGTH: 22
<212> TYPE: RNA
<213> ORGANISM: Homo sapiens

<400> SEQUENCE: 498 caucaucgucucaaaugagucu 22

<210> SEQ ID NO 499
<211> LENGTH: 22
<212> TYPE: RNA
<213> ORGANISM: Homo sapiens

<400> SEQUENCE: 499 caucuuccaguacaguguugga 22

<210> SEQ ID NO 500
<211> LENGTH: 22
<212> TYPE: RNA
<213> ORGANISM: Homo sapiens

<400> SEQUENCE: 500 aucgugcauccuuuuagagugu 22

<210> SEQ ID NO 501
<211> LENGTH: 21
<212> TYPE: RNA
<213> ORGANISM: Homo sapiens

<400> SEQUENCE: 501 ggcuagcaacagcgcuuaccu 21

<210> SEQ ID NO 502
<211> LENGTH: 22
<212> TYPE: RNA
<213> ORGANISM: Homo sapiens

<400> SEQUENCE: 502 accuugccuugcugcccgggcc 22

<210> SEQ ID NO 503
<211> LENGTH: 22
<212> TYPE: RNA
<213> ORGANISM: Homo sapiens

<400> SEQUENCE: 503 uggugggcacagaaucuggacu 22

<210> SEQ ID NO 504
<211> LENGTH: 22
<212> TYPE: RNA
<213> ORGANISM: Homo sapiens

<400> SEQUENCE: 504 aaacauucgcggugcacuucuu 22

<210> SEQ ID NO 505
<211> LENGTH: 22
<212> TYPE: RNA
<213> ORGANISM: Homo sapiens

<400> SEQUENCE: 505 ucuucucuguuuuggccaugug 22

<210> SEQ ID NO 506
<211> LENGTH: 22
<212> TYPE: RNA
<213> ORGANISM: Homo sapiens

<400> SEQUENCE: 506 ccuauucuugguuacuugcacg 22

<210> SEQ ID NO 507
<211> LENGTH: 23
<212> TYPE: RNA
<213> ORGANISM: Homo sapiens

<400> SEQUENCE: 507 aguauguucuuccaggacagaac 23

<210> SEQ ID NO 508
<211> LENGTH: 22
<212> TYPE: RNA
<213> ORGANISM: Homo sapiens

<400> SEQUENCE: 508 uggacggagaacugauaagggu 22

<210> SEQ ID NO 509
<211> LENGTH: 21
<212> TYPE: RNA
<213> ORGANISM: Homo sapiens

<400> SEQUENCE: 509 aucauagaggaaaauccacgu 21

<210> SEQ ID NO 510
<211> LENGTH: 22
<212> TYPE: RNA
<213> ORGANISM: Homo sapiens

<400> SEQUENCE: 510 cguguucacagcggaccuugau 22

<210> SEQ ID NO 511
<211> LENGTH: 24
<212> TYPE: RNA
<213> ORGANISM: Homo sapiens

<400> SEQUENCE: 511 agccuggaagcuggagccugcagu 24

<210> SEQ ID NO 512
<211> LENGTH: 21
<212> TYPE: RNA
<213> ORGANISM: Homo sapiens

<400> SEQUENCE: 512 uggcagggaggcugggagggg 21

<210> SEQ ID NO 513
<211> LENGTH: 22
<212> TYPE: RNA
<213> ORGANISM: Homo sapiens

<400> SEQUENCE: 513 uugagaaugaugaaucauuagg 22

<210> SEQ ID NO 514
<211> LENGTH: 22
<212> TYPE: RNA
<213> ORGANISM: Homo sapiens

<400> SEQUENCE: 514 cuauacaaccuacugccuuccc 22

<210> SEQ ID NO 515
<211> LENGTH: 22
<212> TYPE: RNA
<213> ORGANISM: Homo sapiens

<400> SEQUENCE: 515 ggagaaauuauccuuggugugu 22

<210> SEQ ID NO 516
<211> LENGTH: 22
<212> TYPE: RNA
<213> ORGANISM: Homo sapiens

<400> SEQUENCE: 516 aaagugcuucccuuuggacugu 22

<210> SEQ ID NO 517
<211> LENGTH: 19
<212> TYPE: RNA
<213> ORGANISM: Homo sapiens

<400> SEQUENCE: 517 ugggcguaucuguaugcua 19

<210> SEQ ID NO 518
<211> LENGTH: 20
<212> TYPE: RNA
<213> ORGANISM: Homo sapiens

<400> SEQUENCE: 518 cuguaugcccucaccgcuca 20

<210> SEQ ID NO 519
<211> LENGTH: 21
<212> TYPE: RNA
<213> ORGANISM: Homo sapiens

<400> SEQUENCE: 519 cugacuguugccguccuccag 21

<210> SEQ ID NO 520
<211> LENGTH: 24
<212> TYPE: RNA
<213> ORGANISM: Homo sapiens

<400> SEQUENCE: 520 cugaagugauguguaacugaucag 24

<210> SEQ ID NO 521
<211> LENGTH: 23
<212> TYPE: RNA
<213> ORGANISM: Homo sapiens

<400> SEQUENCE: 521 caaagugcuguucgugcagguag 23

<210> SEQ ID NO 522
<211> LENGTH: 22
<212> TYPE: RNA
<213> ORGANISM: Homo sapiens

<400> SEQUENCE: 522 agggcuuagcugcuugugagca 22

<210> SEQ ID NO 523
<211> LENGTH: 20
<212> TYPE: RNA
<213> ORGANISM: Homo sapiens

<400> SEQUENCE: 523 aggaauguuccuucuuugcc 20

<210> SEQ ID NO 524
<211> LENGTH: 22
<212> TYPE: RNA
<213> ORGANISM: Homo sapiens

<400> SEQUENCE: 524 acacagggcuguugugaagacu 22

<210> SEQ ID NO 525
<211> LENGTH: 21
<212> TYPE: RNA
<213> ORGANISM: Homo sapiens

<400> SEQUENCE: 525 gaaggcgcuucccuuuggagu 21

<210> SEQ ID NO 526
<211> LENGTH: 23
<212> TYPE: RNA
<213> ORGANISM: Homo sapiens

<400> SEQUENCE: 526 uaauccuugcuaccugggugaga 23

<210> SEQ ID NO 527
<211> LENGTH: 24
<212> TYPE: RNA
<213> ORGANISM: Homo sapiens

<400> SEQUENCE: 527 agccugauuaaacacaugcucuga 24

<210> SEQ ID NO 528
<211> LENGTH: 22
<212> TYPE: RNA
<213> ORGANISM: Homo sapiens

<400> SEQUENCE: 528 acugcauuaugagcacuuaaag 22

<210> SEQ ID NO 529
<211> LENGTH: 22
<212> TYPE: RNA
<213> ORGANISM: Homo sapiens

<400> SEQUENCE: 529 ggaggggucccgcacugggagg 22

<210> SEQ ID NO 530
<211> LENGTH: 22
<212> TYPE: RNA
<213> ORGANISM: Homo sapiens

<400> SEQUENCE: 530 aucgggaaugucguguccgccc 22

<210> SEQ ID NO 531
<211> LENGTH: 22
<212> TYPE: RNA
<213> ORGANISM: Homo sapiens

<400> SEQUENCE: 531 gagugccuucuuuuggagcguu 22

<210> SEQ ID NO 532
<211> LENGTH: 22
<212> TYPE: RNA
<213> ORGANISM: Homo sapiens

<400> SEQUENCE: 532 agagguugcccuuggugaauuc 22

<210> SEQ ID NO 533
<211> LENGTH: 22
<212> TYPE: RNA
<213> ORGANISM: Homo sapiens

<400> SEQUENCE: 533 agacccuggucugcacucuauc 22

<210> SEQ ID NO 534
<211> LENGTH: 22
<212> TYPE: RNA
<213> ORGANISM: Homo sapiens

<400> SEQUENCE: 534 caaaaaucucaauuacuuuugc 22

<210> SEQ ID NO 535
<211> LENGTH: 20
<212> TYPE: RNA
<213> ORGANISM: Homo sapiens

<400> SEQUENCE: 535 uaaagagcccuguggagaca 20

<210> SEQ ID NO 536
<211> LENGTH: 23
<212> TYPE: RNA
<213> ORGANISM: Homo sapiens

<400> SEQUENCE: 536 agcugguguugugaaucaggccg 23

<210> SEQ ID NO 537
<211> LENGTH: 21
<212> TYPE: RNA
<213> ORGANISM: Homo sapiens

<400> SEQUENCE: 537 ugucuugcaggccgucaugca 21

<210> SEQ ID NO 538
<211> LENGTH: 22
<212> TYPE: RNA
<213> ORGANISM: Homo sapiens

<400> SEQUENCE: 538 ugaaacauacacgggaaaccuc 22

<210> SEQ ID NO 539
<211> LENGTH: 22
<212> TYPE: RNA
<213> ORGANISM: Homo sapiens -continued

<400> SEQUENCE: 539 uugcauauguaggaugucccau                                            22

<210> SEQ ID NO 540
<211> LENGTH: 23
<212> TYPE: RNA
<213> ORGANISM: Homo sapiens

<400> SEQUENCE: 540 cuaauaguaucuaccacaauaaa                                           23

<210> SEQ ID NO 541
<211> LENGTH: 22
<212> TYPE: RNA
<213> ORGANISM: Homo sapiens

<400> SEQUENCE: 541 aaucauacagggacauccaguu                                            22

<210> SEQ ID NO 542
<211> LENGTH: 23
<212> TYPE: RNA
<213> ORGANISM: Homo sapiens

<400> SEQUENCE: 542 ucuggcuccgugucuucacuccc                                           23

<210> SEQ ID NO 543
<211> LENGTH: 22
<212> TYPE: RNA
<213> ORGANISM: Homo sapiens

<400> SEQUENCE: 543 uauacaagggcagacucucucu                                            22

<210> SEQ ID NO 544
<211> LENGTH: 27
<212> TYPE: RNA
<213> ORGANISM: Homo sapiens

<400> SEQUENCE: 544 auugaucaucgacacuucgaacgcaau                                       27

<210> SEQ ID NO 545
<211> LENGTH: 22
<212> TYPE: RNA
<213> ORGANISM: Homo sapiens

<400> SEQUENCE: 545 ucggauccgucugagcuuggcu                                            22

<210> SEQ ID NO 546
<211> LENGTH: 22
<212> TYPE: RNA
<213> ORGANISM: Homo sapiens

<400> SEQUENCE: 546 uccuguacugagcugccccgag                                            22

<210> SEQ ID NO 547
<211> LENGTH: 22
<212> TYPE: RNA
<213> ORGANISM: Homo sapiens

<400> SEQUENCE: 547 ucagugcacuacagaacuuugu 22

<210> SEQ ID NO 548
<211> LENGTH: 22
<212> TYPE: RNA
<213> ORGANISM: Homo sapiens

<400> SEQUENCE: 548 ugugagguuggcauuguugucu 22

<210> SEQ ID NO 549
<211> LENGTH: 22
<212> TYPE: RNA
<213> ORGANISM: Homo sapiens

<400> SEQUENCE: 549 aaaaguauuugcggguuuuguc 22

<210> SEQ ID NO 550
<211> LENGTH: 21
<212> TYPE: RNA
<213> ORGANISM: Homo sapiens

<400> SEQUENCE: 550 cauaaaguagaaagcacuacu 21

<210> SEQ ID NO 551
<211> LENGTH: 21
<212> TYPE: RNA
<213> ORGANISM: Homo sapiens

<400> SEQUENCE: 551 uuaauaucggacaaccauugu 21

<210> SEQ ID NO 552
<211> LENGTH: 22
<212> TYPE: RNA
<213> ORGANISM: Homo sapiens

<400> SEQUENCE: 552 uaaugccccuaaaaauccuuau 22

<210> SEQ ID NO 553
<211> LENGTH: 22
<212> TYPE: RNA
<213> ORGANISM: Homo sapiens

<400> SEQUENCE: 553 cacccguagaaccgaccuugcg 22

<210> SEQ ID NO 554
<211> LENGTH: 22
<212> TYPE: RNA
<213> ORGANISM: Homo sapiens

<400> SEQUENCE: 554 caucuuacugggcagcauugga 22

<210> SEQ ID NO 555
<211> LENGTH: 22
<212> TYPE: RNA

<213> ORGANISM: Homo sapiens

<400> SEQUENCE: 555 uaacacugucugguaacgaugu 22

<210> SEQ ID NO 556
<211> LENGTH: 21
<212> TYPE: RNA
<213> ORGANISM: Homo sapiens

<400> SEQUENCE: 556 aaagcgcuucccuucagagug 21

<210> SEQ ID NO 557
<211> LENGTH: 25
<212> TYPE: RNA
<213> ORGANISM: Homo sapiens

<400> SEQUENCE: 557 gcugggcagggcuucugagcuccuu 25

<210> SEQ ID NO 558
<211> LENGTH: 22
<212> TYPE: RNA
<213> ORGANISM: Homo sapiens

<400> SEQUENCE: 558 gugaauuaccgaagggccauaa 22

<210> SEQ ID NO 559
<211> LENGTH: 22
<212> TYPE: RNA
<213> ORGANISM: Homo sapiens

<400> SEQUENCE: 559 ucagugcaucacagaacuuugu 22

<210> SEQ ID NO 560
<211> LENGTH: 23
<212> TYPE: RNA
<213> ORGANISM: Homo sapiens

<400> SEQUENCE: 560 agcagcauuguacagggcuauga 23

<210> SEQ ID NO 561
<211> LENGTH: 22
<212> TYPE: RNA
<213> ORGANISM: Homo sapiens

<400> SEQUENCE: 561 ccaaaacugcaguuacuuuugc 22

<210> SEQ ID NO 562
<211> LENGTH: 21
<212> TYPE: RNA
<213> ORGANISM: Homo sapiens

<400> SEQUENCE: 562 cccggagccaggaugcagcuc 21

<210> SEQ ID NO 563
<211> LENGTH: 22

<212> TYPE: RNA
<213> ORGANISM: Homo sapiens

<400> SEQUENCE: 563 uauagggauuggagccguggcg 22

<210> SEQ ID NO 564
<211> LENGTH: 22
<212> TYPE: RNA
<213> ORGANISM: Homo sapiens

<400> SEQUENCE: 564 agaucagaaggugauuguggcu 22

<210> SEQ ID NO 565
<211> LENGTH: 22
<212> TYPE: RNA
<213> ORGANISM: Homo sapiens

<400> SEQUENCE: 565 ucugcccccuccgcugcugcca 22

<210> SEQ ID NO 566
<211> LENGTH: 23
<212> TYPE: RNA
<213> ORGANISM: Homo sapiens

<400> SEQUENCE: 566 gaagugcuucgauuuuggggugu 23

<210> SEQ ID NO 567
<211> LENGTH: 20
<212> TYPE: RNA
<213> ORGANISM: Homo sapiens

<400> SEQUENCE: 567 acucaaacugugggggcacu 20

<210> SEQ ID NO 568
<211> LENGTH: 24
<212> TYPE: RNA
<213> ORGANISM: Homo sapiens

<400> SEQUENCE: 568 agcagaagcagggagguucuccca 24

<210> SEQ ID NO 569
<211> LENGTH: 22
<212> TYPE: RNA
<213> ORGANISM: Homo sapiens

<400> SEQUENCE: 569 uuugugaccugguccacuaacc 22

<210> SEQ ID NO 570
<211> LENGTH: 23
<212> TYPE: RNA
<213> ORGANISM: Homo sapiens

<400> SEQUENCE: 570 acuucaccugguccacuagccgu 23

<210> SEQ ID NO 571

<211> LENGTH: 23
<212> TYPE: RNA
<213> ORGANISM: Homo sapiens

<400> SEQUENCE: 571 caaagcgcuucucuuuagagugu 23

<210> SEQ ID NO 572
<211> LENGTH: 24
<212> TYPE: RNA
<213> ORGANISM: Homo sapiens

<400> SEQUENCE: 572 ucagaacaaaugccgguucccaga 24

<210> SEQ ID NO 573
<211> LENGTH: 22
<212> TYPE: RNA
<213> ORGANISM: Homo sapiens

<400> SEQUENCE: 573 acuuguaugcuagcucagguag 22

<210> SEQ ID NO 574
<211> LENGTH: 22
<212> TYPE: RNA
<213> ORGANISM: Homo sapiens

<400> SEQUENCE: 574 uugugucaauaugcgaugaugu 22

<210> SEQ ID NO 575
<211> LENGTH: 21
<212> TYPE: RNA
<213> ORGANISM: Homo sapiens

<400> SEQUENCE: 575 cacuguguccuuucugcguag 21

<210> SEQ ID NO 576
<211> LENGTH: 22
<212> TYPE: RNA
<213> ORGANISM: Homo sapiens

<400> SEQUENCE: 576 aaauuauuguacaucggaugag 22

<210> SEQ ID NO 577
<211> LENGTH: 22
<212> TYPE: RNA
<213> ORGANISM: Homo sapiens

<400> SEQUENCE: 577 aagauguggaaaaauuggaauc 22

<210> SEQ ID NO 578
<211> LENGTH: 21
<212> TYPE: RNA
<213> ORGANISM: Homo sapiens

<400> SEQUENCE: 578 ucuuguguucucuagaucagu 21

<210> SEQ ID NO 579
<211> LENGTH: 22
<212> TYPE: RNA
<213> ORGANISM: Homo sapiens

<400> SEQUENCE: 579 gacuauagaacuuucccccuca 22

<210> SEQ ID NO 580
<211> LENGTH: 18
<212> TYPE: RNA
<213> ORGANISM: Homo sapiens

<400> SEQUENCE: 580 aucccaccucugccacca 18

<210> SEQ ID NO 581
<211> LENGTH: 17
<212> TYPE: RNA
<213> ORGANISM: Homo sapiens

<400> SEQUENCE: 581 ucgccuccucucuccc 17

<210> SEQ ID NO 582
<211> LENGTH: 21
<212> TYPE: RNA
<213> ORGANISM: Homo sapiens

<400> SEQUENCE: 582 gaacggcuucauacaggaguu 21

<210> SEQ ID NO 583
<211> LENGTH: 22
<212> TYPE: RNA
<213> ORGANISM: Homo sapiens

<400> SEQUENCE: 583 uuuggucccuucaaccagcua 22

<210> SEQ ID NO 584
<211> LENGTH: 22
<212> TYPE: RNA
<213> ORGANISM: Homo sapiens

<400> SEQUENCE: 584 ggguggggauuuguugcauuac 22

<210> SEQ ID NO 585
<211> LENGTH: 22
<212> TYPE: RNA
<213> ORGANISM: Homo sapiens

<400> SEQUENCE: 585 caagcuuguaucuauagguaug 22

<210> SEQ ID NO 586
<211> LENGTH: 22
<212> TYPE: RNA
<213> ORGANISM: Homo sapiens

<400> SEQUENCE: 586 ugagaaccacgucugcucugag 22

```
<210> SEQ ID NO 587
<211> LENGTH: 21
<212> TYPE: RNA
<213> ORGANISM: Homo sapiens

<400> SEQUENCE: 587

uugugcuugaucuaaccaugu                                              21

<210> SEQ ID NO 588
<211> LENGTH: 21
<212> TYPE: RNA
<213> ORGANISM: Homo sapiens

<400> SEQUENCE: 588

caagucacuagugguuccguu                                              21

<210> SEQ ID NO 589
<211> LENGTH: 22
<212> TYPE: RNA
<213> ORGANISM: Homo sapiens

<400> SEQUENCE: 589

ccaauauuacugugcugcuuua                                             22

<210> SEQ ID NO 590
<211> LENGTH: 23
<212> TYPE: RNA
<213> ORGANISM: Homo sapiens

<400> SEQUENCE: 590

cagugcaaugauauugucaaagc                                            23

<210> SEQ ID NO 591
<211> LENGTH: 21
<212> TYPE: RNA
<213> ORGANISM: Homo sapiens

<400> SEQUENCE: 591

ugauauguuugauauuggguu                                              21

<210> SEQ ID NO 592
<211> LENGTH: 22
<212> TYPE: RNA
<213> ORGANISM: Homo sapiens

<400> SEQUENCE: 592

uuuguucguucggcucgcguga                                             22

<210> SEQ ID NO 593
<211> LENGTH: 22
<212> TYPE: RNA
<213> ORGANISM: Homo sapiens

<400> SEQUENCE: 593

uagcaaaaacugcaguuacuuu                                             22

<210> SEQ ID NO 594
<211> LENGTH: 22
<212> TYPE: RNA
<213> ORGANISM: Homo sapiens

<400> SEQUENCE: 594

aggggcuggcuuuccucugguc                                             22
```

<210> SEQ ID NO 595
<211> LENGTH: 22
<212> TYPE: RNA
<213> ORGANISM: Homo sapiens

<400> SEQUENCE: 595 caaagugccucccuuuagagug 22

<210> SEQ ID NO 596
<211> LENGTH: 23
<212> TYPE: RNA
<213> ORGANISM: Homo sapiens

<400> SEQUENCE: 596 uaaaucccauggugccuucuccu 23

<210> SEQ ID NO 597
<211> LENGTH: 20
<212> TYPE: RNA
<213> ORGANISM: Homo sapiens

<400> SEQUENCE: 597 guagaggagauggcgcaggg 20

<210> SEQ ID NO 598
<211> LENGTH: 22
<212> TYPE: RNA
<213> ORGANISM: Homo sapiens

<400> SEQUENCE: 598 acaggugagguucuugggagcc 22

<210> SEQ ID NO 599
<211> LENGTH: 22
<212> TYPE: RNA
<213> ORGANISM: Homo sapiens

<400> SEQUENCE: 599 cuguugccacuaaccucaaccu 22

<210> SEQ ID NO 600
<211> LENGTH: 22
<212> TYPE: RNA
<213> ORGANISM: Homo sapiens

<400> SEQUENCE: 600 cucuagagggaagcacuuucug 22

<210> SEQ ID NO 601
<211> LENGTH: 22
<212> TYPE: RNA
<213> ORGANISM: Homo sapiens

<400> SEQUENCE: 601 aaaguucugagacacuccgacu 22

<210> SEQ ID NO 602
<211> LENGTH: 21
<212> TYPE: RNA
<213> ORGANISM: Homo sapiens

<400> SEQUENCE: 602 uaacagucuccagucacggcc 21

<210> SEQ ID NO 603
<211> LENGTH: 22
<212> TYPE: RNA
<213> ORGANISM: Homo sapiens

<400> SEQUENCE: 603 cgucaacacuugcugguuuccu 22

<210> SEQ ID NO 604
<211> LENGTH: 22
<212> TYPE: RNA
<213> ORGANISM: Homo sapiens

<400> SEQUENCE: 604 ugaguauuacauggccaaucuc 22

<210> SEQ ID NO 605
<211> LENGTH: 22
<212> TYPE: RNA
<213> ORGANISM: Homo sapiens

<400> SEQUENCE: 605 ucaaaacugaggggcauuuucu 22

<210> SEQ ID NO 606
<211> LENGTH: 22
<212> TYPE: RNA
<213> ORGANISM: Homo sapiens

<400> SEQUENCE: 606 aaaaacugagacuacuuuugca 22

<210> SEQ ID NO 607
<211> LENGTH: 21
<212> TYPE: RNA
<213> ORGANISM: Homo sapiens

<400> SEQUENCE: 607 ucuaguaagaguggcagucga 21

<210> SEQ ID NO 608
<211> LENGTH: 22
<212> TYPE: RNA
<213> ORGANISM: Homo sapiens

<400> SEQUENCE: 608 cccugugcccggcccacuucug 22

<210> SEQ ID NO 609
<211> LENGTH: 22
<212> TYPE: RNA
<213> ORGANISM: Homo sapiens

<400> SEQUENCE: 609 uuaugguuugccugggacugag 22

<210> SEQ ID NO 610
<211> LENGTH: 22
<212> TYPE: RNA
<213> ORGANISM: Homo sapiens

<400> SEQUENCE: 610

-continued

| | |
|---|---|
| auguagggcuaaaagccauggg | 22 |

<210> SEQ ID NO 611
<211> LENGTH: 21
<212> TYPE: RNA
<213> ORGANISM: Homo sapiens

<400> SEQUENCE: 611

| | |
|---|---|
| uuaggccgcagaucuggguga | 21 |

<210> SEQ ID NO 612
<211> LENGTH: 22
<212> TYPE: RNA
<213> ORGANISM: Homo sapiens

<400> SEQUENCE: 612

| | |
|---|---|
| uucaacggguauuuauugagca | 22 |

<210> SEQ ID NO 613
<211> LENGTH: 22
<212> TYPE: RNA
<213> ORGANISM: Homo sapiens

<400> SEQUENCE: 613

| | |
|---|---|
| uuugguccccuucaaccagcug | 22 |

<210> SEQ ID NO 614
<211> LENGTH: 22
<212> TYPE: RNA
<213> ORGANISM: Homo sapiens

<400> SEQUENCE: 614

| | |
|---|---|
| gucauacacggcucuccucucu | 22 |

<210> SEQ ID NO 615
<211> LENGTH: 25
<212> TYPE: RNA
<213> ORGANISM: Homo sapiens

<400> SEQUENCE: 615

| | |
|---|---|
| aaaggauucugcugucggucccacu | 25 |

<210> SEQ ID NO 616
<211> LENGTH: 22
<212> TYPE: RNA
<213> ORGANISM: Homo sapiens

<400> SEQUENCE: 616

| | |
|---|---|
| auauaauacaaccugcuaagug | 22 |

<210> SEQ ID NO 617
<211> LENGTH: 22
<212> TYPE: RNA
<213> ORGANISM: Homo sapiens

<400> SEQUENCE: 617

| | |
|---|---|
| aacacaccugguuaaccucuuu | 22 |

<210> SEQ ID NO 618
<211> LENGTH: 22
<212> TYPE: RNA
<213> ORGANISM: Homo sapiens

<400> SEQUENCE: 618 aagacgggaggaaagaagggag 22

<210> SEQ ID NO 619
<211> LENGTH: 22
<212> TYPE: RNA
<213> ORGANISM: Homo sapiens

<400> SEQUENCE: 619 aggcagcgggguguaguggaua 22

<210> SEQ ID NO 620
<211> LENGTH: 22
<212> TYPE: RNA
<213> ORGANISM: Homo sapiens

<400> SEQUENCE: 620 cugcgcaagcuacugccuugcu 22

<210> SEQ ID NO 621
<211> LENGTH: 23
<212> TYPE: RNA
<213> ORGANISM: Homo sapiens

<400> SEQUENCE: 621 ccaguuaccgcuuccgcuaccgc 23

<210> SEQ ID NO 622
<211> LENGTH: 22
<212> TYPE: RNA
<213> ORGANISM: Homo sapiens

<400> SEQUENCE: 622 cagugcaaugaugaaagggcau 22

<210> SEQ ID NO 623
<211> LENGTH: 18
<212> TYPE: RNA
<213> ORGANISM: Homo sapiens

<400> SEQUENCE: 623 gucccuguucaggcgcca 18

<210> SEQ ID NO 624
<211> LENGTH: 22
<212> TYPE: RNA
<213> ORGANISM: Homo sapiens

<400> SEQUENCE: 624 ucaccagcccuguguucccuag 22

<210> SEQ ID NO 625
<211> LENGTH: 22
<212> TYPE: RNA
<213> ORGANISM: Homo sapiens

<400> SEQUENCE: 625 cucuagagggaagcgcuuucug 22

<210> SEQ ID NO 626
<211> LENGTH: 22
<212> TYPE: RNA
<213> ORGANISM: Homo sapiens

<400> SEQUENCE: 626 ugagccccugugccgcccccag 22

<210> SEQ ID NO 627
<211> LENGTH: 21
<212> TYPE: RNA
<213> ORGANISM: Homo sapiens

<400> SEQUENCE: 627 gucagcggaggaaaagaaacu 21

<210> SEQ ID NO 628
<211> LENGTH: 22
<212> TYPE: RNA
<213> ORGANISM: Homo sapiens

<400> SEQUENCE: 628 cggcaacaagaaacugccugag 22

<210> SEQ ID NO 629
<211> LENGTH: 23
<212> TYPE: RNA
<213> ORGANISM: Homo sapiens

<400> SEQUENCE: 629 cuggagauauggaagagcugugu 23

<210> SEQ ID NO 630
<211> LENGTH: 22
<212> TYPE: RNA
<213> ORGANISM: Homo sapiens

<400> SEQUENCE: 630 cuuggcaccuagcaagcacuca 22

<210> SEQ ID NO 631
<211> LENGTH: 21
<212> TYPE: RNA
<213> ORGANISM: Homo sapiens

<400> SEQUENCE: 631 ugagcuaaaugugugcuggga 21

<210> SEQ ID NO 632
<211> LENGTH: 22
<212> TYPE: RNA
<213> ORGANISM: Homo sapiens

<400> SEQUENCE: 632 cacgcucaugcacacacccaca 22

<210> SEQ ID NO 633
<211> LENGTH: 20
<212> TYPE: RNA
<213> ORGANISM: Homo sapiens

<400> SEQUENCE: 633 ucguuugccuuuuucugcuu 20

<210> SEQ ID NO 634
<211> LENGTH: 22
<212> TYPE: RNA

<213> ORGANISM: Homo sapiens

<400> SEQUENCE: 634 acagauucgauucuaggggaau 22

<210> SEQ ID NO 635
<211> LENGTH: 22
<212> TYPE: RNA
<213> ORGANISM: Homo sapiens

<400> SEQUENCE: 635 uaaucucagcuggcaacuguga 22

<210> SEQ ID NO 636
<211> LENGTH: 22
<212> TYPE: RNA
<213> ORGANISM: Homo sapiens

<400> SEQUENCE: 636 ggauaucaucauauacuguaag 22

<210> SEQ ID NO 637
<211> LENGTH: 22
<212> TYPE: RNA
<213> ORGANISM: Homo sapiens

<400> SEQUENCE: 637 gggguuccuggggaugggauuu 22

<210> SEQ ID NO 638
<211> LENGTH: 21
<212> TYPE: RNA
<213> ORGANISM: Homo sapiens

<400> SEQUENCE: 638 uuaagacuugcagugauguuu 21

<210> SEQ ID NO 639
<211> LENGTH: 22
<212> TYPE: RNA
<213> ORGANISM: Homo sapiens

<400> SEQUENCE: 639 uauggcacugguagaauucacu 22

<210> SEQ ID NO 640
<211> LENGTH: 22
<212> TYPE: RNA
<213> ORGANISM: Homo sapiens

<400> SEQUENCE: 640 caaccuggaggacuccaugcug 22

<210> SEQ ID NO 641
<211> LENGTH: 23
<212> TYPE: RNA
<213> ORGANISM: Homo sapiens

<400> SEQUENCE: 641 gcaaagcacacggccugcagaga 23

<210> SEQ ID NO 642
<211> LENGTH: 21

<212> TYPE: RNA
<213> ORGANISM: Homo sapiens

<400> SEQUENCE: 642 cuguacaggccacugccuugc 21

<210> SEQ ID NO 643
<211> LENGTH: 21
<212> TYPE: RNA
<213> ORGANISM: Homo sapiens

<400> SEQUENCE: 643 ucacuccucuccucccgucuu 21

<210> SEQ ID NO 644
<211> LENGTH: 22
<212> TYPE: RNA
<213> ORGANISM: Homo sapiens

<400> SEQUENCE: 644 acagcaggcacagacaggcagu 22

<210> SEQ ID NO 645
<211> LENGTH: 23
<212> TYPE: RNA
<213> ORGANISM: Homo sapiens

<400> SEQUENCE: 645 uaggcagugucauuagcugauug 23

<210> SEQ ID NO 646
<211> LENGTH: 22
<212> TYPE: RNA
<213> ORGANISM: Homo sapiens

<400> SEQUENCE: 646 acuuuaacauggaggcacuugc 22

<210> SEQ ID NO 647
<211> LENGTH: 22
<212> TYPE: RNA
<213> ORGANISM: Homo sapiens

<400> SEQUENCE: 647 gaaguuguucgugguggauucg 22

<210> SEQ ID NO 648
<211> LENGTH: 22
<212> TYPE: RNA
<213> ORGANISM: Homo sapiens

<400> SEQUENCE: 648 acccuaucaauauugucucugc 22

<210> SEQ ID NO 649
<211> LENGTH: 21
<212> TYPE: RNA
<213> ORGANISM: Homo sapiens

<400> SEQUENCE: 649 gugccagcugcagugggggag 21

<210> SEQ ID NO 650

<211> LENGTH: 20
<212> TYPE: RNA
<213> ORGANISM: Homo sapiens

<400> SEQUENCE: 650 agagguauagggcaugggaa 20

<210> SEQ ID NO 651
<211> LENGTH: 22
<212> TYPE: RNA
<213> ORGANISM: Homo sapiens

<400> SEQUENCE: 651 auucugcauuuuuagcaaguuc 22

<210> SEQ ID NO 652
<211> LENGTH: 19
<212> TYPE: RNA
<213> ORGANISM: Homo sapiens

<400> SEQUENCE: 652 ugucucugcuggguuucu 19

<210> SEQ ID NO 653
<211> LENGTH: 20
<212> TYPE: RNA
<213> ORGANISM: Homo sapiens

<400> SEQUENCE: 653 cggcucugggucugugggga 20

<210> SEQ ID NO 654
<211> LENGTH: 21
<212> TYPE: RNA
<213> ORGANISM: Homo sapiens

<400> SEQUENCE: 654 aaggcagggcccccgcucccc 21

<210> SEQ ID NO 655
<211> LENGTH: 22
<212> TYPE: RNA
<213> ORGANISM: Homo sapiens

<400> SEQUENCE: 655 cuauacggccuccuagcuuucc 22

<210> SEQ ID NO 656
<211> LENGTH: 21
<212> TYPE: RNA
<213> ORGANISM: Homo sapiens

<400> SEQUENCE: 656 uccuucugcuccguccccccag 21

<210> SEQ ID NO 657
<211> LENGTH: 22
<212> TYPE: RNA
<213> ORGANISM: Homo sapiens

<400> SEQUENCE: 657 ugcccuaaaugccccuucuggc 22

<210> SEQ ID NO 658
<211> LENGTH: 22
<212> TYPE: RNA
<213> ORGANISM: Homo sapiens

<400> SEQUENCE: 658 aguauucuguaccagggaaggu 22

<210> SEQ ID NO 659
<211> LENGTH: 22
<212> TYPE: RNA
<213> ORGANISM: Homo sapiens

<400> SEQUENCE: 659 uucuccaaaagggagcacuuuc 22

<210> SEQ ID NO 660
<211> LENGTH: 22
<212> TYPE: RNA
<213> ORGANISM: Homo sapiens

<400> SEQUENCE: 660 aacuguuugcagaggaaacuga 22

<210> SEQ ID NO 661
<211> LENGTH: 22
<212> TYPE: RNA
<213> ORGANISM: Homo sapiens

<400> SEQUENCE: 661 ccuguucuccauuacuuggcuc 22

<210> SEQ ID NO 662
<211> LENGTH: 22
<212> TYPE: RNA
<213> ORGANISM: Homo sapiens

<400> SEQUENCE: 662 aucuggagguaagaagcacuuu 22

<210> SEQ ID NO 663
<211> LENGTH: 22
<212> TYPE: RNA
<213> ORGANISM: Homo sapiens

<400> SEQUENCE: 663 uaugugggaugguaaaccgcuu 22

<210> SEQ ID NO 664
<211> LENGTH: 22
<212> TYPE: RNA
<213> ORGANISM: Homo sapiens

<400> SEQUENCE: 664 uauacaagggcaagcucucugu 22

<210> SEQ ID NO 665
<211> LENGTH: 22
<212> TYPE: RNA
<213> ORGANISM: Homo sapiens

<400> SEQUENCE: 665 uuauaaagcaaugagacugauu 22

```
<210> SEQ ID NO 666
<211> LENGTH: 22
<212> TYPE: RNA
<213> ORGANISM: Homo sapiens

<400> SEQUENCE: 666

uaacagucuacagccauggucg                                              22

<210> SEQ ID NO 667
<211> LENGTH: 23
<212> TYPE: RNA
<213> ORGANISM: Homo sapiens

<400> SEQUENCE: 667

uguaguguuuccuacuuuaugga                                             23

<210> SEQ ID NO 668
<211> LENGTH: 22
<212> TYPE: RNA
<213> ORGANISM: Homo sapiens

<400> SEQUENCE: 668

acggguuaggcucuugggagcu                                              22

<210> SEQ ID NO 669
<211> LENGTH: 22
<212> TYPE: RNA
<213> ORGANISM: Homo sapiens

<400> SEQUENCE: 669

cugggagaaggcuguuuacucu                                              22

<210> SEQ ID NO 670
<211> LENGTH: 22
<212> TYPE: RNA
<213> ORGANISM: Homo sapiens

<400> SEQUENCE: 670

gugagucucuaagaaaagagga                                              22

<210> SEQ ID NO 671
<211> LENGTH: 21
<212> TYPE: RNA
<213> ORGANISM: Homo sapiens

<400> SEQUENCE: 671

cggcggggacggcgauugguc                                               21

<210> SEQ ID NO 672
<211> LENGTH: 21
<212> TYPE: RNA
<213> ORGANISM: Homo sapiens

<400> SEQUENCE: 672

ccuguugaaguguaaucccca                                               21

<210> SEQ ID NO 673
<211> LENGTH: 21
<212> TYPE: RNA
<213> ORGANISM: Homo sapiens

<400> SEQUENCE: 673

uuuugcaccuuuuggagugaa                                               21
```

<210> SEQ ID NO 674
<211> LENGTH: 21
<212> TYPE: RNA
<213> ORGANISM: Homo sapiens

<400> SEQUENCE: 674 caucccuugcaugguggaggg 21

<210> SEQ ID NO 675
<211> LENGTH: 21
<212> TYPE: RNA
<213> ORGANISM: Homo sapiens

<400> SEQUENCE: 675 cggggcagcucaguacaggau 21

<210> SEQ ID NO 676
<211> LENGTH: 21
<212> TYPE: RNA
<213> ORGANISM: Homo sapiens

<400> SEQUENCE: 676 aagccugcccggcuccucggg 21

<210> SEQ ID NO 677
<211> LENGTH: 22
<212> TYPE: RNA
<213> ORGANISM: Homo sapiens

<400> SEQUENCE: 677 ugggucuuugcgggcgagauga 22

<210> SEQ ID NO 678
<211> LENGTH: 21
<212> TYPE: RNA
<213> ORGANISM: Homo sapiens

<400> SEQUENCE: 678 uccgguucucagggcuccacc 21

<210> SEQ ID NO 679
<211> LENGTH: 22
<212> TYPE: RNA
<213> ORGANISM: Homo sapiens

<400> SEQUENCE: 679 ugccuacugagcugauaucagu 22

<210> SEQ ID NO 680
<211> LENGTH: 22
<212> TYPE: RNA
<213> ORGANISM: Homo sapiens

<400> SEQUENCE: 680 aguuuugcagguuugcauuuca 22

<210> SEQ ID NO 681
<211> LENGTH: 18
<212> TYPE: RNA
<213> ORGANISM: Homo sapiens

<400> SEQUENCE: 681 gcaugggugguucagugg 18

<210> SEQ ID NO 682
<211> LENGTH: 22
<212> TYPE: RNA
<213> ORGANISM: Homo sapiens

<400> SEQUENCE: 682 auaagacgagcaaaaagcuugu 22

<210> SEQ ID NO 683
<211> LENGTH: 23
<212> TYPE: RNA
<213> ORGANISM: Homo sapiens

<400> SEQUENCE: 683 uauggcuuuuuauuccuauguga 23

<210> SEQ ID NO 684
<211> LENGTH: 22
<212> TYPE: RNA
<213> ORGANISM: Homo sapiens

<400> SEQUENCE: 684 cuagguauggucccagggaucc 22

<210> SEQ ID NO 685
<211> LENGTH: 22
<212> TYPE: RNA
<213> ORGANISM: Homo sapiens

<400> SEQUENCE: 685 aacauucaaccugucggugagu 22

<210> SEQ ID NO 686
<211> LENGTH: 21
<212> TYPE: RNA
<213> ORGANISM: Homo sapiens

<400> SEQUENCE: 686 augauccaggaaccugccucu 21

<210> SEQ ID NO 687
<211> LENGTH: 22
<212> TYPE: RNA
<213> ORGANISM: Homo sapiens

<400> SEQUENCE: 687 cgcaggggccgggugcucaccg 22

<210> SEQ ID NO 688
<211> LENGTH: 21
<212> TYPE: RNA
<213> ORGANISM: Homo sapiens

<400> SEQUENCE: 688 uggguuuacguugggagaacu 21

<210> SEQ ID NO 689
<211> LENGTH: 23
<212> TYPE: RNA
<213> ORGANISM: Homo sapiens

<400> SEQUENCE: 689 uacccuguagauccgaauuugug 23

<210> SEQ ID NO 690
<211> LENGTH: 22
<212> TYPE: RNA
<213> ORGANISM: Homo sapiens

<400> SEQUENCE: 690 aguggggaacccuuccaugagg 22

<210> SEQ ID NO 691
<211> LENGTH: 23
<212> TYPE: RNA
<213> ORGANISM: Homo sapiens

<400> SEQUENCE: 691 aggaccugcgggacaagauucuu 23

<210> SEQ ID NO 692
<211> LENGTH: 23
<212> TYPE: RNA
<213> ORGANISM: Homo sapiens

<400> SEQUENCE: 692 uucucgaggaaagaagcacuuuc 23

<210> SEQ ID NO 693
<211> LENGTH: 22
<212> TYPE: RNA
<213> ORGANISM: Homo sapiens

<400> SEQUENCE: 693 uacucaggagaguggcaaucac 22

<210> SEQ ID NO 694
<211> LENGTH: 20
<212> TYPE: RNA
<213> ORGANISM: Homo sapiens

<400> SEQUENCE: 694 ccccagggcgacgcggcggg 20

<210> SEQ ID NO 695
<211> LENGTH: 23
<212> TYPE: RNA
<213> ORGANISM: Homo sapiens

<400> SEQUENCE: 695 ucucuggagggaagcacuuucug 23

<210> SEQ ID NO 696
<211> LENGTH: 25
<212> TYPE: RNA
<213> ORGANISM: Homo sapiens

<400> SEQUENCE: 696 gggcgacaaagcaagacucuuucuu 25

<210> SEQ ID NO 697
<211> LENGTH: 21
<212> TYPE: RNA
<213> ORGANISM: Homo sapiens

<400> SEQUENCE: 697 aggcggagacuugggcaauug 21

<210> SEQ ID NO 698
<211> LENGTH: 22
<212> TYPE: RNA
<213> ORGANISM: Homo sapiens

<400> SEQUENCE: 698 ugcggggcuagggcuaacagca 22

<210> SEQ ID NO 699
<211> LENGTH: 23
<212> TYPE: RNA
<213> ORGANISM: Homo sapiens

<400> SEQUENCE: 699 agugccugagggaguaagagccc 23

<210> SEQ ID NO 700
<211> LENGTH: 21
<212> TYPE: RNA
<213> ORGANISM: Homo sapiens

<400> SEQUENCE: 700 uacuuggaaaggcaucaguug 21

<210> SEQ ID NO 701
<211> LENGTH: 22
<212> TYPE: RNA
<213> ORGANISM: Homo sapiens

<400> SEQUENCE: 701 uuuagagacggggucuugcucu 22

<210> SEQ ID NO 702
<211> LENGTH: 21
<212> TYPE: RNA
<213> ORGANISM: Homo sapiens

<400> SEQUENCE: 702 aggaggcagcgcucucaggac 21

<210> SEQ ID NO 703
<211> LENGTH: 20
<212> TYPE: RNA
<213> ORGANISM: Homo sapiens

<400> SEQUENCE: 703 cgugccacccuuuuccccag 20

<210> SEQ ID NO 704
<211> LENGTH: 21
<212> TYPE: RNA
<213> ORGANISM: Homo sapiens

<400> SEQUENCE: 704 gaagugugccgugguguguct 21

<210> SEQ ID NO 705
<211> LENGTH: 22
<212> TYPE: RNA
<213> ORGANISM: Homo sapiens

<400> SEQUENCE: 705 cggaugagcaaagaaaguggu u 22

<210> SEQ ID NO 706
<211> LENGTH: 22
<212> TYPE: RNA
<213> ORGANISM: Homo sapiens

<400> SEQUENCE: 706 agaaggaaauugaauucauuua 22

<210> SEQ ID NO 707
<211> LENGTH: 21
<212> TYPE: RNA
<213> ORGANISM: Homo sapiens

<400> SEQUENCE: 707 gcaguccaugggcauauacac 21

<210> SEQ ID NO 708
<211> LENGTH: 22
<212> TYPE: RNA
<213> ORGANISM: Homo sapiens

<400> SEQUENCE: 708 gcugacuccuaguccagggcuc 22

<210> SEQ ID NO 709
<211> LENGTH: 23
<212> TYPE: RNA
<213> ORGANISM: Homo sapiens

<400> SEQUENCE: 709 uuuggcacuagcacauuuuugcu 23

<210> SEQ ID NO 710
<211> LENGTH: 18
<212> TYPE: RNA
<213> ORGANISM: Homo sapiens

<400> SEQUENCE: 710 cagggaggugaaugugau 18

<210> SEQ ID NO 711
<211> LENGTH: 22
<212> TYPE: RNA
<213> ORGANISM: Homo sapiens

<400> SEQUENCE: 711 uucucaaggaggugucguuuau 22

<210> SEQ ID NO 712
<211> LENGTH: 22
<212> TYPE: RNA
<213> ORGANISM: Homo sapiens

<400> SEQUENCE: 712 aaaaguaauugcgguuuuugcc 22

<210> SEQ ID NO 713
<211> LENGTH: 22
<212> TYPE: RNA

<213> ORGANISM: Homo sapiens

<400> SEQUENCE: 713 aggcggggcgccgcgggaccgc 22

<210> SEQ ID NO 714
<211> LENGTH: 20
<212> TYPE: RNA
<213> ORGANISM: Homo sapiens

<400> SEQUENCE: 714 aaaagcuggguugagagggu 20

<210> SEQ ID NO 715
<211> LENGTH: 22
<212> TYPE: RNA
<213> ORGANISM: Homo sapiens

<400> SEQUENCE: 715 aaaagcuggguugagagggcaa 22

<210> SEQ ID NO 716
<211> LENGTH: 22
<212> TYPE: RNA
<213> ORGANISM: Homo sapiens

<400> SEQUENCE: 716 uggugggccgcagaacaugugc 22

<210> SEQ ID NO 717
<211> LENGTH: 20
<212> TYPE: RNA
<213> ORGANISM: Homo sapiens

<400> SEQUENCE: 717 ccucugggcccuuccuccag 20

<210> SEQ ID NO 718
<211> LENGTH: 18
<212> TYPE: RNA
<213> ORGANISM: Homo sapiens

<400> SEQUENCE: 718 uccagugcccuccucucc 18

<210> SEQ ID NO 719
<211> LENGTH: 22
<212> TYPE: RNA
<213> ORGANISM: Homo sapiens

<400> SEQUENCE: 719 cuggcccucucugcccuuccgu 22

<210> SEQ ID NO 720
<211> LENGTH: 22
<212> TYPE: RNA
<213> ORGANISM: Homo sapiens

<400> SEQUENCE: 720 ugagaacugaauuccauaggcu 22

<210> SEQ ID NO 721
<211> LENGTH: 21

<212> TYPE: RNA
<213> ORGANISM: Homo sapiens

<400> SEQUENCE: 721 cgcgggugcuuacugacccuu 21

<210> SEQ ID NO 722
<211> LENGTH: 21
<212> TYPE: RNA
<213> ORGANISM: Homo sapiens

<400> SEQUENCE: 722 ugagugccggugccugcccug 21

<210> SEQ ID NO 723
<211> LENGTH: 22
<212> TYPE: RNA
<213> ORGANISM: Homo sapiens

<400> SEQUENCE: 723 cucggcgcggggcgcgggcucc 22

<210> SEQ ID NO 724
<211> LENGTH: 22
<212> TYPE: RNA
<213> ORGANISM: Homo sapiens

<400> SEQUENCE: 724 uccagcaucagugauuuuguug 22

<210> SEQ ID NO 725
<211> LENGTH: 23
<212> TYPE: RNA
<213> ORGANISM: Homo sapiens

<400> SEQUENCE: 725 cgggucggaguuagcucaagcgg 23

<210> SEQ ID NO 726
<211> LENGTH: 22
<212> TYPE: RNA
<213> ORGANISM: Homo sapiens

<400> SEQUENCE: 726 uggucuaggauuguuggaggag 22

<210> SEQ ID NO 727
<211> LENGTH: 22
<212> TYPE: RNA
<213> ORGANISM: Homo sapiens

<400> SEQUENCE: 727 uucauucggcuguccagaugua 22

<210> SEQ ID NO 728
<211> LENGTH: 21
<212> TYPE: RNA
<213> ORGANISM: Homo sapiens

<400> SEQUENCE: 728 ccaguccugugccugccgccu 21

<210> SEQ ID NO 729

<211> LENGTH: 26
<212> TYPE: RNA
<213> ORGANISM: Homo sapiens

<400> SEQUENCE: 729 gugagggcaugcaggccuggauggggg 26

<210> SEQ ID NO 730
<211> LENGTH: 23
<212> TYPE: RNA
<213> ORGANISM: Homo sapiens

<400> SEQUENCE: 730 aucaacagacauuaauugggcgc 23

<210> SEQ ID NO 731
<211> LENGTH: 22
<212> TYPE: RNA
<213> ORGANISM: Homo sapiens

<400> SEQUENCE: 731 gcccgcguguggagccaggugu 22

<210> SEQ ID NO 732
<211> LENGTH: 22
<212> TYPE: RNA
<213> ORGANISM: Homo sapiens

<400> SEQUENCE: 732 cugguacaggccugggggacag 22

<210> SEQ ID NO 733
<211> LENGTH: 23
<212> TYPE: RNA
<213> ORGANISM: Homo sapiens

<400> SEQUENCE: 733 cucucaccacugcccucccacag 23

<210> SEQ ID NO 734
<211> LENGTH: 22
<212> TYPE: RNA
<213> ORGANISM: Homo sapiens

<400> SEQUENCE: 734 acugcagugaaggcacuuguag 22

<210> SEQ ID NO 735
<211> LENGTH: 19
<212> TYPE: RNA
<213> ORGANISM: Homo sapiens

<400> SEQUENCE: 735 aaaagcuggguugagagga 19

<210> SEQ ID NO 736
<211> LENGTH: 23
<212> TYPE: RNA
<213> ORGANISM: Homo sapiens

<400> SEQUENCE: 736 uacccuguagaaccgaauuugug 23

<210> SEQ ID NO 737
<211> LENGTH: 22
<212> TYPE: RNA
<213> ORGANISM: Homo sapiens

<400> SEQUENCE: 737 acuccagccccacagccucagc 22

<210> SEQ ID NO 738
<211> LENGTH: 23
<212> TYPE: RNA
<213> ORGANISM: Homo sapiens

<400> SEQUENCE: 738 acuuacagacaagagccuugcuc 23

<210> SEQ ID NO 739
<211> LENGTH: 24
<212> TYPE: RNA
<213> ORGANISM: Homo sapiens

<400> SEQUENCE: 739 aaagacauaggauagagucaccuc 24

<210> SEQ ID NO 740
<211> LENGTH: 22
<212> TYPE: RNA
<213> ORGANISM: Homo sapiens

<400> SEQUENCE: 740 uccgucucaguuacuuuauagc 22

<210> SEQ ID NO 741
<211> LENGTH: 22
<212> TYPE: RNA
<213> ORGANISM: Homo sapiens

<400> SEQUENCE: 741 acucaaaacccuucagugacuu 22

<210> SEQ ID NO 742
<211> LENGTH: 21
<212> TYPE: RNA
<213> ORGANISM: Homo sapiens

<400> SEQUENCE: 742 cuccagagggaaguacuuucu 21

<210> SEQ ID NO 743
<211> LENGTH: 21
<212> TYPE: RNA
<213> ORGANISM: Homo sapiens

<400> SEQUENCE: 743 aagcauucuuucauugguugg 21

<210> SEQ ID NO 744
<211> LENGTH: 21
<212> TYPE: RNA
<213> ORGANISM: Homo sapiens

<400> SEQUENCE: 744 uugcucacuguucuucccuag 21

<210> SEQ ID NO 745
<211> LENGTH: 22
<212> TYPE: RNA
<213> ORGANISM: Homo sapiens

<400> SEQUENCE: 745 cugggagguggauguuuacuuc 22

<210> SEQ ID NO 746
<211> LENGTH: 22
<212> TYPE: RNA
<213> ORGANISM: Homo sapiens

<400> SEQUENCE: 746 cuccuacauauuagcauuaaca 22

<210> SEQ ID NO 747
<211> LENGTH: 22
<212> TYPE: RNA
<213> ORGANISM: Homo sapiens

<400> SEQUENCE: 747 gcuacuucacaacaccagggcc 22

<210> SEQ ID NO 748
<211> LENGTH: 22
<212> TYPE: RNA
<213> ORGANISM: Homo sapiens

<400> SEQUENCE: 748 aauccuuugucccugggugaga 22

<210> SEQ ID NO 749
<211> LENGTH: 23
<212> TYPE: RNA
<213> ORGANISM: Homo sapiens

<400> SEQUENCE: 749 caacggaaucccaaaagcagcug 23

<210> SEQ ID NO 750
<211> LENGTH: 23
<212> TYPE: RNA
<213> ORGANISM: Homo sapiens

<400> SEQUENCE: 750 agcagcauuguacagggcuauca 23

<210> SEQ ID NO 751
<211> LENGTH: 23
<212> TYPE: RNA
<213> ORGANISM: Homo sapiens

<400> SEQUENCE: 751 aucgcugcgguugcgagcgcugu 23

<210> SEQ ID NO 752
<211> LENGTH: 21
<212> TYPE: RNA
<213> ORGANISM: Homo sapiens

<400> SEQUENCE: 752 caaagcgcuucccuuuggagc 21

```
<210> SEQ ID NO 753
<211> LENGTH: 21
<212> TYPE: RNA
<213> ORGANISM: Homo sapiens

<400> SEQUENCE: 753

uaaagugcugacagugcagau                                                    21

<210> SEQ ID NO 754
<211> LENGTH: 22
<212> TYPE: RNA
<213> ORGANISM: Homo sapiens

<400> SEQUENCE: 754

aagcccuuaccccaaaaagcau                                                   22

<210> SEQ ID NO 755
<211> LENGTH: 18
<212> TYPE: RNA
<213> ORGANISM: Homo sapiens

<400> SEQUENCE: 755

acguuggcucugguggug                                                       18

<210> SEQ ID NO 756
<211> LENGTH: 22
<212> TYPE: RNA
<213> ORGANISM: Homo sapiens

<400> SEQUENCE: 756

ggcuacaacacaggacccgggc                                                   22

<210> SEQ ID NO 757
<211> LENGTH: 22
<212> TYPE: RNA
<213> ORGANISM: Homo sapiens

<400> SEQUENCE: 757

ucccugagacccuaacuuguga                                                   22

<210> SEQ ID NO 758
<211> LENGTH: 22
<212> TYPE: RNA
<213> ORGANISM: Homo sapiens

<400> SEQUENCE: 758

gucccucuccaaaugugucuug                                                   22

<210> SEQ ID NO 759
<211> LENGTH: 22
<212> TYPE: RNA
<213> ORGANISM: Homo sapiens

<400> SEQUENCE: 759

cuuucagucggauguuugcagc                                                   22

<210> SEQ ID NO 760
<211> LENGTH: 22
<212> TYPE: RNA
<213> ORGANISM: Homo sapiens

<400> SEQUENCE: 760
```

ucuacagugcacgugucuccag 22

<210> SEQ ID NO 761
<211> LENGTH: 22
<212> TYPE: RNA
<213> ORGANISM: Homo sapiens

<400> SEQUENCE: 761 acucggcguggcgucggucgug 22

<210> SEQ ID NO 762
<211> LENGTH: 23
<212> TYPE: RNA
<213> ORGANISM: Homo sapiens

<400> SEQUENCE: 762 cugggaucuccggggucuugguu 23

<210> SEQ ID NO 763
<211> LENGTH: 22
<212> TYPE: RNA
<213> ORGANISM: Homo sapiens

<400> SEQUENCE: 763 caugccuugaguguaggaccgu 22

<210> SEQ ID NO 764
<211> LENGTH: 22
<212> TYPE: RNA
<213> ORGANISM: Homo sapiens

<400> SEQUENCE: 764 caacaaaucacagucugccaua 22

<210> SEQ ID NO 765
<211> LENGTH: 22
<212> TYPE: RNA
<213> ORGANISM: Homo sapiens

<400> SEQUENCE: 765 uagguaguuucauguuguuggg 22

<210> SEQ ID NO 766
<211> LENGTH: 22
<212> TYPE: RNA
<213> ORGANISM: Homo sapiens

<400> SEQUENCE: 766 uuagggcccuggcuccaucucc 22

<210> SEQ ID NO 767
<211> LENGTH: 22
<212> TYPE: RNA
<213> ORGANISM: Homo sapiens

<400> SEQUENCE: 767 gcugcgcuuggauuucgucccc 22

<210> SEQ ID NO 768
<211> LENGTH: 23
<212> TYPE: RNA
<213> ORGANISM: Homo sapiens

<400> SEQUENCE: 768 agcuacauugucugcuggguuuc                                                23

<210> SEQ ID NO 769
<211> LENGTH: 23
<212> TYPE: RNA
<213> ORGANISM: Homo sapiens

<400> SEQUENCE: 769 agguugggaucgguugcaaugcu                                                23

<210> SEQ ID NO 770
<211> LENGTH: 22
<212> TYPE: RNA
<213> ORGANISM: Homo sapiens

<400> SEQUENCE: 770 ucugggcaacaaagugagaccu                                                 22

<210> SEQ ID NO 771
<211> LENGTH: 22
<212> TYPE: RNA
<213> ORGANISM: Homo sapiens

<400> SEQUENCE: 771 cucuagagggaagcacuuucuc                                                 22

<210> SEQ ID NO 772
<211> LENGTH: 20
<212> TYPE: RNA
<213> ORGANISM: Homo sapiens

<400> SEQUENCE: 772 ugagcccuguccucccgcag                                                   20

<210> SEQ ID NO 773
<211> LENGTH: 19
<212> TYPE: RNA
<213> ORGANISM: Homo sapiens

<400> SEQUENCE: 773 uggauuuuuggaucaggga                                                    19

<210> SEQ ID NO 774
<211> LENGTH: 22
<212> TYPE: RNA
<213> ORGANISM: Homo sapiens

<400> SEQUENCE: 774 uacgucaucguugucaucguca                                                 22

<210> SEQ ID NO 775
<211> LENGTH: 22
<212> TYPE: RNA
<213> ORGANISM: Homo sapiens

<400> SEQUENCE: 775 ugagaccucuggguucugagcu                                                 22

<210> SEQ ID NO 776
<211> LENGTH: 23
<212> TYPE: RNA
<213> ORGANISM: Homo sapiens

<400> SEQUENCE: 776 gaacgccuguucuugccaggugg 23

<210> SEQ ID NO 777
<211> LENGTH: 21
<212> TYPE: RNA
<213> ORGANISM: Homo sapiens

<400> SEQUENCE: 777 cuucuugugcucuaggauugu 21

<210> SEQ ID NO 778
<211> LENGTH: 24
<212> TYPE: RNA
<213> ORGANISM: Homo sapiens

<400> SEQUENCE: 778 uugcagcugccugggagugacuuc 24

<210> SEQ ID NO 779
<211> LENGTH: 24
<212> TYPE: RNA
<213> ORGANISM: Homo sapiens

<400> SEQUENCE: 779 uucuccaaaagaaagcacuuucug 24

<210> SEQ ID NO 780
<211> LENGTH: 19
<212> TYPE: RNA
<213> ORGANISM: Homo sapiens

<400> SEQUENCE: 780 aggcacggugucagcaggc 19

<210> SEQ ID NO 781
<211> LENGTH: 22
<212> TYPE: RNA
<213> ORGANISM: Homo sapiens

<400> SEQUENCE: 781 aaccagcaccccaacuuuggac 22

<210> SEQ ID NO 782
<211> LENGTH: 22
<212> TYPE: RNA
<213> ORGANISM: Homo sapiens

<400> SEQUENCE: 782 caaagcgcuccccuuuagaggu 22

<210> SEQ ID NO 783
<211> LENGTH: 23
<212> TYPE: RNA
<213> ORGANISM: Homo sapiens

<400> SEQUENCE: 783 cacccggcugugugcacaugugc 23

<210> SEQ ID NO 784
<211> LENGTH: 21
<212> TYPE: RNA
<213> ORGANISM: Homo sapiens

<400> SEQUENCE: 784 aacauagaggaaauuccacgu 21

<210> SEQ ID NO 785
<211> LENGTH: 22
<212> TYPE: RNA
<213> ORGANISM: Homo sapiens

<400> SEQUENCE: 785 ccaauauuggcugugcugcucc 22

<210> SEQ ID NO 786
<211> LENGTH: 20
<212> TYPE: RNA
<213> ORGANISM: Homo sapiens

<400> SEQUENCE: 786 cugcaaagggaagcccuuuc 20

<210> SEQ ID NO 787
<211> LENGTH: 23
<212> TYPE: RNA
<213> ORGANISM: Homo sapiens

<400> SEQUENCE: 787 guuugcacgggugggccuugucu 23

<210> SEQ ID NO 788
<211> LENGTH: 21
<212> TYPE: RNA
<213> ORGANISM: Homo sapiens

<400> SEQUENCE: 788 gugggcgggggcaggugugug 21

<210> SEQ ID NO 789
<211> LENGTH: 22
<212> TYPE: RNA
<213> ORGANISM: Homo sapiens

<400> SEQUENCE: 789 aguucuucaguggcaagcuuua 22

<210> SEQ ID NO 790
<211> LENGTH: 22
<212> TYPE: RNA
<213> ORGANISM: Homo sapiens

<400> SEQUENCE: 790 ucggccugaccacccaccccac 22

<210> SEQ ID NO 791
<211> LENGTH: 21
<212> TYPE: RNA
<213> ORGANISM: Homo sapiens

<400> SEQUENCE: 791 agggagggacgggggcugugc 21

<210> SEQ ID NO 792
<211> LENGTH: 22
<212> TYPE: RNA

```
<213> ORGANISM: Homo sapiens

<400> SEQUENCE: 792

cugggagaggguuguuuacucc                                              22

<210> SEQ ID NO 793
<211> LENGTH: 22
<212> TYPE: RNA
<213> ORGANISM: Homo sapiens

<400> SEQUENCE: 793

cgucuuacccagcaguguuugg                                              22

<210> SEQ ID NO 794
<211> LENGTH: 21
<212> TYPE: RNA
<213> ORGANISM: Homo sapiens

<400> SEQUENCE: 794

ccgucgccgccacccgagccg                                               21

<210> SEQ ID NO 795
<211> LENGTH: 22
<212> TYPE: RNA
<213> ORGANISM: Homo sapiens

<400> SEQUENCE: 795

aggugguccguggcgcguucgc                                              22

<210> SEQ ID NO 796
<211> LENGTH: 20
<212> TYPE: RNA
<213> ORGANISM: Homo sapiens

<400> SEQUENCE: 796

gugucugggcggacagcugc                                                20

<210> SEQ ID NO 797
<211> LENGTH: 22
<212> TYPE: RNA
<213> ORGANISM: Homo sapiens

<400> SEQUENCE: 797

gugaaauguuuaggaccacuag                                              22

<210> SEQ ID NO 798
<211> LENGTH: 22
<212> TYPE: RNA
<213> ORGANISM: Homo sapiens

<400> SEQUENCE: 798

uuuaacauggggguaccugcug                                              22

<210> SEQ ID NO 799
<211> LENGTH: 22
<212> TYPE: RNA
<213> ORGANISM: Homo sapiens

<400> SEQUENCE: 799

aacccguagauccgaucuugug                                              22

<210> SEQ ID NO 800
<211> LENGTH: 22
```

<212> TYPE: RNA
<213> ORGANISM: Homo sapiens

<400> SEQUENCE: 800 ugagaacugaauuccauggguu 22

<210> SEQ ID NO 801
<211> LENGTH: 21
<212> TYPE: RNA
<213> ORGANISM: Homo sapiens

<400> SEQUENCE: 801 aauauuauacagucaaccucu 21

<210> SEQ ID NO 802
<211> LENGTH: 22
<212> TYPE: RNA
<213> ORGANISM: Homo sapiens

<400> SEQUENCE: 802 gaaagugcuuccuuuuagaggc 22

<210> SEQ ID NO 803
<211> LENGTH: 22
<212> TYPE: RNA
<213> ORGANISM: Homo sapiens

<400> SEQUENCE: 803 aaguucuguuauacacucaggc 22

<210> SEQ ID NO 804
<211> LENGTH: 23
<212> TYPE: RNA
<213> ORGANISM: Homo sapiens

<400> SEQUENCE: 804 aacauucaacgcugucggugagu 23

<210> SEQ ID NO 805
<211> LENGTH: 21
<212> TYPE: RNA
<213> ORGANISM: Homo sapiens

<400> SEQUENCE: 805 acagucugcugagguuggagc 21

<210> SEQ ID NO 806
<211> LENGTH: 24
<212> TYPE: RNA
<213> ORGANISM: Homo sapiens

<400> SEQUENCE: 806 ucccugagacccuuuaaccuguga 24

<210> SEQ ID NO 807
<211> LENGTH: 21
<212> TYPE: RNA
<213> ORGANISM: Homo sapiens

<400> SEQUENCE: 807 ucagugcaugacagaacuugg 21

<210> SEQ ID NO 808

<211> LENGTH: 22
<212> TYPE: RNA
<213> ORGANISM: Homo sapiens

<400> SEQUENCE: 808 uucaccaccuucuccacccagc 22

<210> SEQ ID NO 809
<211> LENGTH: 21
<212> TYPE: RNA
<213> ORGANISM: Homo sapiens

<400> SEQUENCE: 809 uucacaguggcuaaguucugc 21

<210> SEQ ID NO 810
<211> LENGTH: 22
<212> TYPE: RNA
<213> ORGANISM: Homo sapiens

<400> SEQUENCE: 810 ccucuuccccuugucucuccag 22

<210> SEQ ID NO 811
<211> LENGTH: 22
<212> TYPE: RNA
<213> ORGANISM: Homo sapiens

<400> SEQUENCE: 811 aaacaaacauggugcacuucuu 22

<210> SEQ ID NO 812
<211> LENGTH: 21
<212> TYPE: RNA
<213> ORGANISM: Homo sapiens

<400> SEQUENCE: 812 ugagaugaagcacuguagcuc 21

<210> SEQ ID NO 813
<211> LENGTH: 22
<212> TYPE: RNA
<213> ORGANISM: Homo sapiens

<400> SEQUENCE: 813 aacacaccuauucaaggauuca 22

<210> SEQ ID NO 814
<211> LENGTH: 23
<212> TYPE: RNA
<213> ORGANISM: Homo sapiens

<400> SEQUENCE: 814 uggugcggagagggcccacagug 23

<210> SEQ ID NO 815
<211> LENGTH: 17
<212> TYPE: RNA
<213> ORGANISM: Homo sapiens

<400> SEQUENCE: 815 ucccuguucgggcgcca 17

<210> SEQ ID NO 816
<211> LENGTH: 22
<212> TYPE: RNA
<213> ORGANISM: Homo sapiens

<400> SEQUENCE: 816 ggagacgcggcccuguuggagu 22

<210> SEQ ID NO 817
<211> LENGTH: 21
<212> TYPE: RNA
<213> ORGANISM: Homo sapiens

<400> SEQUENCE: 817 acucuuucccuguugcacuac 21

<210> SEQ ID NO 818
<211> LENGTH: 20
<212> TYPE: RNA
<213> ORGANISM: Homo sapiens

<400> SEQUENCE: 818 ucacaccugccucgcccccc 20

<210> SEQ ID NO 819
<211> LENGTH: 22
<212> TYPE: RNA
<213> ORGANISM: Homo sapiens

<400> SEQUENCE: 819 uuuccggcucgcgugggugugu 22

<210> SEQ ID NO 820
<211> LENGTH: 19
<212> TYPE: RNA
<213> ORGANISM: Homo sapiens

<400> SEQUENCE: 820 gagccaguuggacaggagc 19

<210> SEQ ID NO 821
<211> LENGTH: 22
<212> TYPE: RNA
<213> ORGANISM: Homo sapiens

<400> SEQUENCE: 821 ugugacugguugaccagagggg 22

<210> SEQ ID NO 822
<211> LENGTH: 21
<212> TYPE: RNA
<213> ORGANISM: Homo sapiens

<400> SEQUENCE: 822 ccuggaaacacugagguugug 21

<210> SEQ ID NO 823
<211> LENGTH: 22
<212> TYPE: RNA
<213> ORGANISM: Homo sapiens

<400> SEQUENCE: 823 agggacgggacgcggugcagug 22

-continued

<210> SEQ ID NO 824
<211> LENGTH: 22
<212> TYPE: RNA
<213> ORGANISM: Homo sapiens

<400> SEQUENCE: 824 uacccauugcauaucggaguug 22

<210> SEQ ID NO 825
<211> LENGTH: 23
<212> TYPE: RNA
<213> ORGANISM: Homo sapiens

<400> SEQUENCE: 825 cucuugagggaagcacuuucugu 23

<210> SEQ ID NO 826
<211> LENGTH: 22
<212> TYPE: RNA
<213> ORGANISM: Homo sapiens

<400> SEQUENCE: 826 acuggacuuagggucagaaggc 22

<210> SEQ ID NO 827
<211> LENGTH: 21
<212> TYPE: RNA
<213> ORGANISM: Homo sapiens

<400> SEQUENCE: 827 acggugcuggauguggccuuu 21

<210> SEQ ID NO 828
<211> LENGTH: 22
<212> TYPE: RNA
<213> ORGANISM: Homo sapiens

<400> SEQUENCE: 828 ugcccuuaaaggugaacccagu 22

<210> SEQ ID NO 829
<211> LENGTH: 25
<212> TYPE: RNA
<213> ORGANISM: Homo sapiens

<400> SEQUENCE: 829 aggggugguguugggacagcuccgu 25

<210> SEQ ID NO 830
<211> LENGTH: 17
<212> TYPE: RNA
<213> ORGANISM: Homo sapiens

<400> SEQUENCE: 830 ucauauugcuucuuucu 17

<210> SEQ ID NO 831
<211> LENGTH: 22
<212> TYPE: RNA
<213> ORGANISM: Homo sapiens

<400> SEQUENCE: 831 acgcccuucccccccuucuuca 22

<210> SEQ ID NO 832
<211> LENGTH: 24
<212> TYPE: RNA
<213> ORGANISM: Homo sapiens

<400> SEQUENCE: 832 ugccugggucucuggccugcgcgu 24

<210> SEQ ID NO 833
<211> LENGTH: 20
<212> TYPE: RNA
<213> ORGANISM: Homo sapiens

<400> SEQUENCE: 833 ucacuguucagacaggcgga 20

<210> SEQ ID NO 834
<211> LENGTH: 22
<212> TYPE: RNA
<213> ORGANISM: Homo sapiens

<400> SEQUENCE: 834 cagugcaauguuaaaagggcau 22

<210> SEQ ID NO 835
<211> LENGTH: 22
<212> TYPE: RNA
<213> ORGANISM: Homo sapiens

<400> SEQUENCE: 835 uuuugcaauauguuccugaaua 22

<210> SEQ ID NO 836
<211> LENGTH: 23
<212> TYPE: RNA
<213> ORGANISM: Homo sapiens

<400> SEQUENCE: 836 ucuuggaguaggucauugggugg 23

<210> SEQ ID NO 837
<211> LENGTH: 22
<212> TYPE: RNA
<213> ORGANISM: Homo sapiens

<400> SEQUENCE: 837 gaauguugcucggugaaccccu 22

<210> SEQ ID NO 838
<211> LENGTH: 20
<212> TYPE: RNA
<213> ORGANISM: Homo sapiens

<400> SEQUENCE: 838 cugcaaagggaagcccuuuc 20

<210> SEQ ID NO 839
<211> LENGTH: 21
<212> TYPE: RNA
<213> ORGANISM: Homo sapiens

<400> SEQUENCE: 839 uccucuucucccuccucccag 21

<210> SEQ ID NO 840
<211> LENGTH: 20
<212> TYPE: RNA
<213> ORGANISM: Homo sapiens

<400> SEQUENCE: 840 cuuccucgucugucugcccc 20

<210> SEQ ID NO 841
<211> LENGTH: 22
<212> TYPE: RNA
<213> ORGANISM: Homo sapiens

<400> SEQUENCE: 841 ccucuagauggaagcacugucu 22

<210> SEQ ID NO 842
<211> LENGTH: 22
<212> TYPE: RNA
<213> ORGANISM: Homo sapiens

<400> SEQUENCE: 842 cgggguuuugagggcgagauga 22

<210> SEQ ID NO 843
<211> LENGTH: 22
<212> TYPE: RNA
<213> ORGANISM: Homo sapiens

<400> SEQUENCE: 843 cuacaaagggaagcacuuucuc 22

<210> SEQ ID NO 844
<211> LENGTH: 21
<212> TYPE: RNA
<213> ORGANISM: Homo sapiens

<400> SEQUENCE: 844 aguuaggauuaggucguggaa 21

<210> SEQ ID NO 845
<211> LENGTH: 22
<212> TYPE: RNA
<213> ORGANISM: Homo sapiens

<400> SEQUENCE: 845 uagguuauccguguugccuucg 22

<210> SEQ ID NO 846
<211> LENGTH: 24
<212> TYPE: RNA
<213> ORGANISM: Homo sapiens

<400> SEQUENCE: 846 acugggggcuuucgggcucugcgu 24

<210> SEQ ID NO 847
<211> LENGTH: 21
<212> TYPE: RNA
<213> ORGANISM: Homo sapiens

<400> SEQUENCE: 847

-continued uuggccacaaugguuagaac 21

<210> SEQ ID NO 848
<211> LENGTH: 23
<212> TYPE: RNA
<213> ORGANISM: Homo sapiens

<400> SEQUENCE: 848 uuaaugcuaaucgugauaggggu 23

<210> SEQ ID NO 849
<211> LENGTH: 24
<212> TYPE: RNA
<213> ORGANISM: Homo sapiens

<400> SEQUENCE: 849 acuggcuagggaaaaugauuggau 24

<210> SEQ ID NO 850
<211> LENGTH: 21
<212> TYPE: RNA
<213> ORGANISM: Homo sapiens

<400> SEQUENCE: 850 gcccuccgcccgugcaccccg 21

<210> SEQ ID NO 851
<211> LENGTH: 22
<212> TYPE: RNA
<213> ORGANISM: Homo sapiens

<400> SEQUENCE: 851 acggauguuugagcaugugcua 22

<210> SEQ ID NO 852
<211> LENGTH: 23
<212> TYPE: RNA
<213> ORGANISM: Homo sapiens

<400> SEQUENCE: 852 cgcauccccuagggcauuggugu 23

<210> SEQ ID NO 853
<211> LENGTH: 22
<212> TYPE: RNA
<213> ORGANISM: Homo sapiens

<400> SEQUENCE: 853 aagcccuuaccccaaaaaguau 22

<210> SEQ ID NO 854
<211> LENGTH: 21
<212> TYPE: RNA
<213> ORGANISM: Homo sapiens

<400> SEQUENCE: 854 agggggaaaguucuauagucc 21

<210> SEQ ID NO 855
<211> LENGTH: 22
<212> TYPE: RNA
<213> ORGANISM: Homo sapiens

<400> SEQUENCE: 855 cucuagagggaagcgcuuucug 22

<210> SEQ ID NO 856
<211> LENGTH: 22
<212> TYPE: RNA
<213> ORGANISM: Homo sapiens

<400> SEQUENCE: 856 accacugaccguugacuguacc 22

<210> SEQ ID NO 857
<211> LENGTH: 23
<212> TYPE: RNA
<213> ORGANISM: Homo sapiens

<400> SEQUENCE: 857 cccaguguuuagacuaucuguuc 23

<210> SEQ ID NO 858
<211> LENGTH: 21
<212> TYPE: RNA
<213> ORGANISM: Homo sapiens

<400> SEQUENCE: 858 uucacaguggcuaaguuccgc 21

<210> SEQ ID NO 859
<211> LENGTH: 22
<212> TYPE: RNA
<213> ORGANISM: Homo sapiens

<400> SEQUENCE: 859 gaaagcgcuucccuuugcugga 22

<210> SEQ ID NO 860
<211> LENGTH: 22
<212> TYPE: RNA
<213> ORGANISM: Homo sapiens

<400> SEQUENCE: 860 caggauguggucaaguguuguu 22

<210> SEQ ID NO 861
<211> LENGTH: 22
<212> TYPE: RNA
<213> ORGANISM: Homo sapiens

<400> SEQUENCE: 861 uauugcacuugucccggccugu 22

<210> SEQ ID NO 862
<211> LENGTH: 24
<212> TYPE: RNA
<213> ORGANISM: Homo sapiens

<400> SEQUENCE: 862 gcugguuucauauggugguuuaga 24

<210> SEQ ID NO 863
<211> LENGTH: 22
<212> TYPE: RNA
<213> ORGANISM: Homo sapiens

```
<400> SEQUENCE: 863

ucucccaacccuuguaccagug                                          22


<210> SEQ ID NO 864
<211> LENGTH: 23
<212> TYPE: RNA
<213> ORGANISM: Homo sapiens

<400> SEQUENCE: 864

ucaagagcaauaacgaaaaaugu                                         23


<210> SEQ ID NO 865
<211> LENGTH: 25
<212> TYPE: RNA
<213> ORGANISM: Homo sapiens

<400> SEQUENCE: 865

agggaucgcgggcggguggcggccu                                       25


<210> SEQ ID NO 866
<211> LENGTH: 22
<212> TYPE: DNA
<213> ORGANISM: Homo sapiens

<400> SEQUENCE: 866

aactatacaacctactacctca                                          22
```

MIRNA FINGERPRINT IN THE DIAGNOSIS OF LUNG CANCER

CROSS REFERENCE TO RELATED APPLICATION

This application is a 35 U.S.C. 371 National Phase Entry Application from PCT/EP2010/057942, filed Jun. 7, 2010, which claims the benefit of U.S. Provisional Applications Nos. 61/184,452 filed Jun. 5, 2009, 61/213,971 filed Aug. 3, 2009, 61/287,521 filed Dec. 17, 2009 and European Patent Application No. 09015668.8 filed on Dec. 17, 2009, the disclosures of which are incorporated herein in their entirety by reference.

BACKGROUND OF THE INVENTION

MicroRNAs (miRNA) are a recently discovered class of small non-coding RNAs (17-14 nucleotides). Due to their function as regulators of gene expression they play a critical role both in physiological and in pathological processes, such as cancer (Calin and Croce 2006; Esquela-Kerscher and Slack 2006; Zhang, Pan et al. 2007; Sassen, Miska et al. 2008).

There is increasing evidence that miRNAs are not only found in tissues but also in human blood both as free circulating nucleic acids (also called circulating miRNAs) and in mononuclear cells. A recent proof-of-principle study demonstrated miRNA expression pattern in pooled blood sera and pooled blood cells, both in healthy individuals and in cancer patients including patients with lung cancer (Chen, Ba et al. 2008). In addition, a remarkable stability of miRNAs in human sera was recently demonstrated (Chen, Ba et al. 2008; Gilad, Meiri et al. 2008). These findings make miRNA a potential tool for diagnostics for various types of diseases based on blood analysis.

Lung cancer is the leading cause of cancer death worldwide (Jemal, Siegel et al. 2008). Its five-year survival rate is among the lowest of all cancer types and is markedly correlated to the stage at the time of diagnosis (Scott, Howington et al. 2007). Using currently existing techniques, more than two-thirds of lung cancers are diagnosed at late stages, when the relative survival rate is low (Henschke and Yankelevitz 2008). This reality calls for the search of new biomarkers that are able to catch lung cancer while it is still small and locally defined.

Various markers have been proposed to indicate specific types of disorders and in particular cancer. However, there is still a need for more efficient and effective methods and compositions for the diagnosis of diseases and in particular cancer.

SUMMARY OF THE INVENTION

The present invention provides novel methods for diagnosing diseases based on the determination of specific miRNAs that have altered expression levels in disease states compared to healthy or other relevant controls. The present invention particularly provides novel methods for the diagnosis and/or prognosis and/or monitoring of lung cancer or related diseases in human individuals based on miRNA analysis from samples derived from blood.

Subject-matter of the invention is a method for diagnosing lung cancer, comprising the steps (a) determining an expression profile of a predetermined set of miRNAs in a biological sample from a patient; and (b) comparing said expression profile to a reference expression profile, wherein the comparison of said determined expression profile to said reference expression profile allows for the diagnosis of lung cancer.

A "biological sample" in terms of the invention means a sample of biological tissue or fluid. Examples of biological samples are sections of tissues, blood, blood fractions, plasma, serum, etc. A biological sample may be provided by removing a sample of cells from a subject, but can also be provided by using a previously isolated sample. For example, a tissue sample can be removed from a subject suspected of having a disease by conventional biopsy techniques. In a preferred embodiment, a blood sample is taken from the subject. In one embodiment, the blood or tissue sample is obtained from the subject prior to initiation of radiotherapy, chemotherapy or other therapeutic treatment. According to the invention, the biological sample preferably is a blood, plasma, PBMC (peripheral blood mononuclear cell) or a serum sample. Further, it is also preferred to use blood cells, e.g. erythrocytes, leukocytes or thrombocytes.

A biological sample from a patient means a sample from a subject suspected to be affected by a disease. As used herein, the term "subject" refers to any mammal, including both human and other mammals. Preferably, the methods of the present invention are applied to human subjects.

In step (a) of the method of the invention, an expression profile of a predetermined set of miRNAs is determined. The determination may be carried out by any convenient means for determining nucleic acids. For expression profiling, qualitative, semi-quantitative and preferably quantitative detection methods can be used. A variety of techniques are well known to those of skill in the art. In particular, the determination may comprise nucleic acid hybridization and/or nucleic acid amplification steps.

Nucleic acid hybridization may for example be performed using a solid phase nucleic acid biochip array, in particular a microarray, beads, or in situ hybridization. The miRNA microarray technology affords the analysis of a complex biological sample for all expressed miRNAs. Nucleotides with complementarity to the corresponding miRNAs are spotted or synthesized on coated carriers. E.g., miRNAs isolated from the sample of interest may be labelled, e.g. fluorescently labelled, so that upon hybridization of the miRNAs to the complementary sequences on the carrier the resulting signal indicates the occurrence of a distinct miRNA. Preferably, microarray methods are employed that do not require a labeling of the miRNAs prior to hybridization (FIG. 3-4) and start directly from total RNA input. On one miRNA microarray, preferably the whole predetermined set of miRNAs can be analyzed. Examples of preferred hybridization assays are shown in FIGS. 1-4. The design of exemplary miRNA capture probes for use in hybridization assays is depicted in FIGS. 5 and 6.

Further, real-time or quantitative real-time polymerase chain reaction (RT-RCR or qRT-PCR) can be used to detect also low abandoned miRNAs. Furthermore, bead-based assays, e.g. the Luminex platform, are suitable.

Alternative methods for obtaining expression profiles may also contain sequencing, next generation sequencing or mass spectroscopy.

The predetermined set of miRNAs in step (a) of the method of the invention depends on the disease to be diagnosed. The inventors found out that single miRNA biomarkers lack sufficient accuracy, specificity and sensitivity, and therefore it is preferred to analyze more complex miRNA expression patterns, so-called miRNA signatures.

The predetermined set of miRNAs comprises one or more, preferably a larger number of miRNAs (miRNA signatures) that are differentially regulated in samples of a patient affected by a particular disease compared to healthy or other relevant controls.

The expression profile determined in step (a) is subsequently compared to a reference expression profile in step (b). The reference expression profile is the expression profile of the same set of miRNAs in a biological sample originating from the same source as the biological sample from a patient but obtained from a healthy subject. Preferably, both the reference expression profile and the expression profile of step (a) are determined in a blood or serum sample including whole blood, plasma, serum or fractions thereof, or in a sample of peripheral blood mononuclear cells, of erythrocytes, leukocytes and/or thrombocytes. It is understood that the reference expression profile is not necessarily obtained from a single healthy subject but may be an average expression profile of a plurality of healthy subjects. It is preferred to use a reference expression profile obtained from a person of the same gender, and a similar age as the patient. It is also understood that the reference expression profile is not necessarily determined for each test. Appropriate reference profiles stored in databases may also be used. These stored references profiles may, e.g., be derived from previous tests. The reference expression profile may also be a mathematical function or algorithm developed on the basis of a plurality of reference expression profiles.

The method of the invention is suitable for diagnosing lung cancer. The diagnosis may comprise determining type, rate and/or stage of lung cancer. The course of the disease and the success of therapy such as chemotherapy may be monitored. The method of the invention provides a prognosis on the survivor rate and enables to determine a patient's response to drugs.

Figure 9:
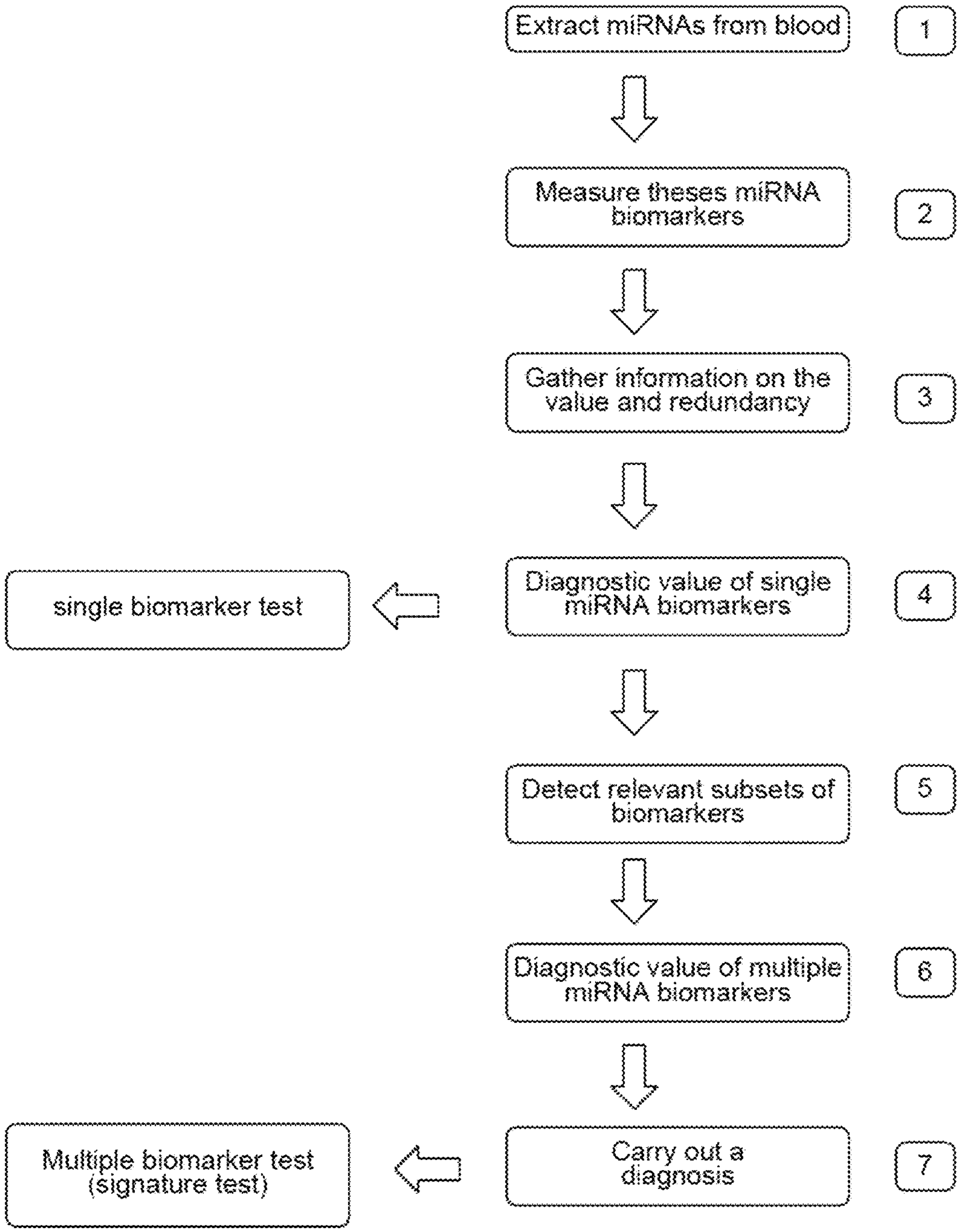

The inventors succeeded in developing a generally applicable approach to arrive at miRNA signatures that are correlated with a particular disease. The general work flow is depicted in FIG. 9. In more detail, the following steps are accomplished:

1. miRNAs are extracted from a biological sample of a patient, preferably a blood or serum sample or a sample comprising erythrocytes, leukocytes or thrombocytes, using suitable kits/purification methods
2. The respective samples are measured using experimental techniques.
   These techniques include but are not restricted to:
   Array based approaches
   Real time quantitative polymerase chain reaction
   Bead-based assays (e.g. Luminex)
   Sequencing
   Next Generation Sequencing
   Mass Spectroscopy
3. Mathematical approaches are applied to gather information on the value and the redundancy of single biomarkers. These methods include, but are not restricted to:
   basic mathematic approaches (e.g. Fold Quotients, Signal to Noise ratios, Correlation)
   statistical methods as hypothesis tests (e.g. t-test, Wilcoxon-Mann-Whitney test), the Area under the Receiver operator Characteristics Curve
   Information Theory approaches, (e.g. the Mutual Information, Cross-entropy)
   Probability theory (e.g. joint and conditional probabilities)
   Combinations and modifications of the previously mentioned examples
4. The information collected in 3) are used to estimate for each biomarker the diagnostic content or value. Usually, however, this diagnostic value is too small to get a highly accurate diagnosis with accuracy rates, specificities and sensitivities beyond the 90% barrier.
   Please note that the diagnostic content for our miRNAs can be found in the attached figures. These figures include the miRNAs with the sequences, the fold quotient, the mutual information and the significance value as computed by a t-test.
5. Thus statistical learning/machine learning/bioinformatics/computational approaches are applied to define subsets of biomarkers that are tailored for the detection of diseases.
   These techniques includes but are not restricted to
   Wrapper subset selection techniques (e.g. forward step-wise, backward step-wise, combinatorial approaches, optimization approaches)
   Filter subset selection methods (e.g. the methods mentioned in 3)
   Principal Component Analysis
   Combinations and modifications of such methods (e.g. hybrid approaches)
6. The diagnostic content of each detected set can be estimated by mathematical and/or computational techniques to define the diagnostic information content of subsets.
7. The subsets, detected in step 5, which may range from only a small number (at least two) to all measured biomarkers is then used to carry out a diagnosis. To this end, statistical learning/machine learning/bioinformatics/computational approaches are applied that include but are not restricted to any type of supervised or unsupervised analysis:
   Classification techniques (e.g. naïve Bayes, Linear Discriminant Analysis, Quadratic Discriminant Analysis Neural Nets, Tree based approaches, Support Vector Machines, Nearest Neighbour Approaches)
   Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression)
   Clustering techniques (e.g. k-means clustering, hierarchical clustering, PCA)
   Adaptations, extensions, and combinations of the previously mentioned approaches The inventors surprisingly found out that the described approach yields in miRNA signatures that provide high diagnostic accuracy, specificity and sensitivity in the determination of lung cancer.

According to the invention, the disease to be determined is lung cancer, e.g. lung carcinoid, lung pleural mesothelioma or lung squamous cell carcinoma, in particular non-small cell lung carcinoma.

The inventors succeeded in determining miRNAs that are differentially regulated in samples from lung cancer patients as compared to healthy controls. A complete overview of all miRNAs that are found to be differentially regulated in blood samples of lung cancer patients is provided in the tables shown in FIGS. 10A and 10B. In the tables shown in FIGS. 10A and 10B, the miRNAs that are found to be differentially regulated are sorted in the order of their mutual information and in the order of their t-test significance as described in more detail below. Mutual information (MI) (Shannon, 1984) is an adequate measure to estimate the overall diagnostic information content of single biomarkers (Keller, Ludwig et al., 2006).

According to the invention mutual information is considered as the reduction in uncertainty about the class labels "0" for controls and "1" for tumor samples due to the knowledge of the miRNA expression. The higher the value of the MI of a miRNA, the higher is the diagnostic content of the respective miRNA. The computation of the MI of each miRNA is explained in the experimental section below.

For example, the predetermined set of miRNAs representative for lung cancer comprises at least 1, 7, 10, 15, 20, 25, 30, 35, 40, 50, 75, 100 of the miRNAs selected from the group consisting of hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p, hsa-miR-93*, hsa-miR-29a, hsa-miR-1248, hsa-miR-210, hsa-miR-19b, hsa-miR-453, hsa-miR-126*, hsa-miR-188-3p, hsa-miR-624*, hsa-miR-505*, hsa-miR-425, hsa-miR-339-3p, hsa-miR-668, hsa-miR-363*, hsa-miR-15b*, hsa-miR-29c*, hsa-miR-550*, hsa-miR-34c-3p, hsa-miR-20a, hsa-miR-374a, hsa-miR-145*, hsa-miR-302b, hsa-miR-106a, hsa-miR-30e, hsa-miR-223, hsa-miR-1269, hsa-let-7b, hsa-miR-542-3p, hsa-miR-516b*, hsa-miR-451, hsa-miR-519c-3p, hsa-miR-1244, hsa-miR-602, hsa-miR-361-3p, hsa-miR-19a*, hsa-miR-433, hsa-miR-1200, hsa-miR-522, hsa-miR-520f, hsa-miR-519c-5p, hsa-miR-192, hsa-miR-1245, hsa-miR-151-5p, hsa-miR-1288, hsa-miR-503, hsa-miR-563, hsa-miR-663b, hsa-let-7d*, hsa-miR-199a-5p, hsa-miR-720, hsa-miR-1246, hsa-miR-338-5p, hsa-miR-297, hsa-miR-1261, hsa-miR-922, hsa-miR-185, hsa-miR-611, hsa-miR-1272, hsa-miR-1299, hsa-miR-335*, hsa-miR-497, hsa-miR-1207-3p, hsa-miR-16, hsa-miR-1, hsa-miR-1291, hsa-miR-138-2*, hsa-miR-136, hsa-miR-548d-3p, hsa-miR-561, hsa-miR-548h, hsa-miR-331-3p, hsa-miR-186*, hsa-miR-145, hsa-miR-17, hsa-miR-30b, hsa-let-7f-1*, hsa-miR-1305, hsa-miR-129-5p, hsa-miR-1204, hsa-miR-106b*, hsa-miR-619, hsa-miR-34a*, hsa-miR-652, hsa-miR-1256, hsa-miR-20b*, hsa-miR-424*, hsa-miR-517a, hsa-miR-1284, hsa-miR-199b-3p, hsa-miR-599, hsa-miR-411, hsa-miR-23b, hsa-miR-1302, hsa-miR-449a, hsa-miR-548f, hsa-miR-597, hsa-miR-603, hsa-miR-1247, hsa-miR-1539, hsa-miR-1911, hsa-miR-325, hsa-miR-409-5p, hsa-miR-182, hsa-miR-658, hsa-miR-215, hsa-miR-147b, hsa-miR-30d, hsa-miR-378*, hsa-miR-221*, hsa-miR-34b, hsa-miR-593*, hsa-miR-552, hsa-miR-378, hsa-miR-143*, hsa-miR-1266, hsa-miR-554, hsa-miR-631, hsa-miR-609, hsa-miR-30c, hsa-miR-28-5p, hsa-miR-23a, hsa-miR-645, hsa-miR-647, hsa-miR-302b*, hsa-miR-607, hsa-miR-1289, hsa-miR-1324, hsa-miR-513a-3p, hsa-miR-939, hsa-miR-29b, hsa-miR-665, hsa-miR-18a, hsa-miR-1224-5p, hsa-miR-10a*, hsa-miR-181a*, hsa-miR-218-2*, hsa-miR-371-3p, hsa-miR-377, hsa-miR-140-5p, hsa-miR-301a, hsa-miR-1277, hsa-miR-130a*, hsa-miR-1912, hsa-miR-193b, hsa-miR-214*, hsa-miR-216b, hsa-miR-302f, hsa-miR-522*, hsa-miR-548j, hsa-miR-568, hsa-miR-648, hsa-miR-662, hsa-miR-222, hsa-miR-1287, hsa-miR-891b, hsa-miR-342-3p, hsa-miR-512-3p, hsa-miR-623, hsa-miR-208b, hsa-miR-16-1*, hsa-miR-551b, hsa-miR-146b-3p, hsa-miR-520b, hsa-miR-449b, hsa-miR-520g, hsa-miR-24-2*, hsa-miR-518f, hsa-miR-649, hsa-miR-32, hsa-miR-151-3p, hsa-miR-454, hsa-miR-101, hsa-miR-19b-1*, hsa-miR-509-5p, hsa-miR-144, hsa-miR-508-5p, hsa-miR-569, hsa-miR-636, hsa-miR-937, hsa-miR-346, hsa-miR-506, hsa-miR-379*, hsa-miR-1184, hsa-miR-579, hsa-miR-23b*, hsa-miR-1262, hsa-miR-153, hsa-miR-520e, hsa-miR-632, hsa-miR-106a*, hsa-miR-31*, hsa-miR-33b*, hsa-miR-654-3p, hsa-miR-99b*, hsa-miR-1278, hsa-miR-135b, hsa-let-7c*, hsa-miR-1468, hsa-miR-374b*, hsa-miR-514, hsa-miR-590-3p, hsa-miR-606, hsa-miR-369-3p, hsa-miR-488, hsa-miR-128, hsa-miR-362-5p, hsa-miR-671-5p, hsa-miR-874, hsa-miR-1911*, hsa-miR-1292, hsa-miR-194, hsa-miR-15b, hsa-miR-342-5p, hsa-miR-125b-2*, hsa-miR-1297, hsa-miR-933, hsa-miR-493*, hsa-miR-105, hsa-miR-141, hsa-miR-181c*, hsa-miR-193a-3p, hsa-miR-302c, hsa-miR-485-5p, hsa-miR-499-3p, hsa-miR-545, hsa-miR-548b-5p, hsa-miR-549, hsa-miR-576-5p, hsa-miR-577, hsa-miR-583, hsa-miR-587, hsa-miR-624, hsa-miR-646, hsa-miR-655, hsa-miR-885-5p, hsa-miR-194*, hsa-miR-299-5p, hsa-miR-337-3p, hsa-miR-493, hsa-miR-497*, hsa-miR-519a, hsa-miR-99a*, hsa-miR-1280, hsa-miR-523*, hsa-miR-198, hsa-miR-934, hsa-miR-30d*, hsa-miR-452*, hsa-miR-548b-3p, hsa-miR-586, hsa-miR-92b, hsa-miR-517b, hsa-miR-548a-3p, hsa-miR-875-5p, hsa-miR-431*, hsa-miR-384, hsa-miR-644, hsa-miR-1185, hsa-miR-29b-2*, hsa-miR-489, hsa-miR-566, hsa-miR-1538, hsa-miR-28-3p, hsa-let-7f-2*, hsa-miR-1322, hsa-miR-1827, hsa-miR-192*, hsa-miR-302e, hsa-miR-411*, hsa-miR-424, hsa-miR-582-3p, hsa-miR-629*, hsa-miR-491-3p, hsa-miR-519b-3p, hsa-miR-1197, hsa-miR-127-5p, hsa-miR-1286, hsa-miR-132*, hsa-miR-33b, hsa-miR-553, hsa-miR-620, hsa-miR-708, hsa-miR-892b, hsa-miR-520h, hsa-miR-500*, hsa-miR-551b*, hsa-miR-186, hsa-miR-558, hsa-miR-26a, hsa-miR-1263, hsa-miR-211, hsa-miR-1304, hsa-miR-220b, hsa-miR-891a, hsa-miR-1253, hsa-miR-1205, hsa-miR-137, hsa-miR-154*, hsa-miR-555, hsa-miR-887, hsa-miR-363, hsa-miR-1537, hsa-miR-219-1-3p, hsa-miR-220a, hsa-miR-222*, hsa-miR-323-3p, hsa-miR-376b, hsa-miR-490-5p, hsa-miR-523, hsa-miR-302a*, hsa-miR-27b*, hsa-miR-591, hsa-miR-888, hsa-miR-376a*, hsa-miR-618, hsa-miR-1182, hsa-miR-532-3p, hsa-miR-181b, hsa-miR-521, hsa-miR-545*, hsa-miR-9*, hsa-miR-920, hsa-miR-571, hsa-miR-635, hsa-miR-200b, hsa-miR-455-5p, hsa-miR-876-3p, hsa-miR-373*, hsa-miR-146a*, hsa-miR-122*, hsa-miR-450b-3p, hsa-miR-24, hsa-miR-484, hsa-miR-103-as, hsa-miR-380, hsa-miR-513a-5p, hsa-miR-509-3-5p, hsa-miR-873, hsa-miR-556-5p, hsa-miR-369-5p, hsa-miR-653, hsa-miR-767-3p, hsa-miR-516a-3p, hsa-miR-520c-3p, hsa-miR-708*, hsa-miR-924, hsa-miR-520d-5p, hsa-miR-512-5p, hsa-miR-374a*, hsa-miR-921, hsa-miR-1206, hsa-miR-1259, hsa-miR-525-5p, hsa-miR-200a*, hsa-miR-1293, hsa-miR-372, hsa-miR-548a-5p, hsa-miR-548k, hsa-miR-1300, hsa-miR-1264, hsa-miR-551a, hsa-miR-196b, hsa-miR-32*, hsa-miR-33a, hsa-miR-548d-5p, hsa-miR-616, hsa-miR-876-5p, hsa-miR-508-3p, hsa-miR-26a-2*, hsa-miR-187, hsa-miR-199a-3p, hsa-miR-96*, hsa-miR-18b, hsa-miR-432*, hsa-miR-509-3p, hsa-miR-1183, hsa-miR-626, hsa-miR-513b, hsa-miR-617, hsa-miR-9, hsa-miR-519e, hsa-miR-204, hsa-miR-29c, hsa-miR-1268, hsa-miR-122, hsa-miR-7-2*, hsa-miR-15a*, hsa-miR-181d, hsa-miR-219-5p, hsa-miR-302d, hsa-miR-34a, hsa-miR-410, hsa-miR-33a*, hsa-miR-502-3p, hsa-miR-379, hsa-miR-498, hsa-miR-518d-5p, hsa-miR-556-3p, hsa-miR-502-5p, hsa-miR-31, hsa-miR-100, hsa-miR-296-3p, hsa-miR-615-5p, hsa-miR-21*, hsa-miR-657, hsa-miR-651, hsa-miR-765, hsa-miR-548m, hsa-miR-219-2-3p, hsa-miR-501-3p, hsa-miR-302a, hsa-miR-202*, hsa-miR-206, hsa-miR-520d-3p, hsa-miR-548i, hsa-miR-511, hsa-miR-30a, hsa-miR-1224-3p, hsa-miR-525-3p, hsa-miR-1225-5p, hsa-miR-223*, hsa-miR-615-3p, hsa-miR-570, hsa-miR-320a, hsa-miR-770-5p, hsa-miR-582-5p, hsa-miR-590-5p, hsa-miR-659, hsa-miR-1251, hsa-miR-664, hsa-miR-488*, hsa-miR-548g, hsa-miR-802, hsa-miR-542-5p, hsa-miR-190, hsa-miR-218-1*, hsa-miR-367*, hsa-miR-450a, hsa-miR-367, hsa-miR-124, hsa-miR- 767-5p, hsa-miR-200c, hsa-miR-572, hsa-miR-526a, hsa-miR-936, hsa-miR-548n, hsa-miR-21, hsa-miR-182*, hsa-miR-34c-5p, hsa-miR-429, hsa-miR-628-5p, hsa-miR-29a*, hsa-miR-370, hsa-let-7a*, hsa-miR-101*, hsa-miR-559, hsa-miR-217, hsa-miR-519b-5p, hsa-miR-30e*, hsa-miR-147, hsa-miR-487b, hsa-miR-888*, hsa-miR-205, hsa-miR-1257, hsa-miR-7, hsa-miR-296-5p, hsa-miR-1255a, hsa-miR-380*, hsa-miR-1275, hsa-miR-330-5p, hsa-miR-1243, hsa-miR-136*, hsa-miR-141*, hsa-miR-517c, hsa-miR-621, hsa-miR-1915*, hsa-miR-541, hsa-miR-543, hsa-miR-942, hsa-miR-26a-1*, hsa-miR-567, hsa-miR-184, hsa-miR-376a, hsa-miR-124*, hsa-miR-1254, hsa-miR-1207-5p, hsa-miR-580, hsa-let-7b*, hsa-miR-539, hsa-miR-520a-3p, hsa-miR-585, hsa-miR-675b, hsa-miR-943, hsa-miR-573, hsa-miR-93, hsa-miR-27a*, hsa-miR-613, hsa-miR-220c, hsa-miR-524-3p, hsa-miR-500, hsa-miR-1201, hsa-miR-20a*, hsa-miR-1914*, hsa-miR-425*, hsa-miR-515-3p, hsa-miR-377*, hsa-miR-504, hsa-miR-548c-3p, hsa-miR-1276, hsa-miR-138, hsa-miR-431, hsa-miR-494, hsa-miR-448, hsa-miR-633, hsa-miR-487a, hsa-miR-149, hsa-miR-300, hsa-miR-1826, hsa-miR-127-3p, hsa-miR-486-5p, hsa-miR-148a, hsa-miR-1294, hsa-miR-548l, hsa-miR-142-5p, hsa-miR-889, hsa-miR-365, hsa-miR-99b, hsa-miR-200b*, hsa-miR-200a, hsa-miR-518e, hsa-miR-612, hsa-miR-183*, hsa-miR-148b, hsa-miR-103, hsa-miR-548o, hsa-miR-1203, hsa-miR-135a*, hsa-miR-383, hsa-miR-1913, hsa-miR-373, hsa-miR-371-5p, hsa-miR-298, hsa-miR-758, hsa-miR-412, hsa-miR-518c, hsa-miR-589*, hsa-miR-643, hsa-miR-592, hsa-miR-892a, hsa-miR-944, hsa-miR-576-3p, hsa-miR-581, hsa-miR-625*, hsa-miR-1260, hsa-miR-1281, hsa-miR-337-5p, hsa-miR-133b, hsa-miR-92a-2*, hsa-miR-100*, hsa-miR-589, hsa-miR-218, hsa-miR-224, hsa-miR-16-2*, hsa-miR-301b, hsa-miR-190b, hsa-miR-375, hsa-miR-548p, hsa-miR-185*, hsa-miR-519d, hsa-miR-605, hsa-miR-877, hsa-miR-125a-3p, hsa-miR-744*, hsa-miR-520c-5p, hsa-miR-148a*, hsa-miR-212, hsa-miR-505, hsa-miR-496, hsa-miR-1323, hsa-miR-548e, hsa-miR-628-3p, hsa-miR-1914, hsa-miR-584, hsa-miR-135b*, hsa-miR-1295, hsa-miR-95, hsa-miR-133a, hsa-miR-485-3p, hsa-miR-541*, hsa-miR-374b, hsa-miR-329, hsa-miR-483-5p, hsa-miR-885-3p, hsa-let-7i*, hsa-miR-935, hsa-miR-130b, hsa-miR-1274a, hsa-miR-1226, hsa-miR-518e*, hsa-miR-1225-3p, hsa-miR-923, hsa-miR-196a*, hsa-miR-1270, hsa-miR-1271, hsa-miR-610, hsa-miR-574-3p, hsa-miR-1282, hsa-miR-10b*, hsa-miR-216a, hsa-miR-144*, hsa-miR-23a*, hsa-miR-499-5p, hsa-miR-183, hsa-miR-490-3p, hsa-miR-330-3p, hsa-let-7g*, hsa-miR-483-3p, hsa-miR-214, hsa-miR-34b*, hsa-miR-302d*, hsa-miR-382, hsa-miR-454*, hsa-miR-1202, hsa-miR-202, hsa-miR-544, hsa-miR-593, hsa-miR-760, hsa-miR-940, hsa-let-7e*, hsa-miR-1237, hsa-miR-18b*, hsa-miR-630, hsa-miR-519e*, hsa-miR-452, hsa-miR-26b*, hsa-miR-516b, hsa-miR-299-3p, hsa-miR-381, hsa-miR-340, hsa-miR-132, hsa-miR-142-3p, hsa-miR-125b-1*, hsa-miR-30c-2*, hsa-miR-627, hsa-miR-1908, hsa-miR-1267, hsa-miR-507, hsa-miR-188-5p, hsa-miR-486-3p, hsa-miR-596, hsa-miR-193a-5p, hsa-miR-671-3p, hsa-miR-24-1*, hsa-miR-19b-2*, hsa-miR-1308, hsa-miR-208a, hsa-miR-135a, hsa-miR-331-5p, hsa-miR-181c, hsa-miR-640, hsa-miR-1909, hsa-miR-629, hsa-miR-10a, hsa-miR-491-5p, hsa-miR-492, hsa-miR-516a-5p, hsa-miR-510, hsa-miR-1915, hsa-miR-518c*, hsa-miR-1273, hsa-miR-25*, hsa-miR-744, hsa-miR-550, hsa-miR-890, hsa-miR-1303, hsa-miR-650, hsa-miR-1227, hsa-miR-595, hsa-miR-1255b, hsa-miR-1252, hsa-miR-455-3p, hsa-miR-345, hsa-miR-96, hsa-miR-1321, hsa-miR-513c, hsa-miR-548c-5p, hsa-miR-663, hsa-miR-320c, hsa-miR-320b, hsa-miR-654-5p, hsa-miR-326, hsa-miR-1825, hsa-miR-328, hsa-miR-146b-5p, hsa-miR-886-3p, hsa-miR-1909*, hsa-miR-1469, hsa-miR-338-3p, hsa-miR-886-5p, hsa-miR-601, hsa-miR-1298, hsa-miR-1910, hsa-miR-1226*, hsa-miR-421, hsa-miR-1471, hsa-miR-150*, hsa-miR-1229, hsa-miR-17*, hsa-miR-320d, hsa-miR-10b, hsa-miR-766, hsa-miR-600, hsa-miR-641, hsa-miR-340*, hsa-miR-616*, hsa-miR-520a-5p, hsa-miR-1179, hsa-miR-1178, hsa-miR-30b*, hsa-miR-155*, hsa-miR-138-1*, hsa-miR-501-5p, hsa-miR-191, hsa-miR-107, hsa-miR-639, hsa-miR-518d-3p, hsa-miR-106b, hsa-miR-129-3p, hsa-miR-1306, hsa-miR-187*, hsa-miR-125b, hsa-miR-642, hsa-miR-30a*, hsa-miR-139-5p, hsa-miR-1307, hsa-miR-769-3p, hsa-miR-532-5p, hsa-miR-7-1*, hsa-miR-196a, hsa-miR-1296, hsa-miR-191*, hsa-miR-221, hsa-miR-92a-1*, hsa-miR-1285, hsa-miR-518f*, hsa-miR-1233, hsa-miR-1290, hsa-miR-598, hsa-miR-769-5p, hsa-miR-614, hsa-miR-578, hsa-miR-1301, hsa-miR-515-5p, hsa-miR-564, hsa-miR-634, hsa-miR-518b, hsa-miR-941, hsa-miR-376c, hsa-miR-195*, hsa-miR-518a-5p, hsa-miR-557, hsa-miR-1228*, hsa-miR-22*, hsa-miR-1234, hsa-miR-149*, hsa-miR-30c-1*, hsa-miR-200c*, hsa-miR-1181, hsa-miR-323-5p, hsa-miR-1231, hsa-miR-203, hsa-miR-302c*, hsa-miR-99a, hsa-miR-146a, hsa-miR-656, hsa-miR-526b*, hsa-miR-148b*, hsa-miR-181a, hsa-miR-622, hsa-miR-125a-5p, hsa-miR-152, hsa-miR-197, hsa-miR-27b, hsa-miR-1236, hsa-miR-495, hsa-miR-143, hsa-miR-362-3p, hsa-miR-675, hsa-miR-1274b, hsa-miR-139-3p, hsa-miR-130b*, hsa-miR-1228, hsa-miR-1180, hsa-miR-575, hsa-miR-134, hsa-miR-875-3p, hsa-miR-92b*, hsa-miR-660, hsa-miR-526b, hsa-miR-422a, hsa-miR-1250, hsa-miR-938, hsa-miR-608, hsa-miR-1279, hsa-miR-1249, hsa-miR-661, hsa-miR-1208, hsa-miR-130a, hsa-miR-450b-5p, hsa-miR-432, hsa-miR-409-3p, hsa-miR-527, hsa-miR-877*, hsa-miR-1238, hsa-miR-517*, hsa-miR-193b*, hsa-miR-524-5p, hsa-miR-1258, hsa-miR-154, hsa-miR-637, hsa-miR-588, hsa-miR-155, hsa-miR-664*, hsa-miR-1470, hsa-miR-105*, hsa-miR-324-5p, hsa-miR-129*, hsa-miR-625, hsa-miR-519a*, hsa-miR-181a-2*, hsa-miR-199b-5p, hsa-miR-27a, hsa-miR-518a-3p, hsa-miR-1265, hsa-miR-92a, hsa-miR-29b-1*, hsa-miR-150, hsa-miR-335, hsa-miR-638.

The miRNAs that provide the highest mutual information in samples from lung cancer patients compared to healthy controls are hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a, hsa-miR-1914*, hsa-miR-29c, hsa-miR-505*, hsa-let-7d, hsa-miR-378, hsa-miR-29b, hsa-miR-604, hsa-miR-29b, hsa-let-7b, hsa-miR-299-3p, hsa-miR-423-3p, hsa-miR-18a*, hsa-miR-1909, hsa-let-7c, hsa-miR-15a, hsa-miR-425, hsa-miR-93*, hsa-miR-665, hsa-miR-30e, hsa-miR-339-3p, hsa-miR-1307, hsa-miR-625*, hsa-miR-193a-5p, hsa-miR-130b, hsa-miR-17*, hsa-miR-574-5p, hsa-miR-324-3p (group (a)).

Figure 12:
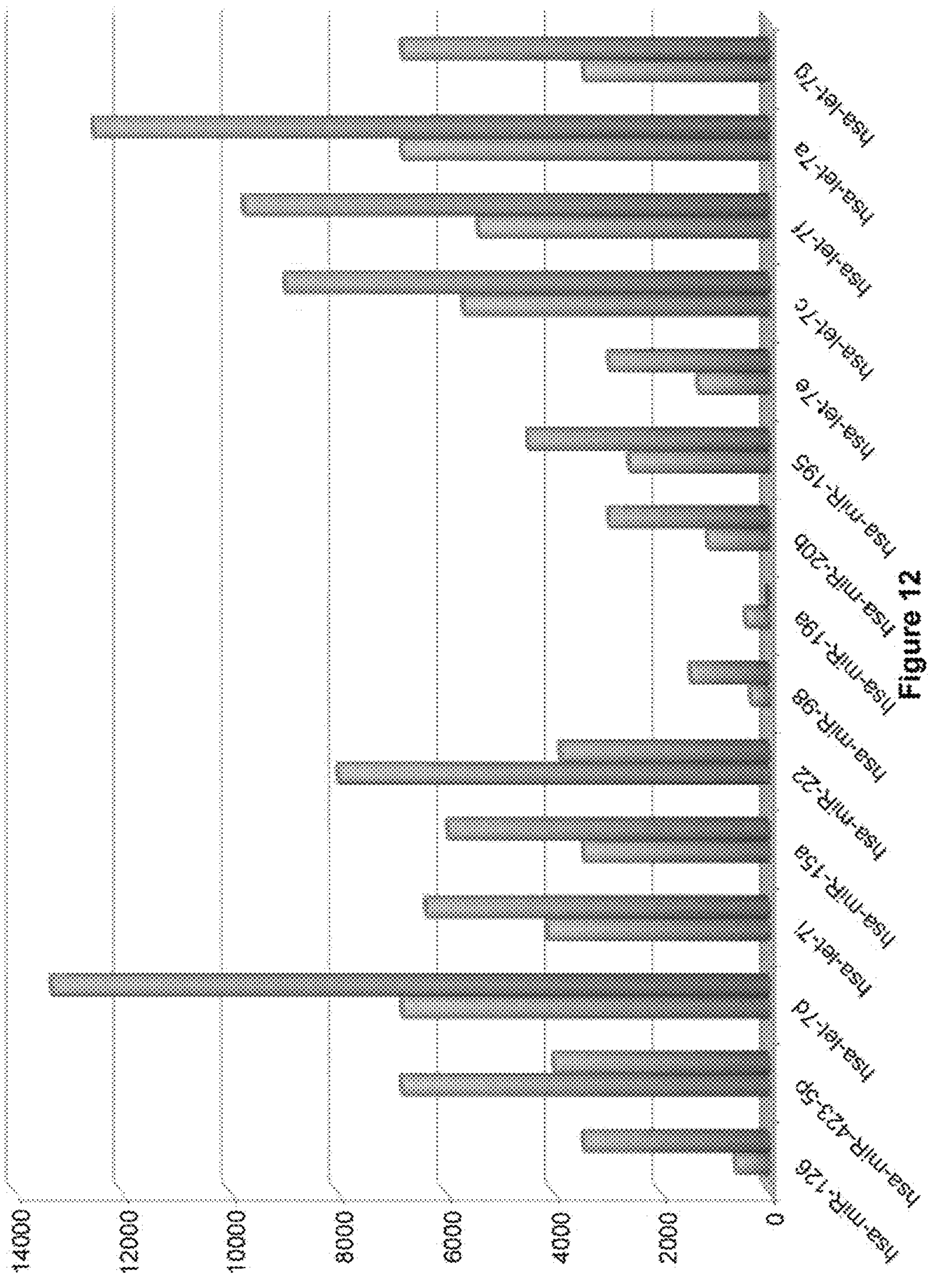

Further, the measured miRNA profiles of FIGS. 10A and 10B were classified according to their significance in t-tests as described in more detail in the experimental section. The miRNAs that performed best according to the t-test results are hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p, hsa-miR-93* (group (b)). A comparison of a subset of 15 of these miRNAs is depicted in FIG. 12.

The miRNAs given above that have been grouped in the order of their performance in the t-tests or in the order of their MI-values provide the highest diagnostic power. Thus, preferably the predetermined set of miRNAs for the diagnosis of lung cancer comprises one or more nucleic acids selected from the above groups (a) and (b) of miRNAs. The predetermined set of miRNAs should preferably comprise at least 7, preferably at least 10, 15, 20 or 24 of the indicated nucleic acids. Most preferably, all of the above indicated miRNAs are included in the predetermined set of miRNAs. It is particularly preferred to include the 24, 20, 15, 10 or at least 7 of the first mentioned miRNAs in the order of their performance in the t-tests or of their MI-values. A comparison of the results obtained by determining 4, 8, 10, 16, 20, 24, 28 or 40 miRNAs provided in FIG. 13A-G shows that the accuracy of the diagnosis is improved, the more miRNAs are measured.

In a particularly preferred embodiment of the method of the invention, the predetermined set of miRNAs includes the miRNAs hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a* and hsa-miR-26b.

In a further particularly preferred embodiment of the method of the invention, the miRNAs are selected from the miRNAs shown in FIG. 11A. The predetermined set of miRNAs should preferably comprise at least 7, preferably at least 10, 15, 20 or 24 of the indicated nucleic acids. It is particularly preferred to include the 24, 20, 15, 10 or at least 7 of the first mentioned miRNAs according to their order in the table in FIG. 11A.

In another embodiment, the predetermined set of miRNAs for the diagnosis of lung cancer comprises at least one preferred signature L1-251 as shown in FIG. 11B. It should be noted that preferred diagnostic sets may also comprise one or more miRNAs of the miRNAs disclosed in FIG. 11B and any combination of the miRNAs together with one or more further diagnostically relevant miRNA from FIG. 10A, 10B or 11A. Preferred predetermined sets of miRNA molecules based on FIG. 11B comprise at least 3, 4, 5, 6, 7, 8, 9 or 10 miRNAs and up to 10, 15, or 20 or more miRNAs.

For the diagnosis of different types of diseases, such as for a different type of cancer, a different predetermined set of miRNAs should be determined in step (a) of the method of the invention. The relevant miRNA signatures can be obtained according to the workflow depicted in FIG. 9 and as explained above.

Another embodiment of the present invention is a kit for diagnosing a disease, comprising means for determining an expression profile of a predetermined set of miRNAs in a biological sample, in particular in a blood, plasma, and/or serum sample including whole blood, plasma, serum or fractions thereof, or in a sample comprising peripheral blood mononuclear cells, erythrocytes, leukocytes and/or thrombocytes. Preferably, one or more reference expression profiles are also provided which show the expression profile of the same set of miRNAs in the same type of biological sample, in particular in a blood and/or serum sample, obtained from one or more healthy subjects. A comparison to said reference expression profile(s) allows for the diagnosis of the disease.

The kit is preferably a test kit for detecting a predetermined set of miRNAs in sample by nucleic acid hybridisation and optionally amplification such as PCR or RT-PCR. The kit preferably comprises probes and/or primers for detecting a predetermined set of miRNAs. Further, the kit may comprise enzymes and reagents including reagents for cDNA synthesis from miRNAs prior to realtime PCR.

A kit for diagnosing lung cancer preferably comprises means for determining the expression profile of one or more miRNAs selected from the group (a) consisting of hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a, hsa-miR-1914*, hsa-miR-29c, hsa-miR-505*, hsa-let-7d, hsa-miR-378, hsa-miR-29b, hsa-miR-604, hsa-miR-29b, hsa-let-7b, hsa-miR-299-3p, hsa-miR-423-3p, hsa-miR-18a*, hsa-miR-1909, hsa-let-7c, hsa-miR-15a, hsa-miR-425, hsa-miR-93*, hsa-miR-665, hsa-miR-30e, hsa-miR-339-3p, hsa-miR-1307, hsa-miR-625*, hsa-miR-193a-5p, hsa-miR-130b, hsa-miR-17*, hsa-miR-574-5p and hsa-miR-324-3p.

According to another embodiment of the invention, the kit for diagnosing lung cancer preferably comprises means for determining the expression profile of one or more miRNAs selected from the group (b) consisting of hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p and hsa-miR-93*.

In a preferred embodiment, the kit comprises means for determining at least 7, preferably at least 10, 15, 20 or 24 of the indicated groups of miRNAs. It is particularly preferred to include means for determining the 24, 20, 15, 10 or at least 7 of the first mentioned miRNAs in the order of their MI-values or their performance in the t-tests as shown in the tables in FIGS. 10 and 11. Most preferably, means for determining all of the above indicated miRNAs are included in the kit for diagnosing lung cancer. The kit is particularly suitable for diagnosing lung cancer in a blood, plasma and/or serum sample or in a sample comprising peripheral erythrocytes, leukocytes and/or thrombocytes.

In a particularly preferred embodiment, the kit comprises means for determining the miRNAs hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a* and hsa-miR-26b.

The means for determining a predetermined set of miRNAs may for example comprise a microarray comprising miRNA-specific oligonucleotide probes. In a preferred embodiment, the microarray comprises miRNA-specific oligonucleotide probes for one or more miRNAs selected from the group consisting of (a) hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a, hsa-miR-1914*, hsa-miR-29c, hsa-miR-505*, hsa-let-7d, hsa-miR-378, hsa-miR-29b, hsa-miR-604, hsa-miR-29b, hsa-let-7b, hsa-miR-299-3p, hsa-miR-423-3p, hsa-miR-18a*, hsa-miR-1909, hsa-let-7c, hsa-miR-15a, hsa-miR-425, hsa-miR-93*, hsa-miR-665, hsa-miR-30e, hsa-miR-339-3p, hsa-miR-1307, hsa-miR-625*, hsa-miR-193a-5p, hsa-miR-130b, hsa-miR-17*, hsa-miR-574-5p and hsa-miR-324-3p or (b) hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a*, hsa-miR-26b, hsamiR-604, hsa-miR-423-3p and hsa-miR-93*. In a preferred embodiment, the microarray comprises oligonucleotide probes for determining at least 7, preferably at least 10, 15, 20 or 24 of the indicated groups (a) and (b) of miRNAs. It is particularly preferred to include oligonucleotide probes for determining the 24, 20, 15, 10 or at least 7 of the first mentioned miRNAs in the order of their MI-values or their performance in the t-tests as shown in the tables in FIGS. 10 and 11. Most preferably, oligonucleotide probes for determining all of the above indicated miRNAs of groups (a) or (b) are included in the microarray for diagnosing lung cancer.

In a particularly preferred embodiment, the microarray comprises oligonucleotide probes for determining the miRNAs hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a* and hsa-miR-26b.

The microarray can comprise oligonucleotide probes obtained from known or predicted miRNA sequences. The array may contain different oligonucleotide probes for each miRNA, for example one containing the active mature sequence and another being specific for the precursor of the miRNA. The array may also contain controls such as one or more sequences differing from the human orthologs by only a few bases, which can serve as controls for hybridization stringency conditions. It is also possible to include viral miRNAs or putative miRNAs as predicted from bioinformatic tools. Further, it is possible to include appropriate controls for non-specific hybridization on the microarray.

The invention also relates to sets of oligo- or polynucleotides for diagnosing lung cancer comprising the sequences of at least 5, preferably at least 7, 10, 15, 20 or all of the indicated miRNAs, and/or the complement of such sequences. It is particularly preferred to include oligo- or polynucleotides for detecting of the most significant miRNAs, which are represented by their order in the table depicted in FIG. 10A, 10B or 11A. In a further embodiment, the set includes oligo- or polynucleotides for detecting the miRNA sets based on FIG. 11B as described above. The oligo- or polynucleotides preferably have a length of 10, 15 or 20 and up to 30, 40, 50, 100 or more nucleotides. The term “oligo- or polynucleotides” includes single- or double-stranded molecules, RNA molecules, DNA molecules or nucleic acid analogs such as PNA or LNA.

Another embodiment of the present invention relates to a method for the assessment of a clinical condition related to lung cancer of a patient.

Recent developments have shown that there is a tendency towards smaller sets of biomarkers for the detection of diseases. However, for single biomarkers and small biomarker sets, there is only a basic understanding whether these biomarkers are specific for only the single diseases or whether they occur in any other disease.

Therefore, the present inventors developed a novel class of diagnostic tests improving the current test scenarios. The inventors found out that a variety of diseases are correlated with a specific expression profile of miRNAs. In case a patient is affected by a particular disease, several miRNAs are present in larger amounts compared to a healthy normal control, whereas the amount of other miRNAs is decreased. Interestingly, the amount of some miRNAs is deregulated, i.e. increased or decreased, in more than one disease. The miRNA profile for a particular disease therefore shows conformity with the miRNA profile of other diseases in regard of individual miRNAs while other miRNAs show significant differences. If the expression profile of a large variety of miRNAs in a biological sample of a patient is measured, the comparison of the expression profile with a variety of reference expression profiles which are each characteristic for different diseases makes it possible to obtain information about the clinical condition of a certain patient and to determine, which disease(s) is/are present in said patient.

A further subject matter of the invention is a method for the assessment of a clinical condition related to lung cancer of a patient comprising the steps (a) providing a sample from the patient, (b) determining a predetermined set of miRNAs in said sample to obtain a miRNA expression profile, (c) comparing said miRNA expression profile with a plurality of miRNA reference expression profiles characteristic for different diseases, and (d) assessing the clinical condition of the patient based on the comparison of step (c).

The inventors found out that the above method for the assessment of a clinical condition makes it possible to carry out an integrative diagnosis of a wide variety of diseases, particularly including lung cancer. Comparing a miRNA profile obtained from a biological sample of a patient whose clinical condition is not known with a plurality of reference profiles characteristic for different diseases enables the diagnosis of a wide variety of diseases with high specificity and sensitivity.

A “biological sample” in terms of the invention means a sample of biological tissue or fluid as described hereinabove. Examples of biological samples are sections of tissues, blood, blood fractions, plasma, serum, urine or samples from other peripheral sources. Preferred biological samples are blood, plasma and/or serum samples including blood fractions such as PBMC.

The set of miRNAs determined in step (d) preferably includes a large number of different miRNAs. It is particularly preferred to use at least 10, 20, 30, 50, preferably at least 100, 200, 500 or 1,000 miRNAs. Most preferably, all known miRNAs are included in the set of miRNAs determined in step (b) Such a complex set of miRNA-biomarkers enables a diagnosis with higher specificity and sensitivity compared to single biomarkers or sets of only a few dozens of such markers.

The determination of the set of miRNAs can be done as described herein above. Preferably, the determination is done on an experimental platform which shows a high degree of automation to minimize experimental variations, measure results time- and cost-efficiently, measures results highly reproduceably and be able for measuring more than one sample at once in order to ensure a high throughput.

Step (c) preferably includes a comparison of the miRNA profile measured for a patient with a large number of different reference profiles to provide information about the presence of as many different diseases as possible. The reference expression profiles may be laid down in a database, e.g. an Internet database, a centralized or a decentralized database. The reference profiles do not necessarily have to include information about all miRNAs included in step (b), which are determined in the sample of the patient. It is, according to the invention, sufficient if the reference profile provides information on those miRNAs which are altered to a large extent compared to the condition of a healthy individual in case of the presence of a disease. Alternatively, the said relevant reference may be a mathematical function or algorithm.

Preferably, an miRNA reference profile or the relevant reference according to the invention provides information on miRNA expression characteristic for a particular disease in the same type of biological sample as used in step (b) for determining a predetermined set of miRNAs in a sample from a patient. This means that, if a patient with an unknown disease is to be classified with the analysis of a blood sample, the comparison is preferably made with miRNA reference expression profiles, which do also relate to the miRNA expression pattern in a blood sample.

The reference profiles or the relevant reference characteristic for particular diseases provide information on one or more miRNAs, which are, in case of the disease, highly deregulated, for example strongly increased or decreased, as compared to a healthy condition. It is not necessary for the reference profiles to provide information about all miRNAs included in the set of biomarkers determined in step (b). However, the more miRNAs are included in the reference profile or relevant reference, the more precise the diagnosis will be. If, for example, a reference profile for lung cancer is included, it is preferred to include the characteristic miRNAs for lung cancer.

Another embodiment of this aspect of the invention is a kit for the assessment of a clinical condition related to lung cancer of a patient comprising (a) means for determining a predetermined set of miRNAs in a biological sample from a patient, and (b) a plurality of miRNA reference expression profiles characteristic for different diseases or a mathematical function that allows for the diagnosis on the basis of the data derived from the miRNA expression profiles of a patient.

The set of miRNAs to be determined in a biological sample from a patient preferably includes a large number of different miRNAs. It is particularly preferred to include all known miRNAs in the set of miRNAs to be determined. In each case, said predetermined set of miRNAs should include those miRNAs for which information is provided in the reference profiles characteristic for particular diseases. It is understood that only in case the set of miRNAs determined in a biological sample from a patient comprises those miRNAs included in the reference profile/reference for a disease, a diagnosis regarding this particular disease can be provided or otherwise the diagnosis may be less informative.

The assessment of a clinical condition of a patient according to the invention is suitable for diagnosing any diseases which are correlated with a characteristic miRNA profile. Accordingly, the kit for the assessment of a clinical condition preferably includes reference profiles/references for a plurality of diseases that are correlated with a characteristic miRNA profile. It is understood that all miRNAs that are significantly deregulated in the disease states for which reference profiles are provided should be included in the set of miRNAs to be determined in a biological sample from a patient. If the kit for the assessment of a clinical condition of a patient should provide information regarding, e.g. lung cancer or multiple sclerosis, a reference profile should be available providing information about the significantly deregulated miRNAs compared to a normal or any other relevant control individual or any other relevant control individual(s). A kit for the assessment of a clinical condition shall provide information on the presence of lung cancer, a reference profile characteristic for lung cancer should be included. Said reference profile preferably includes information on those miRNAs that are most significantly deregulated in the case of lung cancer. The relevant miRNAs are as disclosed hereinabove.

The invention will now be illustrated by the following figures and the non-limiting experimental examples.

FIGURES

FIG. 1:

Scheme of a miRNA hybridization assay for use in the invention.

miRNA capture probes consist of 1 miRNA probe sequence stretch that is linked to support via 3'-end or alternatively by 5'-end (not depicted here)

the miRNA probe sequence stretches are complementary to miRNA target sequences each miRNA capture probe can bind 1 miRNA target sequences the miRNA target sequences are labeled prior to hybridisation (e.g. by biotin labeling)

FIG. 2:

Scheme of an miRNA tandem hybridization assay for use in the invention miRNA capture probes consist of 2 DNA-based miRNA probe sequence stretches that are linked to each other by a spacer element the miRNA probe sequence stretches are complementary to miRNA target sequences each miRNA capture probe can bind 2 miRNA target sequences the spacer sequence consists of 0-8 nucleotides the miRNA target sequences are labeled prior to hybridisation (e.g. by biotin labeling)

FIG. 3:

miRNA RAKE-Assay for use in the invention (PT Nelson et al., Nature Methods, 2004, 1(2), 1)

the miRNA capture probes consist of one miRNA probe sequence stretch (white) and one elongation element "(gray)"

probes are oriented 5'→3', presenting a free terminal 3'-OH the miRNA probe sequence stretch (white) is complementary to miRNA target sequences the elongation sequences (gray) can be freely chosen and is typically between 1-12 nucleotides long, preferably a homomeric sequence each miRNA capture probe can bind 1 miRNA target sequences the miRNA target sequences are NOT labeled prior to hybridisation Labeling occurs after hybridisation during elongation by polymerase extention reaction Biochip is not reusable due to exonuclease treatment

FIG. 4:

miRNA MPEA-Assay for use in the invention (Vorwerk S. et al., Microfluidic-based enzymatic on-chip labeling of miRNAs, N. Biotechnol. 2008; 25(2-3):142-9. Epub 2008 Aug. 20)

the miRNA capture probes consist of one miRNA probe sequence stretch (white) and one elongation element (gray)

probes are oriented 3'→5', presenting a free terminal 5'-OH the miRNA probe sequence stretch (white) is complementary to miRNA target sequences the elongation sequences (gray) can be freely chosen and is typically between 1-12 nucleotides long, preferably a homomeric sequence each miRNA capture probe can bind 1 miRNA target sequences the miRNA target sequences are NOT labeled prior to hybridisation Labeling occurs after hybridisation during elongation by polymerase extention reaction Biochip is reusable after removal of target/elongated target

FIG. 5:

miRNA capture probe design

Depicted is the design of a capture probe (SEQ ID NO:866) for the exemplary miRNA human mature miRNA let-7a (SEQ ID NO:17) for use in the various types of hybridization assays shown in FIGS. 1-4. SP=spacer element; EL=elongation element

FIG. 6:

Spacer Element.

Figure 2:
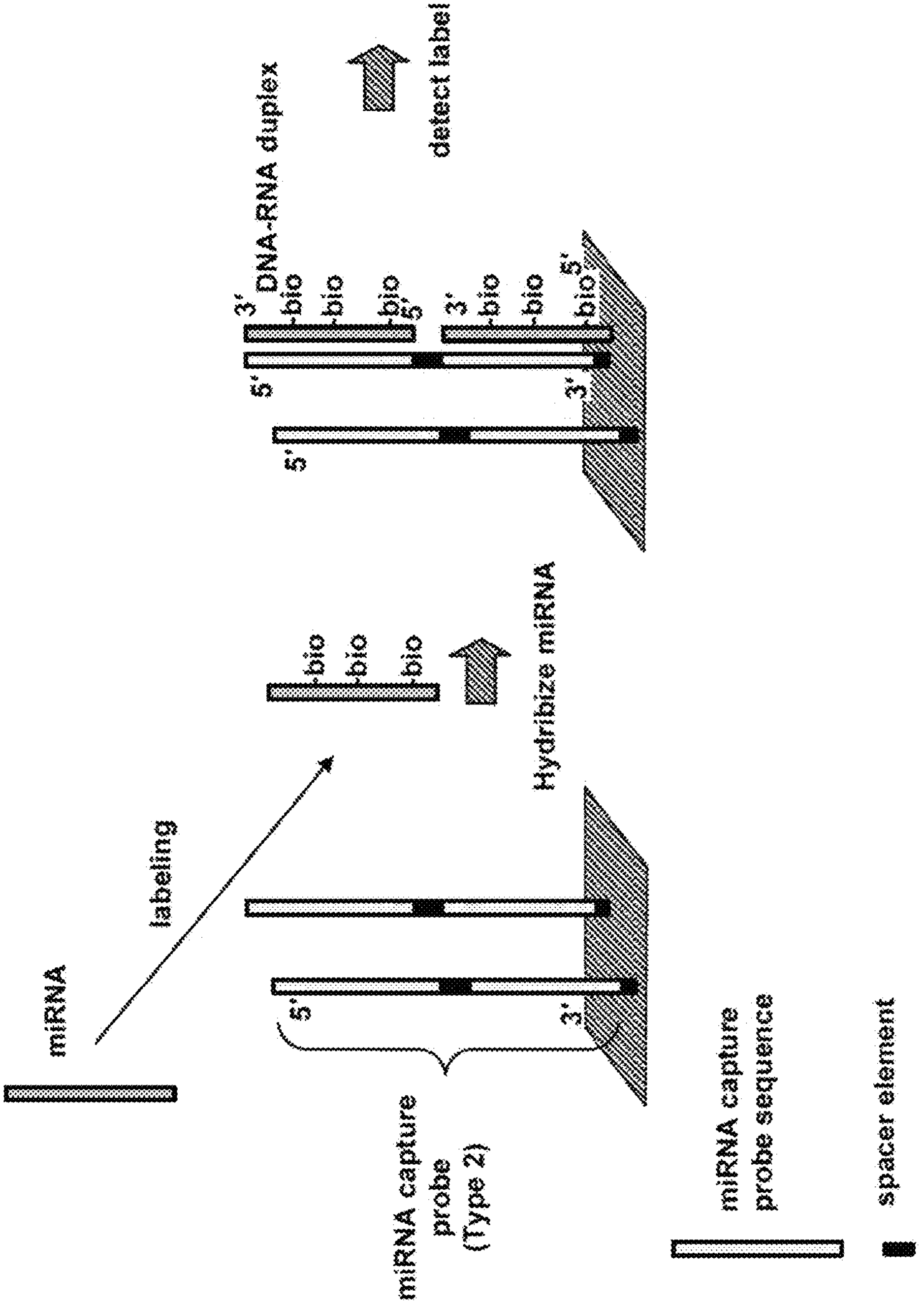

Capture probes (SEQ ID NO:866) for use in e.g. a tandem hybridization assay as shown in FIG. 2 may comprise a spacer element SP. The spacer element represents a nucleotide sequence with n=0-12 nucleotides chosen on the basis of showing low complementarity to potential target sequences, therefore resulting in no to low degree of cross hybridization to target mixture. Preferably, n=0, i.e. there is no spacer between the 2 miRNA probe sequence stretches.

FIG. 7:

Elongation element

Figure 3:
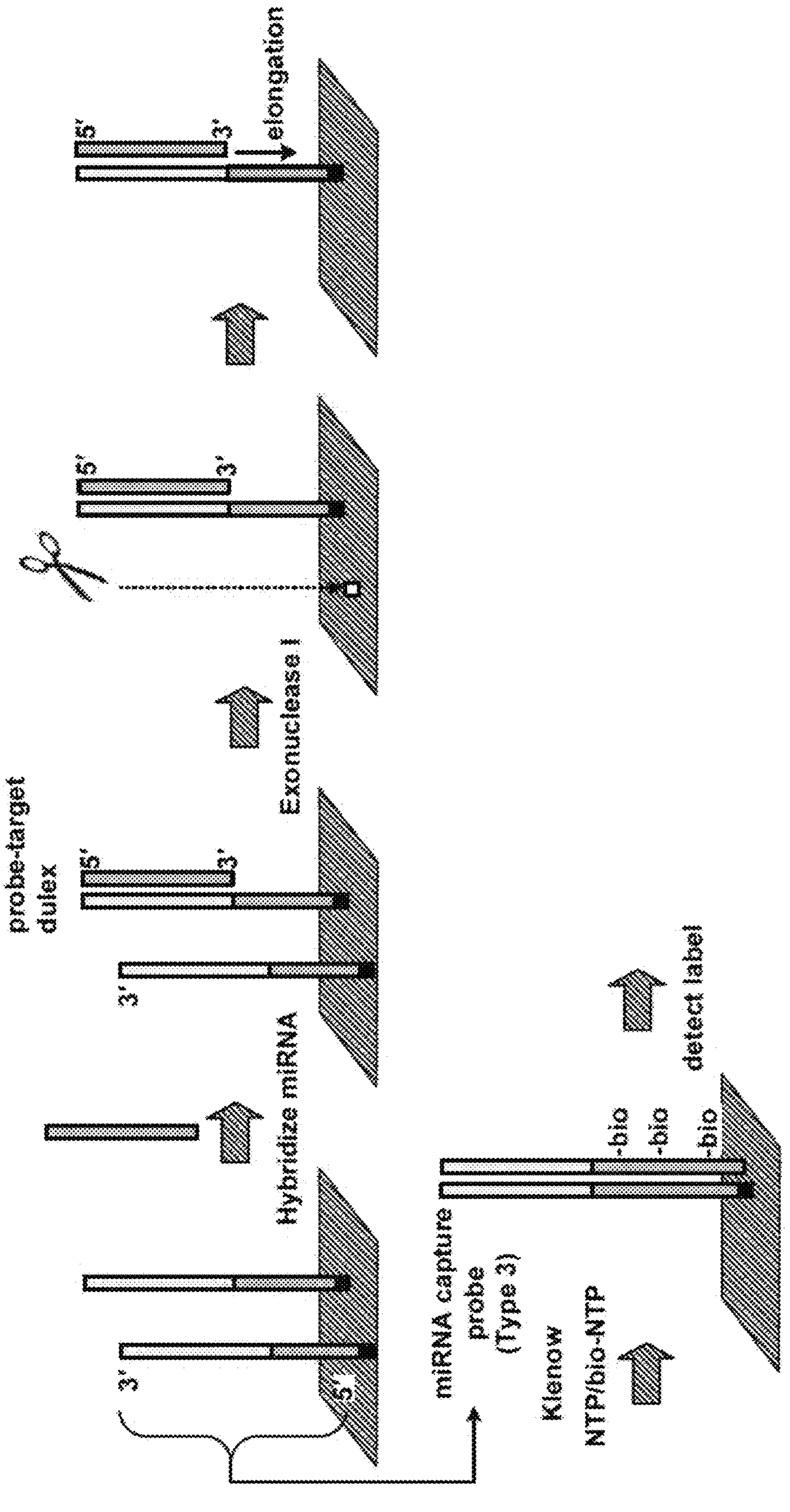
Figure 4:
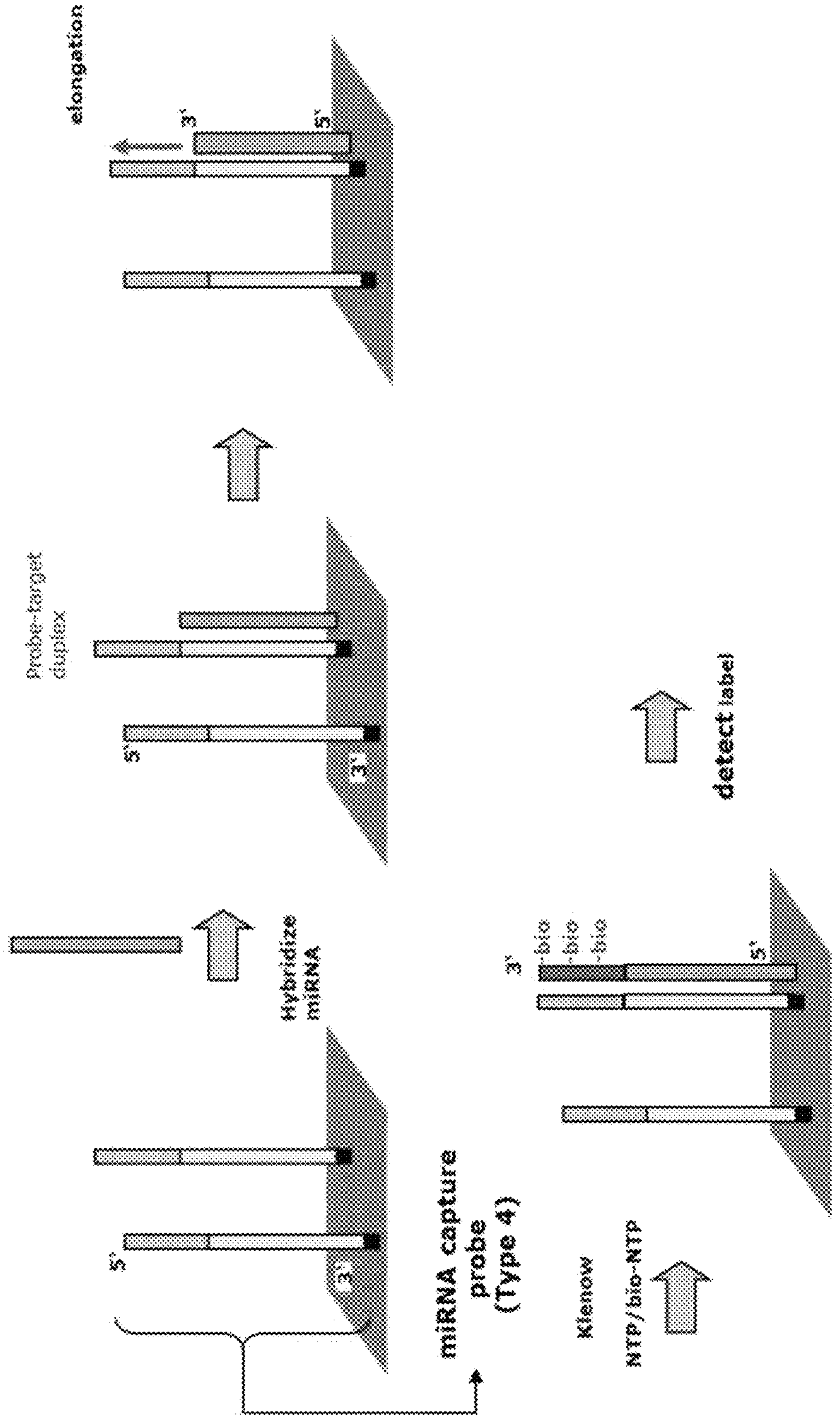

A capture probe (SEQ ID NO:866), e.g. for use in a RAKE or MPEA assay as shown in FIGS. 3 and 4 may include an elongation element. The elongation element comprises a nucleotide sequence with N=0-30 nucleotides chosen on the basis of showing low complementarity to potential target sequences, therefore resulting in no to low degree of cross hybridization to target mixture. Preferred is a homomeric sequence stretch -N.sub.n- with n=1-30, N=A or C, or T, or G. Especially preferred is a homomeric sequence stretch -Nn- with n=1-12, N=A or C, or T, or G.

Figure 8:
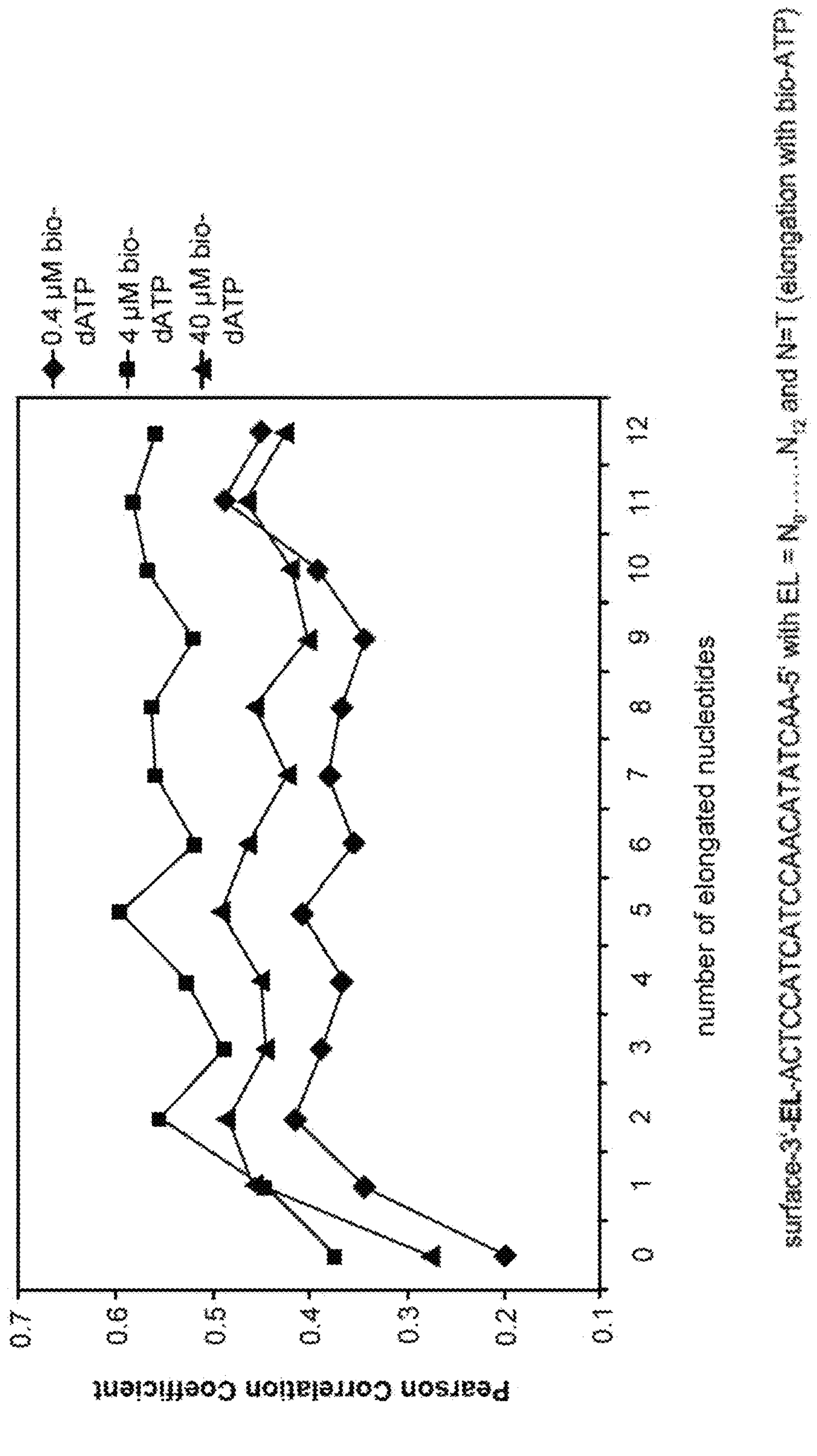

FIG. 8: Pearson Correlation Coefficient depending on the number of elongated nucleotides in capture probes (SEQ ID NO:866) in an MPEA assay.

FIG. 9:

Diagram describing the general approach for determining miRNA signatures for use as biomarkers in disease diagnosis.

FIG. 10A:

Overview of all miRNAs that are found to be differentially regulated in blood samples of lung cancer patients, grouped according to their mutual information (MI).

FIG. 10B:

Overview of all miRNAs that are found to be differentially regulated in blood samples of lung cancer patients, grouped according to their results in t-tests.

FIG. 11A:

Overview of preferred miRNAs that are found to be significantly ($p<0.1$) differentially regulated in blood samples of lung cancer patients.

FIG. 11B:

Overview of preferred signatures of miRNAs for the diagnosis of lung cancer.

FIG. 12:

Expression of some relevant miRNAs. The bar-chart shows for 15 deregulated miRNAs the median value of cancer samples and normal samples. Here, left bars correspond to cancer samples while right bars controls.

FIG. 13:

Bar diagrams showing a classification of the accuracy, specificity and sensitivity of the diagnosis of lung cancer based on blood samples using different sizes of subsets of miRNAs. Blue bars represent accuracy, specificity and sensitivity of the diagnosis using the indicated biomarkers and red bars represent the results of the same experiments of random classifications. The relevant value is the population median (horizontal black lines inside the bars).

Figure 13A:
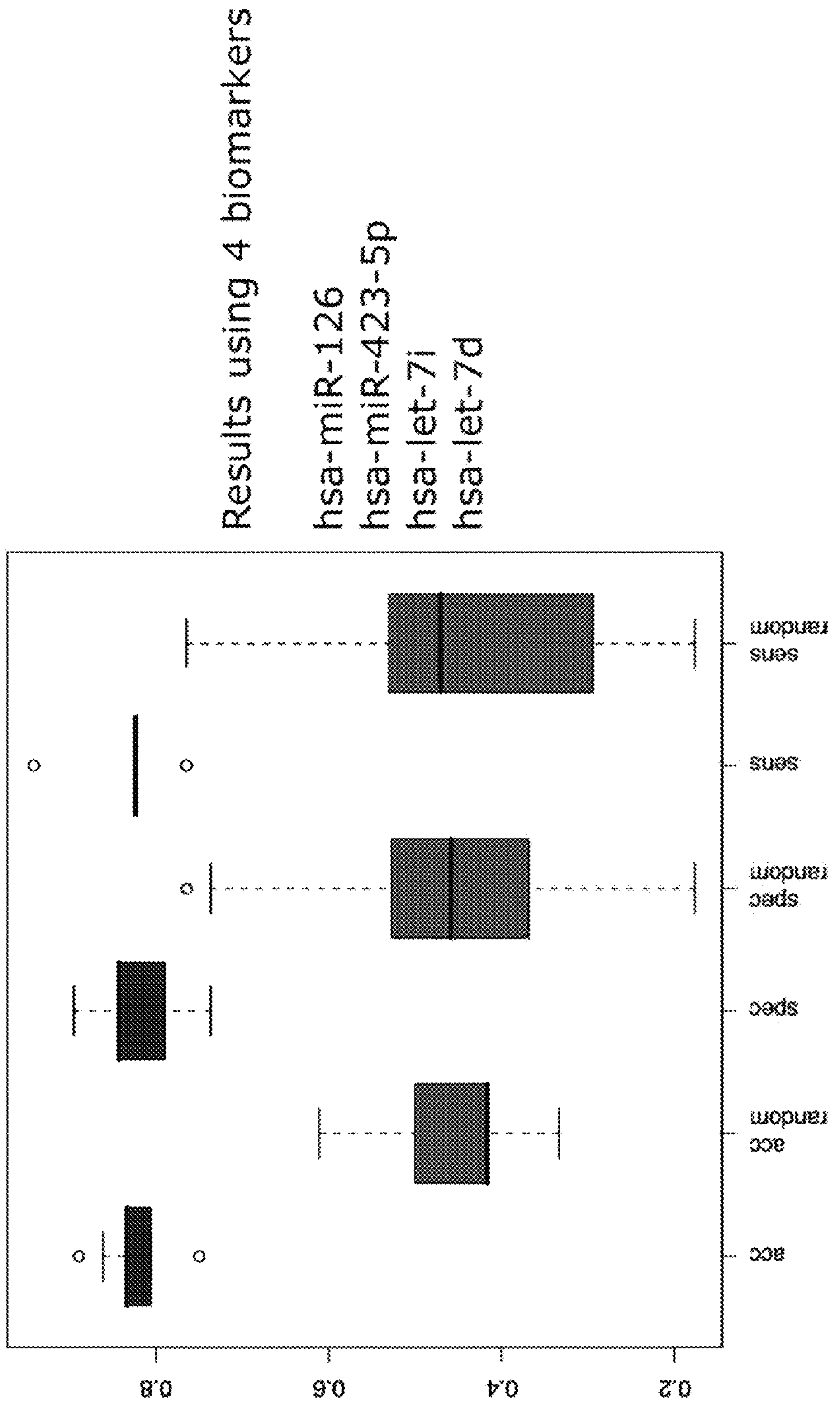
Figure 13B:
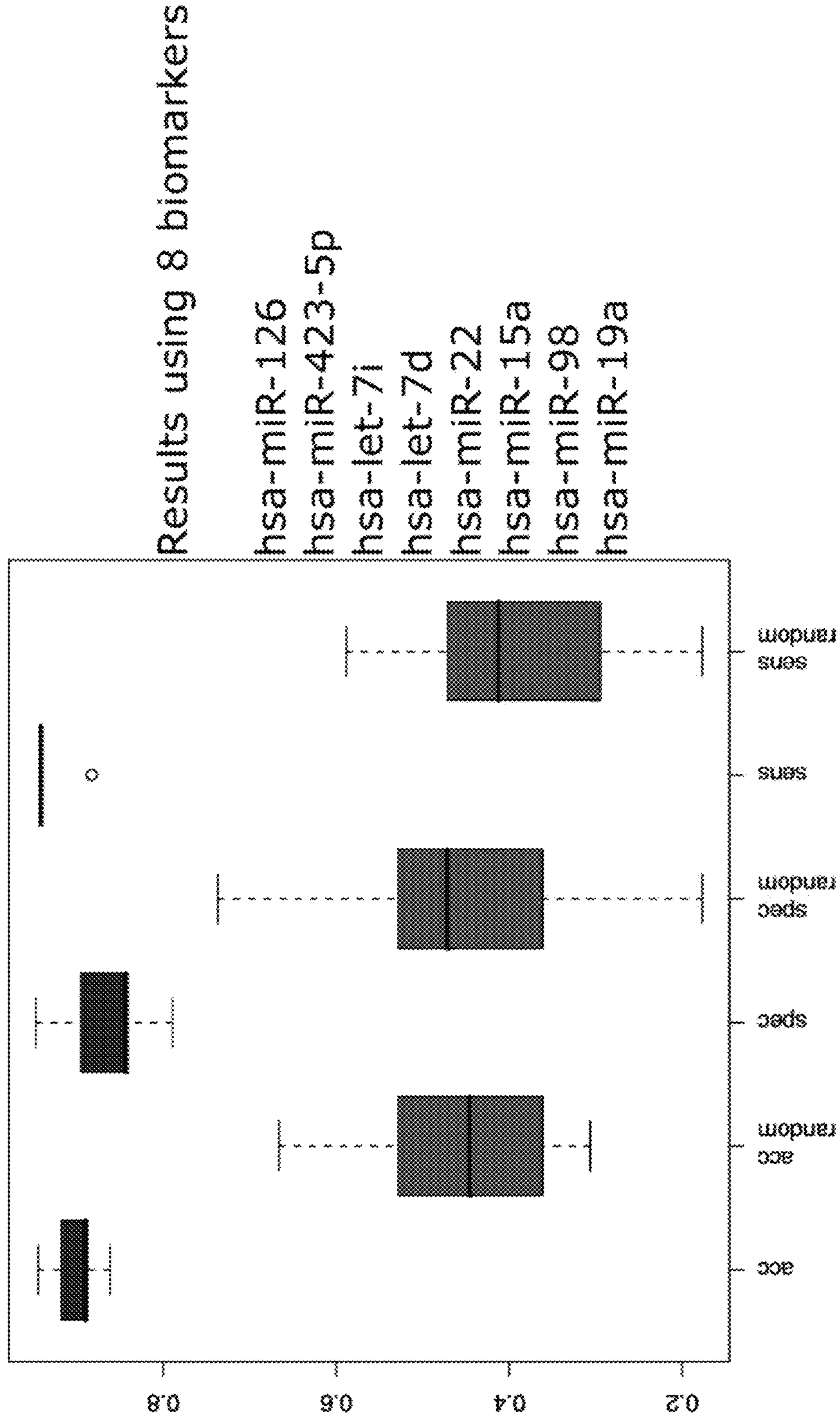
Figure 13C:
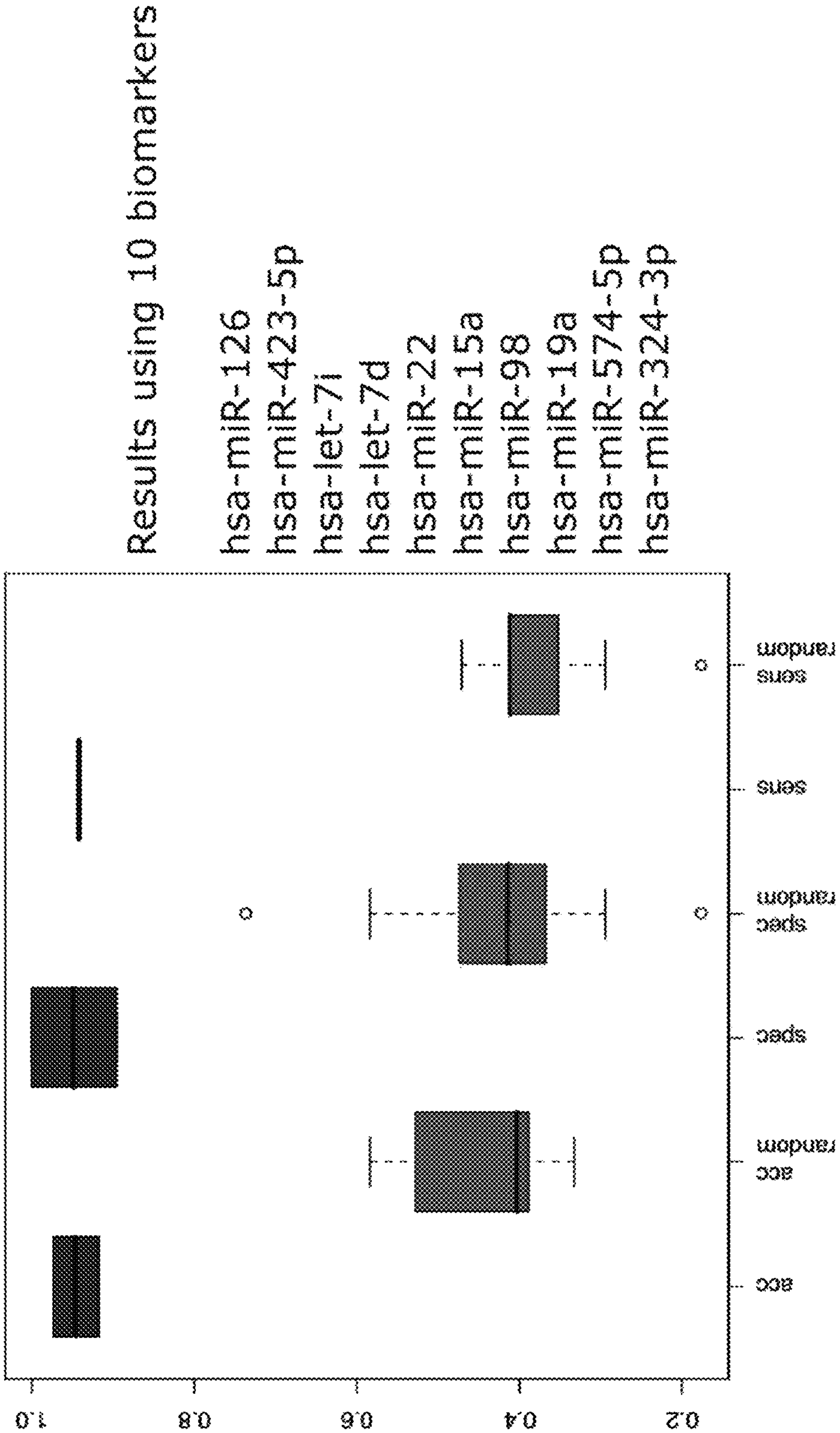
Figure 13D:
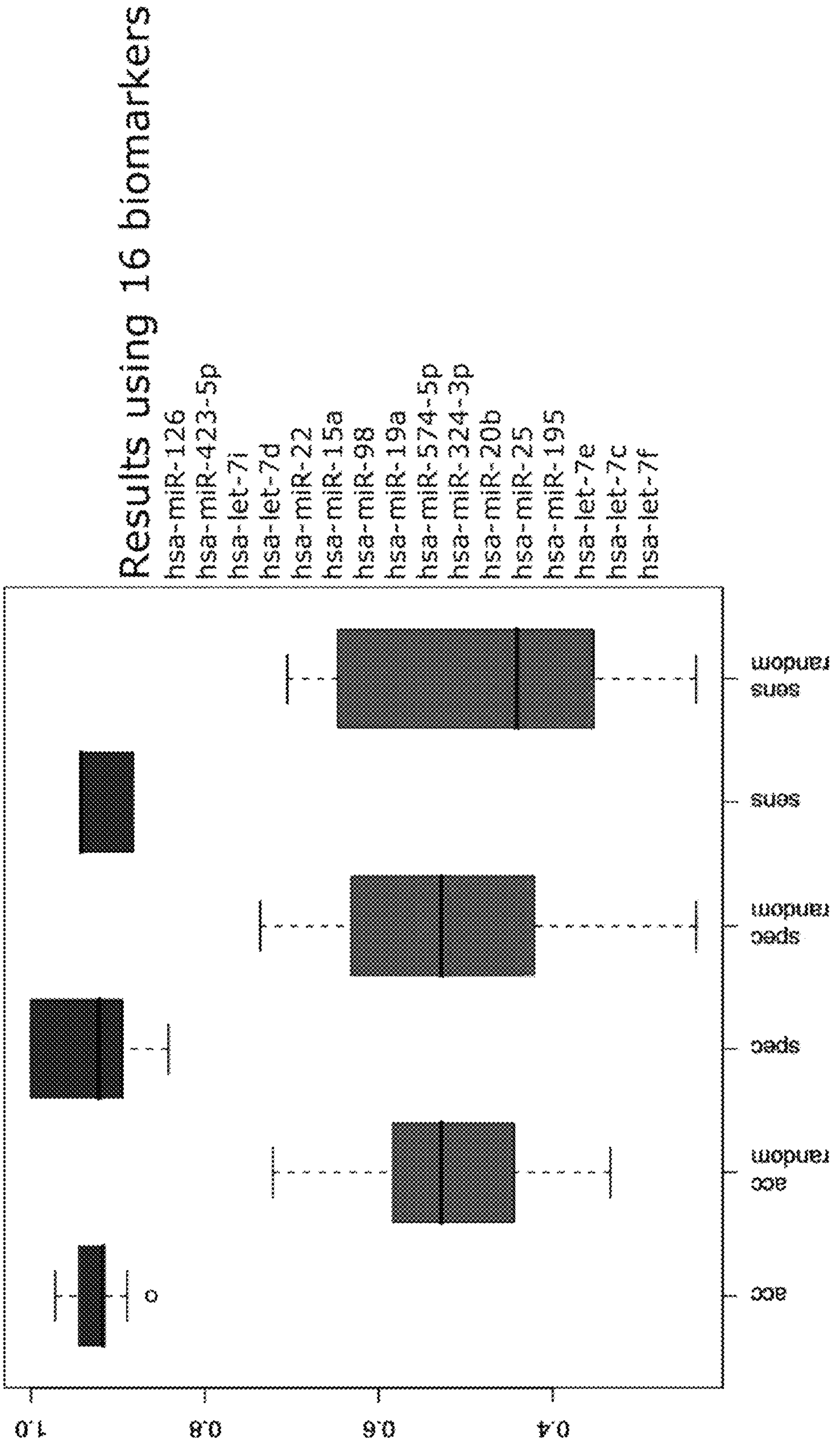
Figure 13E:
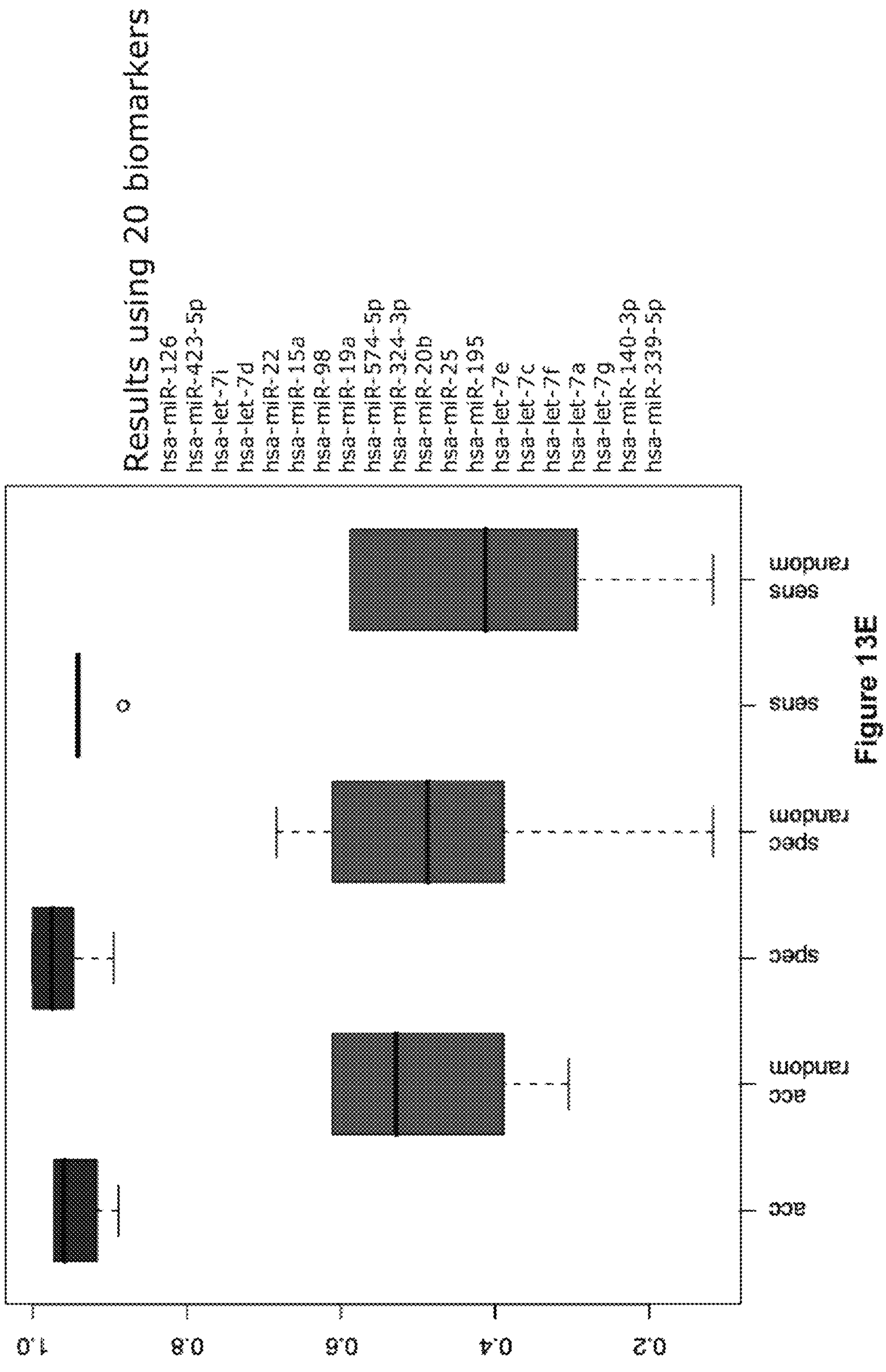
Figure 13F:
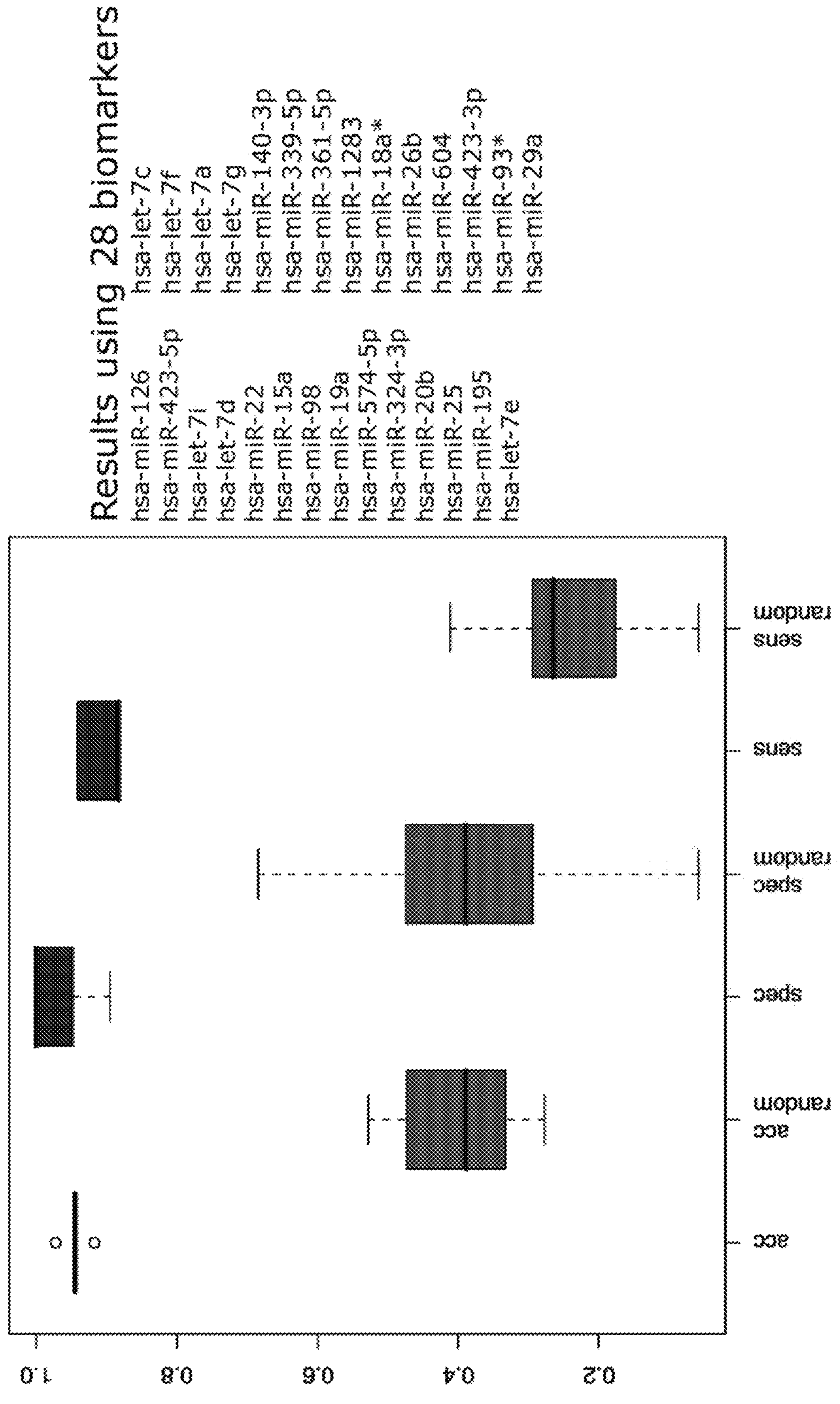
Figure 13G:
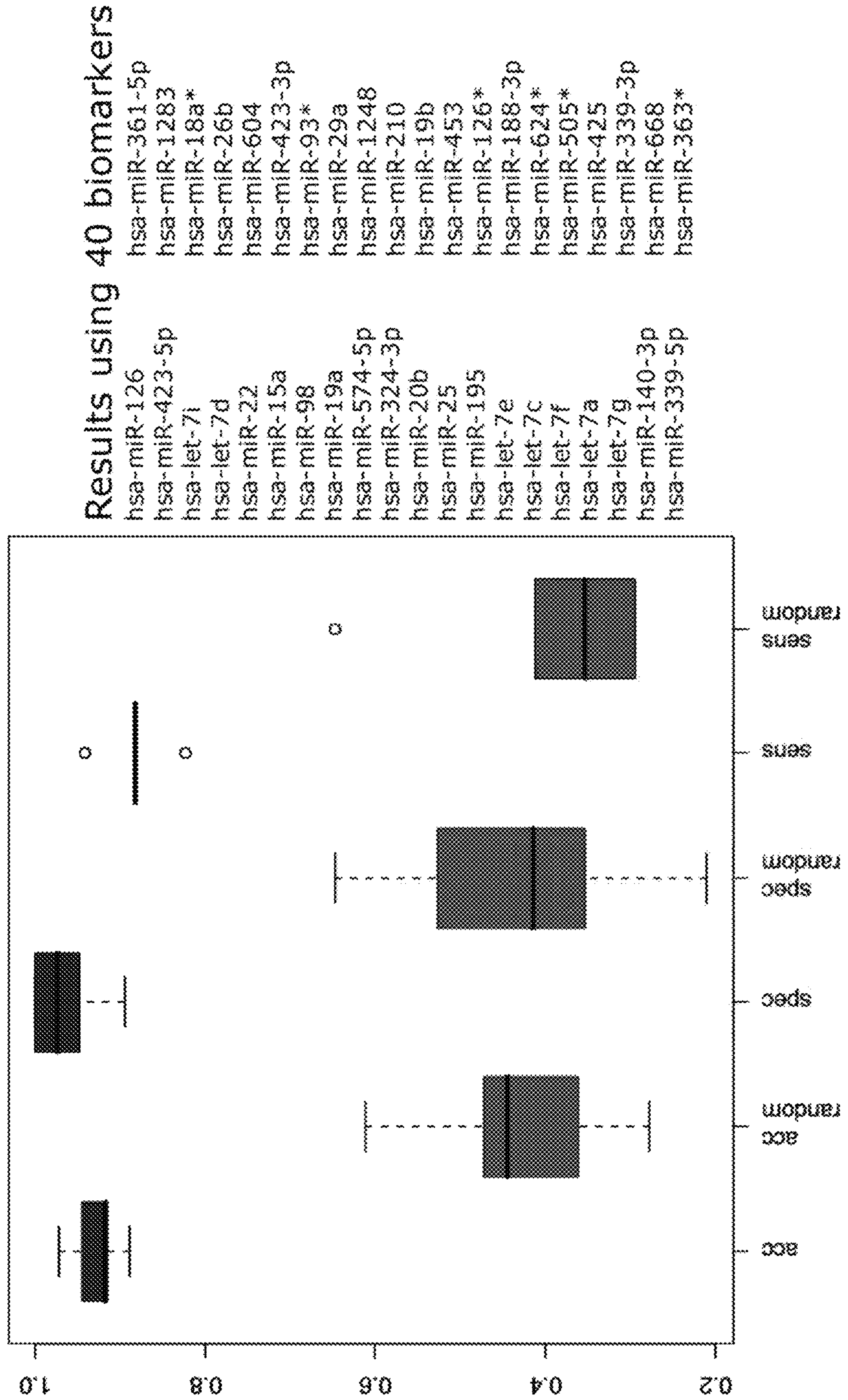
Figure 14:
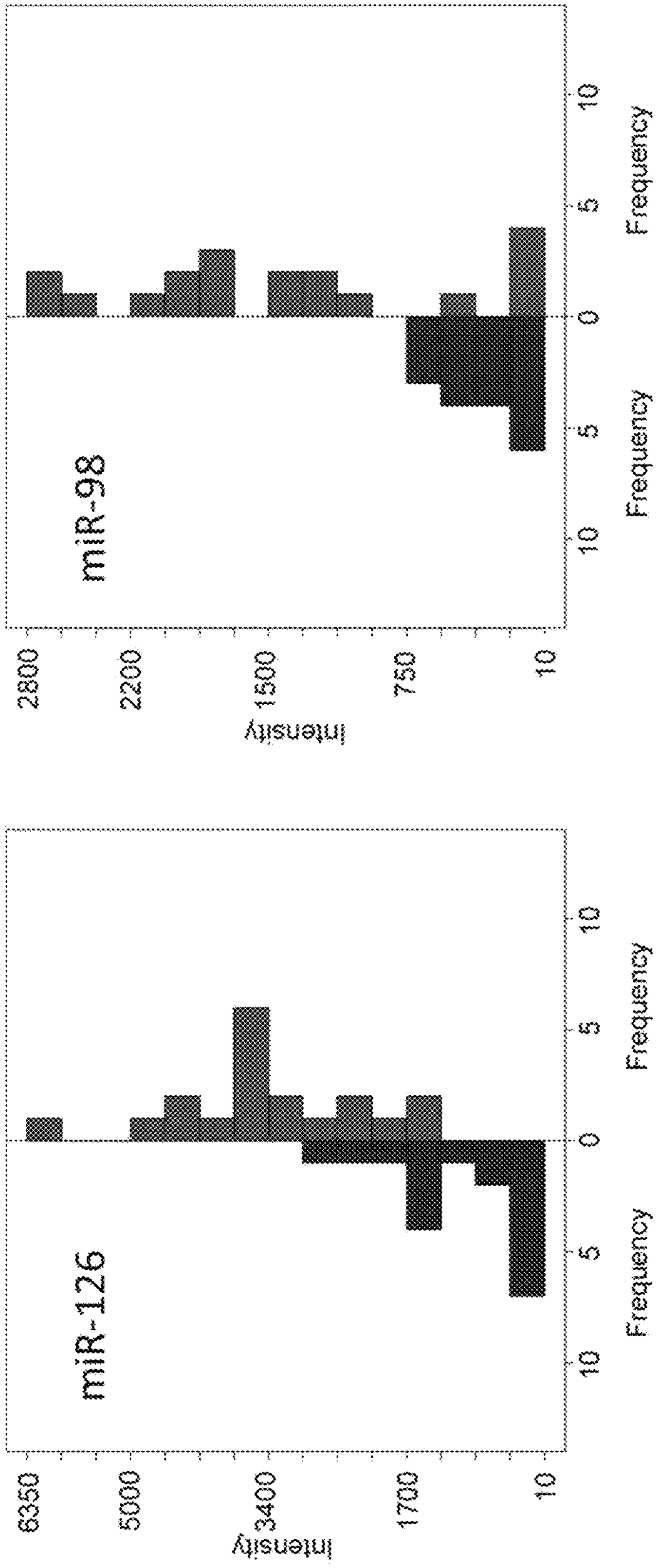
Figure 15:
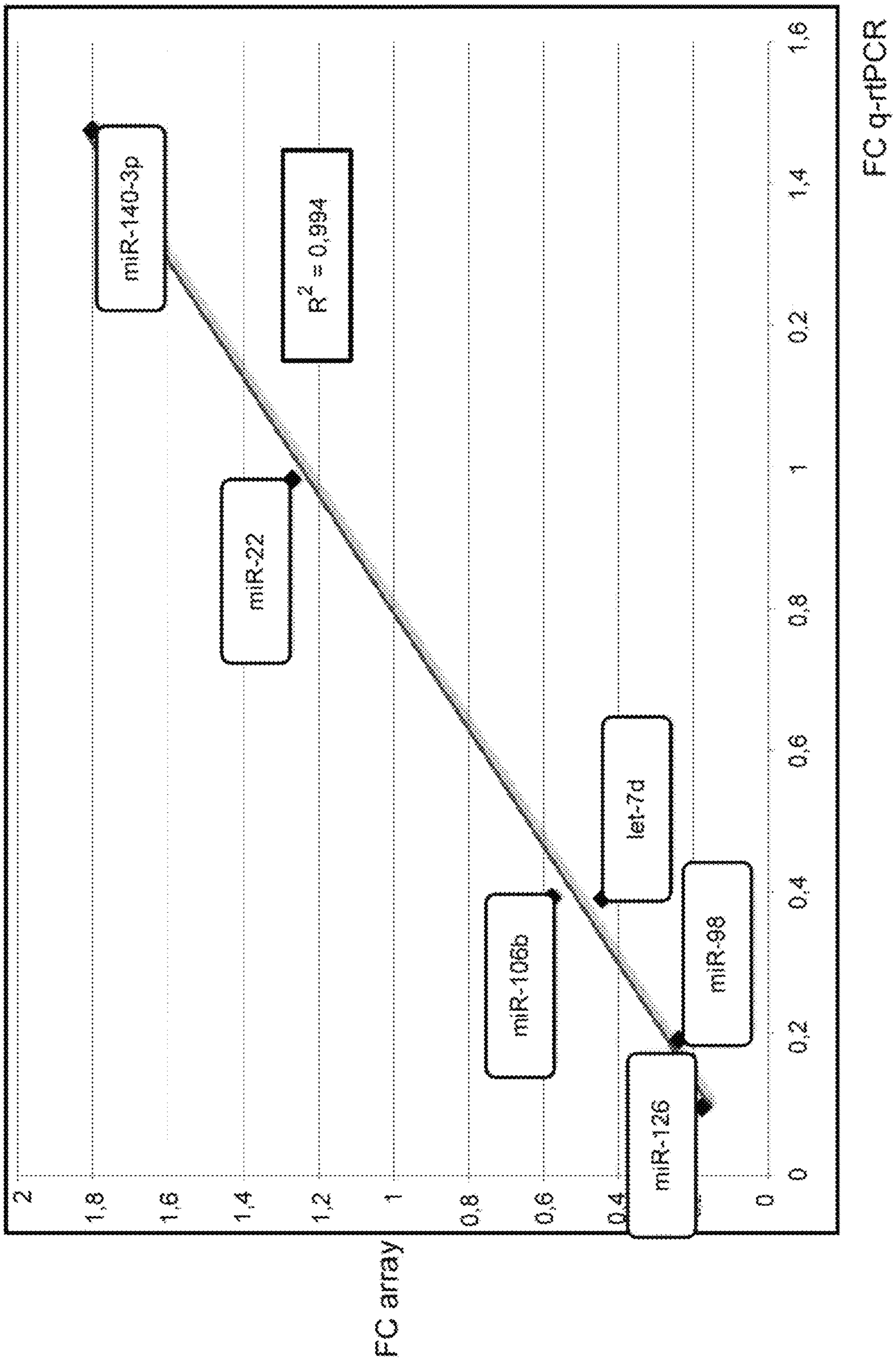

FIG. 13A: 4 biomarkers:

hsa-miR-126, hsa-miR-423-5p, hsa-let-7i and hsa-let-7d;

FIG. 13B: 8 biomarkers:

hsa-miR-126, hsa-miR-423-5p, hsa-let-7i; hsa-let-7d, hsa-miR-22, hsa-miR-15a, hsa-miR-98, and hsa-miR-19a;

FIG. 13C: 10 biomarkers:

hsa-miR-126, hsa-miR-423-5p, hsa-let-7i; hsa-let-7d, hsa-miR-22, hsa-miR-15a, hsa-miR-98, hsa-miR-19a, hsa-miR-574-5p, and hsa-miR-324-3p;

FIG. 13D: 16 biomarkers:

hsa-miR-126, hsa-miR-423-5p, hsa-let-7i; hsa-let-7d, hsa-miR-22, hsa-miR-15a, hsa-miR-98, hsa-miR-19a; hsa-miR-574-5p; hsa-miR-324-3p, hsa-miR-20b, hsa-miR-25, hsa-miR-195, hsa-let-7e, hsa-let-7c, and has-let-7f;

FIG. 13E: 20 biomarkers:

hsa-miR-126, hsa-miR-423-5p, hsa-let-7i; hsa-let-7d, hsa-miR-22, hsa-miR-15a, hsa-miR-98, hsa-miR-19a; hsa-miR-574-5p; hsa-miR-324-3p, hsa-miR-20b, hsa-miR-25, hsa-miR-195, hsa-let-7e, hsa-let-7c, hsa-let-7f; hsa-let-7a, hsa-let-7g, hsa-miR-140-3p and hsa-miR-339-5p;

FIG. 13F: 28 biomarkers:

hsa-miR-126, hsa-miR-423-5p, hsa-let-7i; hsa-let-7d, hsa-miR-22, hsa-miR-15a, hsa-miR-98, hsa-miR-19a; hsa-miR-574-5p; hsa-miR-324-3p, hsa-miR-20b, hsa-miR-25, hsa-miR-195, hsa-let-7e, hsa-let-7c, hsa-let-7f; hsa-let-7a, hsa-let-7g, hsa-miR-140-3p, hsa-miR-339-5p, hsa-miR-36'-5p, hsa-miR-1283, hsa-miR-18a*, hsa-miR-26b, hsa-miR-604, hsa-miR-423-3p, hsa-miR-93*, and hsa-miR-29a;

FIG. 13G: 40 biomarkers:

hsa-miR-126, hsa-miR-423-5p, hsa-let-71; hsa-let-7d, hsa-miR-22, hsa-miR-15a, hsa-miR-98, hsa-miR-19a; hsa-miR-574-5p; hsa-miR-324-3p, hsa-miR-20b, hsa-miR-25, hsa-miR-195, hsa-let-7e, hsa-let-7c, hsa-let-7f; hsa-let-7a, hsa-let-7g, hsa-miR-140-3p, hsa-miR-339-5p, hsa-miR-36'-5p, hsa-miR-1283, hsa-miR-18a*, hsa-miR-26b, hsa-miR-604, hsa-miR-423-3p, hsa-miR-93*, hsa-miR-29a, hsa-miR-1248, hsa-miR-210, hsa-miR-19b, hsa-miR-453, hsa-miR-126*, hsa-miR-188-3p, hsa-miR-624*, hsa-miR-505*, hsa-miR-425, hsa-miR-339-3p, hsa-miR-668, and hsa-miR-363*.

FIG. 14:

Classification of cancer samples versus controls for two individual miRNAs (miR-126 and miR-196). Blue bars correspond to cancer samples, while red bars correspond to controls.

FIG. 15:

Scatterplot of fold quotients of rt-qPCR (x-axis) and microarray experiments (y-axis).

FIG. 16:

The mutual information of all miRNAs that have higher information content than the best permutation test (upper red line). The middle red line denotes the 95% quantile of the 1000 permutation tests and the bottom red line the mean of the permutation experiments, corresponding to the background MI.

FIG. 17:

Box plots of the classification accuracy, specificity and sensitivity of the set of 24 best miRNAs (obtained with radial basis function support vector machine). These miRNAs allow for the discrimination between blood cells of lung cancer patients and blood cells of controls with an accuracy of 95.4% [94.9%-95.9%], a specificity of 98.1% [97.3%-98.8%], and a sensitivity of 92.5%[91.8%-92.5%].

The permutation tests showed significantly decreased accuracy, specificity and sensitivity with 94.2% [47.2%-51.3%], 56.9%[54.5%-59.3%] and 40.6%[37.9%-43.4%], respectively, providing evidence that the obtained results are not due to an overfit of the statistical model on the miRNA fingerprints.

EXAMPLE 1

Lung Cancer
1. Material and Methods
1.1 Samples

Blood samples were obtained with patients' informed consent. The patient samples stem from 17 patients with non-small cell lung carcinoma and normal controls. Normal samples were obtained from 19 different volunteers. More detailed information of patients and controls is given in Table 1.

TABLE 1

Detailed information on lung cancer patients and healthy control subjects

| | blood donors | |
|---|---|---|
| | male | female |
| lung cancer patients | | |
| number | 9 | 8 |
| average age | 67.4 | 60.6 |
| squamous cell lung cancer | 3 | 4 |
| adenocarcinoma | 6 | 1 |
| adenosquamous carcinoma | 0 | 1 |
| broncholaveolar carcinoma | 0 | 1 |
| typical carcinoid | 0 | 1 |
| healthy subjects | | |
| number | 7 | 12 |
| average age | 43.3 | 36.7 |
| lung cancer patients | | |
| number | 9 | 8 |
| average age | 67.4 | 60.6 |
| squamous cell lung cancer | 3 | 4 |
| adenocarcinoma | 6 | 1 |
| adenosquamous carcinoma | 0 | 1 |
| broncholaveolar carcinoma | 0 | 1 |
| typical carcinoid | 0 | 1 |
| healthy subjects | | |
| number | 7 | 12 |
| average age | 43.3 | 36.7 |
| lung cancer patients | | |
| number | 9 | 8 |
| average age | 67.4 | 60.6 |
| squamous cell lung cancer | 3 | 4 |
| adenocarcinoma | 6 | 1 |
| adenosquamous carcinoma | 0 | 1 |
| broncholaveolar carcinoma | 0 | 1 |
| typical carcinoid | 0 | 1 |
| healthy subjects | | |
| number | 7 | 12 |
| average age | 43.3 | 36.7 |

1.2 miRNA Microarray Screening

Blood of lung cancer patients and volunteers without known disease was extracted in blood collection tubes which prevent RNA degradation (PAXgene Blood RNA tubes BD, Franklin Lakes, N.J. USA). For each blood donor, 5 ml of peripheral blood were obtained. Total RNA was extracted from blood cells using the miRNeasy Mini Kit (Qiagen GmbH, Hilden, Germany) and the RNA has been stored at−70.degree. C. Samples were analyzed with the Geniom Realtime Analyzer (GRTA, febit gmbh, Heidelberg, Germany) using the Geniom Biochip miRNA *homo sapiens*. Each array contains 7 replicates of 866 miRNAs and miRNA star sequences as annotated in the Sanger mirBase 12.0 (Griffiths-Jones, Moxon at al. 2005; Griffiths-Jones, Saini et al. 2008). Sample labelling with Biotin has been carried out either by using the miRVANA™ miRNA Labelling Kit (Applied Biosystems Inc, Foster City, Calif. USA) or by multifluidic-based enzymatic on-chip labelling of miRNAs (MPEA (Vorwerk, Canter et al. 2008), incorporated herein by reference).

Following hybridization for 16 hours at 42° C. the biochip was washed automatically and a program for signal enhancement was processed with the GRTA. The resulting detection pictures were evaluated using the Geniom Wizard Software. For each array, the median signal intensity was extracted from the raw data file such that for each miRNA seven intensity values have been calculated corresponding to each replicate copy of mirBase on the array. Following background correction, the seven replicate intensity values of each miRNA were summarized by their median value. To normalize the data across different arrays, quantile normalization (Bolstad, Irizarry et al, 2003) was applied and all further analyses were carried out using the normalized and background subtracted intensity values.

1.3 Statistical Analysis

After having verified the normal distribution of the measured data, parametric t-tests (unpaired, two-tailed) were carried out for each miRNA separately, to detect miRNAs that show a different behavior in different groups of blood donors. The resulting p-values were adjusted for multiple testing by Benjamini-Hochberg (Hochberg 1988; Benjamini and Hochberg 1995) adjustment. Moreover, the Mutual Information (MI) (Shannon 1984) was computed as a measure to access the diagnostic value of single miRNA biomarkers. To this end, all biomarkers were transformed to z-scores and binned in three bins before the MI values of each biomarker, and the information whether the marker has been measured from a normal or lung cancer sample, was computed. In addition to the single biomarker analysis classification of samples using miRNA patterns was carried out using Support Vector Machines (SVM, (Vapnik 2000)) as implemented in the R (Team 2008) e1071 package. In detail, different kernel (linear, polynomial, sigmoid, radial basis function) Support Vector Machines were evaluated, where the cost parameter was sampled from 0.01 to 10 in decimal powers. The measured miRNA profiles were classified using 100 repetitions of standard 10-fold cross-validation. As a subset selection technique a filter approach based on t-test was applied. In detail, the s miRNAs with lowest p-values were computed on the training set in each fold of the cross validation, where s was sampled from 1 to 866. The respective subset was used to train the SVM and to carry out the prediction of the test samples. As result, the mean accuracy, specificity, and sensitivity were calculated together with the 95% Confidence Intervals (95% CI) for each subset size. To check for overtraining permutation tests were applied. Here the class labels were sampled randomly and classifications were carried out using the permuted class labels. All statistical analyzes were performed using R (Team 2008).

2. Results
2.1 miRNA Experiments

The expression of 866 miRNAs and miRNA star sequences was analyzed in blood cells of 17 patients with NSCLC. As a control blood cells of 19 volunteers without known disease were used (see also Materials and Methods).

Following RNA isolation and labeling by miRVANA™ miRNA Labeling Kit, the miRNA expression profiles were measured by the Geniom Bioship miRNA *homo sapiens* in the GRTA (febit gmbh, Heidelberg). Following intensity value computation and quantile normalization of the miRNA profiles (Bolstad, Irizarry et al. 2003), a mean correlation value of 0.97 for technical replicates was determined by using purchased total RNA from Ambion (four heart and four liver replicates). For the biological replicates the different tumor samples were compared between each other and the different normal samples between each other. The biological replicates showed a mean correlation of 0.87 and a variance of 0.009.

2.2 Ruling Out the Influence of Age and Gender

To cross-check that age and gender do not have an influence on our analysis, t-tests were computed for the normal samples. In the case of males versus females there was no statistically significant deregulated miRNA. The most significant miRNA, hsa-miR-423, showed an adjusted significance level of 0.78.

To test for the influence of donor age the profiles obtained from samples obtained from the oldest versus youngest patients were compared by splitting the group in half based on age. Here, the most significant miRNA, miR-890, obtained an adjusted p-value of 0.87. As for gender, there were no deregulated miRNAs, thus providing evidence that age and gender do not have a substantial influence on the miRNA profiles.

2.3 Single Deregulated miRNAs

Hypothesis testing was applied to identify miRNAs deregulated in the blood cells of lung cancer patients as compared to the blood cells of the controls.

Following verification of an approximately normal distribution, two-tailed unpaired t-tests were performed for each miRNA. The respective p-values were adjusted for multiple testing by the Benjamini-Hochberg approach (Hochberg 1988; Benjamini and Hochberg 1995). In total 27 miRNAs significantly deregulated in blood cells of lung cancer patients as compared to the controls were detected. A complete list of deregulated miRNAs is given in the tables in FIGS. 10 and 11. The miRNAs that were most significantly deregulated included hsa-miR-126 with a p-value of 0.00003, hsa-let-7d with a p-value of 0.003, hsa-let-7i with a p-value of 0.003, and hsa-miR-423 with a p-value of 0.001 (FIG. 1 and FIG. 2). Other members of the let-7 family that were also found to be deregulated included hsa-let-7c, hsa-let-7e, hsa-let-7f, hsa-let-7g and hsa-let-7a. Besides miR-423, all above mentioned miRNAs were down-regulated in blood cells of lung cancer patients compared to blood cells of healthy subjects indicating an overall decreased miRNA repertoire.

To validate the findings, the miRNA profiling was repeated using an enzymatic on-chip labeling technique termed MPEA (Microfluidic-based enzymatic on-chip labeling of miRNAs). For this control experiment, 4 out of the 17 lung cancer patients and 10 of the controls were used. Hereby, 100 differentially regulated miRNAs were detected. The miRNAs that were most significantly deregulated include hsa-miR-1253 with a p-value of 0.001, hsa-miR-126 with a p-value of 0.006, hsa-let-7d with a p-value of 0.006, and hsa-let-7f with a p-value of 0.006. Of the previously identified 27 miRNAs 12 were detected to be significant in the second experiment, while the remaining miRNAs showed increased p-values. The correlation of fold changes was 0.62. Also other members of the let-7 family were confirmed as deregulated in blood cells of lung cancer patients. Furthermore, it was confirmed that the majority of the deregulated miRNAs were down-regulated in patients' blood samples. Here, 62% of the deregulated miRNAs showed decreased intensity values in lung cancer samples.

As a further control experiment an expression analysis by qRT-PCR was performed. As a test sample the fold changes of has-miR-106b, miR-98, miR-140-3p, let-7d, mir-126, and miR-22 were analyzed in blood cells of eight tumor patients and five controls. The fold quotients detected by the Geniom Biochip experiments agreed very well with the qRT-PCR experiments, as demonstrated by an excellent $R^2$ value of 0.994. The fold quotients are presented as a scatterplot together with the $R^2$ value and the regression line in FIG. 16.

2.4 Diagnostic Value of miRNA Biomarkers

Mutual Information (MI) (Shannon 1984) is an adequate measure to estimate the overall diagnostic information content of single biomarkers (Keller, Ludwig et al. 2006). In the present study, Mutual Information is considered as the reduction in uncertainty about the class labels '0' for controls and '1' for tumor samples due to the knowledge of the miRNA expression. The higher the value of the MI of a miRNA, the higher is the diagnostic content of the respective miRNA.

Figure 16:
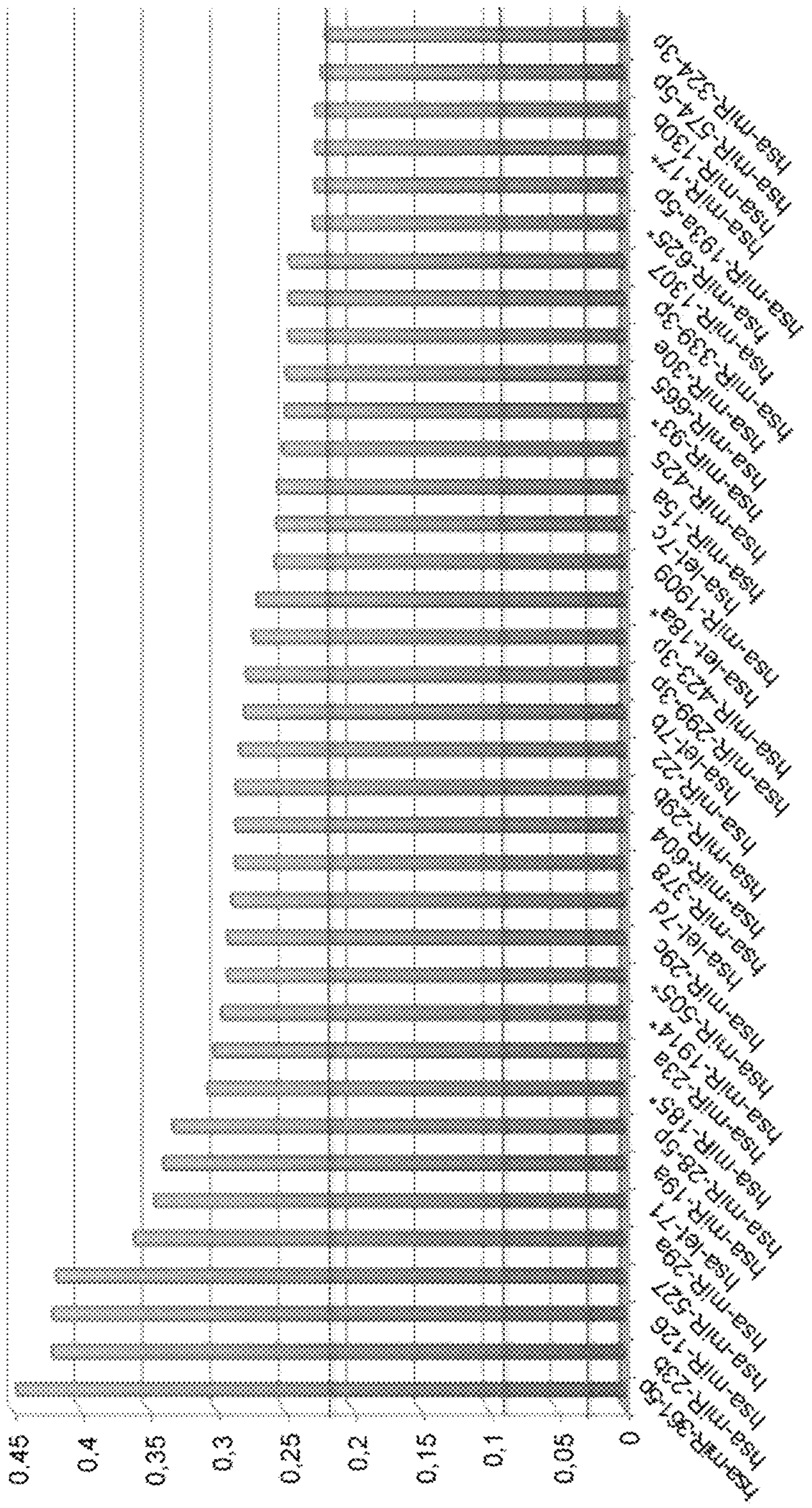
Figure 17:
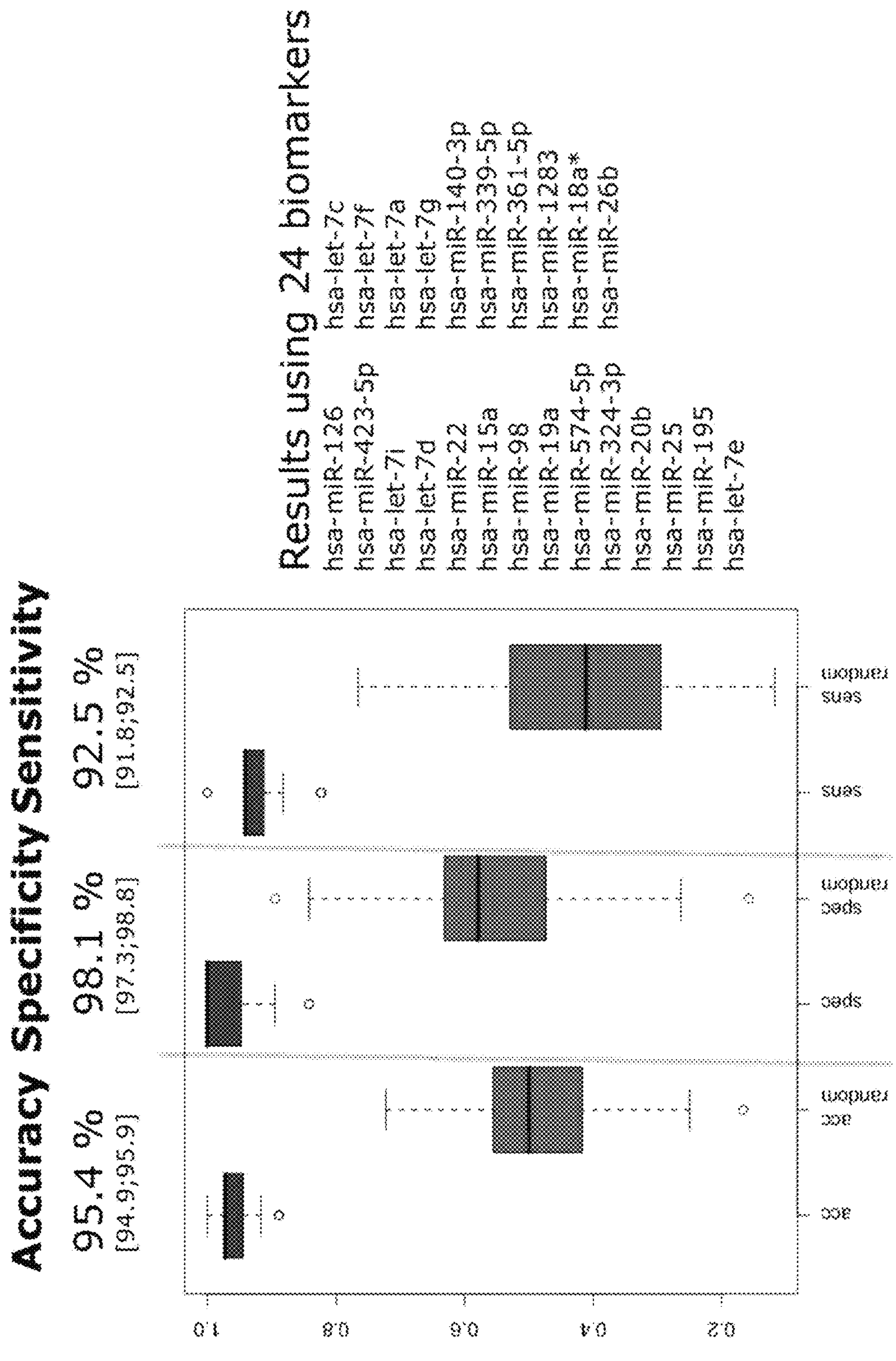

The MI of each miRNA with the class labels was computed. First, a permutation test was carried out to determine the background noise of the miRNAs, e.g. the random information content of each miRNA. 1000 miRNAs (with replacements) were randomly selected and the class labels were sampled for each miRNA. These permutation tests yielded a mean MI value of 0.029, a 95% quantile of 0.096 and a value of 0.217 for the highest random MI. Second, the MI values were calculated for the comparison between the miRNAs in blood cells of tumor patients and controls. The overall comparison of the 866 miRNAs yielded significantly increased MI values with a two-tailed p-value of $\leq 10^{-10}$ as shown by an unpaired Wilcoxon Mann-Whitney test (Wilcoxon 1945; Mann and Wilcoxon 1947). The miRNA hsa-miR-361-5p showed the highest MI with a value of 0.446. The miRNAs with the best significance values as computed by the t-test, namely hsa-miR-126 and hsa-miR-98, were also among the miRNAs showing the highest MI values. In total 37 miRNAs with MI values higher than the highest of 1000 permuted miRNAs and 200 miRNAs with MI values higher than the 95% quantile were detected (FIG. 16). A complete list of miRNAs, the respective MI and the enrichment compared to the background MI is provided in the table in FIG. 10.

2.5 Evaluating Complex Fingerprints

Even single miRNAs with highest MI values are not sufficient to differentiate between blood cells of tumor patients as compared to controls with high specificity. For example, the has-miR-126 separates blood cells of tumor patients from blood cells of healthy individuals with a specificity of 68%, only. In order to improve the classification accuracy the predictive power of multiple miRNAs was combined by using statistical learning techniques. In detail, Support Vector Machines with different kernels (linear, polynomial, sigmoid, radial basis function) were applied to the data and a hypothesis test was carried out based subset selection as described in Material and Methods. To gain statistical significance 100 repetitions of 10-fold cross validation were carried out. Likewise, 100 repetitions for the permutation tests were computed.

The best results were obtained with radial basis function Support Vector Machines and a subset of 24 miRNAs. These miRNAs allowed for the discrimination between blood cells of lung tumor patients and blood cells of controls with an accuracy of 95.4% [94.9%-95.9%], a specificity of 98.1% [97.3%-98.8%], and a sensitivity of 92.5% [91.8%-92.5%]. The permutation tests showed significantly decreased accuracy, specificity, and sensitivity with 49.2% [47.2%-51.3%], 56.9% [54.5%-59.3%] and 40.6% [37.9%-43.4%], respectively (FIG. 5), providing evidence that the obtained results are not due to an overfit of the statistical model on the miRNA fingerprints.

3. Discussion

While complex miRNA expression patterns have been reported for a huge variety of human tumors, information there was only one study analyzing miRNA expression in blood cells derived from tumor patients. In the following the present miRNA expression profiling is related to both the miRNA expression in blood cells and in cancer cells of non-small cell lung cancer patients. A significant down-regulation of has-miR-126 was found that was recently detected in blood cells of healthy individuals, but not in blood cells of lung cancer patients (Chen, Ba et al. 2008). Down-regulation of has-miR-126 was also found in lung cancer tissue in this study. Functional studies on has-miR-126 revealed this miRNA as a regulator of the endothelial expression of vascular cell adhesion molecule 1 (VCAM-1), which is an intercellular adhesion molecule expressed by endothelial cells focuses on the identification of miRNAs in serum of patients with cancer and other diseases or healthy controls. Since most miRNAs are expressed in both, serum and blood cells of healthy controls, most serum miRNAs are likely derived from circulating blood cells. Since there was only a weak correlation between the miRNA expression in serum and blood cell, miRNA expression appears to be deregulated in either serum or blood cells of cancer patients. The present experimental example focused on the analysis of miRNA expression in blood cells of non-small cell lung cancer patients and healthy controls. Significant downregulation of has-miR-126 was found that was recently detected in blood cells of healthy individuals, but not in blood cells of lung cancer patients (Harris, YamakuchiChen, Ba et al. 2008). Downregulation of has-miR-126 was also found in lung cancer tissue (Yanaihara, Caplen et al. 2006). Functional studies on has-miR-126 revealed this miRNA as regulator of the endothelial expression of vascular cell adhesion molecule 1 (VCAM-1), which is an intercellular adhesion molecule expressed by endothelial cells (Harris, Yamakuchi et al. 2008). hsa-miR-126 is also reported to be an inhibitor of cell invasion in non-small cell lung cancer cell lines, and down-regulation of this miRNA 126 might be a mechanism of lung cancer cells to evade these inhibitory effects (Crawford, Brawner et al. 2008). Members of the has-let-7 family that were found down-regulated in the present invention were the first miRNAs reported as deregulated in lung cancer (Johnson, Grosshans et al. 2005). This down-regulation of the let-7 family in lung cancer was confirmed by several independent studies (Takamizawa, Konishi et al. 2004; Stahlhut Espinosa and Slack 2006; Tong 2006; Zhang, Wang et al. 2007; Williams 2008). The present data are also in agreement with a recent study showing the down-regulation of has-let-7a, has-let-7d, has-let-7f, has-let-7g, and has-let-7i in blood cells of lung cancer patients (Chen, Ba et al. 2008). Notably, down-regulation of let-7 in lung cancer was strongly associated with poor clinical outcome (Takamizawa, Konishi et al. 2004). The let-7 family members negatively regulate oncogene RAS (Johnson, Grosshans et al. 2005). The miRNA has-miR-22 that showed a high MI value and up-regulation in the present study, was recently also reported to be up-regulated in blood cells of lung cancer patients (Chen, Ba et al. 2008). The miRNA has-miR-19a that also showed a high MI value and up-regulation in the present study was reported to be up-regulated in lung cancer tissue (Hayashita, Osada et al. 2005; Cahn and Croce 2006). In contrast, has-miR-20a, which is significantly down-regulated in the present experiments, was reported as up-regulated in lung cancer tissue (Hayashita, Osada et al. 2005; Calin and Croce 2006). The up-regulation of has-miR-20a was found in small-cell lung cancer cell lines, the present study investigated only NSCLC. In summary, there is a high degree of consistency between miRNA expression found in the peripheral blood cells of lung cancer patients and miRNA expression in lung cancer tissue (Takamizawa, Konishi et al. 2004; Hayashita, Osada et al. 2005; Lu, Getz et al. 2005; Calin and Croce 2006; Stahlhut Espinosa and Slack 2006; Tong 2006; Volinia, Calin et al. 2006; Yanaihara, Caplen et al. 2006; Zhang, Wang et al. 2007; Williams 2008).

Some of the deregulated miRNAs identified in the present invention are also reported as de-regulated in other cancer entities, e.g. has-miR-346 in gastritic cancer, has-miR-145 in bladder cancer, and has-miR-19a in hepatocellular carcinoma and B-cell leukemia (Alvarez-Garcia and Miska 2005; He, Thomson et al. 2005; Feitelson and Lee 2007; Guo, Huang et al. 2008; Ichimi, Enokida et al. 2009). In addition, miRNAs with high diagnostic potential e.g. high MI value, were found that were not yet related to cancer as for example has-miR-527 or has-mir-361-5p that were both up-regulated in blood cells of lung cancer patients.

Besides the deregulation of single miRNAs, the overall expression pattern of miRNAs in peripheral blood cells of lung cancer patients were analyzed in comparison to the pattern in blood cells of healthy controls. Recently, Chen et al. (Chen, Ba et al. 2008) reported a high correlation of 0.9205 between miRNA profiles in serum and miRNA profiles in blood cells, both in healthy individuals. The correlation of the miRNA profiles between serum and blood cells in lung cancer patients were significantly lower (0.4492). These results are indicative of deregulated miRNAs in blood and/or serum of patients and are in agreement with the present data that show the deregulation of miRNAs in the blood cells of lung carcinoma patients. These deregulated miRNAs can be used to differentiate patients with lung cancer from normal controls with high specificity and sensitivity. This is the first evidence for the diagnostic potential of miRNA expression profiles in peripheral blood cells of cancer patients and healthy individuals.

REFERENCES

Alvarez-Garcia, I. and E. A. Miska (2005). "MicroRNA functions in animal development and human disease." *Development* 132(21): 4653-62.

Benjamini, Y. and Y. Hochberg (1995). "Controlling the false discovery rate: A practical and powerful approach to multiple testing." *J R Statist Soc B* 57: 289-300.

Bolstad, B. M., R. A. Irizarry, et al. (2003). "A comparison of normalization methods for high density oligonucleotide array data based on variance and bias." *Bioinformatics* 19(2): 185-93.

Calin, G. A. and C. M. Croce (2006). "MicroRNA-cancer connection: the beginning of a new tale." *Cancer Res* 66(15): 7390-4.

Calin, G. A. and C. M. Croce (2006). "MicroRNA signatures in human cancers." *Nat Rev Cancer* 6(11): 857-66.

Chen, X., Y. Ba, et al. (2008). "Characterization of microRNAs in serum: a novel class of biomarkers for diagnosis of cancer and other diseases." *Cell Res* 18(10): 997-1006.

Crawford, M., E. Brawner, et al. (2008). "MicroRNA-126 inhibits invasion in non-small cell lung carcinoma cell lines." *Biochem Biophys Res Commun* 373(4): 607-12.

Esquela-Kerscher, A. and F. J. Slack (2006). "Oncomirs—microRNAs with a role in cancer." *Nat Rev Cancer* 6(4): 259-69.

Feitelson, M. A. and J. Lee (2007). "Hepatitis B virus integration, fragile sites, and hepatocarcinogenesis." *Cancer Lett* 252(2): 157-70.

Gilad, S., E. Meiri, at al. (2008). "Serum microRNAs are promising novel biomarkers." *PLoS ONE* 3(9): e3148.

Griffiths-Jones, S., R. J. Grocock, et al. (2006). "miRBase: microRNA sequences, targets and gene nomenclature." *Nucleic Acids Res* 34(Database issue): D140-4.

Griffiths-Jones, S., S. Moxon, et al. (2005). "Rfam: annotating non-coding RNAs in complete genomes." *Nucleic Acids Res* 33(Database issue): D121-4.

Griffiths-Jones, S., H. K. Saini, et al. (2008). "miRBase: tools for microRNA genomics." *Nucleic Acids Res* 36(Database issue): D154-8.

Guo, L., Z. X. Huang, et al. (2008). "Differential Expression Profiles of microRNAs in NIH3T3 Cells in Response to UVB Irradiation." *Photochem Photobiol.*

Harris, T. A., M. Yamakuchi, et al. (2008). "MicroRNA-126 regulates endothelial expression of vascular cell adhesion molecule 1." *Proc Natl Acad Sci USA* 105(5): 1516-21.

Hayashita, Y., H. Osada, et al. (2005). "A polycistronic microRNA cluster, miR-17-92, is overexpressed in human lung cancers and enhances cell proliferation." *Cancer Res* 65(21): 9628-32.

He, L., J. M. Thomson, et al. (2005). "A microRNA polycistron as a potential human oncogene." *Nature* 435 (7043): 828-33.

Henschke, C. I. and D. F. Yankelevitz (2008). "CT screening for lung cancer: update 2007." *Oncologist* 13(1): 65-78.

Hochberg, Y. (1988). "A sharper bonferroni procedure for multiple tests of significance." *Biometrica* 75: 185-193.

Ichimi, T., H. Enokida, et al. (2009). "Identification of novel microRNA targets based on microRNA signatures in bladder cancer." *Int J Cancer.*

Jemal, A., R. Siegel, et al. (2008). "Cancer statistics, 2008." *CA Cancer J Clin* 58(2): 71-96.

Johnson, S. M., H. Grosshans, et al. (2005). "RAS is regulated by the let-7 microRNA family." *Cell* 120(5): 635-47.

Keller, A., N. Ludwig, et al. (2006). "A minimally invasive multiple marker approach allows highly efficient detection of meningioma tumors." *BMC Bioinformatics* 7: 539.

Lee, R. C., R. L. Feinbaum, et al. (1993). "The *C. elegans* heterochronic gene lin-4 encodes small RNAs with antisense complementarity to lin-14." *Cell* 75(5): 843-54.

Lu, J., G. Getz, et al. (2005). "MicroRNA expression profiles classify human cancers." *Nature* 435(7043): 834-8.

Mann, H. and F. Wilcoxon (1947). "On a test whether one of two random variables is stochastically larger than the other." *Ann Mat Stat* 18: 50-60.

Sassen, S., E. A. Miska, et al. (2008), "MicroRNA: implications for cancer." *Virchows Arch* 452(1): 1-10.

Scott, W. J., J. Howington, et al. (2007). "Treatment of non-small cell lung cancer stage I and stage II: ACCP evidence-based clinical practice guidelines (2nd edition)." *Chest* 132(3 Suppl): 234S-242S.

Shannon, C. (1984). "A mathematical theory of communication." *The Bell System Technical Journal* 27: 623-656.

Stahlhut Espinosa, C. E. and F. J. Slack (2006). "The role of microRNAs in cancer." *Yale J Bid Med* 79(3-4): 131-40.

Takamizawa, J., H. Konishi, et al. (2004). "Reduced expression of the let-7 microRNAs in human lung cancers in association with shortened postoperative survival." *Cancer Res* 64(11): 3753-6.

Team, R. D. C. (2008). *R: A Language and Environment for Statistical Computing*. Vienna, Austria, R Foundation for Statistical Computing.

Tong, A. W. (2006). "Small RNAs and non-small cell lung cancer." *Curr Mol Med* 6(3): 339-49.

Vapnik, V. (2000). *The Nature of Statistical Learning Theory.*, Springer.

Volinia, S., G. A. Calin, et al. (2006). "A microRNA expression signature of human solid tumors defines cancer gene targets." *Proc Natl Acad Sci USA* 103(7): 2257-61.

Vorwerk, S., K. Ganter, et al. (2008). "Microfluidic-based enzymatic on-chip labeling of miRNAs." *N Biotechnol* 25(2-3): 142-9.

Wilcoxon, F. (1945), "Individual comparisons by ranking methods." *Biometric Bull* 1: 80-83.

Williams, A. E. (2008). "Functional aspects of animal microRNAs." *Cell Mol Life Sci* 65(4): 545-62.

Yanaihara, N., N. Caplen, et al. (2006). "Unique microRNA molecular profiles in lung cancer diagnosis and prognosis." *Cancer Cell* 9(3): 189-98.

Zhang, B., X. Pan, et al. (2007). "microRNAs as oncogenes and tumor suppressors." *Dev Biol* 302(1): 1-12.

Zhang, B., Q. Wang, et al. (2007). "MicroRNAs and their regulatory roles in animals and plants." *J Cell Physiol* 210(2): 279-89.

The invention claimed is:

1. A method of detecting miRNA, comprising
(a) extracting total intracellular RNA from all blood cells obtained from a whole blood sample taken from a patient, and
(b) determining in said total intracellular RNA an expression profile of an miRNA set consisting of:
(i) hsa-miR-423-5p, hsa-miR-126, and hsa-let-7i;
(ii) hsa-miR-423-5p, hsa-miR-126, hsa-let-7i, and hsa-let-7d;
(iii) hsa-miR-423-5p, hsa-miR-126, hsa-let-7i, hsa-let-7d, and hsa-miR-22; or
(iv) hsa-miR-423-5p, hsa-miR-126, hsa-let-7i, hsa-let-7d, hsa-miR-22, hsa-miR-15a, hsa-miR-98, hsa-miR-19a, hsa-miR-574-5p, and hsa-miR-324-3p.

2. The method of claim 1, wherein the patient is suspected of suffering from lung cancer.

3. The method of claim 1, wherein the lung cancer is selected from the group consisting of lung carcinoid, lung pleural mesothelioma, non-small cell lung carcinoma and lung squamous cell carcinoma.

4. The method of claim 3, wherein the lung cancer is non-small cell lung carcinoma.

5. The method of claim 1, wherein step (b) comprises quantitative or semiquantitative detection of said miRNAs.

6. The method of claim 1, wherein determining said expression profile comprises nucleic acid amplification performed using real-time polymerase chain reaction (PCR).

7. The method of claim 6, wherein determining the expression profile using real-time PCR comprises:
(1) reverse transcribing the total intracellular RNA extracted from said blood cells into cDNA, and
(2) quantifying the cDNA, thereby determining the expression profile of said miRNAs.

8. The method of claim 1, wherein said blood cells comprise a mixture of erythrocytes, leukocytes, and thrombocytes.

9. The method of claim 1, wherein the expression profile of hsa-miR-423-5p, hsa-miR-126, hsa-let-7i, and hsa-let-7d is determined.

* * * * *